United States Patent
Horikawa et al.

(10) Patent No.: US 6,235,481 B1
(45) Date of Patent: May 22, 2001

(54) POLYNUCLEOTIDES ENCODING CALPAIN 10

(75) Inventors: Yukio Horikawa, Kobe; Naohisa Oda, Nagoya, both of (JP); Craig L. Hanis, Houston, TX (US); Graeme I. Bell, Chicago; Nancy J. Cox, Inverness, both of IL (US)

(73) Assignees: ARCH Development Corporation & Board of Regents, Chicago, IL (US); The University of Texas System, Austin, TX (US)

( * ) Notice: Subject to any disclaimer, the term of this patent is extended or adjusted under 35 U.S.C. 154(b) by 0 days.

(21) Appl. No.: 09/422,869

(22) Filed: Oct. 21, 1999

Related U.S. Application Data
(60) Provisional application No. 60/134,175, filed on May 13, 1999, and provisional application No. 60/105,052, filed on Oct. 21, 1998.

(51) Int. Cl.[7] .............................. C07H 1/68; C07H 21/04
(52) U.S. Cl. ............................ 435/6; 536/23.1; 536/24.1
(58) Field of Search ............................... 435/6; 536/23.1, 536/24.1

(56) References Cited

U.S. PATENT DOCUMENTS
5,545,672 8/1996 Knutson ............................... 514/603

FOREIGN PATENT DOCUMENTS
WO 96/09317 3/1996 (WO).
WO 98/11254 3/1998 (WO).
WO 00/09709 2/2000 (WO).

OTHER PUBLICATIONS

Saido et al "Calpain: new perspectives in molecular diversity and physiological–pathologyical involvement" FASEB, vol. 8, pp. 814–822, 1994.*

Carafoli et al "Clapin: a protease in search of a function?" Biochemical and biophysical research communications, vol. 247, pp. 193–203, 1998.*

Genbank Accession Packet with alignments. (No year).*

Braun et al., "Identification of a new calpain–like cDNA in mouse lung," Database EMBL 'Online!, XP002139084 Abstract No year.

Braun et al., "Identification of a new calpain–like cDNA in mouse lung," Database EMBL 'Online!, XP002139083 Abstract No year.

Cox et al., "Loci on chromosomes 2 (NIDDM1) and 15 interact to increase susceptibility to diabetes in Mexican Americans," *Nature Genetics*, 21:213–215, 1999.

Terada et al., "Delayed wallerian degeneration and increased neurofilament phosphorylation in sciatic nerves of rats with streptozocin–induced diabetes," *J Neuro Sci.*, 155:23–30, 1998.

Wang and Yuen, "Calpain inhibition: and overview of its therapeutic potential," *TIPS*, 15:412–417, 1994.

Barnes and Hodgkin, "The tra–3 sex determination gene of *Caenorhabditis elegans* encodes a member of the calpain regulatory protease family," *EMBO J.*, 15(17):4477–4484, 1996.

Barrett et al., "L–trans–epoxysuccinyl–leucylamido(4–guanidino)butane (E–64) and its analogues as inhibitors of cysteine proteinases including cathepsins B, H and L," *Biochem J.*, 201:189–198, 1982.

Carafoli and Molinari, "Calpain: a protease in search of a function?", *Biochem. Biophys. Res. Commun.*, 247:193–203, 1998.

Ciccarese et al., "Preliminary data on a genome search in NIDDM siblings: the NIDDM 1 locus on chromosome 2 is not linked to NIDM in the Sardinian population", *Diabetologia*, 40:1366–1367, 1997.

Dear et al., "A new subfamily of vertebrate calpains lacking a calmodulin–like domain: implications for calpain regulation and evolution", *Genomics*, 45:175–184, 1997.

Emori et al., "Endogenous inhibitor for calcium–dependent cysteine protease contains four internal repeats that could be responsible for its multiple reactive sites", *Proc. Natl. Acad. Sci. USA* 84:3590–3594, 1987.

Figueiredo–Pereira et al., "Comparison of the effect of calpain inhibitors on two extralysosomal proteinases: the multicatalytic proteinase complex and m–calpain", *J Neurochem*, 62:1989–94, 1994.

Flexner, "HIV–protease inhibitors," *N. Engl. J. Med.*, 338:1281–1292, 1998.

Ghosh et al., "A large sample of Finnish diabetic sib–pairs reveals no evidence for a non–insulin–dependent diabetes mellitus susceptibility locus at 2qter", *J. Clin. Invest.*, 102:704–709, 1998.

Hani et al., "Mapping NIDDM susceptibility loci in French families: studies with markers in the region of NIDDM1 on chromosome 2q," *Diabetes*, 46:1225–1226, 1997.

Hanis et al., "A genome–wide search for human non–insulin–dependent (type 2) diabetes genes reveals a major susceptibility locus on chromosome 2," *Nature Genet.*, 13:161–166, 1996.

(List continued on next page.)

Primary Examiner—Lisa B. Arthur
Assistant Examiner—Jeanine Goldberg
(74) Attorney, Agent, or Firm—Fulbright & Jaworski LLP

(57) ABSTRACT

The present invention relates generally to the field of diabetes. More particularly, it concerns the identification of genes responsible for NIDDM1 for use in diagnostic and therapeutic applications. The present invention demonstrates that the NIDDM1 locus is, in fact, the calpain 10 gene. The invention further relates to the discovery that analysis of mutations in calpain genes and gene products can be diagnostic for type 2 diabetes. The invention also contemplates methods of treating diabetes in view of the fact that calpain mutations can cause diabetes. Further, the invention relates to novel polynucleotides of the NIDDM1 locus and polypeptides encoded by such polynucleotides.

88 Claims, 48 Drawing Sheets

OTHER PUBLICATIONS

Hashida et al., "Inhibitions by E–64 derivatives of rat liver cathepsin B and cathepsin L in vitro and in vivo," *J. Biochem*, 88:1805–1811, 1980.

Jackson et al., "Obesity and impaired prohormone processing associated with mutations in the human prohormone convertase 1 gene", *Nature Genet.*, 16:303–306, 1997.

Mahtani et al., "Mapping of a gene for type 2 diabetes associated with an insulin secretion defect by a genome scan in Finnish families", *Nature Genet.*, 14:90–94, 1996.

Naggert et al., "Hyperproinsulinaemia in obese fat/fat mice associated with a carboxypeptidase E mutation which reduces enzyme activity", *Nature Genet.*, 10:135–141, 1995.

O'Dowd et al., "Discovery of three novel G–protein–coupled receptor genes", *Genomics*, 47:310–313, 1998.

Posmantur et al., "A calpain inhibitor attenuates cortical cytoskeletal protein loss after experimental traumatic brain injury in the rat", *Neuroscience*, 77:875–88, 1997.

Richard et al., "Mutations in the proteolytic enzyme calpain 3 cause limb–gridle muscular dystrophy type 2A", *Cell*, 81:27–40, 1995.

Saido et al., "Calpain: new perspectives in mollecular diversity and physiological–pathological involvement," *FASEB J.*, 8:814–822, 1994.

Smith et al., "The insulin–induced down–regulation of IRS–1 in 3T3–L1 adipocytes is mediated by a calcium–dependent thiol protease", *Mol. Cell. Endocrinol.*, 122:81–92, 1996.

Spielman and Ewens, "A sibship test for linkage in the presence of association: the sib transmission/disequilibrium test", *Am. J. Hum. Genet.*, 62:450–458, 1998.

Thomas et al., "Genetic linkage study of a major susceptibility locus (D2S125) in a British population of non–insulin dependent diabetic sib–pairs using a simple non–isotopic screening method," *Hum. Genet.*, 101:212–213, 1997.

Tsujinaka et al., "Synthesis of a new cell penetrating calpain inhibitor calpeptin," Abstract, *Biochem. and Biophys. Res. Comm.*, 153(3): 1201–1208, 1988.

Ueda et al., "Evidence for the participation of the proteasome and calpain in early phases of muscle cell differentiation", *Int. J. Biochem. Cell Biol.*, 30:679–94, 1998.

Villa et al., "Calpain inhibitors, but not caspase inhibitors, prevent actin proteolysis and DNA fragmentation during apoptosis", *J. Cell. Sci.*, 111:713–22, 1998.

Waxman and Krebs, "Identification of two protease inhibitors from bovine cardiac muscle," *J. Biol. Chem.* 253:5888–5891, 1978.

Zimmerman et al., "Inhibition of secretion from isolated rat alveolar epithelial type II cells by the cell permeant calpain inhibitor II (N–acetyl–leucyl–methioninal)", *Cell. Calcium*, 18:1–8, 1995.

* cited by examiner hCAPN5
MFSCVKPYEDQNYSALRQDCRRRK'
MVDVVIDERLPTVNNQLIYCHSNS]
RKVRLGHGLLAFFKSEKLDMIRLR]
QYIFEVKKPEDEVLICIQQRPKRS'
VTQVHVLGAAGLKDSPTGANSYVI:

mCAPN6
MGPPLKLFKNQKYQELKQECMKDG]
EWTEVVIDDLPTINGDLVFSFST:
IRKLRLGERLVEVFSTEKLYMVRL]
IFTVPEDGHKVIMSLQQKDLRTYR]
VTQITVHSAEGLEKKYANETVNPY:

hCAPN3
MPTVISASVAPRTAAEPRSPGPVP]
WFLAAIACLTLNQHLLFRVIPHDQ:
GSLMGCSIDDGTNMTYGTSPSGLN]
QHQVTEDGEFWMSYEDFIYHFTKL]
KQHLQKDFFLYNASKARSKTYINM]
QESEEQQQFRNIFKQIAGDDMEIC¿
MNIDFDSFICCFVRLEGMFRAFHA]

FIG. 5A

```
VLFEDPLFPATDDSLYYKGTPGPAV
RNEFWCALVEKAYAKLAGCYQALDG
NPWGEREWNGPWSDTSEEWQKVSKS
TRREGKGENLAIGFDIYKVEENRQY
IKCEGDKVRSAVQKGTSTPEYNVKG

RLFCDPTFLPENDSLFFNRLLPGKV
SMNEFWNALLEKAYAKLLGCYEALD
RNPLGRQEWSGPWSEISEEWQQLTV
RMGRPDNYIIGFELFKVEMNRRFRL
LIIKCGKEEVRSPVQKNTVHAIFDT

HPAQSKATEAGGGNPSGIYSAIISR
SFIENYAGIFHFQFWRYGEWVDVVI
MGELIARMVRNMDNSLLQDSDLDPR
EICNLTADALQSDKLQTWTVSVNEG
REVSQRFRLPPSEYVIVPSTYEPHQ
ADELKKVLNTVVNKHKDLKTHGFTL
FDKDGDGIIKLNVLEWLQLTMYA  8
```

FIG. 5B

```
RWKRPKGICEDPRLFVDGISSHDLH
GNTADALVDFTGGVSEPIDLTEGDF
EREKMGVTVQDDGEFWMTFEDVCRY
RMHSLQHKAASSIYINSRSVFLRTD
IFYRKKLSQPITVQVWNHRVLKDEF

VWKRPQDISDDPHLIVGNISNHQLI
GLTITDIIMDFTGTLAEIIDMQKGR
TDRKNLGLVMSDDGEFWMSLEDFCH
HHLYIQERAGTSTYIDTRTVFLSKY
QAVFYRRTTDIPIIQVWNSRKFCD

NFPIIGVKEKTFEQLHKKCLEKKVL
DDCLPTYNNQLVFTKSNHRNEFWSA
GSDERPTRTIIPVQYETRMACGLVR
RWVRGCSAGGCRNFPDTFWTNPQYR
EGEFILRVFSEKRNLSEEVENTISV
ESCRSMIALMDTDGSGKLNLQEFHH
21
```

FIG. 5C

```
QGQVGNCWFVAACSSLASRESLWQK
ANDETKRNQLFERMLKVHSRGGLIS
FTDIIKCRVINTSHLSIHKTWEEAR
QPEGRYVIIPTTFEPGHTGEFLLRV
LGQVHLKADPDNLQALHTLHLRDRN

QGRLGNKAMISAFSCLAVQESHWTK
YTDLVEEKYKLFGELYKTFTKGGLI
NFHKLNVCRNVNNPVFGRKELESVV
LKKGSYVLVPTMFQHGRTSEFLLRI
QFLGQVTLDADPSDCRDLKSLYLRK

YVDPEFPPDETSLFYSQKFPIQFVW
LLEKAYAKLHGSYEALKGGNTTEAM
GHAYSVTGLDEVPFKGEKVKLVRLR
LKLLEEDDDPDDSEVICSFLVALMQ
DRPVKKKKTKPIIFVSDRANSNKEL
LWNKIKAWQKIFKHYDTDQSGTINS
```

FIG. 5F hCAPN9

MPYLYRAPGPQAHPVPKDARITHS
IFHFQFWQHSEWLDVVIDDRLPTF
TGIDQVSFRGQRIELIRIRNPWGQ
DEGQEECSFLVALMQKDRRKLKRF
TEEEQRFRALFEQVAGEDMEVTAE
LDFDDFLNCLVRLENASRVFQALS hCAPN1

MSEEIITPVYCTGVSAQVQKQRAR
LLHRVVPHGQSFQNGYAGIFHFQL
DMEAITFKKLVKGHAYSVTGAKQV
PATFWVNPQFKIRLDETDDPDDYG
KSAGTVELDDQIQANLPDEQVLSE
SAGFKLNKKLYELIITRYSEPDLA hCAPN2

MAGIAAKLAKDREAAEGLGSHERA
SFQENYAGIFHFQFWQYGEWVEVV
VKGHAYSVTGAEEVESNGSLQKLI
LIKLEEEDEDEEDGESGCTFLVGL
EANLEEFDISEDDIDDGVRRLFAQ
IVARFADDQLIIDFDNFVRCLVRL

FIG. 5G

```
SGQSFEQMRQECLQRGTLFEDADFP
RDRLVFLHSADHNEFWSALLEKAYA
VEWNGSWSDSSPEWRSVGPAEQKRL
GANVLTIGYAIYECPDKDEHLNKDF
ELEYVLNAVLQKKKDIKFKKLSLIS
TKNKEFIHLNINEFIHLTMNI  690

ELGLGRHENAIKYLGQDYEQLRVRC
WQFGEWVDVVVDDLLPIKDGKLVFV
NYRGQVVSLIRMRNPWGEVEWTGAW
DRESGCSFVLALMQKHRRRERRFGR
EEIDENFKALFRQLAGEDMEISVKE
VDFDNFVCCLVRLETMFRFFKTLDT

IKYLNQDYEALRNECLEAGTLFQDP
VDDRLPTKDGELLFVHSAEGSEFWS
RIRNPWGEVEWTGRWNDCPSWNTI
IQKHRRRQRKMGEDMHTIGFGIYEV
LAGEDAEISAFELQTILRRVLAKRQ
ETLFKIFKQLDPENTGTIELDLISW
```

FIG. 5H

```
SGQSFEQMRQECLQRGTLFEDADFP
RDRLVFLHSADHNEFWSALLEKAYA
VEWNGSWSDSSPEWRSVGPAEQKRL
GANVLTIGYAIYECPDKDEHLNKDF
ELEYVLNAVLQKKKDIKFKKLSLIS
TKNKEFIHLNINEFIHLTMNI  690

ELGLGRHENAIKYLGQDYEQLRVRC
WQFGEWVDVVVDDLLPIKDGKLVFV
NYRGQVVSLIRMRNPWGEVEWTGAW
DRESGCSFVLALMQKHRRRERRFGR
EEIDENFKALFRQLAGEDMEISVKE
VDFDNFVCCLVRLETMFRFFKTLDT

IKYLNQDYEALRNECLEAGTLFQDP
VDDRLPTKDGELLFVHSAEGSEFWS
RIRNPWGEVEWTGRWNDCPSWNTI
IQKHRRRQRKMGEDMHTIGFGIYEV
LAGEDAEISAFELQTILRRVLAKRQ
ETLFKIFKQLDPENTGTIELDLISW
```

FIG. 5I

```
ASNSSLFYSERPQIPFVWKRPGEIV
KLNGSYEALKGGSAIEAMEDFTGGV
CHTALDDGEFWMAFKDFKAHFDKVE
FRYHASRARSKTFINLREVSDRFKL
CKNIISLMDTSGNGKLEFDEFKVFW

LQSGTLFRDEAFPPVPQSLGYKDLG
HSAEGNEFWSALLEKAYAKVNGSYE
SDSSSEWNNVDPYERDQLRVKMEDG
DMETIGFAVYEVPPELVGQPAVHLK
LRTILNRIISKHKDLRTKGFSLESC
DLDGVVTFDLFKWLQLTMFA    714

SFPAIPSALGFKELGPYSSKTRGMR
ALLEKAYAKINGCYEALSGGATTEG
DPEERERLTRRHEDGEFWMSFSDFL
PEELSGQTNIHLSKNFFLTNRARER
DIKSDGFSIETCKIMVDMLDSDGSG
LCFSVL 700
```

FIG. 5J

```
KNPEFILGGATRTDICQGELGDCWL
AETFQTKEAPENFYEILEKALKRGS
ICNLTPDALEEDAIHKWEVTVHQGS
PPGEYILIPSTFEPHQEADFCLRIF
DKLKQWINLFLRFDADKSGTMSTYE

PNSSKTYGIKWKRPTELLSNPQFIV
ALSGGSTSEGFEDFTGGVTEWYELR
EFWMSFRDFMREFTRLEICNLTPDA
RDFFLANASRARSEQFINLREVSTR
RSMVNLMDRDGNGKLGLVEFNILWN

WKRPTEICADPQFIIGGATRTDICQ
FEDFTGGIAEWYELKKPPPNLFKII
RHYSRLEICNLTPDTLTSDTYKKWK
SDTFINLREVLNRFKLPPGEYILVP
KLGLKEFYILWTKIQKYQKIYREID
```

FIG. 5K

```
LAAIASLTLNQKALARVIPQDQSFG
LLGCFIDTRSAAESEARTPFGLIKG
WVRGSTAGGCRNFLDTFWTNPQIKL
SEKKAITRDMDGNVDIDLPEPPKPT
LRTALKAAGFQLSSHLLQLIVLRYA

DGATRTDICQGALGDCWLLAAIASL
KAPSDLYQIILKALERGSLLGCSID
LKSRTIRKWNTTLYEGTWRRGSTAG
FRLPPGEYVVPSTFEPNKEGDFVL
RIRNYLSIFRKFDLDKSGSMSAYEM

GALGDCWLLAAIASLTLNEEILARV
QKALQKGSLLGCSIDITSAADSEAI
LTKMDGNWRRGSTAGGCRNYPNTFW
STFEPNKDGDFCIRVFSEKKADYQA
VDRSGTMNSYEMRKALEEAGFKMPC
```

FIG. 5L

```
PGYAG
HAYSV
SLTEK
PPDQE
DEELQ

TLNDT
ISSVL
GCRNY
RFFSE
RMAIE

VPLNQ
TFQKL
MNPQY
VDDEI
QLHQV
```

FIG. 5M rCAPN8

MAALAAGVSKQRAVAEGLGSNQNA
SFQKDYAGIFHFQFWQYGEWVEVV
VKGHAYSVTGVEEVNFHGRPEKLI
KIHLDEVDEDQEEGTSEPCCTVLL
TVSGHPEPHPRDMDEEDEHVRSL
QQTIAMRYACSKLGVDFNGFVACM hCAPN10

MRAGRGATPARELFRDAAFPAADS
CLAGRLCFSRCQREDVFWLPLLEK
LRIQNPWGRRCWQGLWREGGEGWS
HAADWAGRARALVGDSHTSWSPAS
VQLRGSWRVGQTAGGSRNFASYPT
IDRPSIHSQEMLGQFLQEVSVMAV

FIG. 5N

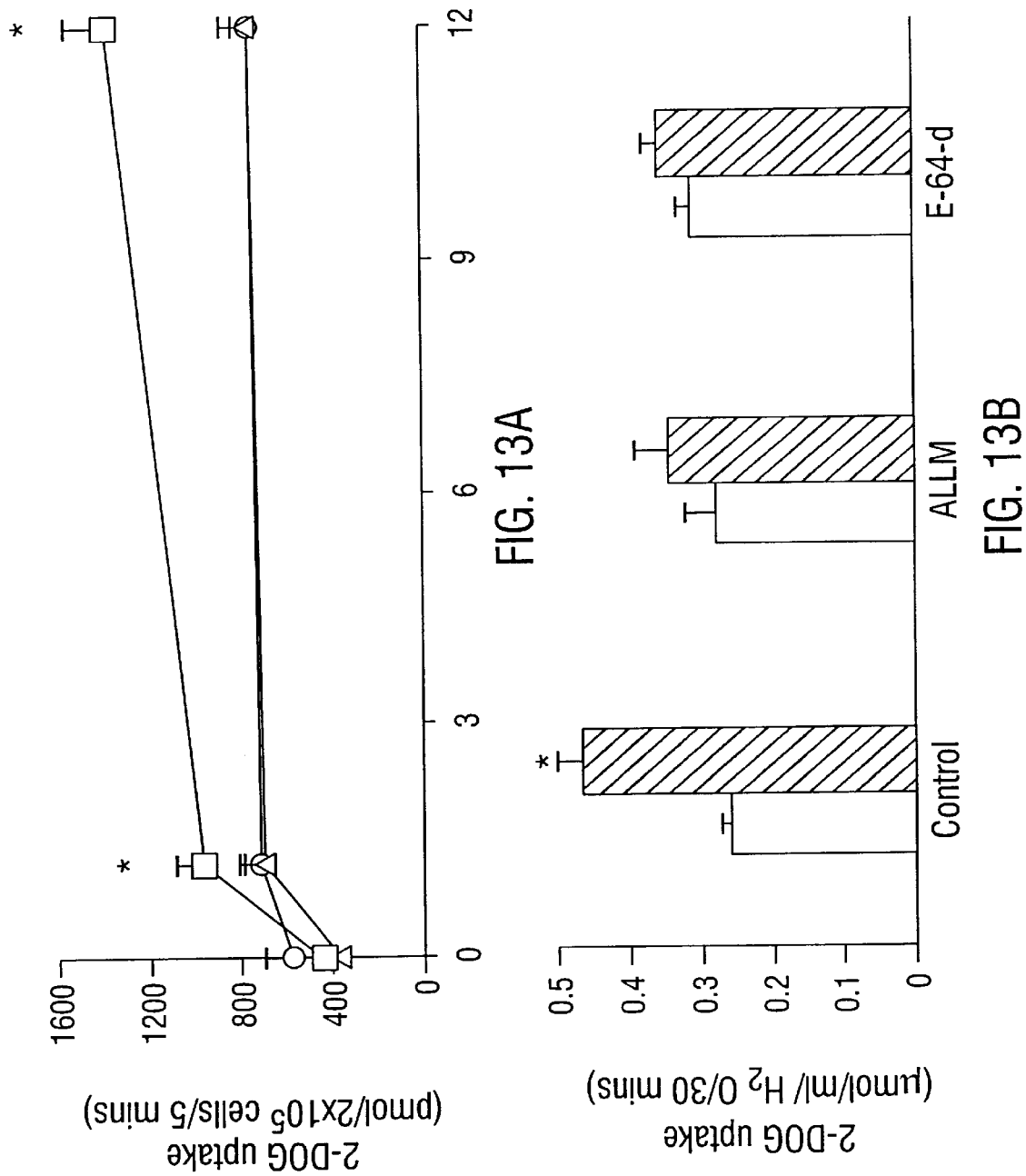

FIG. 25
DMSO
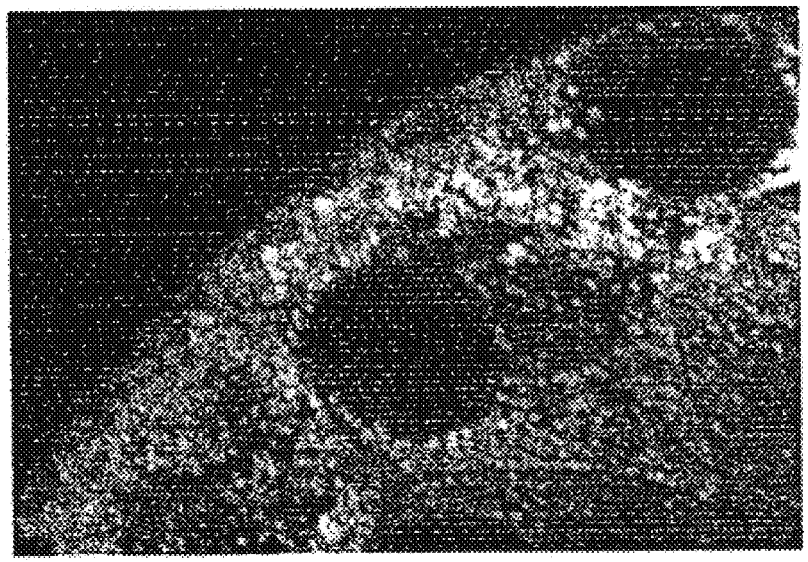
E64d
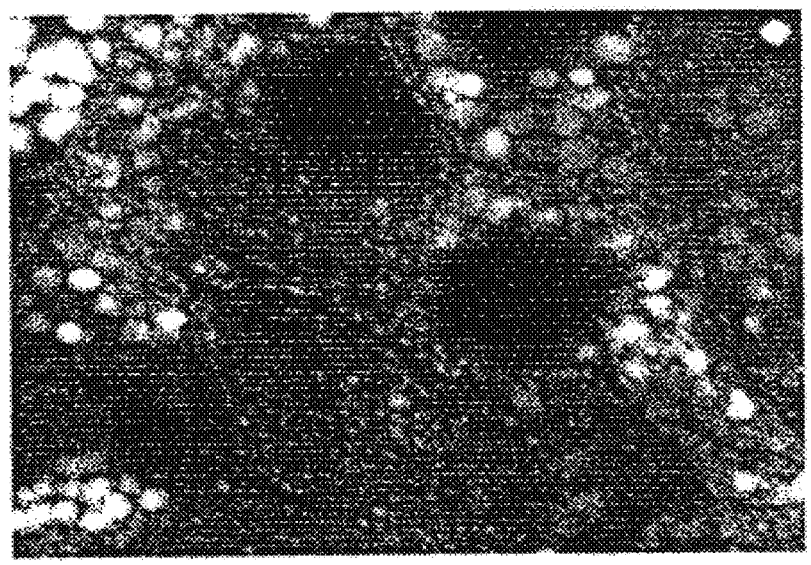
ALLM
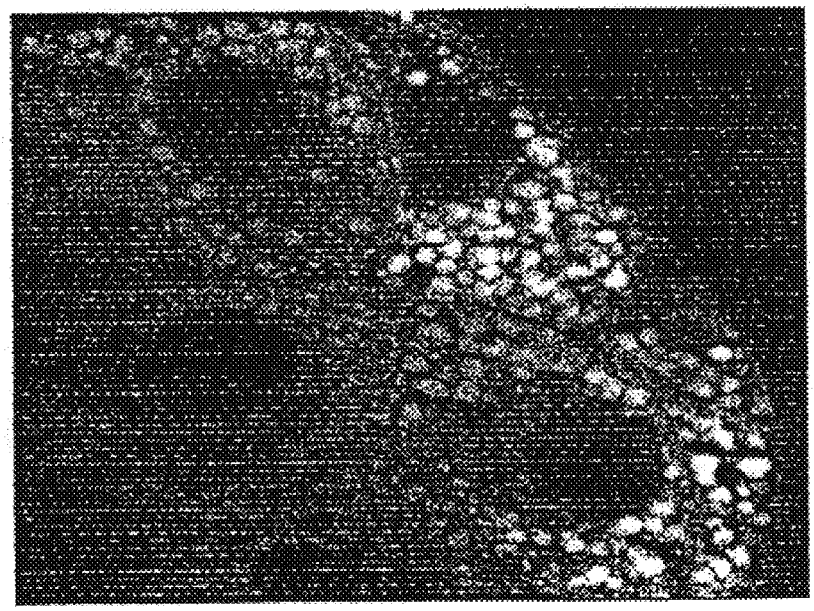

POLYNUCLEOTIDES ENCODING CALPAIN 10

This application claims the benefit of U.S. Provisional Application, Ser. No. 60/105,052, filed Oct. 21, 1998 and U.S. Provisional Application, Ser. No. 60/134,175, filed May 13, 1999.

The government may own rights in the present invention pursuant to grant numbers DK-20595, DK-47486, and DK-47487 from United States Public Health Service.

BACKGROUND OF THE INVENTION

1. Field of the Invention

The present invention relates generally to the field of treatment of diabetes mellitus. More particularly, it concerns methods of diagnosing a propensity for type 2 diabetes mellitus, methods of identifying compounds to treat type 2 diabetes mellitus, and new nucleic acid sequences encoding polypeptides related to type 2 diabetes mellitus.

2. Description of Related Art

Diabetes mellitus is a phenotypically and genetically heterogeneous group of metabolic diseases all of which are characterized by high blood glucose levels resulting from an absolute or relative deficiency of the hormone insulin (The Expert Committee on the Diagnosis and Classification of Diabetes Mellitus, 1997). The chronic hyperglycemia damages the eyes, kidneys, nerves, heart and blood vessels leading to blindness, kidney and heart disease, stroke, loss of limbs and reduced life expectancy. Diabetes mellitus is a major public health problem affecting more than 120 million people worldwide (King et al., 1998). It has an enormous economic impact on society and the direct medical and indirect expenditures attributable to diabetes in 1997 in the United States alone were $98 billion (American Diabetes Assoc., 1998).

Genetics play an important role in the development of diabetes with some forms resulting from mutations in a single gene whereas others are oligogenic or polygenic in origin. The monogenic forms of diabetes may account for 5% of all cases of diabetes and have diverse causes. Diabetes can result from mutations in the insulin (Steiner et al., 1995) and insulin receptor genes (Taylor et al., 1995) as well as the genes encoding the glycolytic enzyme glucokinase (Vionnet et al., 1992) and the transcription factors hepatocyte nuclear factor-1α (HNF-1α), HNF-1β, HNF-4α and insulin promoter factor-1 (IPF-1) (Yamagata et al., 1996a; Horikawa et al., 1997; Yamagata et al., 1996b; Stoffers et al., 1997). Mutations in these genes lead to impaired pancreatic β-cell function or in the case of the insulin receptor to defects in insulin action in target tissues including the pancreatic β-cell. In addition to these nuclear-encoded genes, mutations in maternally-inherited mitochondrial genes can cause diabetes and appear to do so primarily by impairing pancreatic β-cell function (Maassen and Kadowaki, 1996).

The two most common forms of diabetes, type 1 and type 2 diabetes, have a complex mode of inheritance. Type 1 diabetes is a common chronic disorder of children which accounts for about 5–10% of all diabetes. It results from the autoimmunological destruction of the insulin-producing cells of the pancreas leading to an absolute deficiency of insulin and requirement of insulin therapy for survival. Type 1 diabetes was the first genetically complex disorder to be studied by large-scale genome-wide screening for susceptibility genes and these studies showed the importance of the HLA region in determining susceptibility and revealed the locations of other loci with smaller effects on susceptibility (Davies et al., 1994; Hashimoto et al., 1994; Lernark and Ott, 1998).

Type 2 diabetes is the most common form of diabetes accounting for about 90% of all cases of diabetes and affecting 10–20% of those over 45 years of age in many developed countries. It is characterized by defects in insulin action resulting in decreased glucose uptake by muscle and fat and increased hepatic glucose production, and by abnormalities in the normal pattern of glucose-stimulated insulin secretion. Type 2 diabetes results from the joint action of multiple genetic and environmental factors. Linkage studies have led to the localization of susceptibility genes for type 2 diabetes in Mexican Americans (Hanis et al., 1996), in the linguistically-isolated Swedish-speaking population living in the Botnia region on the western coast of Finland (Mahtani et al., 1996), and in the Pima Indians of the southwestern United States (Pratley et al., 1998). Each study localized susceptibility to largely different regions of the genome suggesting that different combinations of susceptibility genes are responsible for type 2 diabetes in these various populations.

Genome-wide screens for susceptibility genes for complex disorders have become de rigueur and genes for a number of different complex disorders have been successfully localized through linkage studies. Although disease genes for complex disorders can be localized through genetic studies, their identification still represents a major challenge if there are no candidates in the region of interest. This is due in part to the fact that recombination events cannot be used to unambiguously define the boundaries of the region containing the susceptibility locus because of heterogeneity within and between families. The location of a gene for a complex disorder is defined by a confidence interval which may be and often is quite large. The future of genetic studies of complex disorders depends on the ability to identify predisposing genes once they have been mapped.

There are no examples of the successful identification of a gene for a complex disease originally mapped by linkage that can be used to guide such studies. It has been proposed that linkage disequilibrium mapping can be used to refine the localization and perhaps identify the disease locus (Spielman and Ewens, 1998). However, it is unclear how successful linkage disequilibrium mapping will be when only affected sibpairs are available for study as is the case for many common late-onset disorders such as type 2 diabetes.

Moreover, experience in identifying genes for complex disorders is so limited that it is not known whether the susceptibility is due to only one or a few variants or many. The presence of a large number of disease-associated variants would confound linkage disequilibrium studies. Thus, there is a need to provide an exemplary protocol for the identification of genes in complex disorder and further, there is a pressing need to identify the elusive type-2 diabetes susceptibility gene. Despite the desirablity of these endeavors these needs remain unfulfilled.

SUMMARY OF THE INVENTION

In some aspects, the present invention relates to methods for screening for diabetes comprising: a) obtaining sample nucleic acid from an animal; and b) analyzing the nucleic acid to detect a polymorphism in a calpain-encoding nucleic acid segment or a protease-encoding nucleic segment; wherein detection of the polymorphism in the nucleic acid is indicative of a propensity for type 2 diabetes mellitus. In some cases, the nucleic acid is analyzed to detect a polymorphism in a cysteine protease-encoding nucleic acid. In some presently preferred methods, the nucleic acid is a calpain-encoding nucleic acid. The nucleic acid may encode a portion of a CAPN10 gene. For example, the nucleic acid may encode UCSNP-43 of the CAPN10 gene, wherein the G-allele has been determined to exist. In particularly preferred embodiments, the nucleic acid encodes a calpain 10 polypeptide, for example: calpain 10a, calpain 10b, calpain 10c, calpain 10d, calpain 10e, calpain 10f, calpain 10g, or calpain 10h. The calpain-encoding nucleic acid segment or protease-encoding nucleic segment may be a DNA, for example a cDNA or genomic DNA. In preferred embodiments, the DNA comprises a gene for a calpain or protease. The nucleic acid may also be an RNA, for example, an mRNA encoding a calpain or protease.

In many cases, the methods of the invention will involve the step of analyzing the nucleic acid by sequencing the nucleic acid to obtain a sequence. The obtained sequence of the nucleic acid may then be compared to a known nucleic acid sequence of a calpain or protease gene to determine whether a polymorphism exists. In some preferred embodiments, the sequenced nucleic acid encodes a portion of a CAPN10 gene, for example, UCSNP-43 of the CAPN10 gene. In other embodiments, the sequenced nucleic acid encodes a calpain 10 polypeptide, for example, a calpain 10a, calpain 10b, calpain 10c, calpain 10d, calpain 10e, calpain 10f, calpain 10g, or calpain 10h. In presently preferred embodiments, the obtained sequence of the nucleic acid is analyzed to detect a presence or absence of the G-allele at UCSNP-43.

Analysis of the nucleic acid for a polymorphism may comprise any of a number of standard molecular biological methods known to those of skill. For example, PCR, an RNase protection assay, or an RFLP procedure may be used.

Presently preferred methods for screening for diabetes according to the above general methods comprise: a) obtaining sample nucleic acid from an animal; and b) analyzing the nucleic acid to detect a polymorphism in a calpain-encoding nucleic segment; wherein a polymorphism in the calpain-encoding nucleic acid is indicative of a propensity for type 2 diabetes mellitus.

In other aspects, the invention relates to methods of regulating or preventing diabetes in an animal comprising the step of modulating calpain function in the animal. Such methods often further comprise diagnosing an animal with diabetes via analysis of a calpain-encoding nucleic acid sequence as described above. In anticipated preferred embodiments, the calpain-encoding sequence is a calpain 10-encoding sequence.

Modulating calpain function may comprise providing a calpain polypeptide to the animal. The calpain polypeptide may be a native calpain polypeptide, for example, a native calpain 10 polypeptide. The native calpain 10 polypeptide may have an amino acid sequence as set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO: 18, and/or may be encoded by a nucleic acid as set forth in SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. The provision of a calpain polypeptide may be accomplished by inducing expression of a calpain polypeptide. For example, the expression of an calpain polypeptide encoded in the animal's genome may induced. Alternatively, the expression of a calpain polypeptide encoded by a nucleic acid provided to the animal may induced. The provision of a calpain polypeptide may be accomplished by a method comprising introduction of a calpain-encoding nucleic acid to the animal. Alternatively, the provision of a calpain polypeptide may be accomplished by injecting the calpain polypeptide into the animal. In some cases, the modulation of calpain function in the animal comprises providing a modulator of calpain function to the animal. For example, the modulator of calpain function may be an agonist or antagonist of a calpain 10 polypeptide. Alternatively, the modulator of calpain function may modulate transcription and/or translation of a calpain 10-encoding nucleic acid. In many cases, modulation will only occur after a diagnosis that an animal has or is susceptible to diabetes via analysis of a calpain-encoding nucleic acid sequence for a polymorphism.

In other aspects, the invention relates to methods of screening for modulators of calpain function comprising the steps of: a) obtaining an calpain polypeptide; b) determining a standard activity profile of the calpain polypeptide; c) contacting the calpain polypeptide with a putative modulator; and d) assaying for a change in the standard activity profile. Often, in such methods, the calpain polypeptide is a calpain 10 polypeptide. The standard activity profile of the calpain 10 polypeptide may be determined by measuring the binding of the calpain 10 polypeptide to a synthetic substrate. An example of such a synthetic substrate is Suc-Leu-Tyr-AMC (Vilei et al., 1997). Frequently, obtaining the calpain polypeptide comprises expressing the polypeptide in a host cell. Although the calpain polypeptide may be isolated away from the host cell prior to contacting the calpain polypeptide with the putative modulator, in many assays known to those of skill in the art, it need not be.

Preferred methods of screening for modulators of calpain function may comprise the steps of: a) obtaining a calpain-encoding nucleic acid segment; b) determining a standard transcription and translation activity of the calpain nucleic acid sequence; c) contacting the calpain-encoding nucleic acid segment with a putative modulator; d) maintaining the nucleic acid segment and putative modulator under conditions that normally allow for calpain transcription and translation; and e) assaying for a change in the transcription and translation activity.

The invention also relates to calpain modulators prepared by a process comprising screening for modulators as described above.

The invention also relates to isolated and purified polynucleotides comprising a calpain 10-encoding sequence. Such polynucleotides may comprise, for example, a sequence encoding any of calpain 10a, calpain 10b, calpain 10c, calpain 10d, calpain 10e, calpain 10f, calpain 10g, calpain 10h, or mouse calpain 10. Such calpains may have an amino acid sequence as set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18. The calpain 10-encoding polynucleotide may have a sequence as set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19.

The invention also relates to isolated and purified calpain 10 polypeptides, for example, polypeptides forming calpain 10a, calpain 10b, calpain 10c, calpain 10d, calpain 10e, calpain 10f, calpain 10g, calpain 10h, or mouse calpain 10. Such polypeptides may have an amino acid sequence as set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

The invention relates to method of obtaining a calpain 10 polypeptide comprising: a) obtaining a calpain 10 encoding-polynucleotide; b) inserting the obtained polynucleotide into a host cell; and c) culturing the host cell under conditions sufficient to allow production of the calpain 10-encoding polypeptide; wherein a calpain 10 polypeptide is thereby obtained. The calpain 10 polypeptide may be any described above, and may be encoded by any calpain 10 encoding nucleotide described above. Such methods of obtaining calpain 10 polypeptides may comprise eventually isolating the calpain 10 polypeptide from the host cell, although this is not required for some applications.

In some aspects, the invention relates to an isolated and purified polynucleotide comprising a sequence encoding the human G-protein coupled receptor as set forth in SEQ ID NO:21. The invention also relates to an isolated and purified polypeptide comprising the amino acid sequence of the human G-protein coupled receptor set forth in SEQ ID NO:20.

The invention further concerns a method of modulating an insulin secretory response in an animal comprising the step of modulating calpain function in the animal. Modulating calpain function can be by providing a modulator of calpain function to the animal. The modulator can be an agonist or antagonist of a calpain polypeptide. In certain embodiments, the modulator may be an inhibitor of a calpain polypeptide. In preferred embodiments, the inhibitor inhibits calpain I and/or calpain II. The inhibitor may be calpeptin or calpain inhibitor 2 (N-Ac-Leu-Leu-methioninal, ALLM). Alternatively, the inhibitor may be a thiol protease inhibitor, such as E-64-d.

The invention also concerns a method of modulating insulin mediated glucose transport in an animal comprising the step of modulating calpain function in the animal. Modulating calpain function can be by providing a modulator of calpain function to the animal. The modulator can be an agonist or antagonist of a calpain polypeptide. In certain embodiments, the modulator may be an inhibitor of a calpain polypeptide. In preferred embodiments, the inhibitor inhibits calpain I and/or calpain II. The inhibitor may be calpeptin or calpain inhibitor 2 (N-Ac-Leu-Leu-methioninal, ALLM). Alternatively, the inhibitor may be a thiol protease inhibitor, such as E-64-d.

Other aspects of the invention concerns a method of increasing an insulin secretory response in an animal comprising the step of modulating calpain function in the animal. Modulating calpain function in the animal can be by providing a modulator of calpain function to the animal. The modulator of calpain function can be an agonist or antagonist of a calpain polypeptide. The modulator may be a thiol protease inhibitor, such as E-64-d.

The invention also concerns a method of treating diabetes in an animal comprising the step of modulating calpain function in the animal. Modulating calpain function can be by providing a modulator of calpain function to the animal. The modulator can be an agonist or antagonist of a calpain polypeptide. In certain embodiments, the modulator may be an inhibitor of a calpain polypeptide. In preferred embodiments, the inhibitor inhibits calpain I and/or calpain II. The inhibitor may be calpeptin or calpain inhibitor 2 (N-Ac-Leu-Leu-methioninal, ALLM). Alternatively, the inhibitor may be a thiol protease inhibitor, such as E-64-d.

The invention further defines methods of treating diabetes by modulating the function of one or more calpains in at least one of a β-cell, muscle cell, or fat cell with a modulator of calpain function. Again, modulating calpain function can be by providing a modulator of calpain function to the animal. The modulator can be an agonist or antagonist of a calpain polypeptide. In certain embodiments, the modulator may be an inhibitor of a calpain polypeptide. In preferred embodiments, the inhibitor inhibits calpain I and/or calpain II. The inhibitor may be calpeptin or calpain inhibitor 2 (N-Ac-Leu-Leu-methioninal, ALLM). Alternatively, the inhibitor may be a thiol protease inhibitor, such as E-64-d.

The methods for treating diabetes can be further defined as a method comprising inhibiting calpain activity in a β-cell with a modulator of calpain function, stimulating calpain activity in a muscle cell or fat cell with a modulator of calpain function, or a combination of these actions.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M and FIG. 5N. Alignment of the predicted amino acid sequence of human calpain 10a with representative members of the large subunit calpain family. The four domains of the calpains are indicated. This alignment was generated with CLUSTAL X. rCAPN8 (SEQ ID NO:27) and hCAPN9 (SEQ ID NO:28) denote nCL-2 and -4, respectively. The mouse and rat sequences for calpain 6 (mCAPN10, SEQ ID NO:26) and calpain 8 (rCAPN10, SEQ ID NO:27) are shown. The GenBank accession numbers and sequence ID listings for the sequences shown here are: hCAPN1, X04366, SEQ ID NO:22; hCAPN2, M23254, SEQ ID NO:23; hCAPN3, X85030, SEQ ID NO:24; hCAPN5, Y10552, SEQ ID NO:25; mCAPN6, Y12582, SEQ ID NO:26; rCAPN8, D14479, SEQ ID NO:27; hCAPN9, AF022799, SEQ ID NO:28; and hCAPN10, AF089088, SEQ ID NO:2.

FIG. 7A. Interaction between NIDDM1 and CYP19. Multipoint allele-sharing analysis of chromosome 15 weighted by the evidence for linkage at NIDDM1 on chromosome 2. FIG. 7B. Interaction between NIDDM1 and CYP19. Multipoint allele-sharing analysis of chromosome 2 weighted by the evidence for linkage at CYP19 on chromosome 15.

FIG. 8A. and FIG. 8B. Insulin secretion by mouse islets incubated in the presence of 2 mM glucose (open bars) and 20 mM glucose (hatched bars) in the absence and presence of 200 $\mu$M E-64-d (FIG. 8A) and 250 $\mu$M ALLM (FIG. 8B). Results are mean ±SEM of 6 studies in each case. *p<0.05 compared to islets incubated in 20 mM glucose in the absence of calpain inhibitors. FIG. 8C and FIG. 8D. Effect of increasing concentrations ($\mu$M) of E-64-d (FIG. 8C) and ALLM (FIG. 8D) on the insulin secretory response to 2 mM glucose (open bars) and 20 mM glucose (hatched bars). Results are mean ±SEM of 5–6 studies in each group. *p<0.05 compared to islets incubated in the absence of calpain inhibitors.

FIG. 9A Insulin secretion by islets incubated at various glucose concentrations in the absence (open bars) and presence (hatched bars) of 100 $\mu$M ALLM. Results are mean ±SEM of 4–7 studies per group. *p<0.05 compared to islets incubated in the absence of ALLM. FIG. 9B. Insulin secretion by perifused islets in response to stimulation with 20 mM glucose (6–20min, solid bar). The perifusate contained 2 mM glucose except where shown. Islets were preincubated for 4 hr either in the absence of calpain inhibitors (■) or in the presence of 100 $\mu$M ALLM (●) or 200 $\mu$M E-64-d (▲). In studies involving inhibitors, ALLM was present throughout the study but E-64-d which is an irreversible cysteine protease inhibitor was present only during the pre-incubation. Results are mean ±SEM of 3 studies in each group. FIG. 9C. Insulin secretion by mouse islets incubated in the presence of 2 mM glucose (2), 8 mM glucose (8), 250 $\mu$M carbachol (CCh) or 50 nM GLP-1 (GLP-1) in the presence of 8 mM glucose and 30 mM KCl in the presence of 2 mM glucose (KCl). Islets were incubated either in the absence (open bars) or presence (hatched bars) of 100 $\mu$M ALLM. Results are mean ±SEM of 6 separate studies. *p<0.05 compared to islets incubated in the absence of ALLM.

FIG. 10A. Representative capacitance traces obtained from a control β-cell (top) and from a different cell pretreated with ALLM (100 $\mu$M, bottom). FIG. 10B. Average peak change in membrane capacitance elicited by trains of depolarizations from control (open bar, n=9) and ALLM pre-treated cells (hatched bar, n=11). Data are mean ±SEM, * indicates p<0.05.

FIG. 11A and FIG. 11B. [$Ca^{2+}$]$_i$ responses to 14 mM glucose (open bar), washout (2 mM glucose) and stimulation with 30 mM KCl in the continued presence of 2 mM glucose (filled bar). 340/380 ratio is an indirect measure of intracellular free calcium ([$Ca^{2+}$]$_i$) Islets were preincubated for 4 hr either in the absence (FIG. 11A) or presence (FIG. 11B) of 100 $\mu$M ALLM inhibitor-2. Similar results were obtained with E-64-d. FIG. 11C. ALLM pre-treatment did not alter whole-cell calcium currents recorded in β-cells. Representative calcium currents recordings obtained from a control cell (0.1% DMSO, top) and from a different cell pre-treated with ALLM (100 $\mu$M, bottom) are shown. FIG. 11D. The average peak calcium current density (peak current divided by cell size) for control (left, open bar, 34.2±2.2 pA/pF, n=18) and for ALLM (100 $\mu$M) pre-treated cells (right, hatched bar, 36.7±3.9 pA/pF, n=15). FIG. 11E and FIG. 11F. Changes in NAD(P)H fluorescence in response to stimulation with 14 mM glucose (open bar) in mouse islets. Islets were preincubated for 4 hr either in the absence (FIG. 11E), or presence (FIG. 11F) of 100 $\mu$M ALLM inhibitor-2.

FIG. 12A Mouse islets were preincubated for 4 hr either in the absence of inhibitors (■) or in the presence of 200 $\mu$M ALLM (●) or 200 $\mu$M E-64-d (▲). Islets were then incubated in KRB containing 10 $\mu$M Boc-Leu-Met-CMAC from 0 min and fluorescence emitted by the calpain proteolytic product was measured following excitation by light at 340 nM. Data represent mean ±SEM of 3–4 separate experiments. FIG. 12B The area under the curve (AUC) of fluorescence generation in the absence of calpain inhibitors (open bar, n=4) and in the presence of ALLM (hatched bar, n=3) and E-64-d (solid bar, n=4) were compared. *p<0.05, compared to islets incubated in the absence of inhibitor.

FIG. 13A, FIG. 13B and FIG. 13C. Effects of protease inhibitors on insulin action in adipocytes and skeletal muscle. FIG. 13A. Effects of insulin alone (■) or insulin in the presence of 100 $\mu$M ALLM (●) or 200 $\mu$M E-64-d (▲) on 2-deoxyglucose uptake into rat adipocytes. Insulin concentrations (nmol/L) are shown on the horizontal axis. * denotes p<0.05 compared to cell incubated in the absence of insulin. FIG. 13B. Effect of ALLM (100 $\mu$M) and E-64-d $\mu$200 (M) on 2-deoxyglucose uptake by skeletal muscle. Soleus muscle strips from normal adult male rats were incubated in the absence (open bars) or presence (hatched bars) of 12 nM insulin and in the absence (control) and presence of protease inhibitors as shown. Results are mean ±SEM of 5 separate studies. # p<0.05 compared to muscles incubated in the absence of inhibitor. FIG. 6c. Effect of ALLM and E-64-d on glycogen synthesis rates in skeletal muscle. Muscle strips were incubated in the absence (open bars) or presence (hatched bars) of 6 nM insulin and in the absence (control) and presence of inhibitor as shown. Results are mean ±SEM of 6 separate studies. * p<0.05 compared to muscles incubated in the absence of insulin, # p<0.05 compared to muscles incubated in the absence of inhibitor.

FIG. 25. Enlarged acidic vesicles in beta cells following 48 hour calpain inhibitor treatment.

DESCRIPTION OF ILLUSTRATIVE EMBODIMENTS

Figure 1:
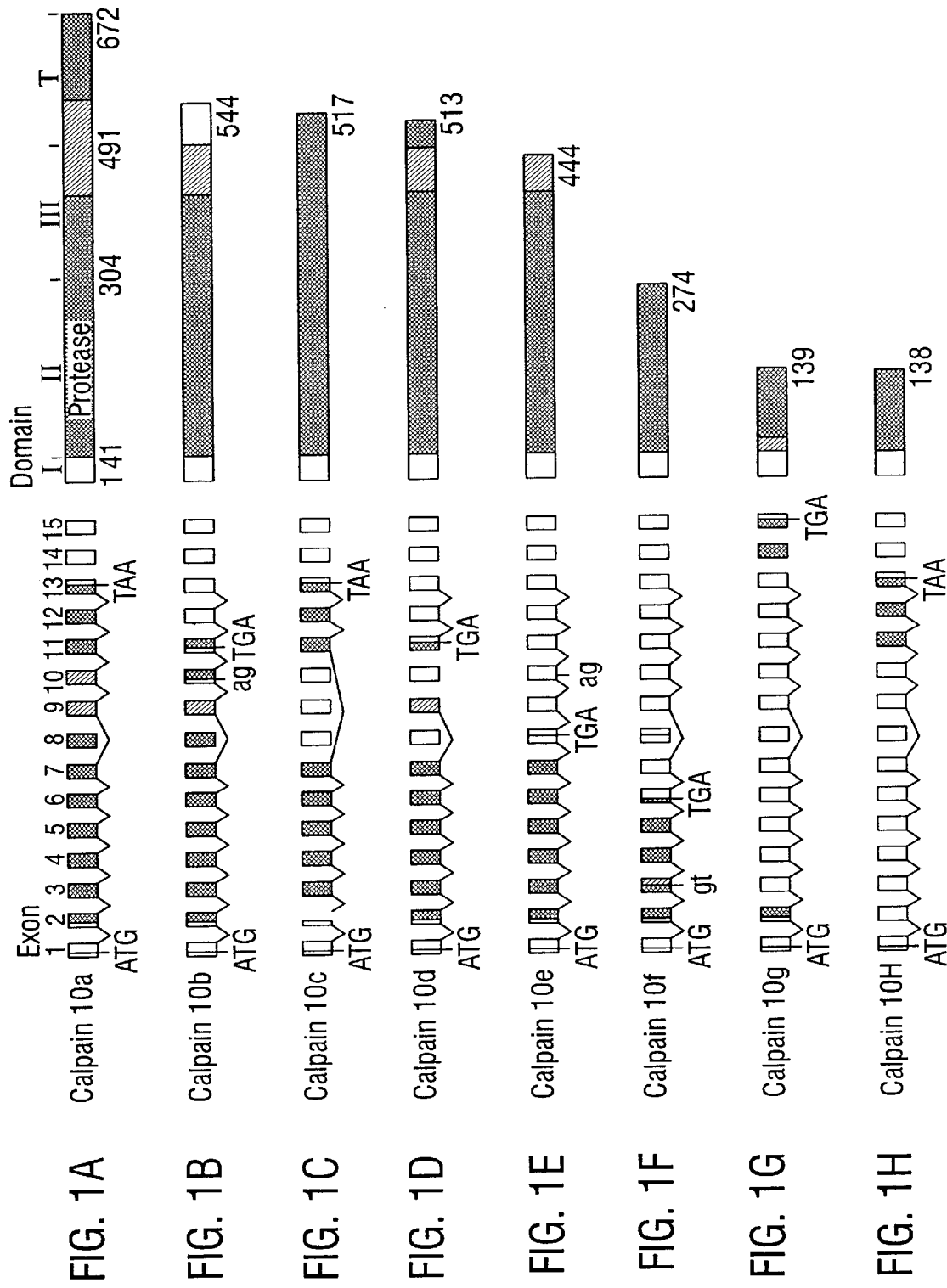
FIG. 1A, FIG. 1B, FIG. 1C, FIG. 1D, FIG. 1E, FIG. 1F, FIG. 1G and FIG. 1H. Alternative splicing of human calpain 10 mRNA generates a family of proteins. The patterns of alternative splicing and the organization of the calpain 10 proteins generated by alternative splicing are shown. The four domains that define calpains are noted as are the amino acid residues that define the boundaries between domains.

Despite the fact that it has been known for many decades that a failure in an absolute or relative deficiency of the hormone insulin lead to diabetes, the genetic basis of susceptibility to diabetes remains elusive. Diabetes is a major cause of health difficulties in the United States. Type 2 diabetes mellitus (also referred to as non-insulin-dependent diabetes mellitus—NIDDM) is a major public health disorder of glucose homeostasis affecting about 5% of the general population in the United States. The causes of the fasting hyperglycemia and/or glucose intolerance associated with this form of diabetes are not well understood.

Type 2 diabetes has onset in mid-life or later. This disorder or maturity-onset diabetes of the young (MODY) shares many features with the more common form(s) of type 2 diabetes the onset of which occurs in mid-life. Maturity-onset diabetes of the young (MODY) is a form of diabetes mellitus that is characterized by an early age at onset, usually before 25 years of age, and an autosomal dominant mode of inheritance (Fajans, 1989). Except for these features, the clinical characteristics of patients with MODY are similar to those with the more common late-onset form(s) of type 2 diabetes. The genes for susceptibility to MODY have been characterized and described in WO 98/11254, which is the PCT counterpart to U.S. patent application Ser. No. 08/927,219, filed Sep. 9, 1997. These documents are incorporated herein by reference in their entirety, as providing disclosure of diagnostic and prognostic aspects of MODY.

Type 2 diabetes results from the joint action of multiple genetic and environmental factors. Linkage studies have led to the localization of susceptibility genes for type 2 diabetes in Mexican Americans, in the linguistically-isolated Swedish-speaking population living in the Botnia region on the western coast of Finland, and in the Pima Indians of the southwestern United States. Each study localized susceptibility to largely different regions of the genome suggesting that different combinations of susceptibility genes are responsible for type 2 diabetes in these various populations.

The genome-wide search for type 2 diabetes genes in the Mexican Americans community of Starr County, Tex., localized a major susceptibility locus, NIDDM1, to the region of D2S125–D2S140 (multipoint lod score=4.03, $P=8.2\times10^{-6}$). The inventors' results and those of others indicate that NIDDM1 has a less important role in determining diabetes susceptibility in non-Hispanic white (German, French, Sardinian, British and Finnish) and Asians (Japanese) populations than it does in Mexican Americans (Hanis et al., 1996; Mahtani et al., 1996; Hanis et al., 1997; Thomas et al., 1997; Ciccarese et al., 1997; Gosh et al., 1998).

The inventors' strategy for positionally cloning NIDDM1 was designed to capitalize on linkage disequilibrium, if it is present, but still recognize disease-associated variation in its absence by utilizing information on the interaction between NIDDM1 and other susceptibility loci. Here, the inventors demonstrate that it is possible to positionally clone a gene for a complex disorder solely on the basis of its map position using standard molecular genetic methods coupled with novel analytic techniques. The inventors show that NIDDM1 encodes a novel calpain-like cysteine protease that the inventors have given the name diabetes calpain or "diapain." This result defines a new pathway leading to the development of type 2 diabetes.

In order to determine whether evidence that the presence of NIDDM1 is associated with increased risk for the development of type 2 diabetes in a predisposed population could be detected, 106 Mexican American subjects from Starr County, Tex., were selected, each of whom had at least two first degree relatives with type 2 diabetes but none of whom had a personal history of previously diagnosed diabetes. The inventors found strong physiological evidence for an important role of this gene as a primary cause of type 2 diabetes. More particularly, the present invention shows that that there are a combination of pathophysiological defects (insulin resistance, impaired glucose tolerance and defective insulin secretion) in subjects who are homozygous GG at UCSNP-43 prior to the onset of overt type 2 diabetes. These results are briefly discussed herein below and discussed in further detail in the Examples.

The inventors used oral glucose tolerance testing to monitor pathophysiological abnormalities associated with NIDDM1. This is a standard test used to measure the response of islet cells to a glucose bolus and is currently recognized as the test in most wide-spread use for diabetes detection. The normal range of fasting glucose concentrations is 110 mg/dl. Following glucose ingestion glucose concentrations increase. The threshold value that defines normal glucose tolerance is below 140 mg/dl, any individual having a glucose concentration value above this threshold is defined, by WHO criteria, as having impaired glucose tolerance.

Using subjects possessing a family history of diabetes who do not have diabetes themselves but who are homozygous GG at UCSNP-43, the inventors were able to demonstrate a number of abnormalities by oral glucose tolerance testing. First, these individuals demonstrate fasting hyperinsulinemia suggesting the presence of insulin resistance. Second, these individuals were shown to have elevated average plasma glucose concentrations 120 min. after ingestion of 75 g glucose orally to within a range that defines impaired glucose tolerance a condition widely recognized to be associated with a significant increased risk for the subsequent development of type 2 diabetes. Further, these individuals characteristically have reduced insulin concentrations 30 min. after ingestion of 75 g glucose. Reduced insulin concentrations in response to the oral ingestion of nutrients is one of the hallmarks of type 2 diabetes. A similar defect is therefore present in subjects homozygous GG at UCSNP-43 even before the onset of diabetes.

Thus, the present invention concerns the early detection, diagnosis, prognosis and treatment of type 2 diabetes. The present invention describes for the first time a sequence and mutations in a diapain gene responsible for type 2 diabetes susceptibility. The specific mutation and identity of the corresponding wild-type genes from diabetic subjects, are disclosed. These mutations are indicators of type-2 related diabetes and are diagnostic of the potential for the development of diabetes. It is envisioned that the techniques disclosed herein will also be used to identify other gene mutations responsible for other forms of diabetes.

Those skilled in the art will realize that the nucleic acid sequences disclosed will find utility in a variety of applications in diabetes detection, diagnosis, prognosis and treatment. Examples of such applications within the scope of the present invention include amplification of markers of NIDDM using specific primers; detection of markers of diapain by hybridization with oligonucleotide probes; incorporation of isolated nucleic acids into vectors and expression of vector-incorporated nucleic acids as RNA and protein; development of immunologic reagents corresponding to gene encoded products; and therapeutic treatment for the identified type 2 diabetes using these reagents as well as anti-sense nucleic acids or other inhibitors specific for the identified type 2 diabetes. The present invention further discloses screening assays for compounds to upregulate gene expression or to combat the effects of the calpain 10 gene(s).

A. Diabetes

Diabetes mellitus affects approximately 5% of the population of the United States and over 120 million people worldwide (King et al., 1998, Harris et al., 1992). A better way of identifying the populace who are at risk of developing diabetes is needed as a subject may have normal plasma glucose compositions but may be at risk of developing overt diabetes. These issues could be resolved if it were possible to diagnose susceptible people before the onset of overt diabetes. This is presently not possible with subjects having classical diabetes due to its multifactorial nature.

The clinical characteristics that are seen in patients with type 2 diabetes include frequent severe fasting hyperglycemia, the need for oral hypoglycemic agents, eventual insulin requirements, and vascular and neuropathic complications (Fajans et al., 1994; Menzel et al., 1995).

The number of genes and allelic variants that influence the development of a complex trait such as type 2 diabetes is uncertain. The inventors' studies in the Mexican American population of Starr County, Tex., indicate that type 2 diabetes in this group results from the interactions of a major gene that accounts for about 35% of the familial clustering with perhaps as many as 11 loci of smaller effect (Hanis et al., 1996). The inheritance of type 2 diabetes in this population appears to be oligogenic with interactions between 2–3 loci in each individual being the primary determinant of susceptibility.

While linkage studies have shown that it is possible to map susceptibility genes, the identification of the gene and nucleotide variants that influence susceptibility is a forbidding task and one for which there is no precedent. Here, the inventors have shown that it is possible to find the one gene in 100,000 and the one nucleotide in 3,300,000,000 that affect susceptibility using positional cloning strategies employed for the identification of mutations in single-gene disorders together with novel analytic techniques. The implications for studies of complex disorders are clear.

Genetic studies of disorders such as type 2 diabetes which have onset in middle-age pose a number of challenges. The late age at onset (the mean age at diagnosis for men and women in the inventors' study population was 50.0±11.6 and 48.7±10.7 (mean ±SD) years, respectively) makes it difficult to identify complete nuclear families. One or both parents are often not available, in part because of the early mortality associated with diabetes, and the children of affected individuals have not yet developed the condition. The inventors have used affected sib-pairs without parents in their studies which limits the types of analyses that can be used to assess linkage disequilibrium to comparisons of allele frequencies between cases and controls from the same community. While this may not be considered optimal, it did not hinder the inventors' search for NIDDM1 and it is unclear that the search would have proceeded differently even if nuclear families had been available thus permitting the use of robust tests of linkage disequilibrium such as the transmission/disequilibrium test (Spielman and Ewens, 1998).

The identification of NIDDM1 proceeded simultaneously with the generation of a physical map, the boundaries of which were defined by the 1-lod confidence interval, the identification of diallelic polymorphisms, usually SNPs, in both ESTs and STSs, and tests of linkage and association of these polymorphisms, and haplotypes formed from adjacent polymorphisms, with type 2 diabetes. The results of each analysis refined the focus of the inventors' search finally identifying a G-to-A polymorphism (UCSNP43) as being responsible for all the evidence for linkage with type 2 diabetes. This polymorphism acts in a recessive manner with individuals homozygous for the high frequency G-allele being at increased risk of developing diabetes.

The inventors identified 166 DNA polymorphisms during the course of this study of which 62 were typed in at least 100 affected and 100 random controls usually by DNA sequencing. In addition, the inventors resequenced a 50 kb region in ten individuals to ensure that they had identified all common variants in the region and could exclude each as being the basis of the evidence of linkage with type 2 diabetes. No other polymorphism exhibited the magnitude of effect attributable to the variation at UCSNP-43. It seems unlikely that the effects at UCSNP-43 are due to chance and that NIDDM1 is another of the SNPs examined that account for substantially less of the evidence of linkage. It is also unlikely that the actual variant lies outside the region that the inventors have sequenced. Such a variant would be more than 6,225 bp from UCSNP-43 and it would have to be in strong linkage disequilibrium with SNP-43 and have a similar frequency. Such a combination is unlikely given the admixture of the Mexican American population—the alleles would have to have been present at similar frequencies in both major founder populations. Nor do the inventors believe that the original evidence for linkage was a false positive and they have merely localized that false positive signal to a single polymorphism. This is unlikely since UCSNP-43 accounts for all the evidence for linkage not only in the original data set but also in a smaller replicate sample. The results strongly suggest that UCSNP-43 is the variant responsible for the effects attributed to NIDDM1.

The nucleotide variant responsible for all the evidence for linkage with type 2 diabetes is located in the gene encoding a novel calpain, calpain 10. The role of this novel calpain, in diabetes is discussed at length herein below.

Existing Diabetes Therapies

Sulfonylureas exert hypoglycemic action and inhibit potassium channel transport by binding to proteins at the potassium channel. Of the compounds commonly known as sulfonylureas, glyburide is considered the most potent because it binds most firmly and for a longer time to the 140 kda protein at the potassium channel of all tissues of the body. Micronized glyburide or small particle glyburide is absorbed more rapidly from the gastrointestinal tract than non-micronized glyburide.

Oral hypoglycemic agents such as tolazamide, tolbutamide, chlorpropamide, micronized and non-micronized glyburide, glimepiride, glypizide, metformin, and phenformin have been available as oral treatments for diabetes, typically non-insulin dependent (Type II) diabetes. Oral hypoglycemic agents in general are disadvantageous because the extent, predictability and duration of the antidiabetic effect is unpredictable and these agents are often characterized by primary or secondary failure. Because oral hypoglycemic agents exhibit inconsistent hypoglycemic benefit, insulin therapy is preferred.

For those diabetics in which current oral medication does not offer sufficient control of their condition, insulin injections are necessary. Daily injections offer a number of risks, including hypoglycemia, wide fluctuations in glucose concentrations requiring multiple daily serum glucose determinations and multiple insulin injections, and strict dietary control which then leads to the issue of poor compliance. Other disadvantages include difficulty in self administration of an accurate dose, especially by the elderly or infirmed patients. Epidemiological data shows that over 85% of insulin treated diabetics in the United States are poorly controlled. As a result, 150 billion dollars per year is spent treating the devastating complications of the illness.

Some patients are virtually impossible to treat with insulin because their cells cannot effectively utilize or are resistant to insulin therapy. As a result of the lack of glycemic control, diabetic patients often experience a variety of conditions including: neuropathy, nephropathy, cardiomyopathy, fetinopathy, coronary and peripherovascular disease and the like. These complications occur due to the unachieved glycemic control that results from failure of the insulin, diet and/or exercise only approach.

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is a critically important approach for the treatment of diabetes.

Type I diabetes (IDDM) is the result of an absolute deficiency of insulin, the hormone which regulates glucose utilization. Type II, noninsulin dependent diabetes mellitus (NIDDM) is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver.

The several treatments for NIDDM, which has not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially high fat-containing food. Increasing the plasma level of insulin by administration of sulfonylureas (e.g. tolbutamide, glipizide) which stimulate the pancreatic .beta.-cells to secrete more insulin or by injection of insulin after the response to sulfonylureas fails, will result in high enough insulin concentrations to stimulate the very insulin-resistant tissues. However, dangerously low levels of plasma glucose can result from these last two treatments and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

Thiazolidinediones (glitazones) are a recently disclosed class of compounds that are suggested to ameliorate many symptoms of NIDDM. These agents increase insulin sensitivity in muscle, liver and adipose tissue in several animal models of NIDDM resulting in complete correction of the elevated plasma levels of glucose, triglycerides and nonesterified free fatty acids without any occurrence of hypoglycemia. However, serious undesirable effects have occurred in animal and/or human studies including cardiac hypertrophy, hemadilution and liver toxicity resulting in few glitazones progressing to advanced human trials.

Biguanide drugs, while not used in this country, are being tested in clinical trials as hypoglycemic agents (Katzung p. 598–599). Likewise, pioglitazone is being tested in clinical trials as a hypoglycemic agent (Hoffman and Colca, Diabetes Care, 15:1075–1078, 1992; Koybayashi et al., Diabetes, 41:476–483, 1992. Although these agents are being tested to evaluate usefulness in decreasing insulin resistance, no mechanism has been described to explain how they exert their effects. As has been found with sulfonylureas, the bignanides and pioglitazone may be found to be ineffective in a large percentage of patients, or the effectiveness of the agents may decline with longterm use. New therapeautic agents to decrease insulin resistance need to be identified and brought to clinical practice.

B. Calpain

Calpain is a calcium-activated neutral protease, also known as CAPN; EC 3.4.22.17. It is an intracellular cysteine protease which is ubiquitously expressed in mammalian tissues (Aoki et al., 1986). Calpain has been implicated in many degenerative diseases including, but not limited to, neurodegeneration (Alzheimer's disease, Huntington's disease, and Parkinson's disease), amyotrophy, stroke, motor neuron damage, acute central nervous system (CNS) injury, muscular dystrophy, bone resorption, platelet aggregation, and inflammation.

Mammalian calpain, including human calpain, is multimeric. It consists of two different subunits, which are a 30 kDa subunit and an 80 kDa subunit, and, therefore, is a heterodimer. There are two forms of calpain, calpain I (um-calpain, umCAPN) and calpain II (m-calpain, mCAPN), which differ in their sensitivities to the concentration of calcium necessary for activation. Calpain I requires only low micromolar concentrations of calcium for activation, whereas calpain II requires high micromolar or millimolar levels (Aoki et al., 1986; DeLuca et al., 1993). The same 30 kDa subunit is common to both forms. The two human calpains differ in the sequences of the DNA encoding their 80 kDa subunit, sharing 62% homology. There is evidence that the 80 kDA subunit is inactive, but that it is autolyzed to a 76 kDa active form in the presence of calcium (Zimmerman et al., 1991). The large catalytic subunit can be divided into four domains: domain I, the N-terminal regulatory domain that is processed upon calpain activation; domain 1I, the protease domain homologous to papain; domain III, a linker domain of unknown function; and domain IV, the calmodulin-like $Ca^{2+}$-binding domain.

Calpain Inhibitors

Commercially available in vitro inhibitors of Calpain include peptide aldehydes such as leupeptin (Ac-Leu-Leu-Arg-H), as well as epoxysuccinates such as E-64. These compounds are not useful in inhibiting Calpain in vivo because they are poorly membrane permeant. Also, many of these inhibitors are poorly specific and will inhibit a wide variety of proteases in addition to Calpain. These commercially available compounds are based upon peptide structures that are believed to interact with the substrate binding site of Calpain. Active groups associated with the Calpain inhibitors then either block or attack the catalytic moiety of Calpain in order to inhibit the enzyme.

In addition, other types of compounds thought to possess in vitro Calpain inhibitory activity that are not commercially available have been reported. Several classes of calpain inhibitors have been identified and found to provide protection against a variety of neurodegenerative diseases and conditions (Bartus et al., WO 92/11850). Other examples of calpain inhibitors include the peptide diazomethanes (Rich, 1986). These peptide diazomethanes are similarly thought to be poorly membrane permeant and non-specific.

Calpeptin is another calpain inhibitor (Tsujinaka, et al., 1988). It was created by modifying the N-terminal of Leu-norleucinal or Leu-methioninal to obtain a cell penetrative peptide inhibitor against calpain. Calpeptin is a potent synthetic inhibitors in terms of preventing the Ca2+-ionophore induced degradation of actin binding protein and P235 in intact platelets.

Calpain inhibitor 2 (N-Ac-Leu-Leu-methioninal, ALLM) has been used in a number of studies looking at its effects on normal cellular physiology. These include secretion from isolated rat alveolar epithelial cells (Zimmerman et al., 1995), muscle cell differentiation (Ueda et al., 1998), apoptosis in embryonic chicken neurons (Villa et al., 1998), and extralysosomal proteolysis in cells, such as what occurs following cellular injury (Posmantur et al., 1997; Figueiredo-Pereira et al., 1994). Calpain inhibitor 2 preferentially inhibits milli (m)-calpain, while calpain inhibitor 1 (N-acetyl-leucyl-leucyl-norleucinal) preferentially inhibits micro (mu)-calpain.

There is some evidence that certain particular inhibitors of Calpain have certain therapeutic utilities. For example, leupeptin can facilitate nerve repair in primates. Loxastatin (also known as EST, Ep-460 or E-64d), a derivative of E-64, is believed to have utility in the treatment of muscular dystrophy. E-64d, while not having significant protease inhibitory activity itself, is believed to be converted to more potent forms, such as to E-64c, inside a mammalian body. E-64 is commercially available from CalBiochem (San Diego, Calif.), Sigma Chemical Co. (St. Louis, Mo.), and Boehringer Mannheim (Indianapolis, Ind.). Other acceptable thiol protease inhibitors include analogs of E-64 (Hashida et al., 1980; Barrett et al; Hanada et al., 1983) and the reversible protease inhibitor, leupeptin (Umezawa, 1976).

Calpastatin

Endogenous protein inhibitors of calpains, called calpastatins, are heat-stable polypeptides with high specificity for calcium-dependent proteinases. Calpastatins are essential factors in the in vivo regulation of CAPN activity, and perturbations of this ratio of inhibitor to enzyme in non-neural tissues have the predicted consequences on CAPN activity in cells.

Calpastatins, the specific protein inhibitors of CAPN, are also widely distributed among tissues. First identified in 1978 (Waxman et al., 1978), calpastatins have since been purified from several different sources. Although each of the purified species shares the properties of heat stability and strict specificity for CAPN, there is no consensus on the number of forms of calpastatin within single cells or among different cell types. The recent characterization of a calpastatin cDNA isolated from a rabbit cDNA library (Emori et al., 1987) revealed a deduced sequence of 718 amino acid residues ($M.sub.r=76,964$) containing four consecutive internal repeats of approximately 140 amino acid residues, each expressing inhibitory activity (Emori, et al., 1987). This deduced molecular weight is significantly lower than the molecular weight of rabbit skeletal muscle calpastatin ($M.sub.r=110,000$), suggesting that the inhibitor migrates anomalously on SDS gels and may be post-translationally modified.

Other studies suggest that additional molecular forms of calpastatin may be present in tissues. Although 110 kDa calpastatin is observed in rabbit and bovine skeletal muscle (Nakamura et al., 1985; Otsuka et al., 1987), porcine cardiac muscle (Takano et al., 1986) and human liver (Imajoh et al., 1984), other molecular forms of calpastatin have also been isolated, including a 68 kDa form from chick skeletal muscle (Ishiura et al., 1982) and porcine erythrocytes (Takano et al., 1986), a 50 kDa heterodimer from rabbit skeletal muscle (Nakamura et al., 1984) and 34 kDa forms from rabbit skeletal muscle (Takahashi-Nakamura et al., 1981) and rat liver (Yamato et al., 1983). The sensitivity of calpastatin to proteolysis has suggested that smaller polypeptide chains containing inhibitory activity might be derived from larger precursors during purification, or in vivo. Although certain of these low molecular weight calpastatins resemble the higher molecular weight forms, their derivation from the same gene product has not been established.

Calpastatin which is a specific inhibitory protein as to calpain, is known, and is expected to be applicable as an effective therapeutic agent for various excessive calpain-related syndromes. Calpastatin is, however, a high molecular weight protein and hence it will be difficult to use as a medicine.

Calpain 10 is a Novel Calpain-like Protease.

Calpain 10 is a "diapain" that has been identified by the present invention. Calpain 10 is encoded by a sequence in a 49,136 base pair region located on chromosome 2 (SEQ ID NO:1). The following list shows the exon regions of this 49,136 base pair region that are differentially spliced to create mRNAs encoding different isomers of calpain 10. Nucleotide positions (nt) are shown relative to SEQ ID NO:1.

Exon 1 nt 1235–1515 (cds 1375–1515)
Exon 2 nt 3813–3944
Exon 3 nt 5283–5479 or Exon 3* 5283–5468

Exon 4 nt 6401–6618
Exon 5 nt 8373–8514
Exon 6 nt 9010–9175 (TGA,9013–9015)
Exon 7 nt 9491–9771
Exon 8 nt 10400–10618 (TGA, 10455–10457)
Exon 9 nt 10785–10987
Exon 10 nt 11147–11408 or Exon 10* 11316–11408
Exon 11 nt 12354–12553 (TGA, 12412–12414)
Exon 12 nt 12818–12863
Exon 13 nt 13117–13569 (TAA, 13144–13146)
Exon 14 nt 30857–30980
Exon 15 nt 31446–32175 (TGA, 31466–31468)

There are a number of calpain 10 isoforms that result from alternative splicing of the CAPN10 gene. Alternative splicing generates eight related but structurally distinct proteins. The structures of the mRNAs encoding each isoform are defined by unique combinations of exons and splice donor and acceptor sites (see Table 1, FIG. 1A, FIG. 1B, FIG. 1C, FIG. 1D, FIG. 1E, FIG. 1F, FIG. 1G and FIG. 1H).

TABLE 1

Description of calpain 10 isoforms.

| Calpain 10 Isoform | Encoded by Exons | Polypeptide Length (aa) | SEQ ID NO |
|---|---|---|---|
| Calpain 10a | 1–7, 9–13 | 672 | 2 |
| Calpain 10b | 1–7, 9, 10*, 11–13 | 544 | 4 |
| Calpain 10c | 1–7, 11–13 | 517 | 6 |
| Calpain 10d | 1–7, 9, 11–13 | 513 | 8 |
| Calpain 10e | 1–10*, 11–13 | 444 | 10 |
| Calpain 10f | 1–3*, 4–7, 9–13 | 274 | 12 |
| Calpain 10g | 1, 2, 14, 15 | 139 | 14 |
| Calpain 10h | 1, 11–13 | 138 | 16 |

There is a G/A polymorphism at nt 6225 of (relative to SEQ ID NO:1) in intron 3 of the Calpain 10 gene that is responsible for the evidence of linkage with type 2 diabetes. Further, there is a GPR35 (G-protein coupled receptor most closely related in sequence to the human ATP receptor subtype P2Y9, amino acid sequence shown as SEQ ID NO:20 and nucleic acid sequence shown as SEQ ID NO:21). There is a polyadenylation signal that is defined by nucleotides 43195–44927 of Exon 1(relative to SEQ ID NO:1). The coding sequence between nucleotides 43390–44574 (inc. TAA, found in SEQ ID NO:1) yields a 394 amino acid protein.

Figure 6:
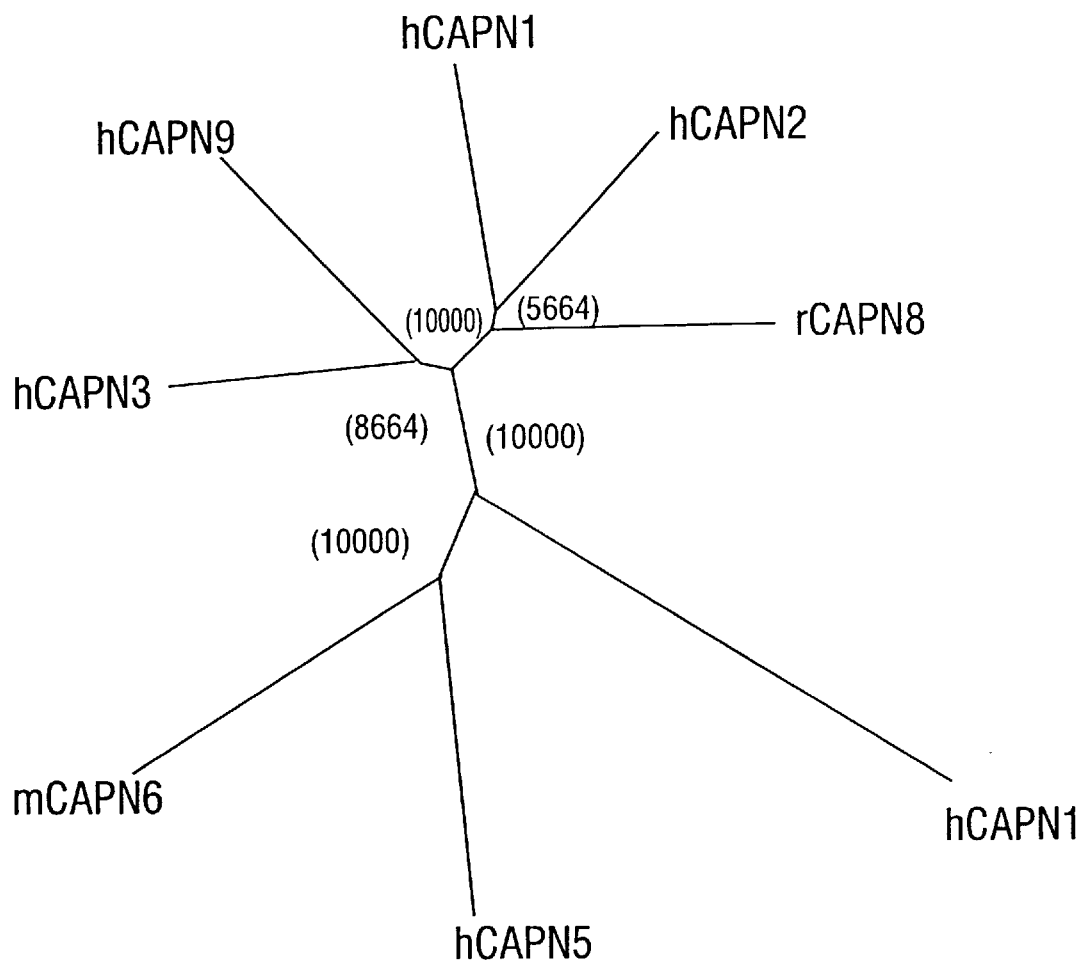
FIG. 6. Unrooted phylogenetic tree of calpain large subunit family. Multiple sequence alignment was performed with CLUSTAL X. The phylogenetic tree was generated using the neighbor joining method based on the number of amino acid substitutions. Branch lengths are proportional to the inferred phylogenetic distances. The tree was drawn using TREEVIEW.

Calpain 10 diapain is an atypical calpain and is similar in structural organization to the other atypical calpains, calpain 5 and calpain 6, in that it has domains I-to-III, lacks the calmodulin-like $Ca^{2+}$-binding domain and has a divergent C-terminal domain, domain T (Dear et al., 1997). Calpains 5, 6 and 10 define a distinct subfamily (FIG. 6). Calpains are found in all tissues and are processing proteases, cleaving specific substrates at a limited number of sites, and causing activation or inactivation of protein function. They have been implicated in the regulation of a variety of cellular functions including intracellular signaling, proliferation and differentiation, and may be responsible for insulin-induced down-regulation of insulin receptor substrate-1 (Smith et al., 1996), a key mediator of insulin action.

Mutations in calpain 3, p94, are the cause of the recessive disorder limb-girdle muscular dystrophy type 2A, indicating a vital role for proteolysis in the determining normal muscle functional (Richard et al., 1995). Calpains have also been implicated in sexual development in *Caenorhabditis elegans* and mutations in the sex determination gene tra-3, the orthologue of human calpain 5, affect correct sexual development of the soma and germ cells (Barnes and Hodgkin, 1996).

The results of the present invention indicate that a single nucleotide polymorphism in intron 3 of the calpain 10 gene affects diabetes susceptibility. The location of the causal variant within an intron suggests that it might function as an enhancer affecting regulation of transcription, or perhaps by its effects on alternative splicing. Diabetes results from defects in insulin secretion and insulin action. Calpain 10 is ubiquitously expressed and thus could affect both processes or, alternatively, have specific effects on muscle, liver and pancreatic β-cell, the three most important tissues controlling glucose homeostasis. An understanding of the role of calpain 10 in diabetes must await the identification of the cell types sensitive to calpain 10 activity and its specific substrates.

The present invention reveals a new regulatory network involved in the pathophysiology of this diabetes. This network likely includes, in addition to calpain 10, its substrates, inhibitors and activators. Calpain 10 does not appear to act alone in determining susceptibility to type 2 diabetes but rather interacts with the product of a gene on chromosome 15. The inventors have shown that NIDDM1 acts in concert with an unknown gene on chromosome 15 to increase susceptibility to type 2 diabetes in Mexican Americans, and this combination may be a primary determinant of susceptibility in 45% of families in this community.

The gene product on chromosome 15 could be a substrate, inhibitor or activator of calpain 10. Given that the present invention has identified the sequence of calpain 10, the compositions of the present invention will allow one of skill in the art to identify the gene product on chromosome 15 that has long been sought after as a gene involved in diabetes.

Furthermore, the identification of the causal variant at NIDDM1 also allows the inventors to re-examine the linkage studies in other populations. The G-allele at UCSNP-43 has a frequency in unrelated nondiabetic non-Hispanic whites (German ancestry), Asians (Japanese) and African Americans of 0.71, 0.94 and 0.90, respectively. Its high frequency in Asians and African Americans indicates that its effects on susceptibility may not be detected by linkage analysis. Its effect on susceptibility in non-Hispanic whites needs to re-evaluated taking into account the interaction with the diabetes gene on chromosome 15.

Calpain 10 is the third example of a protease contributing to the development of diabetes. Mutations in prohormone-processing carboxypeptidase E and prohormone convertase-1 are associated with a diabetes and obesity (Naggert et al., 1995; Jackson et al., 1997). The mutation in the carboxypeptidase E gene is responsible for impaired glucose tolerance or diabetes in a mammalian animal model system. The carboxypeptidase E gene product is known to cleave C-terminal amino acid residues from substrate proteins, and is a principal enzyme involved in the processing of precursor forms of peptide hormones into their mature, biologically active forms. The B-chain of insulin, immediately following the excision of the connector (C-) peptide from the proinsulin precursor by endopeptidase action, is carboxypeptidase E substrate. Carboxypeptidase E activity is required to remove a diarginyl remnant of the C-peptide at the C-terminus of the insulin .beta. chain. Without such removal, the C-terminal extended form has only a fraction of the activity of the processed form. Further, a defect carboxypeptidase E activity leads to an accumulation of proinsulin which also has low biological activity.

Given the great diversity of proteases and the myriad functions they perform, additional proteases may be implicated in diabetes susceptibility. In this regard, it has been noted that one of the side effects of the long-term use of protease inhibitors in patients with AIDS is diabetes (Flexner, 1998). Since it is a variant in the calpain 10 gene that is associated with diabetes, the inventors suggest that the protein encoded by this gene be called diapain-1 (diabetes calpain). As such the terms "calpain 10" and diapain-1 are used interchangeably herein.

It is likely that additional diapain-1-like proteases may be identified that are intrinsically involved in diabetes. As discussed above, there are numerous isoforms of calpain 10 that are formed as a consequence of alternative splicing of calpain 10 mRNA as described above. These include calpain 10a, calpain 10b, calpain 10c, calpain 10d, calpain 10e, calpain 10f, calpain 10g, and calpain 10h, as described in Table 1 and FIG. 1A, FIG. 1B, FIG. 1C, FIG. 1D, FIG. 1E, FIG. 1F, FIG. 1G and FIG. 1H. Additional alternative splicing may provide other calpain 10 proteins. Further, it is contemplated that other calpain or calpain-like proteins will be identified that are involved in the development of diabetes or any other manifestation of diabetes. Given the recent findings with regard to different factors involved in the regulation of expression and activity of the HNF transcription factors which are responsible for susceptibility to MODY1, MODY3 and MODY5 (WO 98/11254), it is likely that another such pathway may be defined for type 2 diabetes, with calpain 10 being one of the key factors in the pathway. From the inventors' investigations, it is conceivable that aberrations at any point along such pathway or any factors affecting the pathway directly or indirectly will result in β-cell dysfunction and diabetes mellitus, either as type 2 diabetes, another manifestation of type 2 diabetes or perhaps in diabetes as a whole (i.e., type 1 and type 2 diabetes).

With respect to calpains, or indeed proteases in general, being involved in diabetic states other than type 2 diabetes, it is of note that one of the side effects of the long-term use of protease inhibitors in patients with AIDS is diabetes (Flexner, 1998). Thus, it is an aspect of the present invention to contemplate therapeutic strategies that provide amelioration of a diabetes-type phenotype by providing therapies that alleviate an aberration in protease gene expression, protein activity or function. These therapies may be based on gene therapy to provide wild-type proteases, or may employ modulators of proteases (calpains and diapains) identified according to the present invention. Such modulators may be small molecule inhibitors, antibody compositions or any other composition that will alleviate, overcome or otherwise circumvent the deleterious effects of protease mutations in diabetes.

C. Linkage Analysis of Increased Susceptibility to Type 2 Diabetes

In one aspect of the present invention, the inventors describe an approach to assessing the evidence for statistical interactions between unlinked regions that allows multipoint allele-sharing analysis to take the evidence for linkage at one region into account in assessing the evidence for linkage over the rest of the genome. Using this method, the inventors show that the interaction of genes on chromosomes 2 (NIDDM1) and 15 (near CYP19) makes a major contribution to susceptibility to type 2 diabetes in Mexican Americans from Starr County, Tex.

The correlation in scores assessing the evidence for linkage across families (e.g., non-parametric linkage scores—NPL (Kruglyak et al., 1996)) can be used to determine preliminary evidence for statistical interaction between unlinked regions. Unless the regions chosen for study actually contain loci which contribute susceptibility to disease, there is no expectation that NPL scores from unlinked regions will be correlated, even if the regions are selected because they show some evidence for linkage. However, there is not always a simple correspondence between the biological interactions of genes and the statistical interactions that can be detected. For example, while some models of epistatic interaction generate positive correlations between NPL scores from the regions to which the interacting loci map, many models of biological interaction would not generate detectable correlations. Moreover, negative correlations between regions can be generated when nonoverlapping sets of families provide evidence for linkage due to genetic heterogeneity, in the absence of biological interactions between the susceptibility loci from these regions. Thus, finding significant correlations between NPL scores at unlinked regions provides additional evidence that loci from those regions contribute to disease susceptibility and generates insight into the models most consistent with the type of correlation (positive or negative) observed.

Once preliminary studies provide evidence for statistical interaction between regions, it is possible to incorporate linkage evidence from one region in assessing evidence for linkage at a second region (or multiple regions) by weighting families according to their evidence for linkage. The multipoint allele-sharing approach described by Kruglyak et al. (1996) and extended by Kong and Cox (1997) to efficiently utilize incomplete information was designed to allow families to be weighted individually, but these original implementations assigned each family equal weight. The inventors' newest extension (GENEHUNTER-PLUS v2.0) allows users to specify individual weights for each family based, for example, on pedigree structure, number of affecteds, and/or their evidence for linkage at a particular location. Family-specific weighting can be used to model positive interactions (such as epistasis) by assigning weight 0 to families with 0 or negative linkage scores and weight 1 to families with positive linkage scores (weight$_{0-1}$), or to model heterogeneity by assigning weight 1 to families with negative linkage scores and weight 0 to families with 0 or positive linkage scores (weight$_{1-0}$). More complex family-specific weights proportional to the evidence for linkage (weight$_{prop}$) can also be constructed.

Determining the significance of apparent interactions requires care. The nominal P-values associated with the sample correlations are calculated using the Pearson's correlation test (a t-test), which is likely to be appropriate for large sample sizes. The significance associated with the increased lod when evidence for linkage at a particular location is taken into account using family-specific weights can be determined either by simulation, or by using a conservative $\chi^2$ test with one degree of freedom as follows. If the inventors consider a more general one-degree-of-freedom family of weights in which weight$_{0-1}$, and weight$_{1-0}$, are the two extremes, then the increase over baseline of the MLS for the family weighting yielding the maximum load multiplied by 2 log(10) is asymptotically distributed as a $\chi^2$ with one degree of freedom under the null hypothesis of no interaction. The test is conservative because the inventors are not actually maximizing the lod with respect to the weighting factors, and currently consider only a few family-specific weights. However, interpretation of such studies still requires taking multiple comparisons into account.

To limit the Bonferroni adjustment, it seems prudent to focus on the top signals from the primary linkage analysis and perhaps a small number of candidate regions. Even with this adjustment, such secondary analyses may increase the overall false positive rate became they are designed to strengthen the support for regions that do not themselves meet genome-wide criteria for significance. Given that, and the absence of information on the a priori likelihood of such interactions, it is appropriate to use more stringent criteria for determining significance, i.e. 0.01 instead of 0.05. The evidence for interaction between the CYP19-NIDDM1 regions meets these criteria after the Bonferroni adjustment where that between NIDDM1 and HNF-1α does not (Table 6). More research will be necessary to determine whether such statistical interactions will be common in complex traits, and how criteria that have been suggested for assessing genome-wide significance (Lander and Kruglyak, 1995) should be modified when the evidence for linkage at multiple susceptibility loci is considered simultaneously. Example 5 herein describes the data generated from linkage between CYP19 and NIDDM1.

D. Nucleic Acids

As described in the Examples, the present invention discloses the calpain 10 gene at the NIDDM1 locus of chromosome 2. Mutations in this gene are responsible for susceptibility to type 2 diabetes. The gene at this locus has been designated as a calpain-like protein, calpain 10 or otherwise referred to herein as diapain-1. In particular, the nucleotide variant showing all the evidence for linkage with type 2 diabetes, UCSNP-43, is located in intron 3 of the calpain 10 gene, CAPN10 (see FIG. 4), 746 bp downstream of the splice donor site and 176 bp upstream of the splice acceptor site. The molecular mechanism by which the G-to-A polymorphism at UCSNP-43 affects susceptibility to type 2 diabetes is unclear. As shown in FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M and FIG. 5N, there is alternative splicing of intron 3.

In one embodiment of the present invention, the nucleic acid sequences disclosed herein find utility as hybridization probes or amplification primers. In certain embodiments, these probes and primers consist of oligonucleotide fragments. Such fragments should be of sufficient length to provide specific hybridization to an RNA or DNA sample extracted from tissue. The sequences typically will be 10–20 nucleotides, but may be longer. Longer sequences, e.g., 40, 50, 100, 500 and even up to full length, are preferred for certain embodiments.

Nucleic acid molecules having contiguous stretches of about 10, 15, 17, 20, 30, 40, 50, 60, 75 or 100 or 500 nucleotides from a sequence selected from the group listed in in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, fragments thereof, mRNAs and cDNAs encoding any of calpains 10a–10h, or any other calpain 10, and mutants of each are contemplated. Molecules that are complementary to the above mentioned sequences and that bind to these sequences under high stringency conditions also are contemplated. SEQ ID NO:21 is the human G protein coupled receptor within the NIDDM1 region. SEQ ID NO:19 is the mouse calpain 10 protease. These probes will be useful in a variety of hybridization embodiments, such as Southern and northern blotting. In some cases, it is contemplated that probes may be used that hybridize to multiple target sequences without compromising their ability to effectively diagnose diabetes and in particular, type 2 diabetes. In certain embodiments, it is contemplated that multiple probes may be used for hybridization to a single sample.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The value of n in the algorithm above for the nucleic acid sequence is n=49,136 for the calpain 10 gene. The value of n for a cDNA encoding any of calpains 10a–10h may be calculated by adding up the number of nucleic acids in the exons that are spliced to form the mRNA from which the particular calpain 10 is expressed.

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional analogs of these sequences.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

In an alternative embodiment, the diapain-1 encoding nucleic acids employed may actually encode antisense constructs that hybridize, under intracellular conditions, to an diapain-1 encoding or other calpain encoding nucleic acid.

The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the diapain-1 gene sequence may be employed in the context of antisense construction, short oligonucleotides are easier to make and increase in vivo accessibility. However, both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

Preferred promoters include those derived from HSV, and calpain 10, additionally, other calpain promoters also may be useful. The sequence of the human, calpain 10 gene including promoter has also been identified by the present inventors and deposited in the GenBank database. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 1 and 2 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| α-Globin |
| β-Globin |
| c-fos |
| c-HA-ras |
| Insulin |
| Neural Cell Adhesion Molecule (NCAM) |
| $α_1$-Anti-trypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |

TABLE 2-continued

| PROMOTER |
| --- |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

Use of the baculovirus system will involve high level expression from the powerful polyhedron promoter.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In various embodiments of the invention, the expression construct may comprise a virus or engineered construct derived from a viral genome. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papoviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

In some embodiments, the vector is HSV. Because HSV is neurotropic, it has generated considerable interest in treating nervous system disorders. Since insulin-secreting pancreatic β-cells share many features with neurons, HSV may be useful for delivering genes to β-cells and for gene therapy of diabetes. Moreover, the ability of HSV to establish latent infections in non-dividing neuronal cells without integrating into the host cell chromosome or otherwise altering the host cell's metabolism, along with the existence of a promoter that is active during latency. And though much attention has focused on the neurotropic applications of HSV, this vector also can be exploited for other tissues.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings.

E. Encoded Proteins

Once the entire coding sequence of a particular gene has been determined, the gene can be inserted into an appropriate expression system. In this case, the inventors have identified diapain-1 as a type 2 diabetes susceptibility gene. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as E. coli, yeast such as Saccharomyces cerevisia and Pichia pastoris, baculovirus, and mammalian expression systems such as in COS or CHO cells. In one embodiment, polypeptides are expressed in E. coli and in baculovirus expression systems. A complete gene can be expressed or, alternatively, fragments of the gene encoding portions of polypeptide can be produced.

In one embodiment, the gene sequence encoding the polypeptide is analyzed to detect putative transmembrane sequences. Such sequences are typically very hydrophobic and are readily detected by the use of standard sequence analysis software, such as DNA Star (DNA Star, Madison, Wis.). The presence of transmembrane sequences is often deleterious when a recombinant protein is synthesized in many expression systems, especially *E. coli,* as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Therefore, antibodies to these sequences will not prove useful for in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene. The skilled practitioner will realize that such changes must be designed so as not to change the translational reading frame for downstream portions of the protein-encoding sequence.

In one embodiment, computer sequence analysis is used to determine the location of the predicted major antigenic determinant epitopes of the polypeptide. Software capable of carrying out this analysis is readily available commercially, for example DNA Star (DNA Star, Madison, Wis.). The software typically uses standard algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides can be prepared that contain at least the essential features of the antigenic determinant and that can be employed in the generation of antisera against the polypeptide. Minigenes or gene fusions encoding these determinants can be constructed and inserted into expression vectors by standard methods, for example, using PCR methodology.

The gene or gene fragment encoding a polypeptide can be inserted into an expression vector by standard subcloning techniques. In one embodiment, an *E. coli* expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (New England Biolabs, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of that are known to be poorly antigenic and which do not adversely affect folding of the polypeptide to its native conformation. Other fusion systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example *E. coli,* are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

In another embodiment, the expression system used is one driven by the baculovirus polyhedron promoter. The gene encoding the polypeptide can be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., A MANUAL OF METHODS FOR BACULOVIRUS VECTORS AND INSECT CELL CULTURE PROCEDURES, Texas Agricultural Experimental Station.

As an alternative to recombinant polypeptides, synthetic peptides corresponding to the antigenic determinants can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, amino acid sequence variants of the polypeptide can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR™ can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY,* Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

TABLE 4

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1);

glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

F. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

G. Expression and Purification of Encoded Proteins

1. Expression of Proteins from Cloned cDNAs

The cDNA species specified in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21 can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* χ 1776 (ATCC No. 31537) as well as *E. coli* W3110 (F-, lambda-, prototrophic, ATCC No. 273325); bacilli such as Bacillus subtilis; and other enterobacteriaceae such as *Salmonella typhimurium, Serratia marcescens,* and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid contains the trpl gene, which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, WI38, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3', SEQ ID NO:30) if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk⁻, hgprt⁻ or aprt⁻ cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin.

It is contemplated that the isolated nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., *Biochem. Biophys. Res. Comm.,* 76:425, 1977). It will therefore be appreciated that under differing electrophoresis conditions, the apparent molecular weights of purified or partially purified expression products may vary.

H. Preparation of Antibodies Specific for Encoded Proteins
Antibody Generation

For some embodiments, it will be desired to produce antibodies that bind with high specificity to the protein product(s) of an isolated nucleic acid selected from the group comprising the sequences in SEQ ID NO:1, or any mutant of calpain 10. Means for preparing and characterizing antibodies are well known in the art (See, e.g., Antibodies: A Laboratory Manual, Cold Spring Harbor Laboratory, 1988, incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate monoclonal antibodies (MAbs). For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art (Goding, 1986). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length gene or of gene fragments in *E. coli*.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc, are other useful labels that can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SnCl_2$, a buffer solution such as sodium-potassium phthalate solution, and the antibody.

It will be appreciated by those of skill in the art that monoclonal or polyclonal antibodies specific for calpain 10 (or any other calpain-like protein involved in diabetes) will have utilities in several types of applications. These can include the production of diagnostic kits for use in detecting or diagnosing type 2 diabetes. The skilled practitioner will realize that such uses are within the scope of the present invention.

I. Immunodetection Assays

The immunodetection methods of the present invention have evident utility in the diagnosis of conditions such as type 2 diabetes. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with type 2 diabetes, the detection of an antigen encoded by a calpain 10 encoding nucleic acid, or an increase or decrease in the levels of such an antigen, in comparison to the levels in a corresponding biological sample from a normal subject is indicative of a patient with type 2 diabetes. The basis for such diagnostic methods lies, in part, with the finding that the nucleic acid calpain 10 mutants identified in the present invention are responsible for an increased susceptibility to type 2 diabetes.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

1. Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a calpain 10 mutant encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a calpain 10 antigen, such as a muscle cell, a homogenized tissue extract, an isolated cell, a cell membrane preparation, separated or purified forms of any of the above protein-containing compositions, or even any biological fluid that comes into contact with diabetic tissue, including blood.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

2. Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of diabetic tissue. The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" diabetic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

3. ELISA

As noted, it is contemplated that the encoded proteins or peptides of the invention will find utility as immunogens, e.g., in immunohistochemistry and in ELISA assays. One evident utility of the encoded antigens and corresponding antibodies is in immunoassays for the detection of calpain 10 wild-type and mutant proteins, as needed in diagnosis and prognostic monitoring of type 2 diabetes.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the diapain mutant, such as a clinical sample, is added to the wells. After binding and washing to remove non-specifically bound immune complexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the calpain 10 antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the calpain 10 protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control, type 2 diabetes and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween™. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween™).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention will be used to quantify and localize the expression of the encoded marker proteins.

The antibody, for example, will be labeled by any one of a variety of methods and used to visualize the localized concentration of the cells producing the encoded protein. Such an assay also will reveal the subcellular localization of the protein, which can have diagnostic and therapeutic applications.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}$Gd, $^{55}$Mn, $^{162}$Dy, $^{52}$Cr, and $^{56}$Fe.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example, 30 minutes to 48 hours, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the encoded calpain 10 proteins in human patients. The present invention provides methods for the in vivo diagnosis of type 2 diabetes in a patient. Such methods generally comprise administering to a patient an effective amount of a calpain 10-specific antibody, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

5. Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

J. Methods for Screening Active Compounds

The present invention also contemplates the use of calpain 10 and active fragments, and nucleic acids coding therefor, in the screening of compounds for activity in either stimulating calpain 10 activity, overcoming the lack of calpain 10 activity or blocking the effect of a calpain 10 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound.

Compounds thus identified will be capable of promoting gene expression, and thus can be said to have up-regulating activity. In as much as decreased levels of calpain 10 indicate an increased susceptibility to type 2 diabetes, any positive substances identified by the assays of the present invention will be anti-diabetic drugs. Before human administration, such compounds would be rigorously tested using conventional animal models known to those of skill in the art.

As stated earlier, the present invention provides the complete sequence of the calpain 10 gene. The sequence predicts a protein with extensive homology with representative members of the large subunit calpain family. The calpain 10 protein acts in concert with the protein product of an unknown gene on chromosome 15 to increase susceptibility to type 2 diabetes. Thus, in certain embodiments, the binding partner for calpain 10 may be the protein encoded by a gene on chromosome 15. This gene may be involved in diabetes. Thus the present invention also will be useful in isolating and identifying the gene on chromosome 15 that has long since been suspected to be involved in diabetes. Alternatively, the binding partner may be any agent or protein that is cleaved by the action of the protease.

Virtually any candidate substance may be analyzed by these methods, including compounds which may interact with calpain 10, calpain 10 binding protein(s), and substances such as enzymes which may act by physically altering one of the structures present. Of course, any compound isolated from natural sources such as plants, animals or even marine, forest, or soil samples, may be assayed, as may any synthetic chemical or recombinant protein.

1. In Vitro Assays

In one embodiment, the invention is to be applied for the screening of compounds that bind to the calpain 10 wild-type molecule, mutant or fragment thereof. The wild-type or mutant polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of calpain 10 to a natural or artificial substrate or binding partner. Competitive binding assays can be performed in which one of the agents (calpain 10, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with calpain 10 and washed. Bound polypeptide is detected by various methods.

Purified calpain 10 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the calpain 10 active region to a solid phase.

Various cell lines containing wild-type or natural or engineered mutations in calpain 10 can be used to study various functional attributes of calpain 10 and how a candidate compound affects these attributes. Methods for engineering mutations are described elsewhere in this document, as are naturally-occurring mutations in calpain 10 that lead to, contribute to and/or otherwise cause diabetes. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of calpain 10, or related pathways, may be explored. This may involve assays such as those for protein expression, enzyme function, substrate utilization, phosphorylation states of various molecules, cAMP levels, mRNA expression (including differential display of whole cell or polyA RNA) and others.

2. In Vivo Assays

The present invention also encompasses the use of various animal models. Here, the identity seen between calpain 10 and other calpains provides an excellent opportunity to examine the function of calpain 10 in relation to other proteases in a whole animal system where it is normally expressed. By developing or isolating mutant cells lines that fail to express normal calpain 10, one can generate diabetes models in mice that will be highly predictive of diabetes in humans and other mammals.

Alternatively, one may increase the susceptibility of an animal to diabetes by providing agents known to be responsible for this susceptibility, i.e., providing a mutant calpain 10. Finally, transgenic animals (discussed below) that lack a wild-type calpain 10 may be utilized as models for type 2 diabetes development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection and regional administration via blood or lymph supply.

Determining the effectiveness of a compound in vivo may involve a variety of different criteria. Such criteria include, but are not limited to, survival, improvement of hyperglycemia, diminished need for hypoglycemic agents, diminished need for insulin requirements, increased insulin synthesis, improved protease activity, improvement in immune effector function and improved food intake.

3. Reporter Genes and Cell-Based Screening Assays

Cellular assays also are available for screening candidate substances to identify those capable of stimulating calpain 10 activity and gene expression. In these assays, the increased expression of any natural or heterologous gene under the control of a functional calpain 10 promoter may be employed as a measure of stimulatory activity, although the use of reporter genes is preferred.

A reporter gene is a gene that confers on its recombinant host cell a readily detectable phenotype that emerges only under specific conditions. In the present case, the reporter gene may be placed under the control of the same promoter as the calpain 10 and will thus generally be repressed under conditions where the calpain 10 is not being expressed and will generally be expressed in the conditions where calpain 10 is being expressed.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. A reporter gene often used is chloramphenicol acetyltransferase (CAT) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neo gene which protects host cells against toxic levels of the antibiotic G418, and genes encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes of potential for use in screening assays are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

To create an appropriate vector or plasmid for use in such assays one would ligate the promoter, whether a hybrid or the native diapain-1 promoter, to a DNA segment encoding the reporter gene by conventional methods. The diapain-1 promoter sequences may be obtained by in vitro synthesis or recovered from genomic DNA and should be ligated upstream of the start codon of the reporter gene. The present invention provides the promoter region for human calpain 10 gene. The sequences associated with the novel calpain 10 gene of the present invention are shown in Apendix A, including the calpain 10 promoter region. Any of these promoters may be particularly preferred in the present invention. An AT-rich TATA box region should also be employed and should be located between the calpain 10 sequence and the reporter gene start codon. The region 3' to the coding sequence for the reporter gene will ideally contain a transcription termination and polyadenylation site. The promoter and reporter gene may be inserted into a replicable vector and transfected into a cloning host such as *E. coli,* the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney (HEK)-293, CHO, W138, BHK, COS-7, and MDCK cell lines, with monkey CV-1 cells being particularly preferred.

In one embodiment, the screening assay typically is conducted by growing recombinant host cells in the presence and absence of candidate substances and determining the amount or the activity of the reporter gene. To assay for candidate substances capable of exerting their effects in the presence of calpain 10 gene products, one would make serial molar proportions of such gene products that alter calpain 10-mediated activity. One would ideally measure the reporter signal level after an incubation period that is sufficient to demonstrate mutant-mediated repression of signal expression in controls incubated solely with mutants. Cells containing varying proportions of candidate substances would then be evaluated for signal activation in comparison to the suppressed levels.

Candidates that demonstrate dose related enhancement of reporter gene transcription or expression are then selected for further evaluation as clinical therapeutic agents. The stimulation of activity may be observed in the absence of calpain 10, in which case the candidate compound might be a positive stimulator of calpain 10 expression. Alternatively, the candidate compound might only give a stimulation in the presence of a calpain 10 protein having the G-allele, which would indicate that it functions to oppose the G-allele-mediated suppression of activity. Candidate compounds of either class might be useful therapeutic agents that would combat type 2 diabetes.

4. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for calpain 10 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a calpain 10-specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved calpain 10 activity or which act as stimulators, inhibitors, agonists, antagonists of calpain 10 or molecules affected by calpain 10 function. By virtue of the availability of cloned calpain 10 sequences, sufficient amounts of calpain 10 can be produced to perform crystallographic studies. In addition, knowledge of the polypeptide sequences permits computer employed predictions of structure-function relationships.

K. Detection and Quantitation of Nucleic Acid Species

One embodiment of the instant invention comprises a method for identification of calpain 10 mutants in a biological sample by amplifying and detecting nucleic acids corresponding to calpain 10 mutants. The biological sample can be any tissue or fluid in which these mutants might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies (Sambrook et al, 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to calpain 10 mutants are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a reference group of normal subjects or indeed patients with type 2 and type 1 diabetes. In this way, it is possible to correlate the amount of calpain 10 mutants detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989); Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS,* Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al, 1989), incorporated herein by reference in its entirety.

3. RNase Protection Assay

Methods for genetic screening by identifying mutations associated with most genetic diseases such as diabetes must be able to assess large regions of the genome. Once a relevant mutation has been identified in a given patient, other family members and affected individuals can be screened using methods which are targeted to that site. The ability to detect dispersed point mutations is critical for genetic counseling, diagnosis, and early clinical intervention as well as for research into the etiology of cancer and other genetic disorders. The ideal method for genetic screening would quickly, inexpensively, and accurately detect all types of widely dispersed mutations in genomic DNA, cDNA, and RNA samples, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others (Cotton, 1989). The more common procedures currently in use include direct sequencing of target regions amplified by PCR™ and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay as first described by Melton et al. (1984) was used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations by Myers and Maniatis (1985) and by Winter and Perucho (1985). In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used (Gibbs and Caskey, 1987; Winter and Perucho, 1985). If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches (Ellis et al., 1994; Lishanski et al., 1994).

By hybridizing each strand of the wild type probe in RNase cleavage mismatch assays separately to the complementary Sense and Antisense strands of the test target, two different complementary mismatches (for example, A-C and G-U or G-T) and therefore two chances for detecting each mutation by separate cleavage events, was provided. Myers et al. (1985) used the RNase A cleavage assay to screen 615 bp regions of the human β-globin gene contained in recombinant plasmid targets. By probing with both strands, they were able to detect most, but not all, of the β-globin mutations in their model system. The collection of mutants included examples of all the 12 possible types of mismatches between RNA and DNA: rA/dA, rC/dC, rU/dC, rC/dA, rC/dT, rU/dG, rG/dA, rG/dG, rU/dG, rA/dC, rG/dT, and rA/dG.

Myers et. al. (1985) showed that certain types of mismatch were more frequently and more completely cleaved by RNase A than others. For example, the rC/dA, rC/dC, and rC/dT mismatches were cleaved in all cases, while the rG/dA mismatch was only cleaved in 13% of the cases tested and the rG/dT mismatch was almost completely resistant to cleavage. In general, the complement of a difficult-to-detect mismatch was much easier to detect. For example, the refractory rG/dT mismatch generated by probing a G to A mutant target with a wild type sense-strand probe, is complemented by the easily cleaved rC/dA mismatch generated by probing the mutant target with the wild type antisense strand. By probing both target strands, Myers and Maniatis (1986) estimated that at least 50% of all single-base mutations would be detected by the RNase A cleavage assay. These authors stated that approximately one-third of all possible types of single-base substitutions would be detected by using a single probe for just one strand of the target DNA (Myers et al., 1985).

In the typical RNase cleavage assays, the separating gels are run under denaturing conditions for analysis of the cleavage products. This requires the RNase to be inactivated by treating the reaction with protease (usually Proteinase K, often in the presence of SDS) to degrade the RNase. This reaction is generally followed by an organic extraction with a phenol/chloroform solution to remove proteins and residual RNase activity. The organic extraction is then followed by concentration and recovery of the cleavage products by alcohol precipitation (Myers et al., 1985; Winter et al., 1985; Theophilus et al., 1989).

4. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

5. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

6. Kit Components

All the essential materials and reagents required for detecting type-2 diabetes markers in a biological sample may be assembled together in a kit. This generally will comprise pre-selected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:1 along with any other cDNAs for calpain 10. In other embodiments preferred pairs of primers for amplification are selected to amplify any of the regions specified in SEQ ID NO:1.

In another embodiment, such kits will comprise hybridization probes specific for calpain 10, chosen from a group including nucleic acids corresponding to the sequence specified in SEQ ID NO:1. Such kits generally will comprise, in suitable means, distinct containers for each individual reagent and enzyme as well as for each marker hybridization probe.

L. Use of RNA Fingerprinting to Identify Type 2 Diabetes Markers

RNA fingerprinting is a means by which RNAs isolated from many different tissues, cell types or treatment groups can be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Some of the experiments described herein were performed similarly to Donahue et al., *J. Biol. Chem.* 269: 8604–8609, 1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT and any two of the four deoxynucleosides. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from for example tumor versus normal tissue samples using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in diabetes.

1. Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from type 2 diabetes patients. By determining that the concentration of a specific mRNA species varies, it is shown that the gene encoding the specific mRNA species is differentially expressed. This technique can be used to confirm that mRNA transcripts shown to be differentially regulated by RNA fingerprinting are differentially expressed in type 2 diabetes.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

M. Methods for Calpain 10 Gene Expression

In one embodiment of the present invention, there are provided methods for the increased calpain 10 gene expression or activation in a cell. This is particularly useful where there is an aberration in the gene product or gene expression is not sufficient for normal function. This will allow for the alleviation of symptoms of type 2 diabetes experienced as a result of deficiency of calpain 10. Further, given that calpain 10 is a protease and that there is a great diversity of proteases and the myriad functions they perform, additional proteases may be implicated in diabetes susceptibility. Specifically, one of the side effects of the long-term use of protease inhibitors in patients with AIDS is diabetes (Flexner, 1998). Thus, calpain 10 gene expression could be increased or activated in such patients.

The general approach to increasing calpain 10 activity according to the present invention, will be to provide a cell with an calpain 10 polypeptide. While it is conceivable that the protein may be delivered directly, a preferred embodiment involves providing a nucleic acid encoding a calpain 10 polypeptide, i.e., a calpain 10 gene, to the cell. Following this provision, the calpain 10 polypeptide is synthesized by the host cell's transcriptional and translational machinery, as well as any that may be provided by the expression construct. Cis-acting regulatory elements necessary to support the expression of the calpain 10 gene will be provided, in the form of an expression construct. It also is possible that expression of virally-encoded calpain 10 could be stimulated or enhanced, or the expressed polypeptide be stabilized, thereby achieving the same or similar effect.

In order to effect expression of constructs encoding calpain 10 and other calpain 10-like genes, the expression construct must be delivered into a cell. One mechanism for delivery is via viral infection, where the expression construct is encapsidated in a viral particle which will deliver either a replicating or non-replicating nucleic acid. In certain embodiments an HSV vector is used, although virtually any vector would suffice.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et. al., 1990), and receptor-mediated transfection (Wu and Wu, 1987; Wu and Wu, 1988). Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver a nucleic acid encoding a calpain 10 transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al, 1994). Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

N. Methods for Blocking Calpain 10 Action

In another embodiment of the present invention, there is contemplated the method of blocking the function of calpain 10 in type 2 diabetes. In this way, it may be possible to curtail the effects of excess calpain 10 in diabetes. In addition, it may prove effective to use this sort of therapeutic intervention in combination with more traditional diabetes therapies, such as the administration of insulin.

The general form that this aspect of the invention will take is the provision, to a cell, of an agent that will inhibit calpain 10 function. Four such agents are contemplated. First, one may employ an antisense nucleic acid that will hybridize either to the calpain 10 gene or the calpain 10 gene transcript, thereby preventing transcription or translation, respectively. The considerations relevant to the design of antisense constructs have been presented above. Second, one may utilize a calpain 10-binding protein or peptide, for example, a peptidomimetic or an antibody that binds immunologically to calpain 10. The binding of either will block or reduce the activity of the calpain 10. The methods of making and selecting peptide binding partners and antibodies are well known to those of skill in the art. Third, one may provide to the cell an antagonist of calpain 10, for example, an inhibitor, alone or coupled to another agent. Fourth, one may provide an agent that binds to the calpain 10 substrate (s) without the same functional result as would arise with calpain 10 binding.

The compounds anticipated herein have activity as inhibitors of proteases, such cysteine proteases, including calpain. It is believed by those of skill in this art that excessive activation of the $Ca^{2+}$-dependent protease calpain plays a role in the pathology of a variety of disorders, including cerebral ischaemia, cataract, myocardial ischaemia, muscular dystrophy and platelet aggregation. Thus, compounds that have activity as calpain inhibitors are considered by those of skill in this art to be useful (U.S. Pat. No. 5,081,284; Sherwood et al., 1993). Assays that measure the anti-calpain activity of selected compounds are known to those of skill in the art (U.S. Pat. No. 5,081,284). Activities of inhibitors in such in vitro assays at concentrations ($IC_{50}$) in the nanomolar range or lower are indicative of therapeutic activity. Such compounds also have utility in the purification of proteinases, such as cysteine proteases, on affinity columns of these compounds (U.S. Pat. No. 5,081,284). Also, calpain inhibtors, such as N-Acetylleucylleucyinorleucinal (EP 0 504 938 A2; Sherwood et al, 1993 are used as reagents in the study of protein trafficking and other cellular processes (Sharma et al., 1992). Finally, inhibitors of cysteine proteases strongly inhibit the growth of Plasmodium falciparumand Schistosoma mansoni (Scheibel et al, 1984).

Provision of a calpain 10 gene, a calpain 10 protein, or a calpain 10 antagonist, would be according to any appropriate pharmaceutical route. The formulation of such compositions and their delivery to tissues is discussed below. The method by which the nucleic acid, protein or chemical is transferred, along with the preferred delivery route, will be selected based on the particular site to be treated. Those of skill in the art are capable of determining the most appropriate methods based on the relevant clinical considerations.

Many of the gene transfer techniques that generally are applied in vitro can be adapted for ex vivo or in vivo use. For example, selected organs including the liver, skin, and muscle tissue of rats and mice have been bombarded in vivo (Yang et al., 1990; Zelenin et al., 1991). Naked DNA also has been used in clinical settings to effect gene therapy. These approaches may require surgical exposure of the target tissue or direct target tissue injection. Nicolau et al (1987) accomplished successful liposome-mediated gene transfer in rats after intravenous injection.

Dubensky et al (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus, it is envisioned that DNA encoding an antisense construct also may be transferred in a similar manner in vivo.

Where the embodiment involves the use of an antibody that recognizes a calpain 10 polypeptide, consideration must be given to the mechanism by which the antibody is introduced into the cell cytoplasm. This can be accomplished, for example, by providing an expression construct that encodes a single-chain antibody version of the antibody to be provided. Most of the discussion above relating to expression constructs for antisense versions of the calpain 10 gene will be relevant to this aspect of the invention. Alternatively, it is possible to present a bifunctional antibody, where one antigen binding arm of the antibody recognizes a calpain 10 polypeptide and the other antigen binding arm recognizes a receptor on the surface of the cell to be targeted. Examples of suitable receptors would be an HSV glycoprotein such as gB, gC, gD, or gH. In addition, it may be possible to exploit the Fc-binding function associated with HSV gE, thereby obviating the need to sacrifice one arm of the antibody for purposes of cell targeting.

Advantageously, one may combine this approach with more conventional diabetes therapy options.

O. Transgenic Animals/Knockout Animals

In one embodiment of the invention, transgenic animals are produced which contain a functional transgene encoding wild-type or calpain 10 polypeptides. Transgenic animals expressing calpain 10 transgenes, recombinant cell lines derived from such animals and transgenic embryos may be useful in methods for screening for and identifying agents that induce or repress function of calpain 10. Such models will be useful in identifiying new and novel agents that will be useful in a diabetes therapeutic context. Transgenic animals of the present invention also can be used as models for studying indications of abnormal calpain 10 expression in diabetes.

In one embodiment of the invention, a calpain 10 transgene is introduced into a non-human host to produce a transgenic animal expressing a human calpain 10. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety). Addiitional descriptions for generating transgenic animal models may be found in numerous published patents inlcuding but not limited to U.S. Pat. Nos. 5,817,912; 5,817,911; 5,814,716; 5,814,318; 5,811,634; 5,741,957; 5,731,489; 5,770,429; 5,718,883, each of these patents is specifically incorporated herein by reference as teaching methods and compositions for the production of transgenic animals.

It may be desirable to replace the endogenous calpain 10 by homologous recombination between the transgene and the endogenous gene; or the endogenous gene may be eliminated by deletion as in the preparation of "knock-out" animals. Typically, a calpain 10 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to rodents, reptiles, amphibians, birds, mammals, and fish. Within a particularly preferred embodiment, transgenic mice are generated which overexpress calpain 10 or express a mutant form of the polypeptide. Alternatively, the absence of a calpain 10 in "knock-out" mice permits the study of the effects that loss of calpain 10 protein has on a cell in vivo. Knock-out mice also provide a model for the development of calpain 10-related abnormalities such as diabetes.

As noted above, transgenic animals and cell lines derived from such animals may find use in certain testing experiments. In this regard, transgenic animals and cell lines capable of expressing wild-type or calpain 10 may be exposed to test substances. These test substances can be screened for the ability to enhance wild-type calpain 10 expression and/or function or impair the expression or function of calpain 10.

P. Pharmaceuticals and In vivo Methods for the Treatment of Disease

Aqueous pharmaceutical compositions of the present invention will have an effective amount of a calpain 10 expression construct, an antisense calpain 10 expression construct, an expression construct that encodes a therapeutic gene along with calpain 10, a protein or compound that inhibits mutated calpain 10 function respectively, such as an anti-calpain 10 antibody. Pharmaceutical compositions of the present invention may also have an effective amount of a calpain inhibitor, such as calpeptin, calpain inhibitor 1, calpain inhibitor 2 (N-acetyl-leucyl-leucyl-methioninal, ALLM), or E-64-d. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the substance, the condition of the patient, the type of treatment, the location of the lesion, etc.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other antidiabetic agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains calpain inhibitory compounds alone or in combination with a conventional diabetes therapy agents as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Q. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Generation of a Physical Map and Sequence of the NIDDM1 Region

YAC clones containing sequences of interest were identified by screening the CEPH 'A' and 'B' Human YAC DNA pools (Research Genetics, Huntsville, Ala.) using PCR™ and standard methods. PAC (PAC-6539; Genome Systems, St. Louis, Mo.) and BAC clones (CITB Human BAC DNA Pools—Release IV, Research Genetics) were identified in a similar manner.

DNA was prepared from each clone and tested directly for the presence of each STS. STSs were selected from the Généthon human genetic linkage map and the human transcript map in the interval around D2S125–D2S140 (http://www.ncbi.nlm.nih.gov). Additional STSs were generated by sequencing ends of clones and by sequencing random PstI fragments from the PACs and BACs after cloning in pGEM-4Z. The sequences of these clones were compared to those in the nonredundant GenBank database to identify unmapped ESTs from this region.

The sequence of a 50 kb region including NIDDM1 was assembled from the sequences of restriction enzyme— (EcoRI, BamHI, HindII, PstI and Sau 3 AI) of PCR™-generated fragments of b204E21 and p278G8. This sequence was examined for putative exons using the exon prediction and gene modeling program Grail 2 (http:H/compbio.ornl.gov) and for homology with known sequences in the GenBank database (http://www.ncbi.nlm.nih.gov) using the BLAST suite of programs. The sequence was screened for repeated sequences using the programs Grail 2 and RepeatMasker (Smit AFA, Green P-RepeatMasker at http://ftp.genome.washington.edu/RM/RepeatMasker.html).

The calpain-like protein and G-protein coupled receptor were examined for sequence motifs using the program PROSITE (http://www.ebi.ac.uk). Multiple alignment of amino acid sequences was carried using the CLUSTAL X software package (http://www.igbmc.u-strasbg.fr/BioInfo/clustal). Phylogenetic trees were constructed using the neighbor joining method based on the number of amino acid substitutions. Bootstrap tests were performed using a random number generator and number of bootstrap trials of 1,000 and 10,000, respectively. The tree was drawn using the TREEVIEW package (http://taxonomy.zoology.gla.ac.uk/rod/treeview).

RNA Expression Studies

Calpain 10 and GPR35 cDNA fragments were labeled by random priming and hybridized to Human RNA Master and Multiple Tissue Northern (MTN™) Blots (Clontech, Palo Alto, Calif.). Membranes were washed under high-stringency conditions (55° and 0.1×SSC and 0.1% SDS) before exposure to X-ray film. The human calpain 10 probe was a 2,484 bp fragment containing the entire coding region and 41 and 427 nucleotides of 5'- and 3'-untranslated region, respectively, and the probe for GPR35 was a 1,558 bp fragment that included the entire 309 amino acid coding region and 464 and 167 nucleotides of 5'- and 3'-untranslated region, respectively. The tissue distribution of mouse calpain 10 was determined by hybridization of a mouse cDNA probe encoding entire coding region to a mouse MTN™ blot.

cDNA Cloning

Human calpain 10 cDNA sequences were obtained by sequencing EST yg33d10 (IMAGE Consortium, Research Genetics), vector-primer and primer-primer amplification of various human cDNA libraries, and 5'- and 3'-RACE. The 3'-RACE was carried out using human pancreas Marathon-Ready™ cDNA (Clontech). Vector-primer amplification of a heart 5'-stretch cDNA library (Clontech) identified a clone having 65 nucleotides upstream of the putative ATG codon. Efforts to obtain additional 5'-untranslated sequence were unsuccessful possibly because of the GC-rich character of the sequence. The sequence of mouse calpain 10 cDNA was obtained in a similar manner including 5'-RACE using liver, heart and skeletal muscle RNA. The sequence of human GPR35 cDNA was obtained as described for human calpain 10 including 5'- and 3'-RACE.

Identification of SNPs

SNPs were identified by resequencing ESTs, STSs and a 50 kb segment in ten affected individuals, eight from families in which NIDDM1 was likely to be segregating and two from families in which variation at NIDDM1 was unlikely to contribute to the development of type 2 diabetes. Only ten subjects were examined because the inventors were primarily interested in identifying SNPs with relatively high frequency. Once a SNP was identified, it was typed by direct sequencing or PCR™-RFLP in 100 additional patients thus giving the inventors information on one affected subject from each of 110 families from the original genome-wide screen (including the 10 individuals used for the original identification of the SNP) and in 112 randomly ascertained Mexican American controls. All patients and controls were from Starr County, Texas, and surrounding area.

Association Studies

The strategy to identify linkage disequilibrium within the NIDDM1 region was based on the comparison of allele and haplotype frequencies at SNPs in 110 patients and 112 random controls. Initial analyses were conducted on allele frequencies, using a chi-square test to assess the significance of differences between patients and controls. Additional analyses were conducted by comparing the estimates of frequencies of haplotypes composed of successive SNPs in patients and controls.

A likelihood ratio test was calculated with significance assessed through simulation studies using random permutation of genotypes within the patient and control groups. The rationale for considering haplotype frequency differences was that the inventors might be able to detect linkage disequilibrium across a region defined by successive SNPs even if they could not detect linkage disequilibrium via the association tests at the individual SNPs. Since the 110 patients were from the original families used in the genome-wide screen for type 2 diabetes genes, the inventors had considerable additional information on the probability that these individuals actually derived susceptibility from NIDDM1, thereby allowing the inventors to conduct analyses to confirm the consistency of any findings.

Positive findings were followed up by making further comparisons between the control group and 1) a subset of patients from families providing strong evidence for linkage to NIDDM1 (NPL>0.7, n=37) and 2) a smaller subset of patients from families with strong evidence for linkage to the NIDDM1 region of chromosome 2 and the CYP19 region of chromosome 15 (NPL>0.7 at both, n=20). The inventors had the expectation that any allele or haplotype frequency differences between the overall patient group and controls that reflected actual linkage disequilibrium between the haplotype or allele and NIDDM1 should be even stronger in comparisons of the controls with subsets of patients most likely to have the variation at NIDDM1. This strategy was designed to maximize the ability to detect disequilibrium by looking for it at both the level of the allele and the haplotype, but minimize the potential for misleading false positive results.

Linkage Studies—110 Families

Once UCSNP-43 was identified through the association studies as a possible candidate for being NIDDM1, the inventors examined the evidence for linkage (using all chromosome 2 markers genotyped for the original genome scan) in subsets of the data defined on the basis of the genotype at UCSNP-43 in the single member of the 110 families in which an individual was typed.

Linkage analyses were conducted using a version of GENEHUNTER (Kruglyak et al., 1996) modified to allow assessment of the evidence for linkage that is not conservative in the presence of missing data Kong and Cox, 1997), and all analyses were conducted using the S(pairs) scoring function. These analyses were facilitated by development of a recent extension that allows weights for families to be specified. Thus, families in which no member was typed were assigned weight 0 and similarly, families in which the single typed member had a non-associated genotype were assigned weight 0, while families in which the single typed individual had an associated genotype were assigned weight 1.

The primary calculations are done but once, and then alternative weighting files can be used to determine the evidence for linkage in any subset of the data defined on the basis of SNP genotypes in the 110 individuals routinely typed. The inventors compared results of linkage analyses in subsets of the families defined on the basis of genotypes in the 110 typed individuals at UCSNP-43 with results of linkage analyses in subset of the families defined on the basis of genotypes at the other SNPs. Dominant (1,1+1,2 vs 2,2) and recessive (1,1 vs 1,2+2,2) models were considered for each SNP.

Linkage Studies—All Families

Linkage analyses for SNPs typed in all members of the 170 sibships were carried out after first constructing data sets reflecting dominant and recessive transmission of the associated allele. The use of a pair-based scoring function allows the inventors to calculate the evidence for linkage in completely non-overlapping sets of affected sib pairs that are defined on the basis of their genotypes at SNPs. For each model (dominant and recessive), two data sets were constructed, each of which contained the full genotypic information at chromosome 2 markers used to determine the probability distribution of the complete inheritance vector for each family included in that data set but which included completely non-overlapping sets of affected sib pairs. For example, if allele 1 is the associated allele, the recessive data set for allele 1 was comprised of all families with at least two sibs with the 1,1 genotype. All individuals within these families were included in analyses for obtaining information on the complete inheritance vectors, but only those individuals who were 1,1 homozygotes were considered as affected and therefore only those individuals contributed to the assessment of the evidence for linkage. A complementary group of sibships was constructed from all sibships not included in the "associated" group. In addition, sibships in which at least two but not all members had the at-risk genotype were included in this group.

In constructing the complementary set of affected sib pairs, it is sometimes necessary to duplicate sibships in order to obtain the necessary complementarity without sacrificing any of the information. Thus, when a sibship contains multiple sibs with and multiple sibs without the associated genotypes, it is duplicated (number of duplicates=number of sibs with associated genotypes), and affection status of sibs are adjusted so that no pair is included more than once but all pairs are present in one or the other of the complementary data sets.

Example 2

Physical Mapping of NIDDM1

Initial linkage studies localized NIDDM1 to the distal long arm of chromosome 2 near D2S125. Further genotyping and refinement of the genetic map placed NIDDM1 near D25140 at 263.56 cM in the genetic map (Broman et al., 1998) with a 1-lod confidence interval from 257–269 cM, a 12 cM interval which included D25125 (260.63 cM). Although the 1-lod confidence interval for NIDDM1 was quite large and thus made the identification of NIDDM1 a rather formidable task, subsequent genetic studies identified a region on chromosome 15 near CYP19 which interacts with NIDDM1 to affect susceptibility to type 2 diabetes.

Taking the evidence for linkage at chromosome 15 into account in linkage analyses on the NIDDM1 region of chromosome 2 increased the lod score from 4.0 to 7.3 and decreased the 1-lod confidence interval from 12 to 7 cM (i.e. from 259–266 cM). The inventors focused the inventors' search for NIDDM1 in the 7 cM interval from 259–266 cM, knowing that the inventors might have to extend the inventors' search if the inventors did not find the variation responsible for NIDDM1 in this region.

A combined YAC, BAC and PAC contig (FIG. 2A, FIG. 2B and FIG. 2C) centered on D2S140 was generated using information in public databases and by screening YAC, BAC and PAC libraries with markers from the Genethon human genetic linkage map and STSs for known genes and ESTs that had been localized to the region of NIDDM1. Additional STSs were generated from the ends of PAC and BAC clones and by random sequencing of fragments of these clones. This contig was defined by 73 STSs and spanned a region of about 1.7 Mb. It included the 5.1 cM interval between D2S2285 and D2S140 (258.49–263.56 cM) and a smaller interval of unknown genetic size telomeric to D2S140 (FIG. 2A, FIG. 2B and FIG. 2C). Thus, this contig may encompass most if not all of the region defined by the 1-lod confidence interval (259–266 cM) based on the interaction between NIDDM1 and the locus on chromosome 15 near CYP19. Fluorescent in situ hybridization with PAC 179G9 placed this contig in chromosome band 2q37.3, the most distal band of the long arm of chromosome 2.

Comparison of the sizes of the genetic and physical maps indicated that the NIDDM1 region was characterized by higher than average recombination so that 1 cM corresponded to about 240 kb, a result consistent the telomeric location. This result was advantageous in that it reduced the size of the interval over which the search for NIDDM1 would be conducted. However, it also represented a disadvantage in that the levels of linkage disequilibrium would likely be decreased over this region.

The physical map enabled the inventors to begin a systematic search for NIDDM1. The inventors focused the inventors' attention initially on the expressed sequences localized in the physical map in this region identified during the course of assembling the contig. These included several known genes (GPC1, ATSV, AGXT, HDLBP, NEDD5, sds22-like, serine/threonine kinase-like), none of which were obvious candidates, and 15 ESTs (FIG. 2A, FIG. 2B and FIG. 2C). SNPs were identified in these expressed sequences by resequencing STSs in a panel of ten unrelated diabetic subjects, eight of whom were selected because they were members of sibships in which NIDDM1 was likely to be segregating and two were from sibships in which variation at NIDDM1was unlikely to contribute to the development of type 2 diabetes. Only ten subjects were examined because the inventors were primarily interested in identifying SNPs with relatively high frequency. Once a SNP was identified, it was typed by direct sequencing or PCR-RFLP in 100 additional patients thus giving the inventors information on one affected subject from each of 110 families from the original genome-wide screen (including the 10 individuals used for the original identification of the SNP) and in 112 random controls.

Example 3

Identification of NIDDM1

Allele and haplotype frequencies were compared among controls (n=112), patients (patients all, n=110), the subgroup of patients from families most likely to have susceptibility at NIDDM1 (patients NIDDM1, n=37) and subsequently with a smaller subgroup from families most likely to have susceptibility at NIDDM1 and the interacting locus near CYP19 on chromosome 15 (patients NIDDM1/CYP29, n=20), once this interaction became evident. The expectation was that the degree of association would increase as the inventors examined those patients with type 2 diabetes due to variation at NIDDM1 or to the interaction between NIDDM1 and the unknown diabetes susceptibility locus on chromosome 15. The inventors began the search for NIDDM1 by first typing SNPs that the inventors had identified in known genes and ESTs and comparing the frequencies of alleles and estimated haplotypes formed between adjacent markers (most haplotypes were between two adjacent markers although occasionally three were examined if the STS contained multiple SNPs) (FIG. 2A, FIG. 2B and FIG. 2C, Table 5).

The results of these comparisons were used to focus the inventors' search including the identification of new SNPs found by shotgun sequencing of fragments of the BAC and PAC clones in ten unrelated diabetic subjects.

The control and various patient groups did not differ in allele frequencies at any of the first 15 SNPs examined (UCSNP-1-to-15, FIG. 2A, FIG. 2B and FIG. 2C; Table 5). However, comparison of estimated haplotype frequencies between controls and patients (patients all) revealed a significant difference (P<0.05) in the frequencies of haplotypes comprised of the three markers UCSNP-1, -2 and -15. Moreover, the haplotype frequencies estimated from the subset of patients from families with evidence for linkage at NIDDM1 were also significantly different (P<0.01) from those estimated in controls even though the sample size was reduced by 50%. Therefore, the region between UCSNP-15 and UCSNP-1 -to-4, a region of about 250 kb, became the primary focus of the inventors' search although the inventors also continued to type SNPs outside this region in order to reinforce the inventors' conclusions with regard to the location of NIDDM1. The inventors observed significant allele frequency differences between patients and controls at UCSNP-18 (P=0.019) which was distal to the inventors' primary region of interest; however, allele frequencies did not differ between controls and either subgroup of patients suggesting that NIDDM1 was unlikely to be in the region of this marker (Table 5).

TABLE 5

Linkage and linkage disequilibrium in the NIDDM1 region

| | | q (1) | | | Dominant | | Recessive | | Recessive | | Dominant | |
|---|---|---|---|---|---|---|---|---|---|---|---|---|
| | | | Patients | Patients | Patients | (1,1 + 1,2) | | (2,2) | | (1,1) | | (1,2 + 2,2) | |
| SNP | Nucleotide | Controls | All | NIDDM1 | NIDDM1/CYP19 | Lod | N | Lod | N | Lod | N | Lod | N |
| 15 | | 0.77 | 0.70 | 0.70 | 0.71 | 1.70 | 89 | 1.90 | 12 | 1.19 | 56 | 2.16 | 45 |
| 20 | | 0.85 | 0.83 | 0.86 | 0.89 | | 99 | | 3 | 3.45 | 72 | 0.42 | 30 |
| 57 | 5801 | | 0.91 | 0.91 | 0.93 | | 97 | | 2 | 3.40 | 84 | 0.19 | 15 |
| 46 | 6154 | 0.95 | 1.00[b] | 0.99 | 0.98 | | 102 | | 0 | | 101 | | 1 |
| 45 | 6168 | 0.94 | 0.91 | 0.88 | 0.85 | | 101 | | 1 | 1.68 | 86 | 2.26 | 16 |
| | | | | | | | 169 | | 1 | 3.34 | 134 | 1.41 | 36 |
| 44 | 6214 | 0.94 | 0.90 | 0.91 | 0.93 | | 102 | | 0 | 2.45 | 82 | 1.02 | 20 |
| | | | | | | | 169 | | 1 | 3.70 | 130 | 0.30 | 40 |
| 43 | 6225 | 0.75[a] | 0.80 | 0.88[b] | 0.95[a] | | 95 | | 7 | 4.15 | 67 | 0.08 | 35 |
| | | | | | | 4.03 | 153 | 0.00 | 17 | 10.19 | 84 | 0.00 | 86 |
| 56 | 6788 | | 0.60 | 0.58 | 0.55 | 1.06 | 81 | 3.06 | 16 | 1.30 | 36 | 1.49 | 61 |
| 59 | 7391 | | 0.58 | 0.52 | 0.50 | 0.55 | 74 | 3.46 | 17 | 0.68 | 33 | 1.71 | 58 |
| 60 | 8895 | | 0.91 | 0.91 | 0.92 | | 92 | | 1 | 2.82 | 79 | 0.31 | 14 |
| 19 | 9291 | 0.57 | 0.58 | 0.50 | 0.50 | 0.99 | 83 | 3.63 | 17 | 0.75 | 34 | 2.67 | 66 |
| 48 | 12470 | 0.53 | 0.58 | 0.53 | 0.50 | 0.87 | 80 | 3.78 | 18 | 0.81 | 35 | 2.31 | 63 |
| 58 | 13123 | | 0.98 | 0.98 | 0.97 | | 95 | | 0 | | 91 | | 4 |
| 47 | 14911 | 0.88 | 0.90 | 0.89 | 0.90 | | 102 | | 2 | 2.87 | 87 | 0.56 | 17 |
| 30 | 16483 | 0.54 | 0.58 | 0.53 | 0.50 | 3.68 | 85 | 1.04 | 18 | 1.04 | 35 | 2.18 | 68 |
| 32 | 31043 | 0.78 | 0.72 | 0.68 | 0.63 | | 96 | | 7 | 1.22 | 51 | 2.09 | 52 |
| 42 | 33450 | 0.54 | 0.58 | 0.57 | 0.58 | 2.88 | 77 | 0.18 | 25 | 2.87 | 31 | 1.14 | 71 |
| 55 | 35721 | 0.55 | 0.64[a] | 0.66 | 0.72 | 2.96 | 88 | 0.23 | 13 | 2.72 | 40 | 0.81 | 61 |
| 54 | 35760 | 0.73 | 0.68 | 0.61 | 0.58 | | 94 | | 8 | 1.13 | 45 | 1.68 | 57 |
| 26 | 36827 | 0.92 | 0.83[b] | 0.80[b] | 0.88 | | 99 | | 4 | 1.65 | 72 | 1.52 | 31 |
| 25 | 36876 | 0.50 | 0.61[a] | 0.54 | 0.52 | 2.73 | 91 | 0.86 | 12 | 0.28 | 36 | 4.00 | 67 |
| 23 | 37157 | 0.85 | 0.76[a] | 0.70[b] | 0.73 | | 97 | | 6 | 1.02 | 60 | 2.55 | 43 |
| 22 | 37170 | 0.61 | 0.49[b] | 0.47[a] | 0.50 | 3.40 | 76 | 0.38 | 27 | 0.06 | 26 | 3.89 | 77 |
| | | | | | | 2.70 | 129 | 1.68 | 39 | 0.11 | 44 | 5.00 | 124 |

TABLE 5-continued

Linkage and linkage disequilibrium in the NIDDM1 region

| | | | q (1) | | | Dominant | | Recessive | | Recessive | | Dominant | |
| | | | | | | (1,1 + 1,2) | | (2,2) | | (1,1) | | (1,2 + 2,2) | |
| | | Patients | Patients | Patients | | | | | | | | | |
| SNP | Nucleotide | Controls | All | NIDDM1 | NIDDM1/CYP19 | Lod | N | Lod | N | Lod | N | Lod | N |
|---|---|---|---|---|---|---|---|---|---|---|---|---|---|
| 39 | 38805 | 0.65 | 0.67 | 0.67 | 0.71 | | 94 | | 9 | 1.53 | 41 | 149 | 62 |
| 41 | 41144 | 0.69 | 0.76 | 0.73 | 0.71 | | 94 | | 5 | 1.28 | 60 | 1.91 | 39 |
| 36 | 42880 | 0.86 | 0.84 | 0.89 | 0.89 | | 97 | | 4 | 2.92 | 71 | 0.54 | 30 |
| 37 | 42906 | 0.62 | 0.49 | 0.57 | 0.55 | 3.22 | 75 | 0.14 | 26 | 2.17 | 22 | 1.36 | 79 |
| 49 | 43314 | 0.84 | 0.83 | 0.89 | 0.89 | | 97 | | 5 | 3.04 | 71 | 0.58 | 31 |
| 50 | 43320 | 0.97 | 0.98 | 0.99 | 0.97 | | 102 | | 0 | | 98 | | 4 |
| 51 | 43330 | 0.97 | 0.93[a] | 0.91 | 0.87[b] | | 102 | | 0 | 1.79 | 88 | 1.35 | 14 |
| 52 | 43604 | 0.61 | 0.51[a] | 0.58 | 0.61 | 3.09 | 78 | 0.10 | 25 | 2.71 | 26 | 1.15 | 77 |
| 53 | 43967 | 0.90 | 0.85 | 0.85 | 0.92 | | 102 | | 1 | 1.95 | 72 | 1.18 | 31 |
| 38 | 44524 | 0.62 | 0.50[b] | 0.54 | 0.53 | 3.02 | 77 | 0.20 | 24 | 2.16 | 22 | 1.43 | 79 |
| 40 | 44666 | 0.73 | 0.82[a] | 0.79 | 0.76 | | 99 | | 2 | 1.72 | 70 | 1.34 | 31 |
| 35 | 47005 | 0.72 | 0.81[a] | 0.78 | 0.74 | | 100 | | 2 | 1.62 | 68 | 1.58 | 34 |
| 34 | | 0.82 | 0.77 | 0.76 | 0.78 | | 97 | | 5 | 2.21 | 59 | 1.04 | 43 |
| 31 | | 0.86 | 0.83 | 0.86 | 0.87 | | 99 | | 3 | 2.51 | 70 | 1.05 | 32 |
| 33 | | 0.85 | 0.83 | 0.88 | 0.86 | | 96 | | 3 | 2.80 | 74 | 0.85 | 25 |
| 27 | | 0.86 | 0.86 | 0.88 | 0.87 | | 101 | | 0 | 3.74 | 71 | 0.31 | 30 |
| 28 | | 0.56 | 0.61 | 0.56 | 0.55 | 2.71 | 85 | 0.50 | 16 | 0.39 | 37 | 4.23 | 64 |
| | | | | | | 2.50 | 112 | 1.86 | 58 | 1.10 | 72 | 3.80 | 98 |
| 29 | | 0.77 | 0.85[a] | 0.82 | 0.79 | | 99 | | 2 | 1.35 | 71 | 1.93 | 30 |
| 1 | | 0.55 | 0.60 | 0.61 | 0.66 | 3.07 | 89 | 0.22 | 14 | 0.98 | 34 | 2.15 | 69 |
| 2 | | 0.83 | 0.85 | 0.88 | 0.87 | | 102 | | 1 | 2.30 | 76 | 0.74 | 27 |
| 3 | | 0.52 | 0.53 | 0.50 | 0.55 | 2.17 | 84 | 1.46 | 19 | 0.48 | 24 | 2.44 | 79 |
| 4 | | 0.99 | 1.00 | 0.99 | 1.00 | | 103 | | 0 | | 102 | | 1 |
| 21 | | 0.45 | 0.44 | 0.53 | 0.55 | 2.12 | 79 | 0.89 | 24 | 1.70 | 35 | 1.39 | 68 |
| 17 | | 0.75 | 0.73 | 0.74 | 0.71 | | 96 | | 5 | 1.70 | 50 | 1.34 | 51 |
| 18 | | 0.84 | 0.75[a] | 0.74 | 0.74 | | 93 | | 7 | 1.14 | 57 | 2.65 | 43 |
| 13 | | 0.56 | 0.55 | 0.55 | 0.56 | 1.74 | 82 | 0.49 | 18 | 0.87 | 28 | 1.46 | 72 |
| 14 | | 0.59 | 0.65 | 0.67 | 0.68 | 2.55 | 84 | 0.42 | 15 | 1.99 | 43 | 1.34 | 56 |
| 10 | | 0.73 | 0.70 | 0.73 | 0.74 | | 89 | | 8 | 2.43 | 46 | 1.15 | 51 |
| 11 | | 0.76 | 0.74 | 0.76 | 0.74 | | 91 | | 6 | 2.20 | 52 | 1.04 | 45 |
| 12 | | 0.74 | 0.74 | 0.76 | 0.76 | | 97 | | 6 | 2.38 | 54 | 1.14 | |
| 5 | | 0.93 | 0.92 | 0.90 | 0.92 | | 102 | | 0 | 2.53 | 85 | 1.01 | 1 |
| 16 | | 0.84 | 0.78 | 0.80 | 0.81 | | 93 | | 6 | 1.69 | 63 | 1.37 | 36 |
| 8 | | 0.88 | 0.86 | 0.83 | 0.88 | | 101 | | 1 | 2.62 | 75 | 0.73 | 27 |
| 9 | | 0.75 | 0.74 | 0.71 | 0.73 | | 96 | | 6 | 1.26 | 53 | 2.32 | 49 |
| 6 | | 0.95 | 0.97 | 0.99 | 0.97 | | 103 | | 0 | | 96 | | 7 |
| 7 | | 0.76 | 0.75 | 0.75 | 0.79 | | 98 | | 5 | 1.49 | 55 | 1.76 | 48 |

Figure 2:
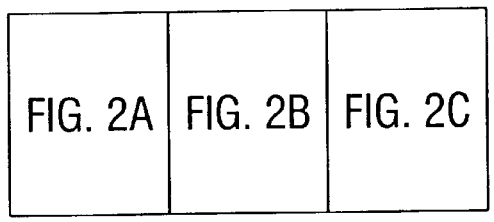
FIG. 2A, FIG. 2B and FIG. 2C. Physical map of the NIDDM1 region of chromosome 2. This contig spans a region of about 1.7 Mb (259–266 cM of the genetic map) and is defined by 73 STSs. SNPs (designated UCSNP-1-to-21) are numbered in the order in which they were identified and studied.
Figure 2A:
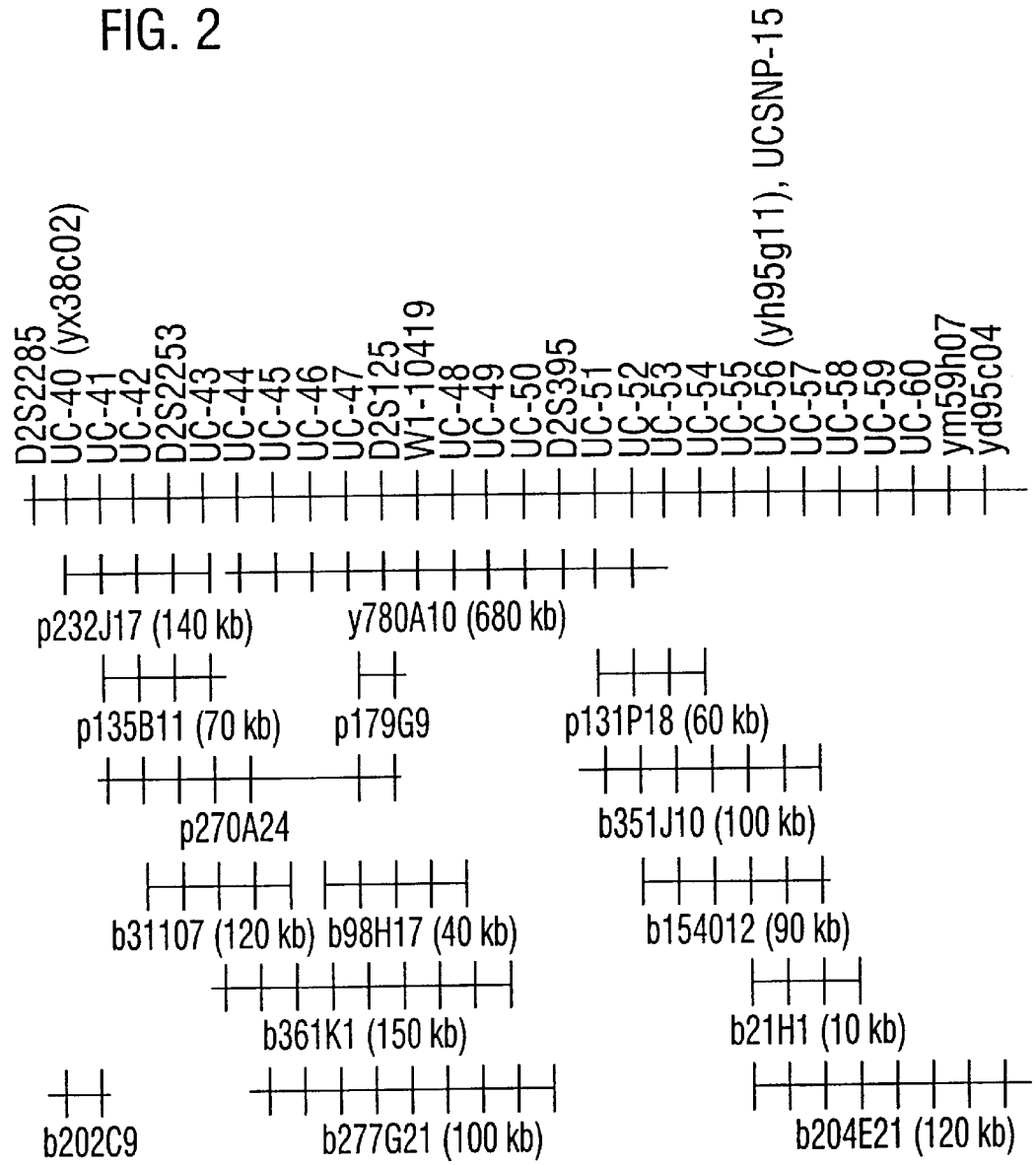
Figure 2B:
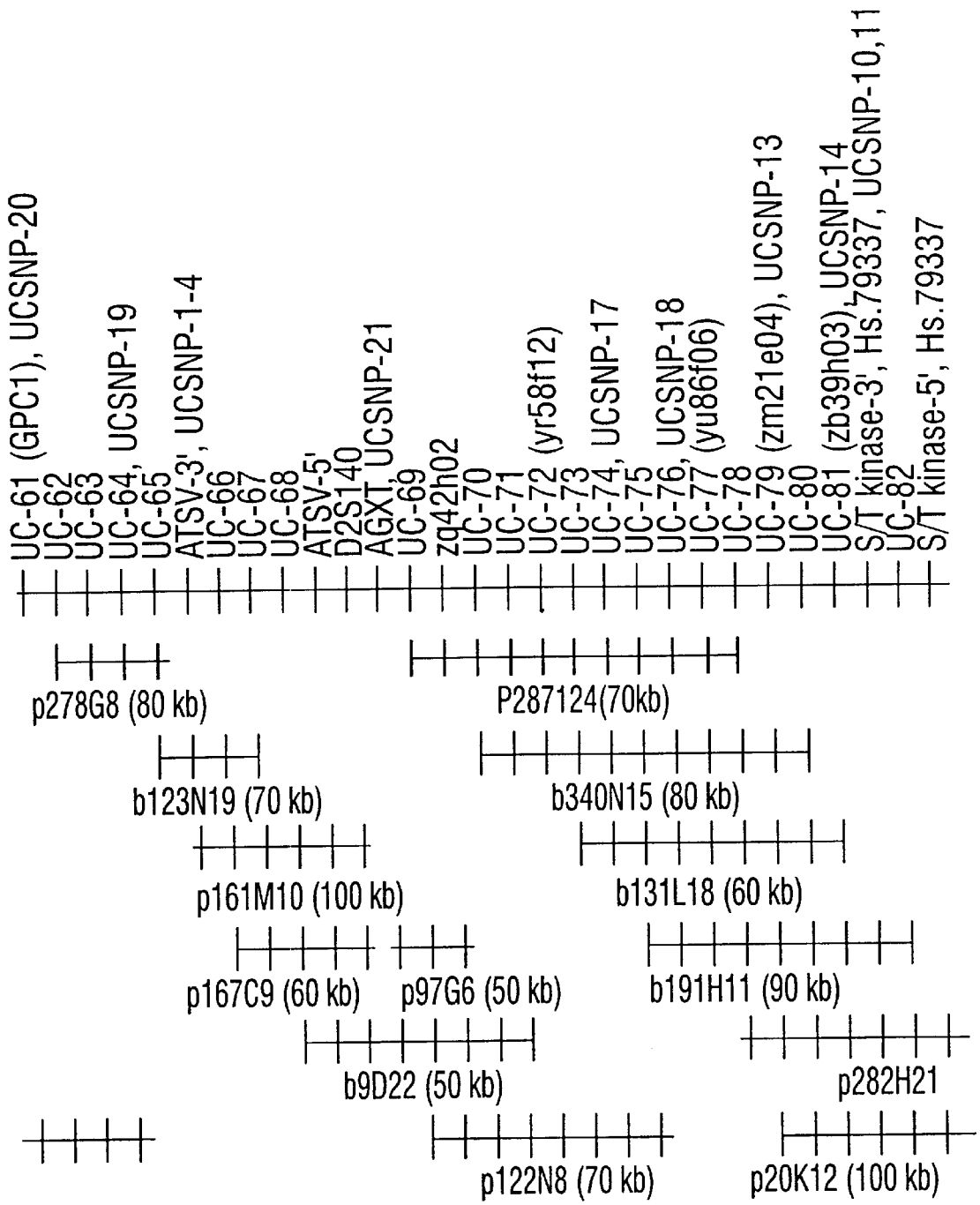
Figure 2C:
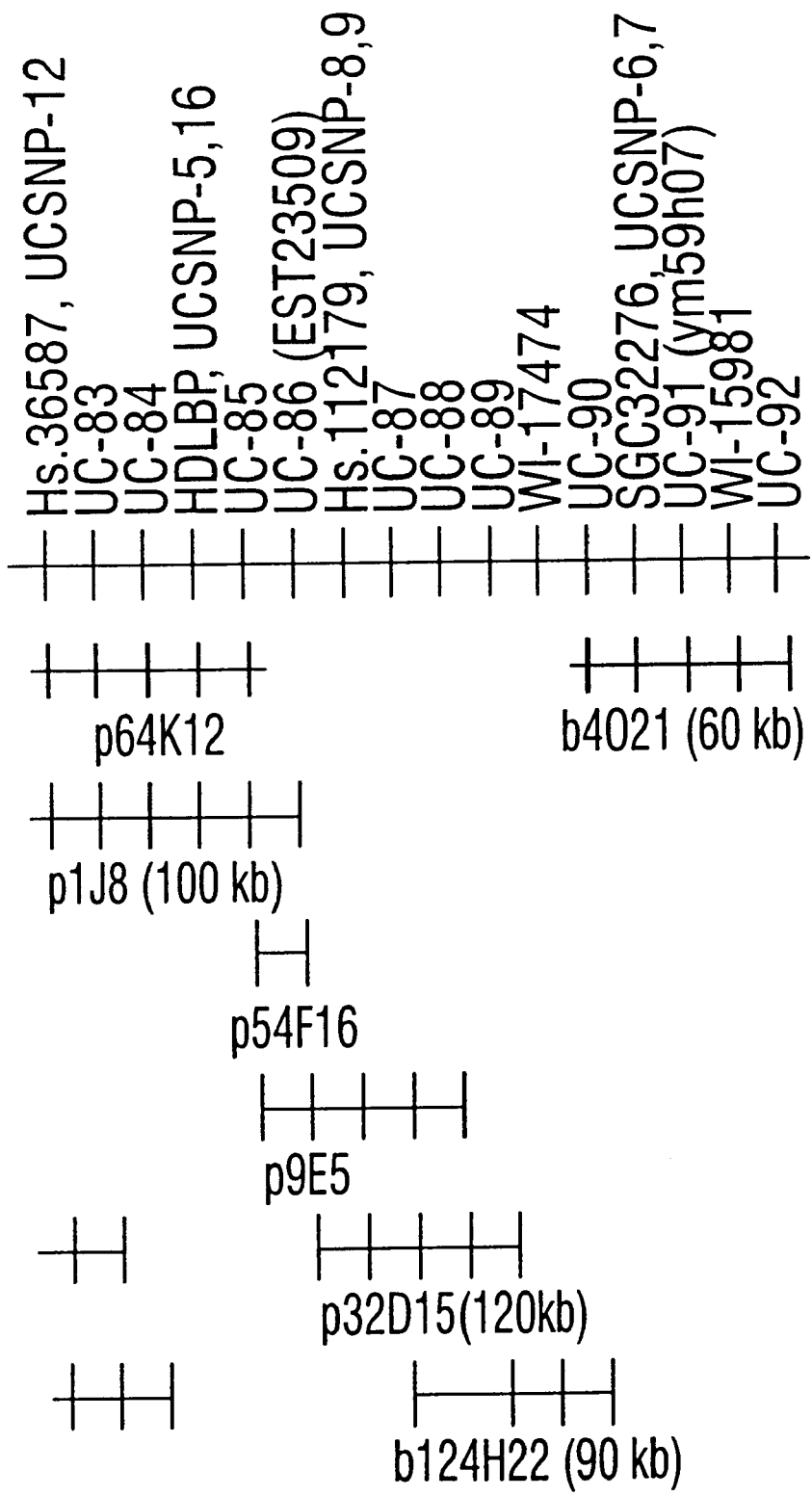
Figure 3:
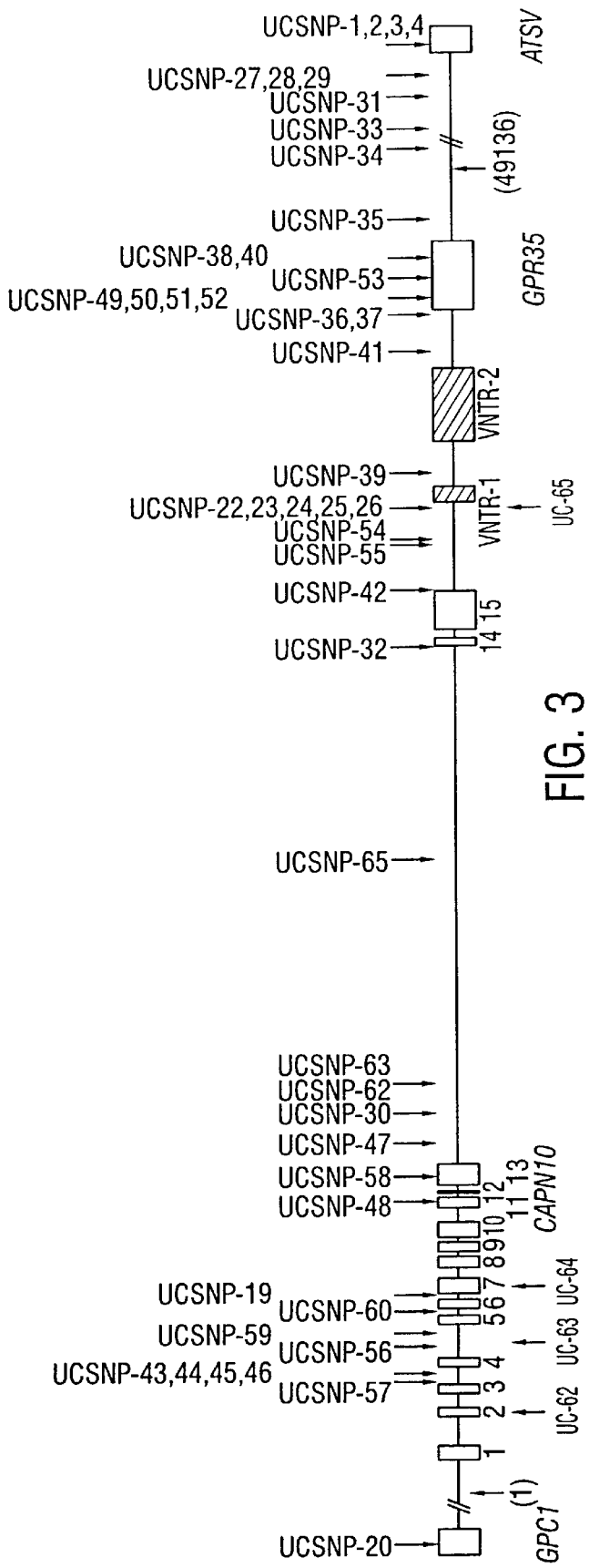
FIG. 3. Organization of the NIDDM1 region. The 49,136 bp region (SEQ ID NO:1) that was sequenced is shown. The intron-exon organizations of the two genes found in the sequenced interval, CAPN10 and GPR35 are indicated. The locations of the SNPs typed in patients and controls are shown. The absolute distances between the two flanking genes GPC1 and ATSV and this region have not been determined precisely but are estimated to be <100 kb. VNTR-2 is estimated to be ~4 kb and consist of 100 or more copies of an imperfect 29 bp repeat (range 26–39 bp), the consensus sequence of which is TCTCAGAGTGGGGT-GAGGCTGTGATGGGG (SEQ ID NO:29). This region is unstable and was deleted in the BAC and PAC clones that the inventors examined with b123N19 having only 12 repeats and p278G8 having only 3. VNTR-2 could not by typed by PCR™. VNTR-1 is a perfect 19 bp repeat that could be typed by PCR™.

The SNPs are listed in order from centromere to qter as shown in FIGS. 2 and 3. The nucleotide indicates the location of the SNP in the 49,136 bp region (SEQ ID NO:1) that was sequenced. The frequency, q(1), of the most common allele of each SNP is shown and is indicated for controls and for all the patients as well as for the subgroups of patients showing evidence of linkage with NIDDM1 and with NIDDM1 and CYP19. N indicates the number of families included in calculating the lod score determined under each model. Each SNP was typed in 112 controls and 110 patients except for SNPs 56–60 that were only typed in the patients. SNPs 45, 43, 22 and 28 were also typed in all affected sib pairs used for the linkage studies - 170 sibships and 330 affected sib pairs, and these results are shown in the line below.
[a]$P < 0.05$, indicated patient group vs. controls
[b]$P < 0.0167$, indicated patient group vs. controls (i.e., significant after correction for thre comparisons)

A cluster of four SNPs in the interval between UCSNP-15 and UCSNP-1 -to-4 showed a significant difference in allele frequencies between patients and controls: UCSNP-26, P=0.020; UCSNP-25, P=0.034; UCSNP-23, P=0.020; and UCSNP-22, P=0.0129 (Table 5). As expected because of their proximity to one another, there was strong linkage disequilibrium between these four SNPs. The associated alleles were also present at higher frequency on the haplotypes that lead the inventors to focus on this region in the first instance. The consistency of the findings led the inventors to focus the inventors' attention on the region around UCSNP-22-to-26 and new SNPs flanking this cluster. The results of this continuing search suggested that NIDDM1 was in the interval between UNSNP-20 and the cluster of SNPs, UCSNP-22 -to-26.

At UCSNP-43, the inventors observed a striking increase in the frequency of the common allele in the patient and patient subgroups compared to controls (Table 5, FIG. 3). The increasing frequency of the associated allele at UCSNP-43 from 0.73 in controls to 0.95 in the patient-NIDDM1/CYP19 subgroup raised the possibility that NIDDM1 was transmitted as a high frequency recessive. The inventors therefore examined the evidence for linkage in the subgroups of patients defined by SNP genotypes in the single typed individual. UCSNP-43 generated a lod score of 4.15 in just 67 of 110 sibships in which the single typed patient was homozygous for the common allele. Thus, UCSNP-43 was associated with type 2 diabetes, provided disproportionate evidence for linkage in the families of patients homozygous for the common allele and was the first marker to show compelling evidence for both (Table 5, FIG. 3). UCSNP-43 was then typed in all members of the 170 sibships comprising the primary affected sibpair dataset. Sibships in which all sibs were homozygotes for the common "G" allele accounted for 49% of all sibships and the affected sibpairs from these families accounted for 45% of the 330 affected sib pairs. The multipoint lod score in these families was 10.19. The multipoint lod score in the complement of the data (51% of families and 55% of affected sib pairs) was 0 across the entire 2qter region. Thus, all the evidence for linkage between type 2 diabetes and the NIDDM1 region can be accounted for by homozygosity of the G-allel at UCSNP-43. UCSNP-43 is the prime candidate for being the variation responsible for NIDDM1.

In order to be certain that there were no other SNPs that might provide comparable or even stronger evidence for being NIDDM1, and to be sure that no other variants in the gene containing UCSNP-43 might be alternative NIDDM1 susceptibility alleles, a 50 kb region around this SNP was resequenced in ten patients to identify all the variation in this region. All high frequency SNPs, i.e. allele frequencies between 0.25–0.75, not in complete linkage disequilibrium with a previously typed SNP (the inventors found that SNPs with perfect genotypic correspondence in the ten unrelated patients were invariably in strong linkage disequilibrium with each other) were then typed in at least the 110 patients for comparison with the results obtained with UCSNP-43. In addition, all members of the 170 sibships comprising the primary affected sibpair dataset were typed at SNPs selected for their proximity and strong linkage disequilibrium to UCSNP-43, association with type 2 diabetes or disproportionate evidence for linkage (Table 5). Of the 60 SNPs examined, only UCSNP-43 can adequately account for the linkage of this region with type 2 diabetes.

Some of the polymorphisms studied exhibited a stronger baseline association with type 2 diabetes in the comparison of allele frequencies between cases and controls than does UCSNP-43. However, many of the associations (e.g., UCSNP-38 and -39) become weaker rather than stronger as the inventors consider the subgroups of patients most likely to come from families segregating for NIDDM1, and the evidence for linkage in subsets of families defined on the basis of genotypes (in the single typed member of the family) at these loci is largely proportional to the number of families in the subset. In contrast, the allelic associations at UCSNP-43 became stronger when examined in subgroups of patients most likely to come from families segregating for NIDDM1. Moreover, the evidence for linkage in subsets of families defined by SNP genotype also increased and this increase was disproportionate to the number of families in the subset of the data examined.

Fourteen of the 60 SNPs examined (Table 5) showed nominal evidence for association with type 2 diabetes (i.e. P<0.05) in comparisons of control and patient-all groups. In fact, some were more than 40 kb from NIDDM1/UCSNP-43 which itself did not show evidence for association in a direct comparison of controls and patients-all but was associated in the patient-NIDDM1 and -NIDDM1/CYP19 subgroups. The failure to achieve statistical significance in the patient-all group is due to the high frequency of the associated allele and the relatively small sample size. Thus consideration of only the association data between controls and the patient-all groups would not have provided the identity of NIDDM1. The analyses that addressed the evidence for linkage enabled the inventors to distinguish which polymorphism was NIDDM1.

In addition to typing UCSNP-43 in the primary set of 170 sibships (330 possible affected sibpairs) used in the genome-wide screen for type 2 diabetes genes, the inventors also typed it in a second smaller group of 76 sibships (110 affected sibpairs) that also provided evidence for linkage with markers near NIDDM1. Homozygosity for the common G-allele at UCSNP-43 can account for all of the evidence for linkage originally reported in this sample as well (Table 5).

Example 4

NIDDM1 is a Novel Calpain-like Protease

The analysis of the sequence of the 49,136 bp region (SEQ ID NO:1) around UCSNP-43 revealed two genes, one encoding a novel calpain-like cysteine protease, designated calpain 10 (gene symbol CAPN10) (Saido et al., 1994; Carafoli and Molinari, 1997; Dear et al., 1997) part of which was homologous to the ESTs yg33d10, nf61d12 and yb22d04, and the second, a recently described G-protein coupled receptor GPR35 (O'Dowd et al., 1998), most similar in sequence to the P2Y-family of ATP receptors. No other excellent or good potential coding regions were predicted using Grail 2. The entire 49,136 bp region is found as SEQ ID NO:1.

Figure 4:
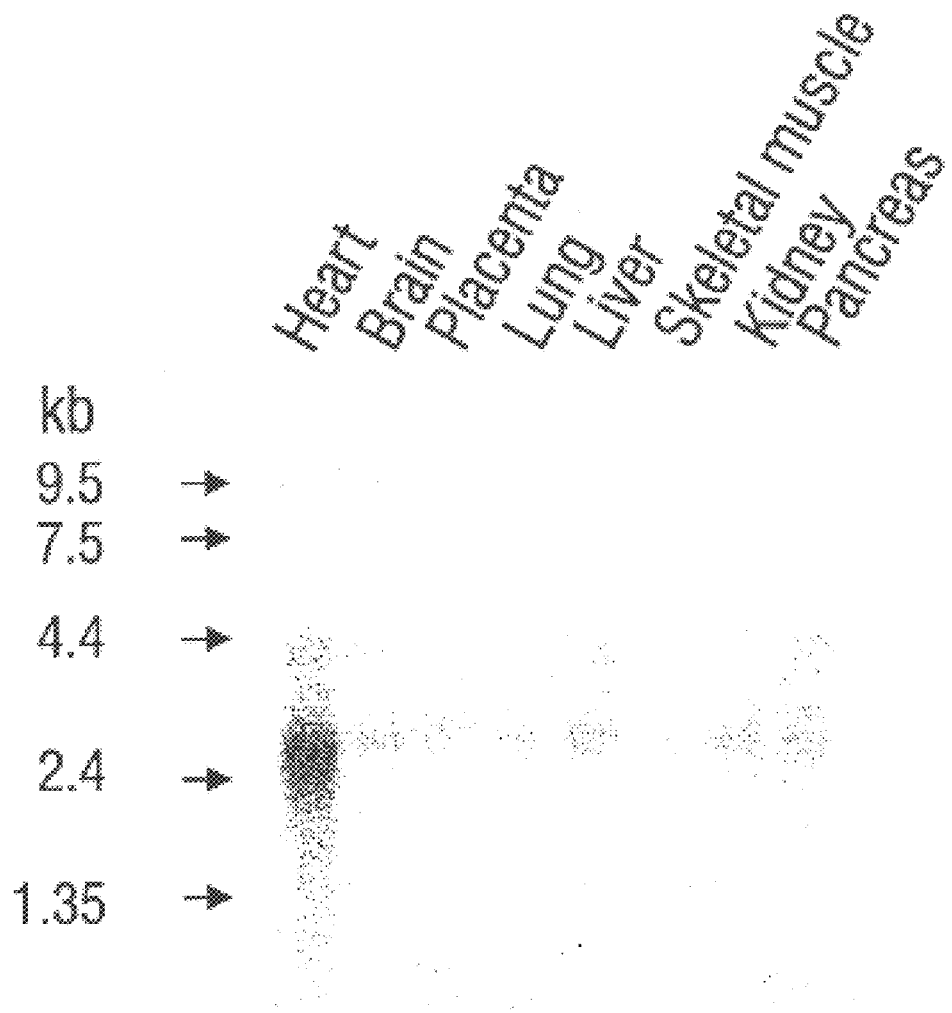
FIG. 4. RNA blot showing expression of calpain 10 mRNA in human tissues. The positions of RNA size markers are shown on the left.
Figure 5E:
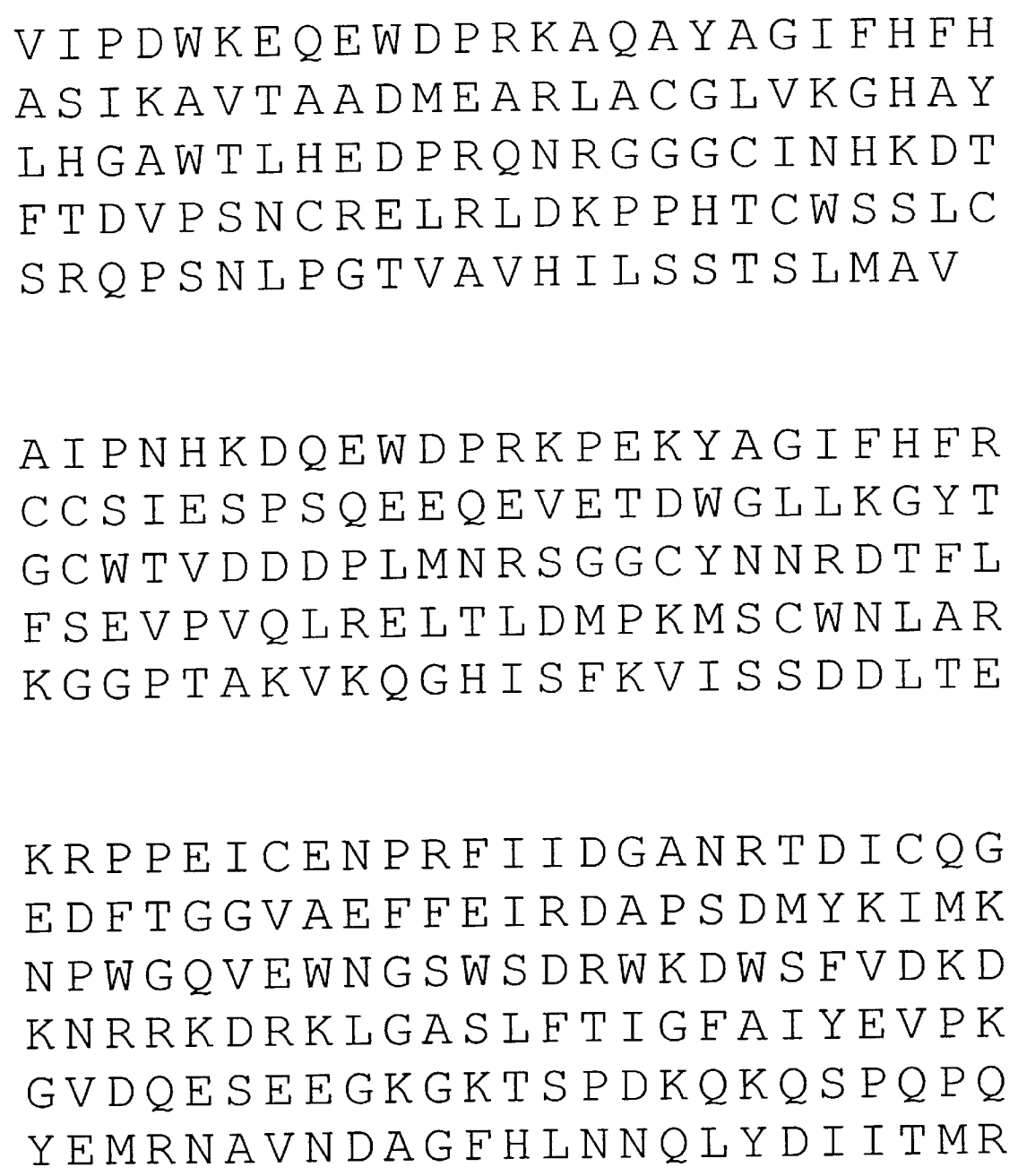

RNA blotting studies showed that calpain 10 mRNA was ubiquitously expressed and the major 2.7 kb transcript could be readily detected in all human adult and fetal tissues examined (FIG. 4). The isolation and characterization of human calpain cDNAs gave a composite sequence of 2,620 nucleotides excluding polyA tract and including 177 nucleotides of putative 5'-untranslated region. This sequence is shown as SEQ ID NO:3. This sequence contains an ORF that encodes a protein of 672 amino acids (SEQ ID NO:2) related in structural organization and sequence with members of the calpain large subunit superfamily (FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M and FIG. 5N). This ORF begins with the second ATG codon (both ATG codons are in an adequate context to be start sites for translation) (Kozak et al., 1996) and is not preceded by an in-frame stop codon.

Conceptual translation beginning at the first ATG predicts the sequence of a protein of 65 amino acids that is unrelated to any in the GenBank data base. Since translation usually begins with the first ATG codon (Kozak et al., 1996), this result suggests that the human calpain 10 cDNA may lack the authentic initiator codon. Using 5'-RACE and other strategies, the inventors were unable to obtain additional 5'-untranslated sequence. Thus, in order to confirm this ORF, the inventors isolated cDNA clones encoding the mouse orthologue since they expected the homology between the human and mouse sequences to be well conserved in the protein coding region and more divergent in the 5'- and 3'-untranslated regions. The 2,511 bp composite mouse calpain 10 cDNA (SEQ ID NO:19) encoded a protein of 666 amino acids (SEQ ID NO:18) having 81.7% identity with the human protein. There is 83.4% identity between the sequences of the predicted coding regions of the mouse and human cDNAs and the homology dissipates outside of these regions. The longest ORF in mouse calpain 10 mRNA begins with the third ATG codon which is preceded upstream by an in-frame stop codon. The first and second ATG are in the same frame and are preceded by a in-frame stop codon. There are stop codons in all three reading frames in the 109 bp upstream of the putative start of translation. The sequence around the first ATG codon is highly divergent between human and mouse and becomes more similar in the region of the second out-of-frame ATG codon. The inventors infer from these results that translation is initiated at the second ATG codon in the human sequence and at the third in the mouse. The implications of the presence of upstream ATG codons for the regulation of expression of calpain 10 are unknown.

The human CAPN10 consists of 15 exons spanning 32 kb (FIG. 3). The analysis of human cDNA clones revealed a complex pattern of alternative splicing generating in addition to the protein of 672 amino acids described above (SEQ ID NO:2), proteins of 544 (SEQ ID NO:4), 517 (SEQ ID NO:6), 513 (SEQ ID NO:8), 444 (SEQ ID NO:10), 274 (SEQ ID NO:12), 139 (SEQ ID NO:14) and 138 amino acids (SEQ ID NO:16), designated calpain 10a to 10h (FIG. 1A, FIG. 1B, FIG. 1C, FIG. 1D, FIG. 1E, FIG. 1F, FIG. 1G and FIG. 1H). RT-PCR® studies suggest that transcripts encoding calpain 10a are the most abundant in the various tissues examined. Calpain 10b, 10c and 10g were readily detectable in many tissues including skeletal muscle and islets, and calpain 10h was present at moderate levels only in islets of the tissues tested. The other forms, calpain 10d to 10f are much less abundant. Studies of mouse calpain 10 expression showed a 2.7 kb transcript that could be detected in all tissues examined. Thus, calpain 10 appears to be ubiquitously expressed in both mouse and human tissues.

The nucleotide variant showing all the evidence for linkage with type 2 diabetes, UCSNP-43, is located in intron 3 of CAPN10 (FIG. 4) 746 bp downstream of the splice donor site and 176 bp upstream of the splice acceptor site. The molecular mechanism by which the G-to-A polymorphism at UCSNP-43 affects susceptibility to type 2 diabetes is unclear. As shown in FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M and FIG. 5N, there is alternative splicing of intron 3. However, the inventors' RT-PCR® studies suggest that this is an relatively rare event and it remains to be determined whether it is influenced by the polymorphism at UCSNP-43. The inventors have also considered the possibility that there is a gene embedded within this intron. Translation of intron 3 in all frames revealed a small ORF in the reverse strand that could encode a protein of 95 amino acids. This protein has no homology with any in the GenBank database and the variant at UCSNP-43 would be a silent mutation. In addition, this ORF is not conserved in the sequence of intron 3 of the mouse gene strongly suggesting that it is not an exon.

There are only three polymorphisms in exons of the CAPN10: exon 11, a silent substitution in codon 620 (UCSNP-48, Table 5); and exon 13, a nucleotide substitution resulting in a Val-to-Ile change in codon 666 (q(1)=0.98) (UCSNP-58); and a polymorphism in the 3'-untranslated region. None of these can account for the evidence of linkage of this region with type 2 diabetes.

In addition to CAPN10, the NIDDM1 interval included the gene encoding a recently identified member of the G-protein coupled receptor superfamily, GPR35 (O'Dowd et al., 1998). The sequence of GPR35 is most similar to that of a putative purinoceptor P2Y$_9$ (34.4% identity) suggesting that ATP or other nucleotide may be its ligand. Hybridization to a RNA Master Blots showed low levels of GPR35 mRNA in all adult and fetal tissues with relatively higher levels in adult lung, small intestine, colon and stomach. In these tissues, there are two major transcripts of 2.4 and 4.4 kb whereas in skeletal muscle there is a single transcript of 9.4 kb. The composite cDNA is 1,875 bp (exclusive of polyA tract, SEQ ID NO:21) and may lack about 400 bp of the 5-untranslated region. It encodes a protein of 309 amino acids (SEQ ID NO:20) having all the features of a G-protein coupled receptor including seven membrane-spanning segments. Translation is predicted to begin at the third ATG codon which is preceded by an in-frame stop codon (the two upstream ATG codons which are in the same reading frame and closely followed by a stop codon are in a poor context to serve as translational start codons). The putative initiation codon is also in a poor context for initiation and translation may start at codon 14 which is in a strong context. The GPR35 cDNA and gene sequences are colinear suggesting that GPR35 gene consists of a single exon. The sequence of the GPR35 gene is also highly polymorphic with six nucleotide substitutions associated with amino acid polymorphisms (including UCSNP-38 and -53), three silent substitutions and three and two polymorphisms in the 5'- (UCSNP-49, -50 and -51) and 3'-untranslated (UCSNP-40) regions of the mRNA, respectively. While there is association of several of these polymorphisms with type 2 diabetes in Mexican Americans, they cannot account for the evidence of linkage (Table 6).

Example 5

Improved Localization of NIDDM1 by Linkage Analyses

A previous genome-wide screen for type 2 diabetes genes in Mexican Americans localized a major susceptibility gene, NIDDM1, to the D2S125-D2S140 region of chromosome 2 (Hanis et al., 1996) (multipoint lod score=4.03). This was the only region in the primary analyses to meet genome-wide criteria for significance. Animal studies have suggested that type 2 diabetes may result, at least in part, from epistatic interactions between genes (Terauchi et al., 1997; Brunning et al., 1997). In addition, some alleles at genes associated with monogenic forms of diabetes such as maturity onset diabetes of the young (MODY, a genetically heterogeneous form of diabetes characterized by autosomal dominant inheritance, onset usually before age 25 and pancreatic β-cell dysfunction) may cause a form of diabetes that resembles type 2 diabetes (Mahtani et al., 1996; Iwasaki et al.; 1997).

The inventors examined the evidence for statistical interactions between NIDDM1 and the ten other autosomal regions providing nominal evidence for linkage (p<0.05) in the study by Hanis et al. (1996) as well as five regions containing genes assorted ninth MODY (Table 6). Two regions, CYP19 on chromosome 15, and the hepatocyte nuclear factor (HNF)-1α/MODY3 gene on chromosome 12, showed significant correlations between their NPL scores and NPL scores at NIDDM1 even after Bonferroni correction for the number of correlations examined. The methods and results related to these studies are described in further detail below.

TABLE 6

Correlations between NPL Scores at NIDDM1 and Autosomal Regions Nominally Significant in Genome-Wide Screen of type 2 Diabetes and Five Loci Associated with MODY

| Region | Correction | Corrected P-value | Baseline LOD | NIDDM1-Weighted LOD |
|---|---|---|---|---|
| CYP19 | 0.288 | $2.1 \times 10^{-3}$ | 1.27 | 4.00 (Weight$_{0-1}$) |
| D7S502 | 0.180 | 0.29 | 0.76 | 1.31 (Weight$_{0-1}$) |
| D3S3054 | 0.098 | ns | 0.81 | 0.42 (Weight$_{0-1}$) |
| D2S377 | 0.085 | ns | 1.28 | 1.50 (Weight$_{0-1}$) |
| D15S104 | 0.066 | ns | 0.93 | 1.20 (Weight$_{0-1}$) |
| D3S2452 | 0.031 | ns | 1.24 | 0.81 (Weight$_{0-1}$) |
| D2S441 | 0.027 | ns | 0.78 | 0.50 (Weight$_{0-1}$) |
| D12S379 | -0.012 | ns | 0.68 | 0.30 (Weight$_{1-0}$) |
| D11S1314 | -0.059 | ns | 0.78 | 0.71 (Weight$_{0-1}$) |
| D17S1298 | -0.172 | 0.39 | 0.73 | 1.21 (Weight$_{1-0}$) |
| GCK | 0.124 | ns | 0.01 | 0.26 (Weight$_{0-1}$) |
| HNF-1α | -0.228 | 0.04 | 0.01 | 1.03 (Weight$_{1-0}$) |
| HNF-1β | 0.010 | ns | 0.00 | 0.00 (Weight$_{0-1}$) |

TABLE 6-continued

Correlations between NPL Scores at NIDDM1 and Autosomal Regions Nominally Significant in Genome-Wide Screen of type 2 Diabetes and Five Loci Associated with MODY

| Region | Correction | Corrected P-value | Baseline LOD | NIDDM1-Weighted LOD |
|---|---|---|---|---|
| HNF-4α | 0.003 | ns | 0.38 | 0.35 (Weight$_{1-0}$) |
| IPF1 | −0.187 | 0.24 | 0.32 | 1.11 (Weight$_{1-0}$) |

*P-values corrected by multiplying the nominal P-value by the number of correlations examined (15), and numerical values are given only for those loci in which the uncorrected P-values were nominally significant (P < 0.05). The marker used for HNF-1α was GATA32A10, for HNF-1β was D17S1788, for HNF-4α was ADA, and for IPF1 was D13S221.

Methods

Genome scan data on 524 autosomal markers genotyped in 424 individuals from 170 Mexican American sibships originally described in Hanis et al. (1996) were used for the analyses described here. A region near D2S140 provided strong evidence for linkage to type 2 diabetes in Mexican Americans (NIDDM1, lod=4.03, P<8×10$^{-6}$) NPL scores from this region were used in calculating correlations with each of the other ten autosomal regions providing nominally significant (P<0.05, MLS>0.59) evidence for linkage. Correlations were also calculated between the NPL scores at NIDDM1 and five regions from which MODY genes have been characterized (GCK (Frogel et al., 1993), HNF-1α (Yamagata, 1996a), HNF-1β (Horikawa et al., 1997), HNF-4α (Yamagata, 1996b) and IPF1 (Stoffers et al., 1997).

Analyses in which the evidence for linkage at NIDDM1 was used to weight the contribution from families in linkage analyses on these 15 regions were also conducted. In the weight$_{0-1}$, family weighting, families were assigned weight 0 if their NPL score at NIDDM1, (D2S140, the location providing the strongest evidence for linkage in the NIDDM1 region) was 0 or negative and weight 1 if their NPL score at NIDDM1 was positive. In the weight$_{0-1}$, family weighting, families were assigned weight 1 if their NPL score at NIDDM1 was negative and weight 0 if their NPL score at NIDDM1 was 0 or positive. In the weight$_{PROP}$ family weighting, the weight for families with positive NPL scores was calculated as NPL/NPL$_{max}$ where NPL$_{max}$ was the maximum NPL score observed in any family, and the weight for families with negative NPL scores was 0.

Simulation studies were used to assess the significance of the increase in lod score at CYP19 using the weights$_{0-1}$ family weighting with respect to the evidence for linkage at NIDDM1. At D2S140 there were 95 families with positive NPL scores and 75 families with 0 or negative NPL scores. Simulations based on the weight$_{0-1}$, or weight$_{1-0}$ family weighing can be rapidly conducted using the extension which allows families to be weighted individually. The basic GENEHUNTER analysis need be conducted only once on the actual data (in this case, from chromosome 15), and then many replicate weighting files can be generated randomly (in this example, 95 randomly chosen families are given weight and the remaining 75 families are given weight 0) and used to calculate the final lod scores.

The software described in this manuscript is distributed as GENEHUNTER-PLUS (version 2.0 or later) and is available via anonymous ftp at galton.uchicago.edu on the /pub/kong directory. The allele-sharing method which is used is described in Kong and Cox (1997) and version 2.0 introduces an option to provide a family-specific weight in the lod score computation.

Results

Figure 7A:
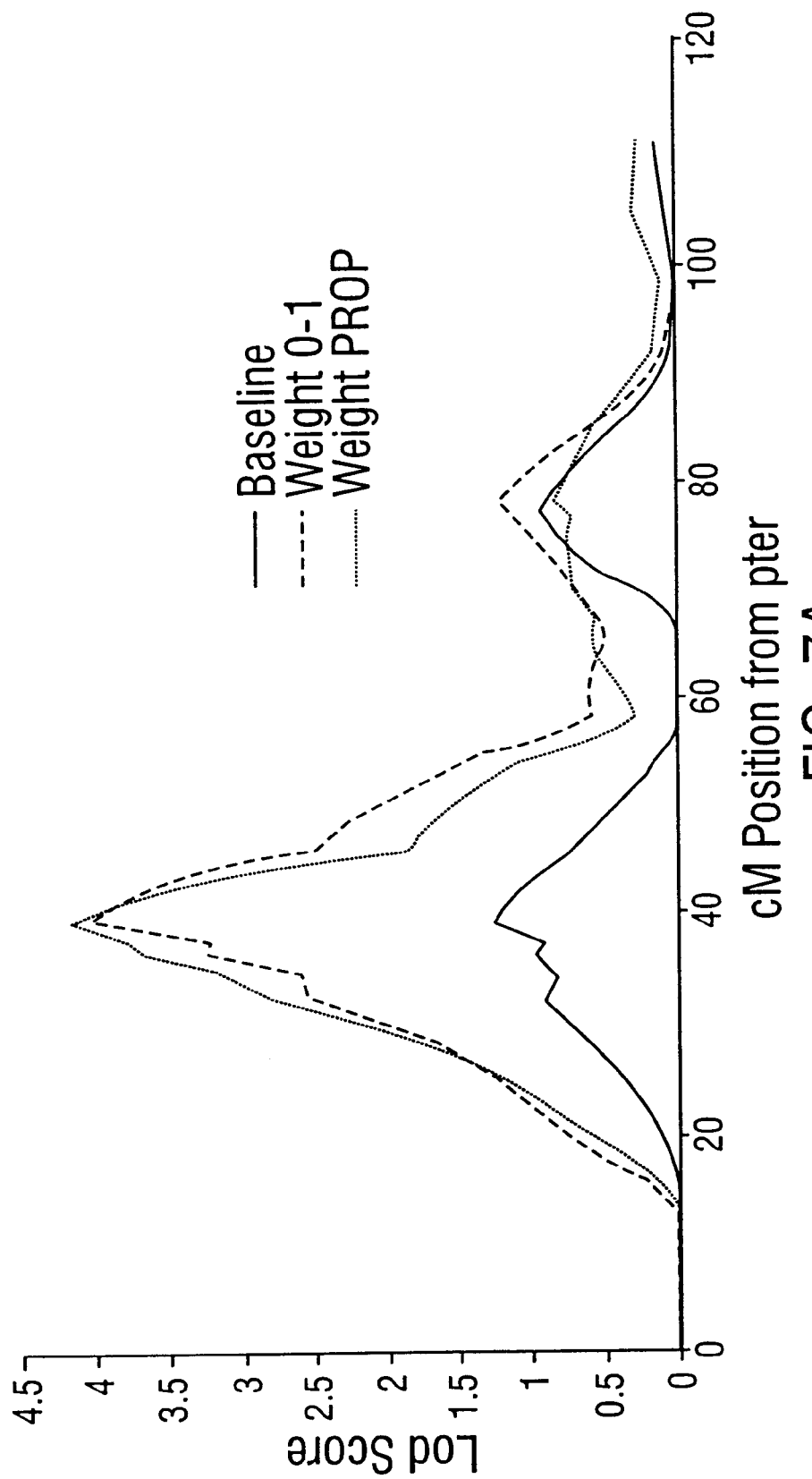
FIG. 7A and FIG. 7B.
Figure 7B:
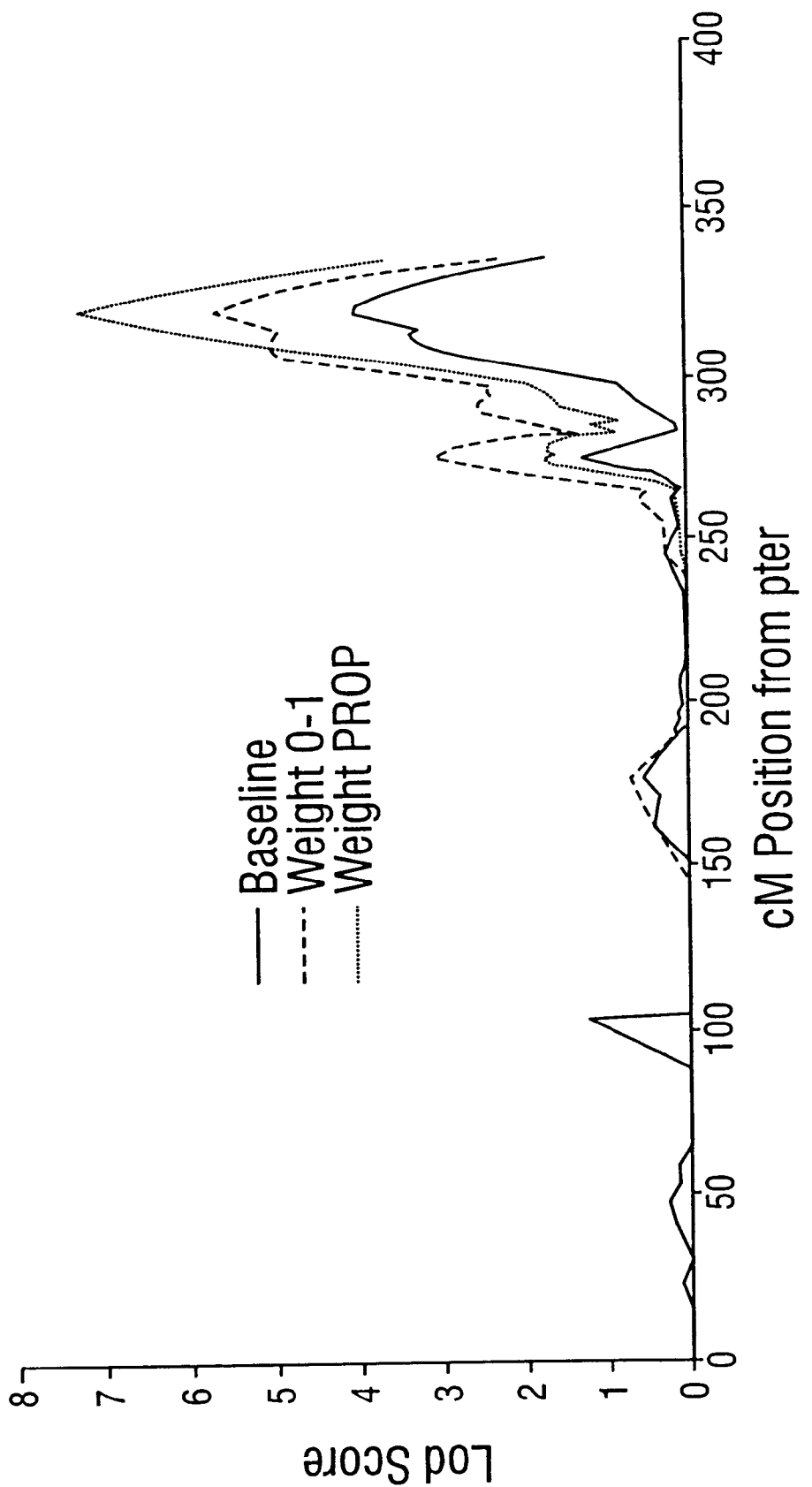

The lod in the CYP19 region was 1.3 in baseline analysis but increased to 4.0 when the families were weighted by their evidence for linkage at NIDDM1 using weight$_{0-1}$, and to 4.1 when families were weighted by their evidence for linkage using weighing FIG. 7A). Note that the more distal region of chromosome 15 with similar baseline evidence for linkage does not show a comparable increase in lod when the evidence for linkage at NIDDM1 is taken into account. However, the lod score at NIDDM1 rises from 4.0 in the baseline analyses to 5.6 when families were weighted by their evidence for linkage at CYP19 using weight$_{0-1}$ asset to 7.3 using weight$_{PROP}$ (FIG. 7B). In simulations conducted to determine the significance of the increase in the lod at CYP19 from 1.3 to >4.0, the inventors found that none of 10,000 replicates from a simulation in which 95 families (the number of families in these data and positive NPL scores at NIDDM1) were randomly chosen and analyzed for the actual 15 data had a lod score as large as 4.0, although 4 (of 10.000) yielded lods between 3.5 and 4.0. Thus, a reasonable estimate of the nominal significance of the increase in lod from 1.3 to 4.0 based on simulation is 0.0001), or 0.0015 corrected for the number of regions examined. The conservative $\chi^2$ test described above would be calculated as 2 log(10)(4.0−1.3)=12.4, giving a P-value of 0.0004. The P-value obtained in this way is indeed comparable to the P-values obtained from the correlation test and the simulations, but is more modest (conservative) because the inventors have not actually maximized the evidence for linkage over a family-specific weights (for example, the lod score for weight$_{PROP}$ is 4.1).

The CYP19 region of chromosome 15 was the only location besides NIDDM1 to be replicated (P<0.05) in a smaller, independent sample of Mexican American families (Hanis et al., 1996). This, as well as the evidence for statistical interaction between these regions, suggests that in collections of Mexican American families similar in size to that in the original genome scan, the evidence for linkage in analyses of chromosome 15 might sometimes be more prominent than that for NIDDM1, and that in many such collections, the signals from both regions might be comparable and only modest unless the interaction is properly taken into account. Thus, it is possible that some of the difficulties recognized in replicating results obtained in genome scans for complex disorders (Suarez et al., 1994) might be alleviated by conducting analyses to identify potential interactions. Finally, the improvement in localization offered by linkage analyses which allow for the contributions of multiple susceptibility loci may be critical to the successful positional cloning of genes for complex disorders.

Example 6

The Presence of NIDDM1 is Associated with Increased Risk for the Development of Type 2 Diabetes in a Predisposed Population In order to determine whether evidence that the presence of NIDDM1 is associated with increased risk for the development of type 2 diabetes in a predisposed population could be detected, 106 Mexican American subjects from Starr County, Tex., were selected, each of whom had at least two first degree relatives with type 2 diabetes but none of whom had a personal history of previously diagnosed diabetes.

Each subject underwent a standard oral glucose tolerance test. This is a standard test used to measure the response of islet cells to a glucose bolus and is currently recognized as the test in most wide-spread use for diabetes detection. After an overnight fast, blood samples for the measurement of glucose and insulin were obtained before (−15 min and 0 min) and after (30, 60, 90 and 120 min) the ingestion of 75 g glucose orally. The subjects were classified into two groups. The first was homozygous for the G allele at UCSNP-43 (GG n=57) and the second was either homozygous for the A-allele (AA, n=15) or heterozygous (GA, n=34) at UCSNP-43 (combined AA/GA n=49). The results of this study are shown in Table 7 below which depicts average glucose and insulin concentrations in both groups of subjects before and after glucose ingestion.

TABLE 7

Average glucose and insulin concentrations in homozygous and heterozygous individuals

|  | Genotype | −15 mins. | 0 min. | 30 min. | 60 min. | 90 min. | 120 min. |
|---|---|---|---|---|---|---|---|
| Glucose (mg/dl) | GG | 103 | 103 | 181 | 193 | 175 | 147 |
| Glucose (mg/dl) | AA/GA | 101 | 101 | 180 | 187 | 160 | 133 |
| Insulin (µU/ml) | GG | 15.8 | 17.2 | 97.8 | 144.9 | 138.3 | 120.9 |
| Insulin (µU/ml) | AA/GA | 16.4 | 17 | 123.6 | 157.2 | 130.5 | 108.9 |

Fasting glucose concentrations were within the normal range (<110 mg/dl) in both groups. Following glucose ingestion glucose concentrations increased as expected. In the AA/GA subjects, the average glucose concentration had fallen to below 140 mg/dl by 120 min. This is the threshold value that defines normal glucose tolerance. However, in the GG subjects, glucose concentrations remained elevated, and at 120 min had fallen to only 147 mg/dl a level defined as impaired glucose tolerance by WHO criteria.

Insulin concentrations were elevated in both groups after the overnight fast, i.e., at −15 and 0 min. In normal insulin sensitive individuals the fasting insulin concentration is usually around 7 µU/ml and rarely exceeds 10 µU/ml. The presence of fasting hyperinsulinemia suggests the presence of insulin resistance. After glucose ingestion, there was a rapid increase in insulin levels in the AA/GA subjects, and this brisk insulin secretory response is presumably responsible for the normal response in glucose concentrations. In the GG subjects however the insulin secretory response to glucose ingestion is significantly reduced at 30 min. Thus, at 30 min after glucose ingestion, the increment in insulin levels over baseline values in the subjects with the GG genotype was significantly lower than in the subjects with the AA/GA genotype (82.0 vs. 107.3 uU/ml, P<0.043). At 90 and 120 min, insulin concentrations were higher in the subjects with the GG genotype, presumably as a response to the continued elevation in plasma glucose concentrations.

Thus, Mexican American subjects possessing a family history of diabetes who do not have diabetes themselves but who are homozygous GG at UCSNP-43 demonstrate a number of abnormalities on oral glucose tolerance testing. First, these individuals demonstrate fasting hyperinsulinemia suggesting the presence of insulin resistance. Second, these individuals have elevated average plasma glucose concentrations 120 min after ingestion of 75 g glucose orally to within a range that defines impaired glucose tolerance a condition widely recognized to be associated with a significant increased risk for the subsequent development of type 2 diabetes. Further, these individuals characteristically have reduced insulin concentrations 30 min after ingestion of 75 g glucose. Reduced insulin concentrations in response to the oral ingestion of nutrients is one of the hallmarks of type 2 diabetes. A similar defect is therefore present in subjects homozygous GG at UCSNP-43 even before the onset of diabetes.

The G-allele at UCSNP-43 has a frequency of 0.75 in Mexican Americans, 0.71 in non-Hispanic whites of German ancestry, 0.90 in African Americans and 0.94 in Asians (Japanese). Its high frequency in African Americans and Asians implies that 81% and 88%, respectively, of the nondiabetic subjects in these two populations have the at-risk genotype at UCSNP-43 and are thus at increased risk of diabetes due to variation at this locus. This may account, at least in part, for the higher frequency of type 2 diabetes in these populations (Diabetes in American, 2nd Edition. NIH Publication No. 95–1468, 1995).

Thus, the combination of pathophysiological defects (insulin resistance, impaired glucose tolerance and defective insulin secretion) in subjects who are homozygous GG at UCSNP-43 prior to the onset of overt type 2 diabetes provides strong supporting evidence for an important role of this gene as a primary cause of type 2 diabetes.

Example 7

Studies to Elucidate Linkage of Homozygous GG at UCSNP-43 to Type 2 Diabetes in Additional Populations and to Determine Whether This Mutation Leads to Similar Physiological Effects in Other Populations The homozygous GG at UCSNP-43 is a common genotype in populations other than the Mexican American subjects studied above. In view of the studies above, it is now possible to determine whether: (1) the linkage between this genotype and type 2 diabetes extends across other populations, and (2) similar physiological effects of this genotype are seen in other populations. Studies are underway to assess these two questions.

The inventors are presently genotyping persons from populations, other than the Starr County, Tex., Mexican American population, who have relatives with type 2 diabetes to determine whether they are homozygous GG, homozygous AA, or heterozygous at the relevant location in UCSNP-43. Once these genotypes have been determined, appropriate subjects from each will be subjected to the glucose tolerance test described in Example 6 and perhaps other appropriate tests. The goals of this testing will be to allow one to determine whether the GG genotype impairs the ability of β-cells to increase insulin in response to glucose in these patients, whether insulin resistance and/or other defects of glucose metabolism are present, and whether there is a linkage found between this genotype and type 2 diabetes in this population.

Example 8

Regulation of Insulin Secretion and Insulin Action by Calpains

As demonstrated above, a substantial part of the genetic risk for diabetes in a Mexican American cohort is due to a common polymorphism in the intron of a gene encoding a novel calpain-like cysteine protease, termed calpain 10. Calpains are ubiquitously expressed cysteine proteases that are thought to act as intracellular processing enzymes with significant substrate specificity that allows them to regulate a variety of cellular functions including intracellular signaling, proliferation and differentaiation (Mellgren, 1997; Carafoli and Molinari, 1998; Murray et al., 1997; Ueda et al., 1998). Although they have been implicated in the regulation of a variety of normal cellular functions and in the pathophysiology of various disease states (Richard et al., 1995; Chen and Fernandez, 1998; Blomgren et al, 1995; Yokota et al, 1995), a role for calpains in glucose homeostasis has not been defined.

In this Example, the inventors show that inhibition of calpain activity with calpain inhibitor 2 (N-Ac-Leu-Leu-methioninal, ALLM), a cell permiable calpain inhibitor that inhibits calpains I and II, reduces insulin secretory responses to glucose and other insulin secretagogues in isolated mouse islets and the isolated perfused mouse pancreas. These effects are dose dependent and reversible, are mediated, in part, by reduced responses in intracellular $Ca^{2+}$, and do not involve a reduction in glucose metabolism in the pancreatic islet. In contrast to calpain inhibitor 2, E-64-d, a cell permeable thiol protease inhibitor, resulted in an increase in glucose induced insulin secretion. In addition, ALLM reduced insulin mediated glucose transport in isolated rat muscle strips and isolated adipocytes and incorporation of glucose to glycogen in muscle. These results therefore document a previously unappreciated role for calpain sesitive pathways in mediating insulin secretion in the pancreatic β cell and insulin action in muscle and fat. Since inhibition of calpain activity can reproduce the two defects that are most characteristic of type 2 diabetes, i.e. insulin resistance and reduced insulin secretory responses to glucose and other secretagogues, these results indicate that alterations in calpain activity play an important role in the pathophysiology of type 2 diabetes.

Methods

Animals. Studies were performed on islets obtained from non-fasted 9–13 wk old C57BL/6J mice (Jackson, Bar Harbor, Me.) and adipocytes and soleus muscles isolated from 8–12 wk old normal Wistar rats (Harlan Sprague-Dawley, Indianapolis, Ind.). The calpain inhibitors used were ALLM (N-Ac-Leu-Leu-methioninal, Calbiochem-Novabiochem, Inc, San Diego, Calif.) and E-64-d (ethyl (+)-(2S,3S)-3-[(S)-3-Methyl-1-(3-methylbutylcarbamoyl) butyl-carbamoyl]-2-oxiranecarboxylate, Matreya Inc., Pleasant Gap, Pa.). The calpain inhibitors were dissolved in DMSO. GLP-1 (7-36 amide) was from Peninsula Laboratory (Belmont, Calif.).

Static incubation of isolated pancreatic islets. Isolation of mouse pancreatic islets was accomplished using collagenase digestion as previously described (Pontoglio et al., 1998). Following overnight incubation in RPMI 1640 medium (11.6 mM glucose), islets were exposed to varying concentrations of inhibitors in the same medium for 4 hr at 37° C. Islets were then pre-incubated in KRB containing 2 mM glucose and similar concentrations of inhibitors for 60 min at 37° C. Triplicate groups of 5 islets were then incubated in borosilicate tubes containing 1 ml of KRB with the same concentration of inhibitor and various insulin secretagogues for one hour in a moving water bath at 37° C. The reaction was stopped by placing the tubes on ice and an aliquot of the buffer was removed for measurement of insulin levels. Control studies, in which the incubation mixture contained vehicle (0.1% DMSO) only, were performed using aliquots of the same batch of islets.

Insulin secretion from perifused islets. Insulin secretion from perifused islets was measured using a modification of a previously described protocol (Pontoglio et al., 1998; Sreenan et al., 1998).

Measurement of islet $[Ca^{2+}]_i$, and NAD(P)H. Islet $[Ca^{2+}]_i$ and NAD(P)H were measured as previously described (Pontoglio et al., 1998; Dukes et al., 1998).

Isolation of pancreatic β-cells. Single β-cells were obtained from isolated islets dispersed by gentle trituration (120 strokes through a 200 μl pipette tip) in $Ca^{2+}$ and $Mg^{2+}$-free PBS containing 10% trypsin. Cells were plated on glass coverslips and maintained in culture in RPMI containing 11.6 mM glucose for 48–96 hr.

Patch-clamp electrophysiology. Calcium current measurements were obtained in the whole-cell patch-clamp configuration. Calcium currents were activated by step depolarizations to either +10 or +20 mV for either 20 ms or 100 ms, from HP=−80 mV. All current records are corrected for leak and capacitance. The data was filtered at 2 kHz and then sampled every 100 μs. Pipette resistances were 1.5–2.5 MΩ. Series resistance was partially compensated (~80%) using the compensation circuit of the Axopatch-1C amplifier.

Cells were incubated for 3–4 hr in RPMI at 37° C. in either 0.1% DMSO (control) or 100 μM ALLM and then transferred for a further 1–2 hr to KRB containing similar concentrations of DMSO or ALLM. For recording, cells were bathed in a solution containing (in mM): 145 NaCl, 2 KCl, 1 $MgCl_2$, 2 glucose, 10 HEPES, 10 $CaCl_2$, pH 7.3 (adjusted with NaOH) and either DMSO or ALLM. After establishing the whole cell configuration the bath solution was exchanged for a TEA based recording medium which contained (in mM): 155 TEA-Cl, 2 glucose, 10 HEPES, 10 $CaCl_2$ and 100 nM TTX, pH=7.3 (adjusted with TEA OH) and either DMSO or ALLM. The intracellular pipette solution consisted of (in mM): 110 CsCl, 4 $MgCl_2$, 20 HEPES, 10 EGTA, 0.35 GTP, 4 ATP, 14 creatine phosphate, pH=7.3 (adjusted with CsOH).

Capacitance recordings. Capacitance measurements were made with the phase-tracking technique in which a 60 mV peak-to-peak sine wave was superimposed on a holding potential of −80 mV as previously described. Conductance and capacitance values were continuously generated and recorded. The whole-cell capacitance was canceled with the slow capacitance compensation; unbalancing the slow capacitance compensation by 100 fF provided the capacitance calibration signal used to calculate changes in membrane capacitance. The sinusoidal voltage template was interrupted to deliver depolarizations to a cell. Beta cells were stimulated with a train of ten step depolarizations to +20 mV (HP=−80 mV). Each step depolarization lasted 150 ms and was separated by 400 ms interpulse duration. Capacitance measurements were carried out in the perforated whole-cell configuration. The data were collected at a 500 μsec sampling rate and filtered at 5 kHz. Recordings with series resistance >20 MΩ were discarded. Series resistance compensation was applied in all recordings.

The recording solution for the capacitance measurements contained (in mM): 130 NaCl, 2 glucose, 10 Na-HEPES, 1 $MgCl_2$, 2 KCl, and 5 $CaCl_2$, pH 7.3 with NaOH. The pipette solution contained (in mM): 135 Cs-glutamate, 10 Na-HEPES, 9.5 NaCl, 0.5 TEACl, and 0.5 $CaCl_2$, pH7.3 with CsOH. The pipettes were backfilled with an identical solution to which amphotericin B (final concentration of 0.5 mg/ml) was added and then sonicated. The amphotericin B stock solution (125 mg/ml) was kept frozen at −20° C. and used for one week. ALLM pre-treatment was as described above (see patch-clamp electrophysiology section). All electrophysiological recordings were carried out at room temperature (22–24° C.)

Measurement of calpain activity in mouse pancreatic islets. Islets were loaded with the fluorogenic, membrane-permeant calpain substrate t-butoxycarbonyl-Leu-Met-7-amino-4-chloromethylcoumarin (Boc-Leu-Met-CMAC (10

μM), Molecular Probes, Eugene, Oreg.) in Hepes (10 mM) buffered KRB with 2 mM glucose, and the fluorescence emitted from the proteolytic product in islets was measured with a bandpass combination between 400 and 500 nm following excitation by light at 340 nM. Studies were performed after a 4 hr incubation in the presence either of 200 μM ALLM, 200 μM E-64-d or vehicle.

Glucose utilization and oxidation rates. Glucose utilization and oxidation rates were measured as previously described (Dukes et al., 1998; Zhou et al., 1996) in mouse islets cultured as described above in the presence or absence of calpain inhibitors.

Glycogen synthesis rates in skeletal muscle. Measurement of glycogen synthesis rates was performed using a modification of a previously described protocol (Burant et al., 1984) in soleus muscle strips isolated from non-fasted normal Wistar rats and incubated in KRB/5 mM glucose/10 mM HEPES, 0.2% BSA in the presence and absence of 100 μM ALLM, 200 μM E-64-d or vehicle.

2-Deoxyglucose uptake into skeletal muscle and adipose tissue. 2-deoxyglucose (2-DOG) uptake by isolated strips of soleus muscle from normal Wistar rats was measured using a modification of a previously described protocol (Burant et al., 1984). Following a 30 min pre-incubation in KRB containing no glucose, 2 mM pyruvate, 10 mM HEPES, 0.2% BSA and ALLM or E-64-d, the muscle strips were transferred to identical medium containing 0.1 mM 2-deoxy-[2,6-$^3$H]glucose (0.5 μCi/ml) and 0.1 mM [$^{14}$C]-sucrose (0.2 μCi/ml) and incubated for another 30 min at 37° C. Muscles were then extracted and 2-DOG uptake calculated as previously described (Burant et al., 1984).

Adipocytes were isolated from epididymal fat pads of 3 month old male Wistar rats as described previously (Robdell, 1964) with the following modification: fat pads were minced to 1–2 mm pieces and incubated for ~25 min at 37° C. with collagenase I (1 mg/ml, Worthington Biochemicals, Lakewood, N.J.) in KRB containing 10 mM Hepes (pH 7.4), 0.2% BSA and 2 mM sodium pyruvate. The cell suspension was filtered through a nylon mesh (134 μM, Spectrum Lab., Laguna Hills, Calif.) washed three times by floating and allowed to rest for 45 min in the KRB. For the measurement of basal and insulin-stimulated transport of glucose, aliquots of 200 μl of adipocytes (2×10$^5$ cells/ml) were incubated for 120 min at 37° C. in KRB with different concentrations of insulin either with or without 100 M ALLM or E-64-d. Then another 50 μl of KRB containing 5 mM 2-DOG (final concentration 1 mM), 0.5 μCi of 2-deoxy-[2,6-$^3$H]glucose was added and cells were incubated for a further 5 min at 25° C. The transport was stopped by adding cytochalasin B (final concentration 50 μM) and cells were spun through 250 μl of dinonyl phthalate oil (Fisher Scientific, Pittsburgh, Pa.). Cells were then transferred to scintillation vials for counting.

Assay methods. Insulin concentrations were measured by a double antibody radioimmunoassay using a rat insulin standard. The intra-assay coefficient of variation for this technique is 7%. All samples were assayed in duplicate.

Statistical analysis. Results are expressed as mean (SEM. In each experimental protocol summary measures of the experimental response e.g. areas under the insulin, NAD (P)H or [Ca$^{2+}$]$_i$ response curves were compared in the presence and absence of calpain inhibitor. The statistical significance of differences in the presence and absence of the inhibitor was assessed at the 5% level using the non-paired student's t-test, paired t-test, ANOVA or Wilcoxon rank sum test where appropriate.

Results

Figure 8A:
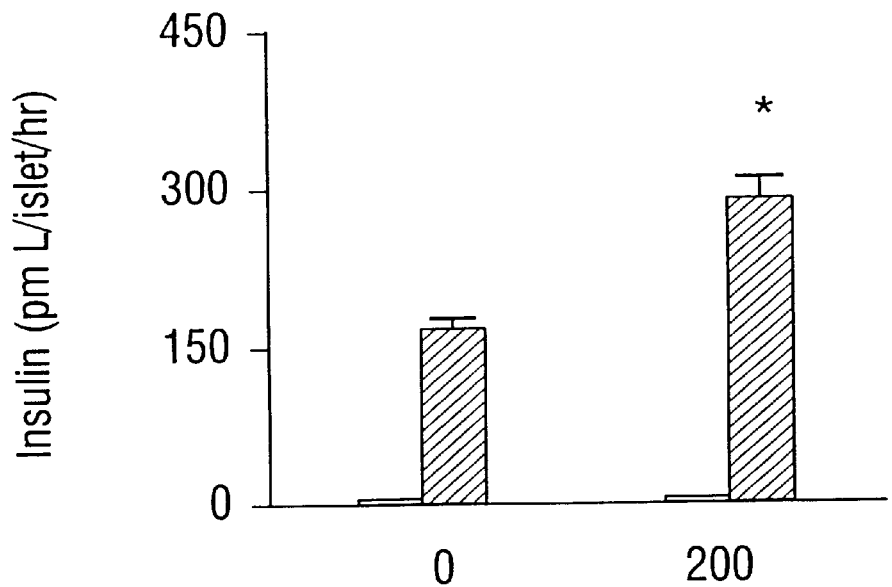
FIG. 8A, FIG. 8B, FIG. 8C.
Figure 8B:
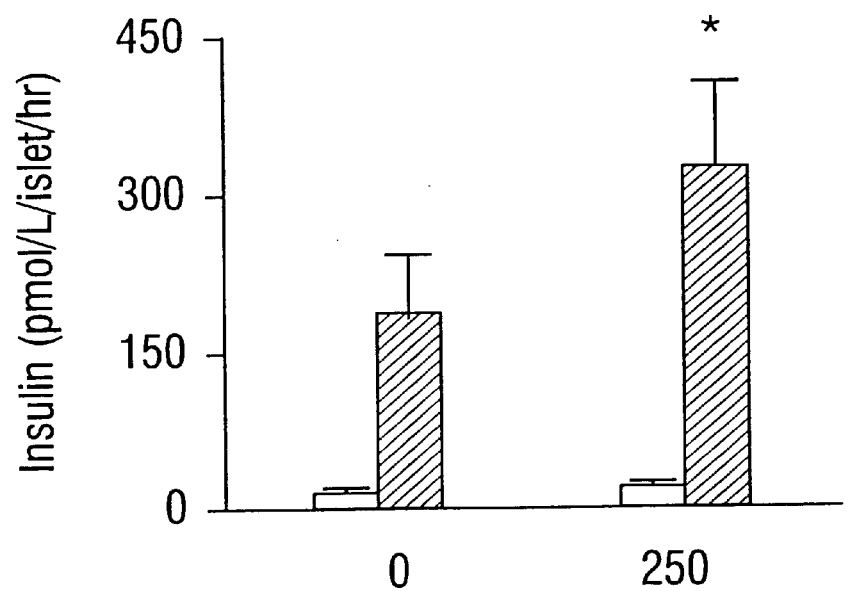
Figure 8C:
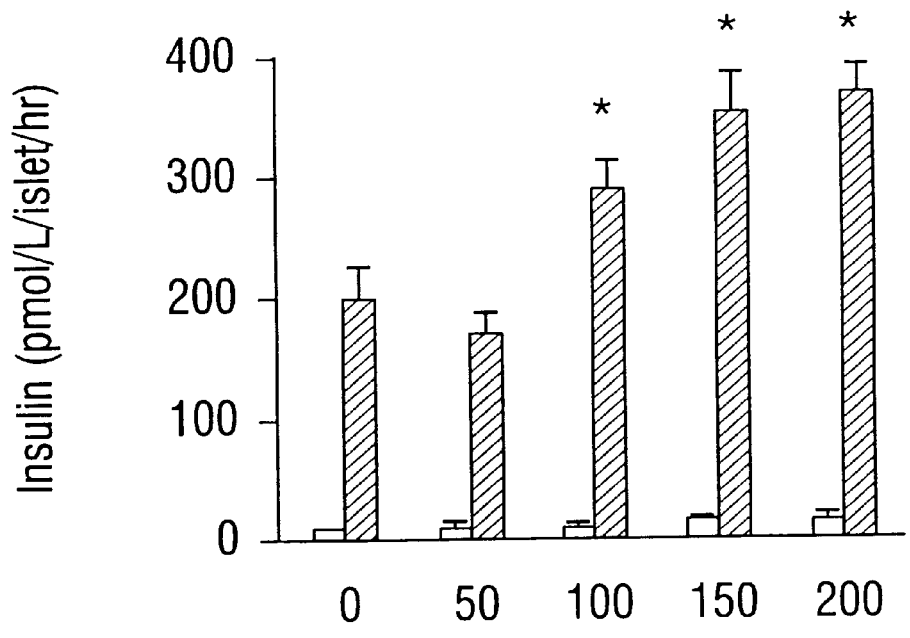
Figure 8D:
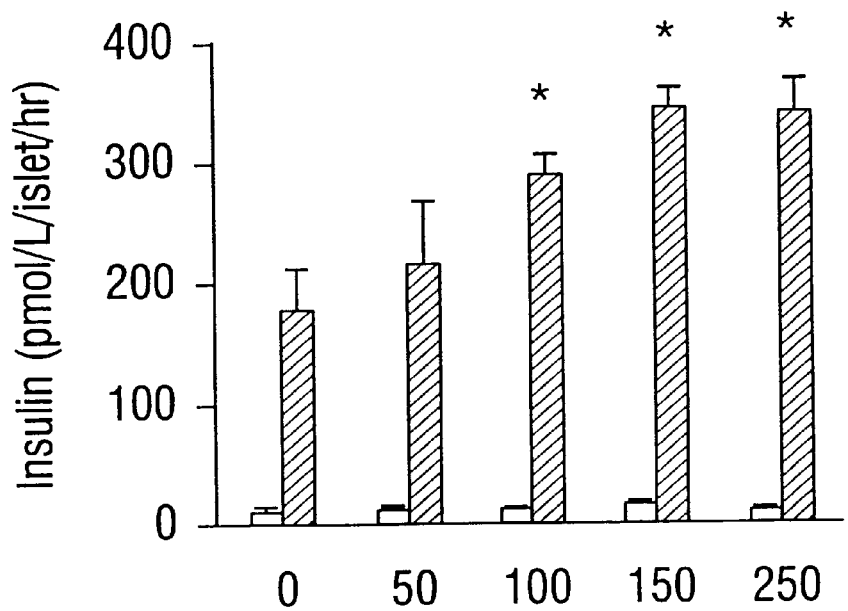
FIG. 8D. Effect of protease inhibitors on the insulin secretory response to glucose in mouse pancreatic islets.
Figure 9A:
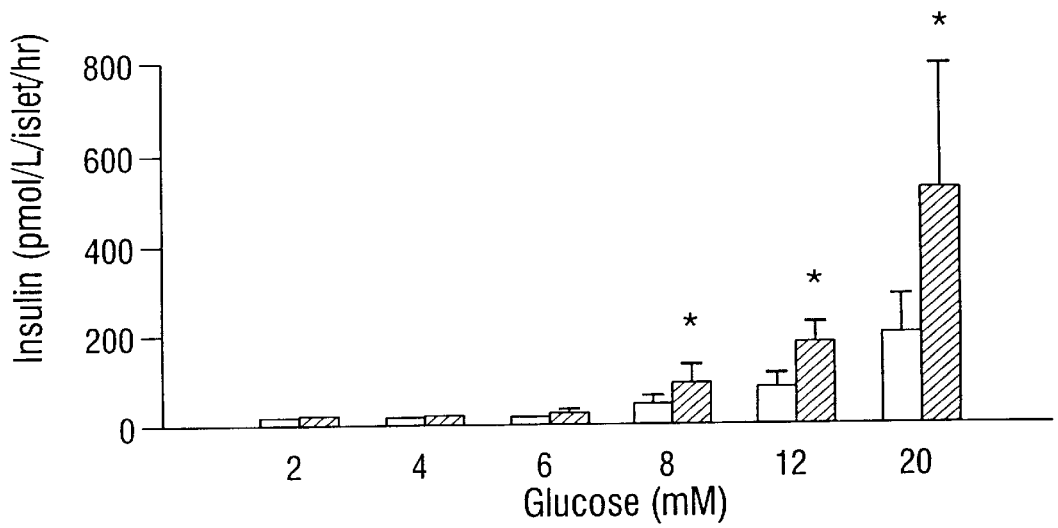
FIG. 9A, FIG. 9B and FIG. 9C. Effect of protease inhibitors on the insulin secretory response to glucose and other secretagogues in mouse pancreatic islets.
Figure 9B:
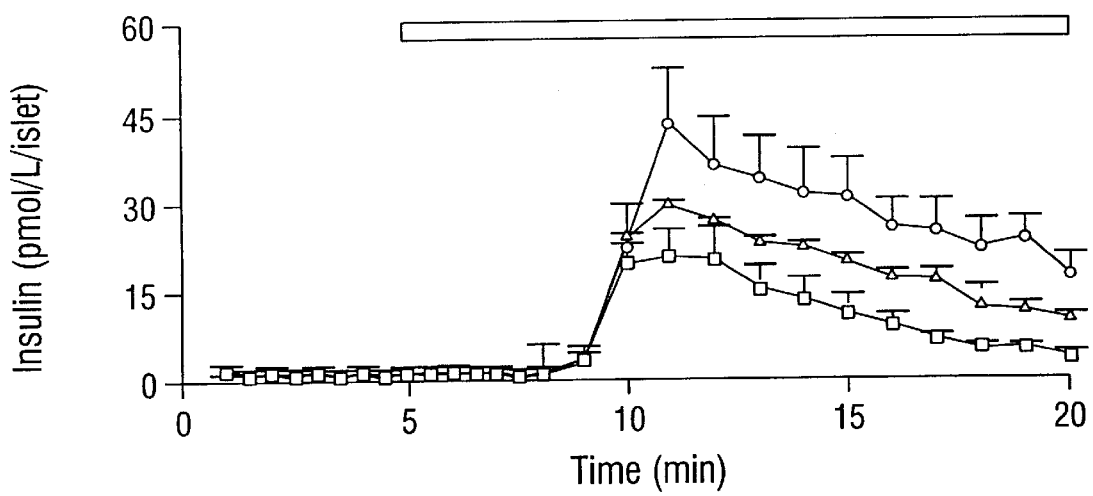
Figure 9C:
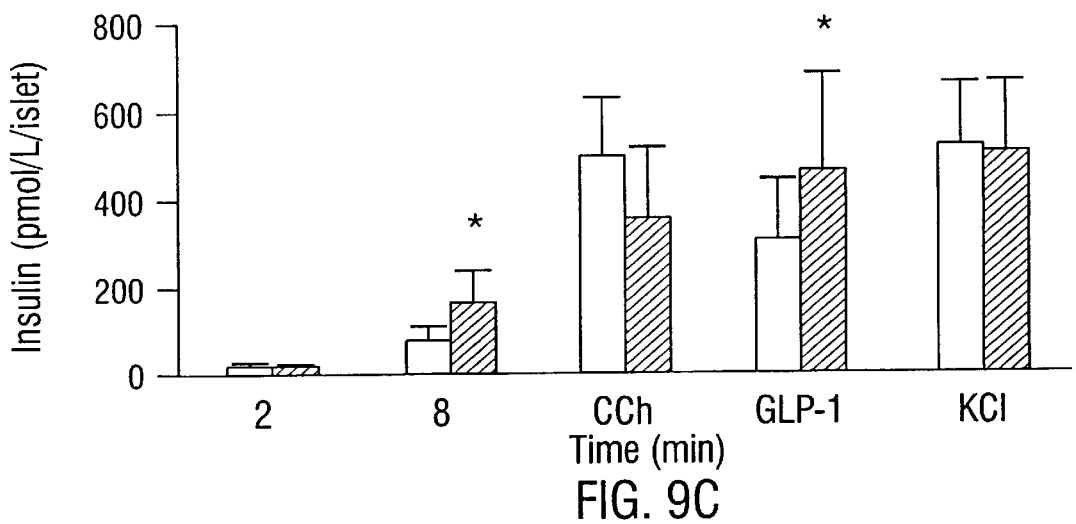

ALLM (250 μM) and E-64-d (200 μM) increased the insulin secretory responses to 20 mM glucose in isolated pancreatic islets by 1.97±0.3-fold (n=5, p<0.01, (mean±SEM)) and 1.77±0.1-fold (n=6, p<0.001), respectively (FIG. 8A and FIG. 8B). These effects were not observed at 2 mM glucose. The effects of ALLM and E-64-d on the insulin secretory response to 20 mM glucose (FIG. 8C and FIG. 8D) were seen at inhibitor concentrations greater than 100 μM and were glucose dependent in that the insulin secretory response was enhanced at glucose concentrations above 8 mM glucose but significant effects were not observed at 2,4 or 6 mM glucose (FIG. 9A). The enhancement of the insulin secretory response to 20 mM glucose by ALLM and E-64-d was also observed in a dynamic islet perifusion system (FIG. 9B). ALLM produced a small but statistically significant increase in the insulin secretory response to 50 nM GLP-1 (1.55±0.2-fold, n=6, p<0.05), an agent which stimulates adenyl cyclase. ALLM did not however significantly increase the insulin secretory responses to 30 mM KCl, an agent which directly depolarizes the β-cell (FIG. 9C) or 100 μM carbachol (CCh) which mobilizes Ca$^{2+}$ from intracellular stores.

Figure 10A:
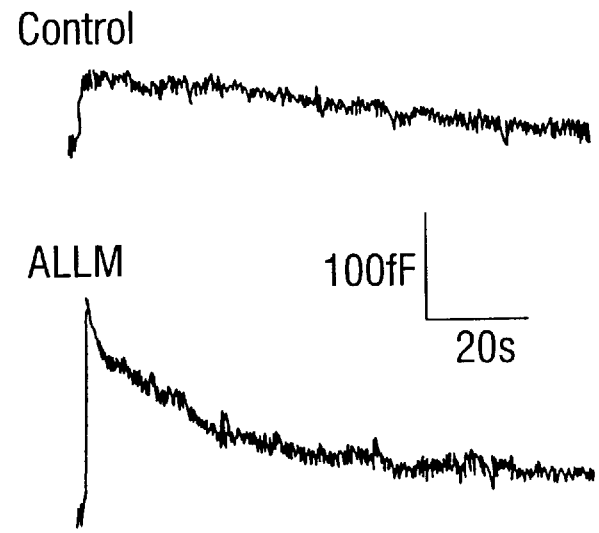
FIG. 10A and FIG. 10B. Measurements of membrane capacitance in isolated β-cells. Capacitance measurements reveal a large increase in insulin secretion after pretreatment with ALLM (100 $\mu$M). Using the perforated whole-cell recording configuration, β-cells were stimulated with a train of ten step depolarizations to +20 mV (HP=−80 mV). Each depolarization lasted 150 ms and was separated by 400 ms interpulse duration.
Figure 10B:
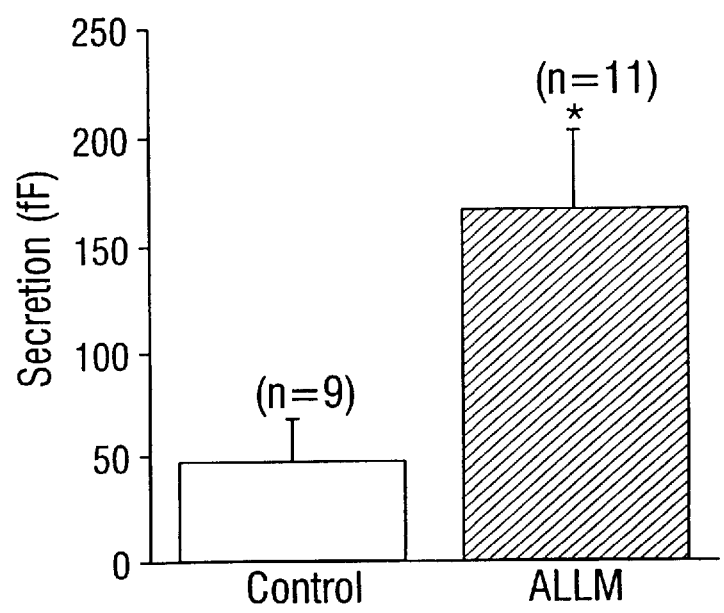

Membrane capacitance measurements confirm the large enhancement of insulin secretion observed after ALLM pre-treatment (FIG. 10). Representative capacitance changes, elicited by a train of depolarizations, from control (top) and ALLM pre-treated cells (bottom) are shown in FIG. 10A. Stimulation induced much larger average changes in membrane capacitance in ALLM pre-treated cells in comparison to control cells (FIG. 10B).

Figure 11A:
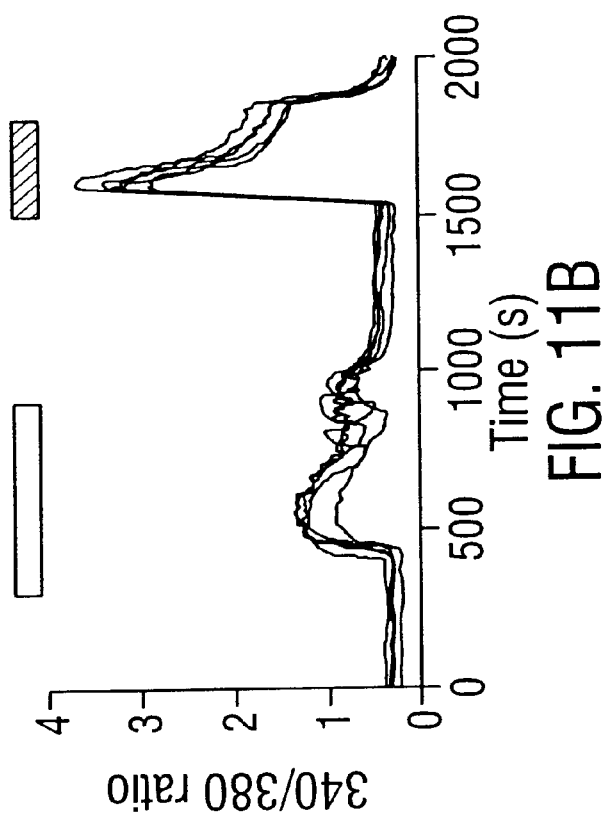
FIG. 11A, FIG. 11B, FIG. 11C, FIG. 11D, FIG. 11E and FIG. 11F. Effect of protease inhibitors on [$Ca^{2+}$]$_i$, whole cell calcium currents and NAD(P)H responses to glucose in mouse islets.
Figure 11B:
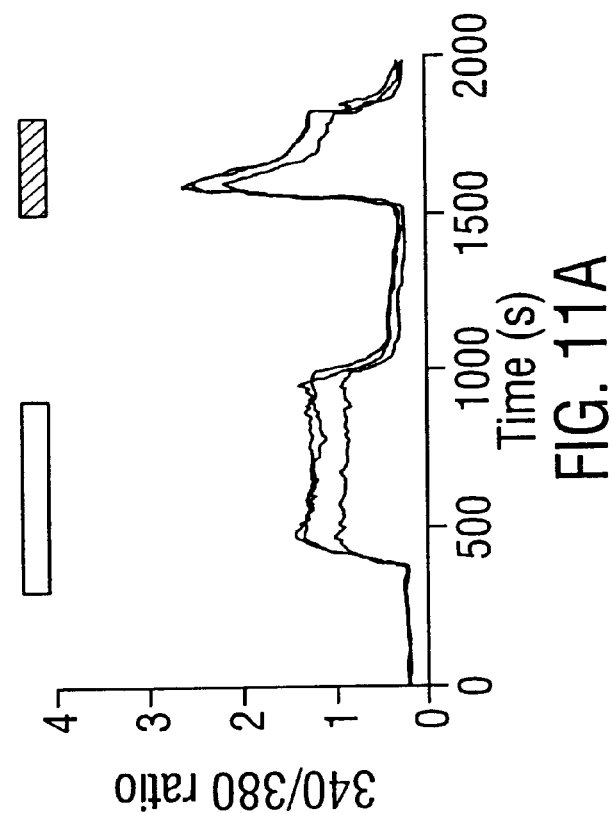
Figure 11D:
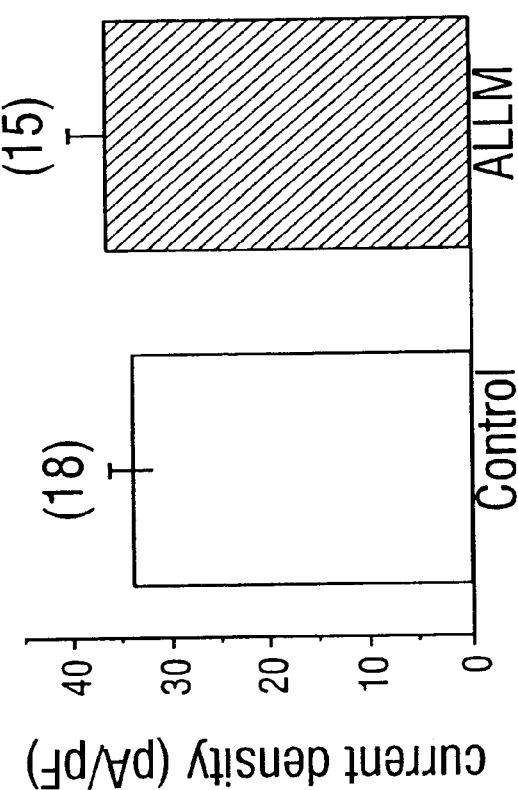
Figure 11C:
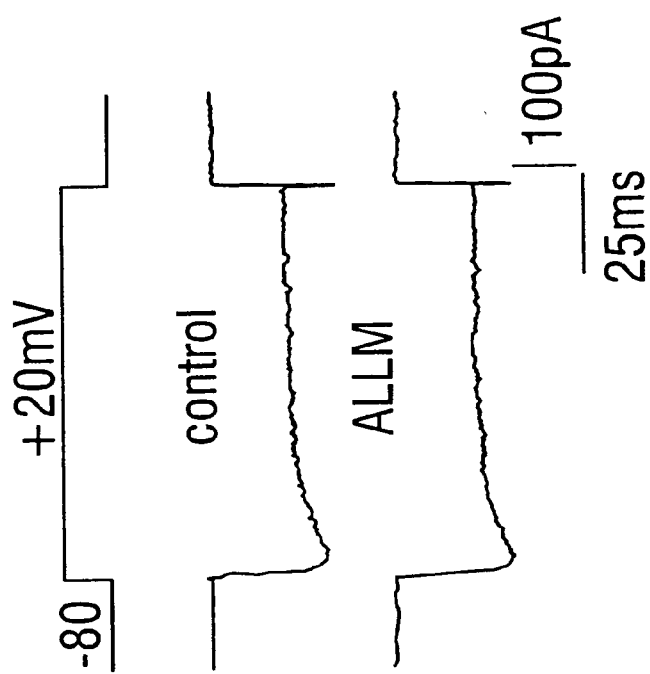

The stimulatory effects of ALLM and E-64-d on insulin secretion in response to high glucose were not associated with increases in [Ca$^{2+}$]$_i$ (FIG. 11A and FIG. 11B). This observation was confirmed by the observation that calcium currents were similar in control and ALLM treated cells (FIG. 11C); no differences in amplitude or kinetics were apparent. In addition, no shifts in voltage-dependence were observed and the average peak calcium current density obtained in control and ALLM pre-treated cells were comparable (FIG. 11D).

Figure 11E:
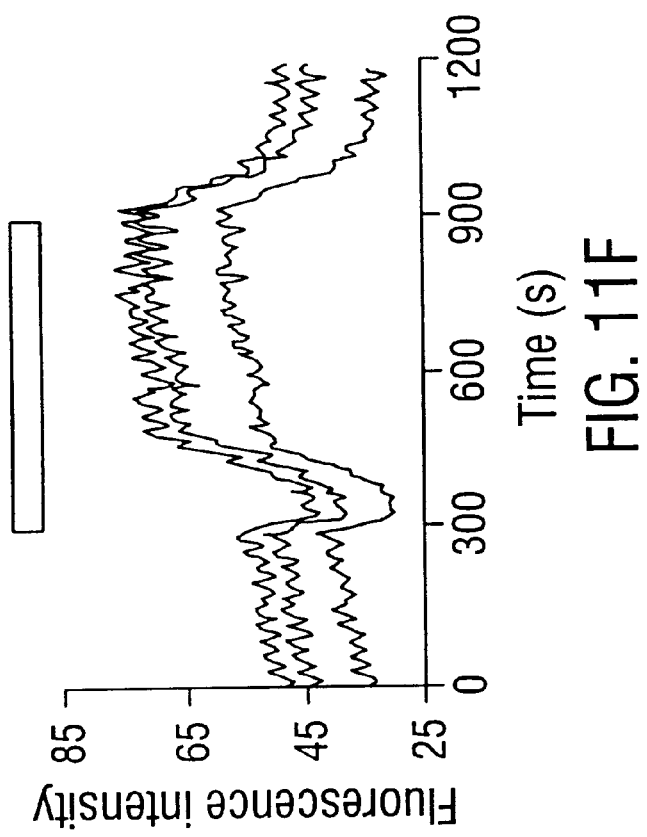
Figure 11F:
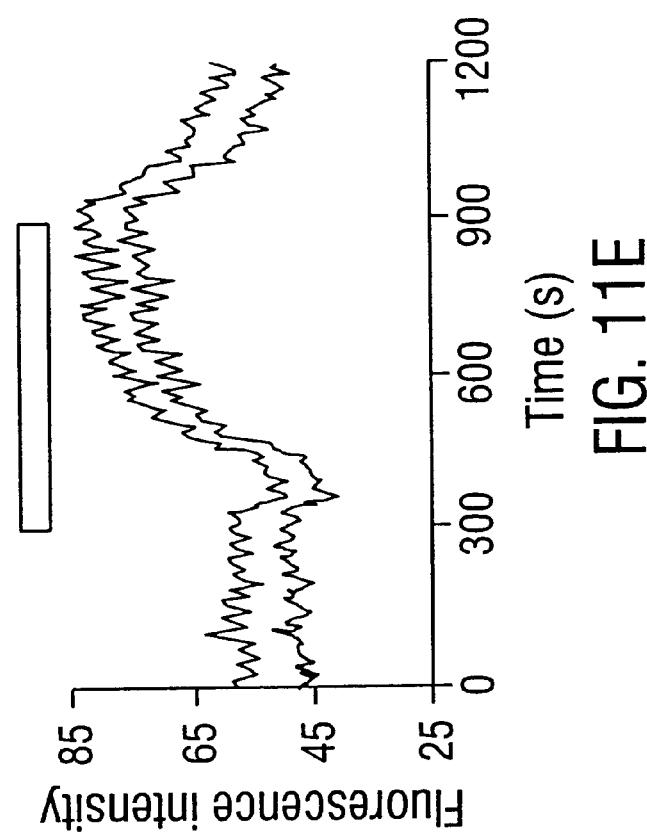

Rates of glucose utilization at basal (2 mM glucose) and stimulatory glucose concentrations (20 mM) in the presence of 100 μM ALLM (14.5±3.6 and 89.5±3.0 pmol/islet/hr, respectively) or 200 μM E-64-d (15.5±4 and 79.5±9.5 pmol/islet/hr respectively) were not significantly different from those in islets incubated in their absence (14.5±2.1 and 76.5±6.5 pmol/islet/hr, n=3 in each case). Similarly, there was no significant difference in the glucose oxidation rates at basal or stimulatory glucose concentrations in the presence of ALLM (6.0±0.7 and 39.5±4.1 pmol/islet/hr) and E-64-d (5.2±0.4 and 40.0±2.4) compared to those measured in the absence of inhibitor (4.4±0.8 and 32.5±6.5 pmol/islet/hr, n=3 in each case). Consistent with a lack of effect of ALLM and E-64-d on β-cell glucose metabolism, the NAD (P)H response to an increase in the glucose concentration from 2 to 14 mM in the presence of 100 μM ALLM (2.7±0.4-fold increase, n=4) and E-64-d (2.8±0.3-fold increase, n=2) was not significantly different from controls (2.6±0.2-fold increase, FIG. 11E and FIG. 11F).

Figure 12A:
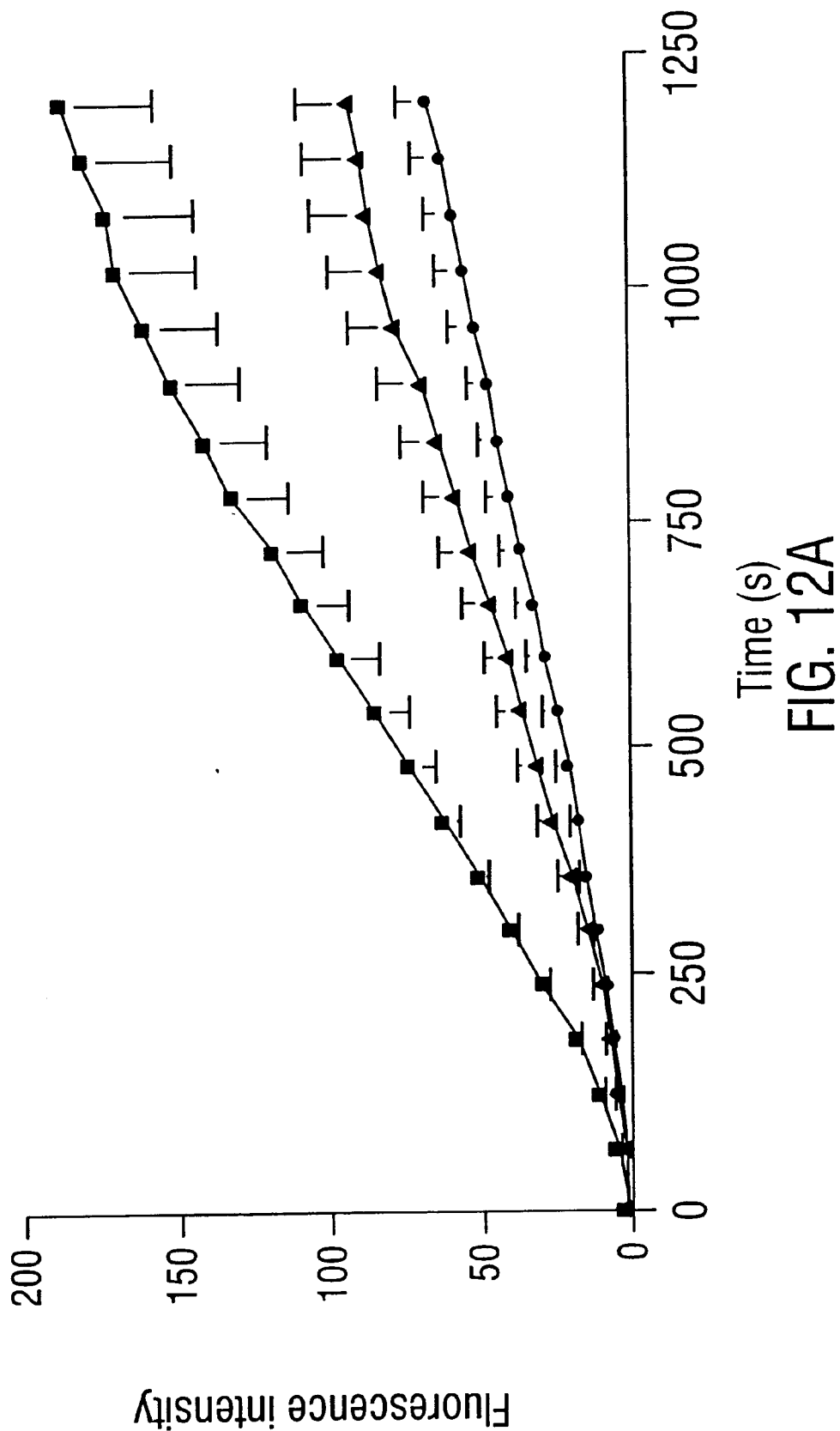
FIG. 12A and FIG. 12B. Effects of protease inhibitors on calpain activity in islets.
Figure 12B:
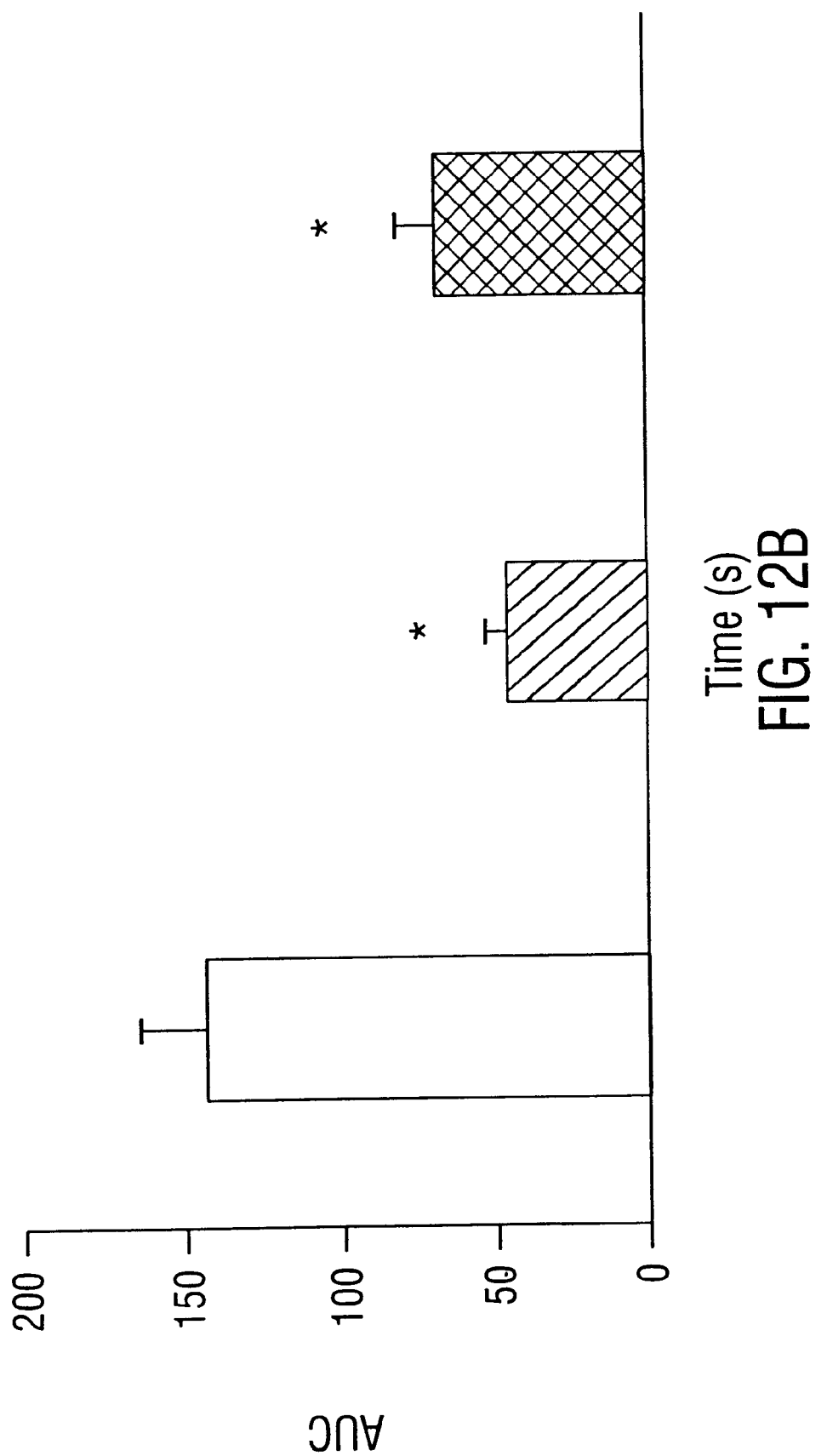

In order to document that ALLM and E-64-d were indeed inhibiting calpains rather than other cysteine proteases, calpain activity was measured in isolated islets using the fluorogenic calpain specific substrate Boc-Leu-Met-CMAC (FIG. 12). Although this compound does not allow us to distinguish between different calpain isozymes, it does appear to be a substrate for calpains and not for other lysosomal proteases under physiological conditions. In islets incubated in the presence of 200 μM ALLM or 200 μM E-64-d, the rate of generation of the fluorescent signal was lower than in islets incubated in the absence of the calpain inhibitors. The area under the curve measuring the rate of generation of the fluorescent product was reduced to 35±4% (n=3, p<0.05) and 45±5% (n=4, p<0.05) of control values in the presence of ALLM (200 μM) and of E-64-d (200 μM) respectively.

The inventors also examined the effects of other protease inhibitors on insulin secretion. Insulin secretory responses to 20 mM glucose were not altered in the presence of pepstatin A (100 μM), an aspartic protease inhibitor, or Cathepsin B inhibitor 2 (100 μM), a lysosomal cysteine protease inhibitor, indicating that the inhibitory effects of ALLM and E-64-d on insulin secretion are not seen with all protease inhibitors.

Since decreased insulin action in peripheral tissues defines insulin resistance and is a prominent feature of type 2 diabetes, we determined whether ALLM and E-64-d affected insulin stimulated 2-deoxyglucose (2-DOG) uptake in muscle and fat cells. The uptake of 2-DOG into normal rat adipocytes (FIG. 13A as increased approximately 3-fold from 456.5±59 pmol/2×10$^5$ cells/5 min (n=6) to 1384±178 pmol/2×10$^5$ cell (p<0.05, n=4) by the addition of insulin (12 nmol/L). However in the presence of 100 μM ALLM, insulin failed to increase 2-DOG uptake into adipocytes significantly (598±102 vs. 751±71 pmol/2×10$^5$ cells/5 min, n=4, p>0.05). Similarly, in the presence of 200 μM E-64-d, insulin failed to increase 2-DOG uptake into adipocytes significantly (361±29 vs. 749±129 pmol/2×10$^5$ cells/5 min, n=4, p>0.05).

Insulin mediated glucose transport into strips of soleus muscle was also reduced by 100 μM ALLM or 200 μM E-64-d (FIG. 13B). Insulin (12 nM) increased 2-deoxyglucose uptake into rat soleus muscle strips from 0.26±0.01 to 0.47±0.03 (mol/ml H$_2$O/30 mins, p<0.05, n=5). However in the presence of ALLM (0.28±0.04 vs. 0.34±0.05 (mol/ml H$_2$O/30 mins, n=5, p>0.05) or E-64-d (0.31±0.02 vs. 0.36±0.02 (mol/ml H$_2$/30 mins, n=5, p>0.05) insulin failed to stimulate a significant increase in muscle glucose uptake.

Figure 13C:
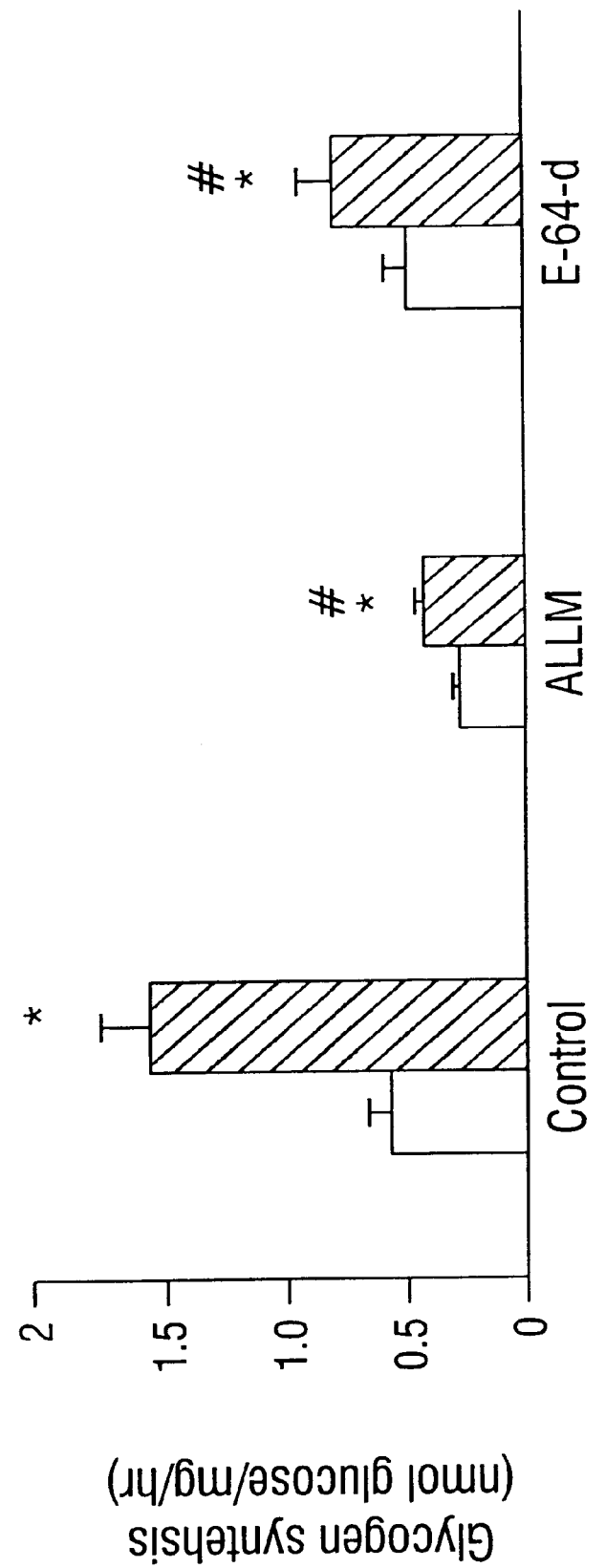

Rates of glycogen synthesis were measured in soleus muscle strips (FIG. 13C). Insulin (6 nM) increased the rate of muscle glycogen synthesis from 0.58±0.08 to 1.55±0.20 nmol glucose/mg/hr (n=6, p<0.005). In the presence of 100 μM ALLM (0.27±0.03 vs. 0.40±0.05 nmol glucose/mg/hr, n=6, p<0.01) and 200 μM E-64-d (0.49±0.08 vs. 0.80±0.14 nmol glucose/mg/hr, n=6, p<0.04), insulin caused a significant increase in muscle glycogen synthesis. However the magnitude of the increase was significantly lower in the presence of both ALLM (0.13±0.03 nmol glucose/mg/hr, p<0.01) and E-64-d (0.31±0.09 nmol glucose/mg/hr) than in islets not exposed to these inhibitors (0.97±0.19 nmol glucose/mg/hr, p<0.01).

The specific calpain isozyme(s) or cysteine protease(s) implicated in the control of insulin secretion and insulin action in the studies described above is unknown. Isozyme-specific inhibitors are not available and ALLM and E-64-d inhibit both calpains and cathepsins. However, the inhibition of hydrolysis of the substrate Boc-Leu-Met-CMAC by ALLM and E-64-d in pancreatic islets supports the hypothesis that ALLM and E-64-d increase insulin secretion by inhibiting calpain activity rather than affecting lysosomal cysteine proteases such as the cathepsins. The identification of the specific calpain(s) involved must await the development of more specific inhibitors. The concordance of the present results with those from molecular genetic and clinical studies showing a role for calpain 10 in the development of type 2 diabetes and insulin resistance suggests that this calpain isozyme is important in mediating the observed effects.

The present studies also provide insight into the molecular mechanism by which ALLM and E-64-d increase the insulin secretory responses to glucose and GLP-1. These agents did not lead to an increase in $[Ca^{2+}]_i$, rates of glucose oxidation and utilization, or NAD(P)H generation. Thus, they do not affect pathways in the β-cell responsible for the uptake and metabolism of glucose. Rather, the inventors believe that the most likely site(s) of action are in pathways that regulate the movement or fusion of insulin secretory granules with the plasma membrane.

In addition to a role in insulin secretion, the inventors have demonstrated that calpain inhibition results in reduced insulin stimulated glucose transport into fat and muscle and reduced muscle glycogen synthesis and thus reproduces the defects in insulin action that are the hallmarks of insulin resistant states including type 2 diabetes. Taken in conjunction with genetic and physiological studies showing that a common polymorphism in calpain 10 is associated with an increased risk of type 2 diabetes, decreased muscle mRNA levels and insulin resistance, these findings provide additional support for the notion that calpains play an important role in the regulation of insulin action, perhaps by down-regulating IRS-1 or promoting adipocyte differentiation. It is interesting to note that insulin resistance in muscle and fat is commonly associated with hypersecretion of insulin in subjects predisposed to the later development of type 2 diabetes. Alterations in calpain expression and/or calpain activity in diverse tissues may therefore represent a common unifying pathogenetic mechanism for the development of type 2 diabetes that accounts for both insulin resistance and the resulting compensatory increase in insulin secretion.

Example 9

Long-term Effects of Calpain Inhibition on Beta Cell Function

Figure 14:
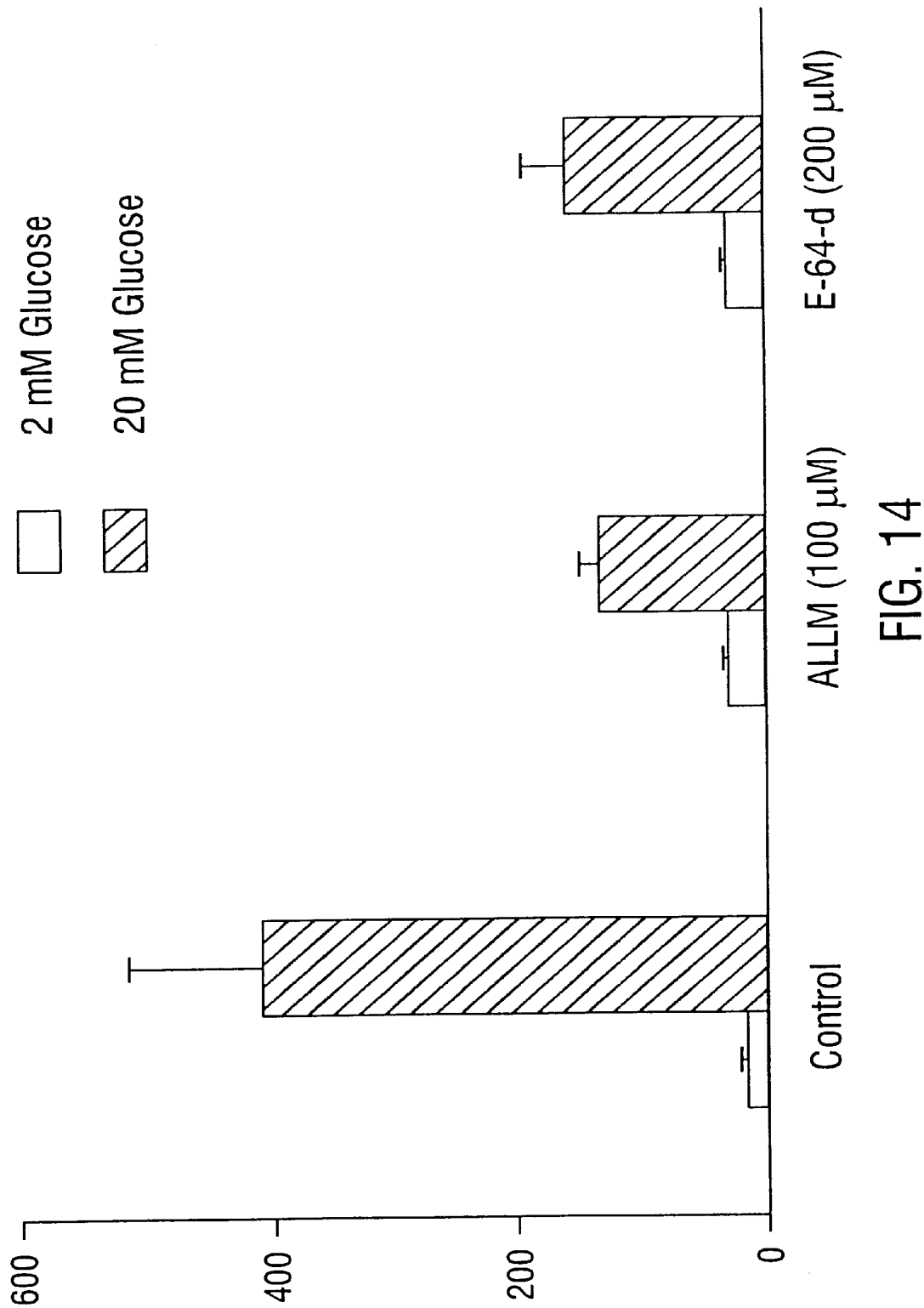
FIG. 14. Effect on glucose stimulated insulin secretion by islets following 48 hour exposure to calpain inhibitors, ALLM or E64-d.
Figure 15:
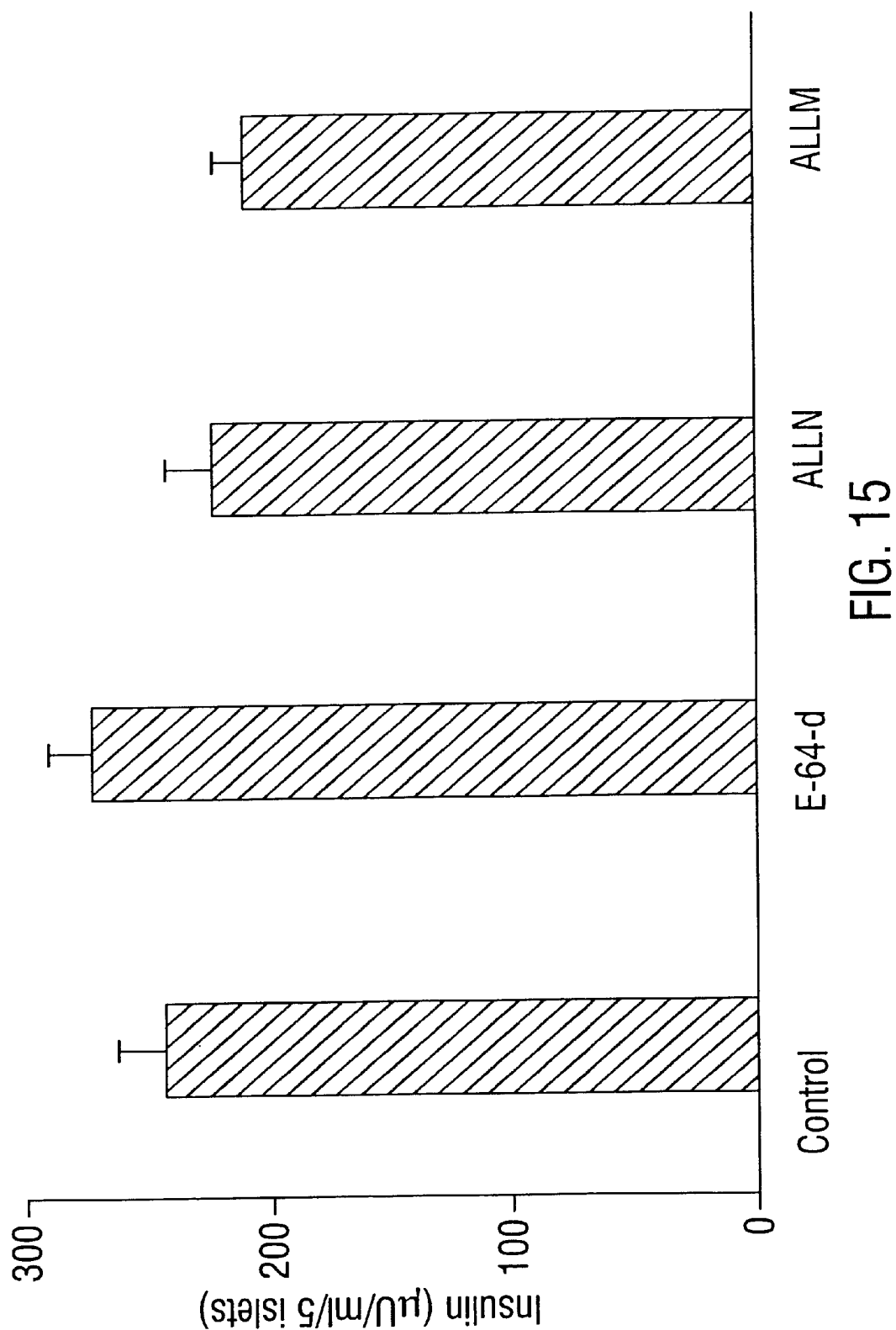
FIG. 15. Insulin content of islets following 48 hour exposure to calpain inhibitors, ALLM or E64-d.
Figure 16:
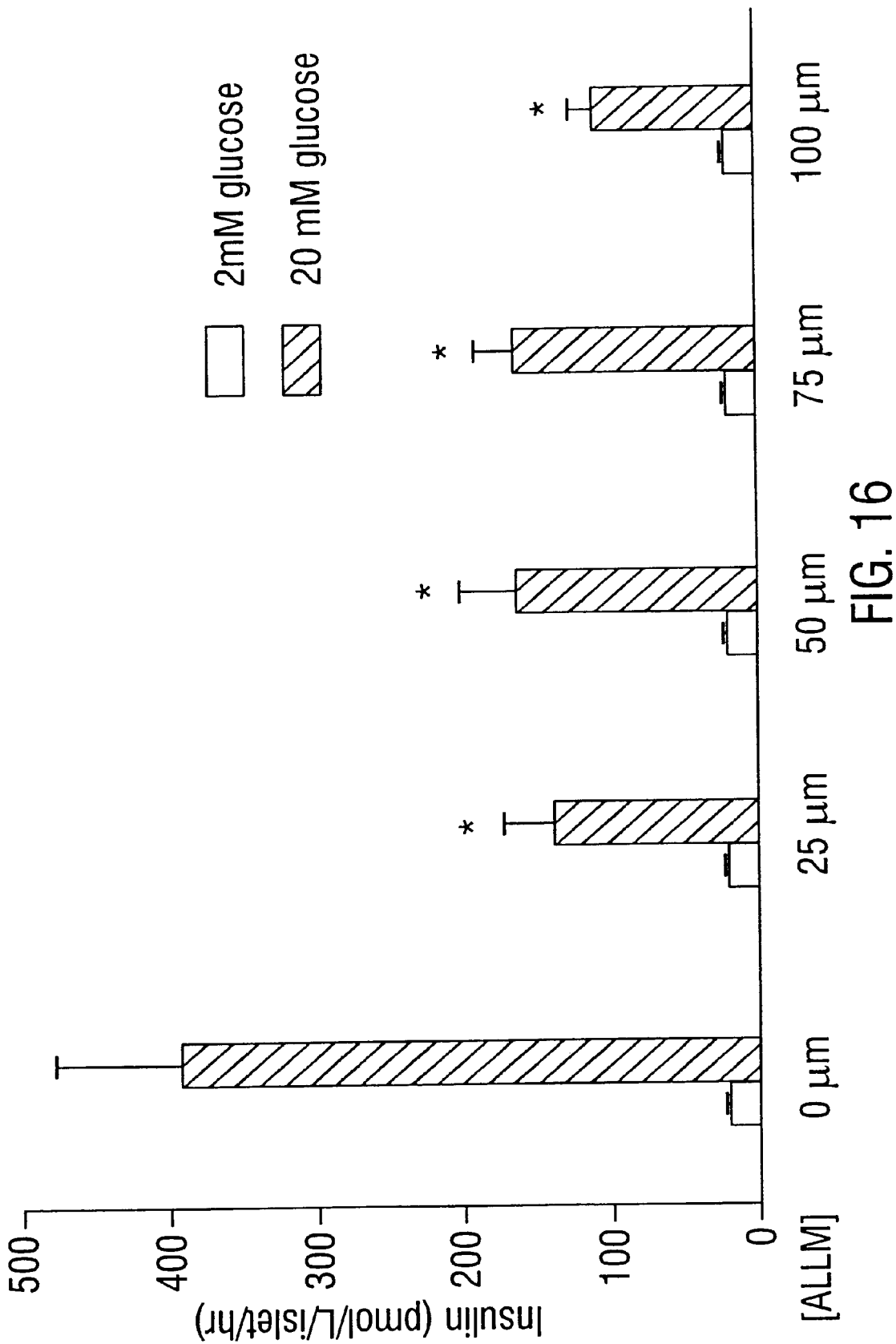
FIG. 16. Dose response of glucose stimulated insulin secretion by calpain inhibitor II.
Figure 17A:
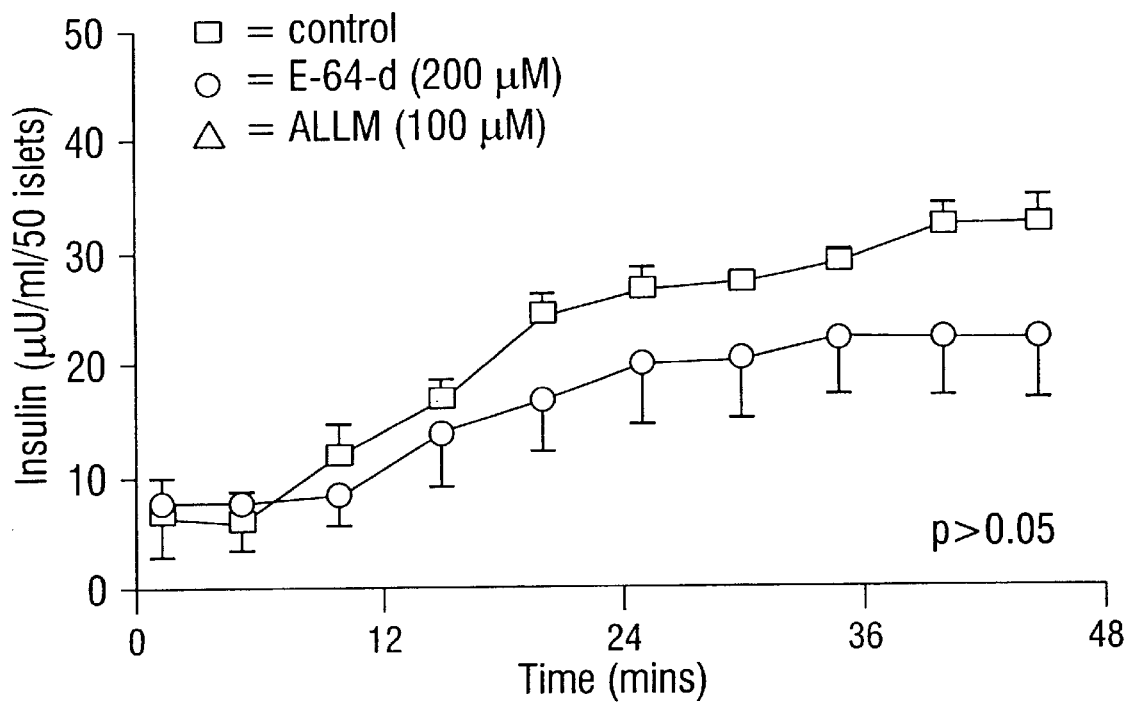
FIG. 17A and FIG. 17B. Long term inhibitory effects of calpain inhibitors on glucose stimulated insulin secretion of perfused islets.
Figure 17B:
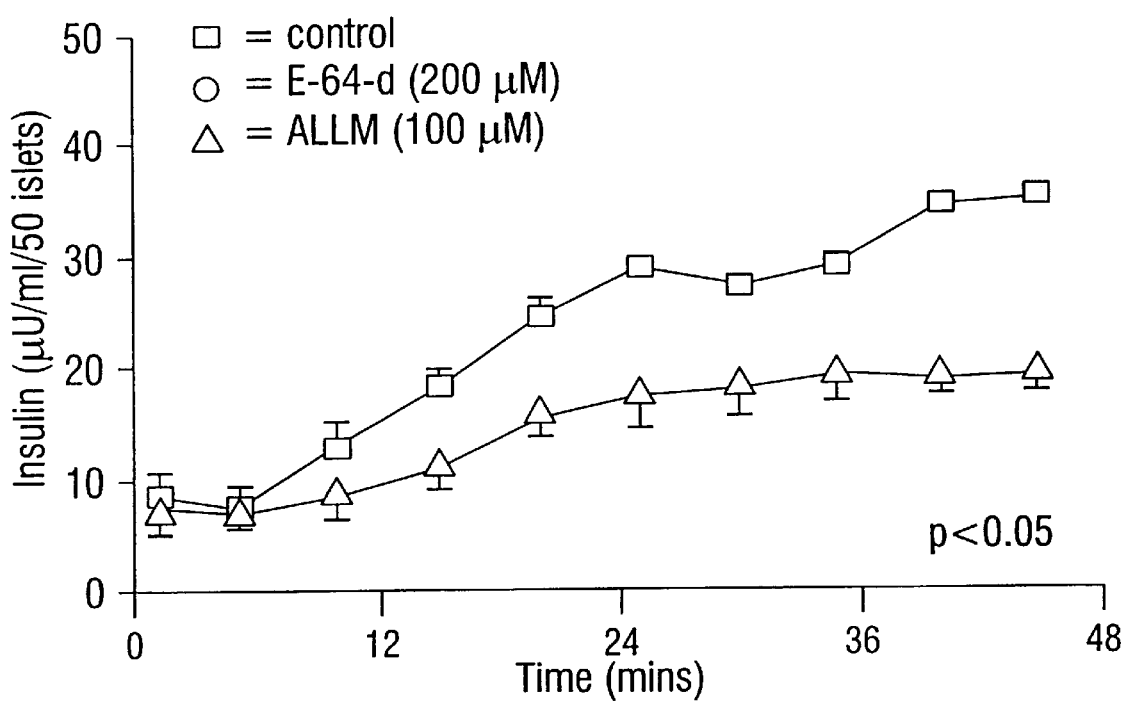
Figure 18:
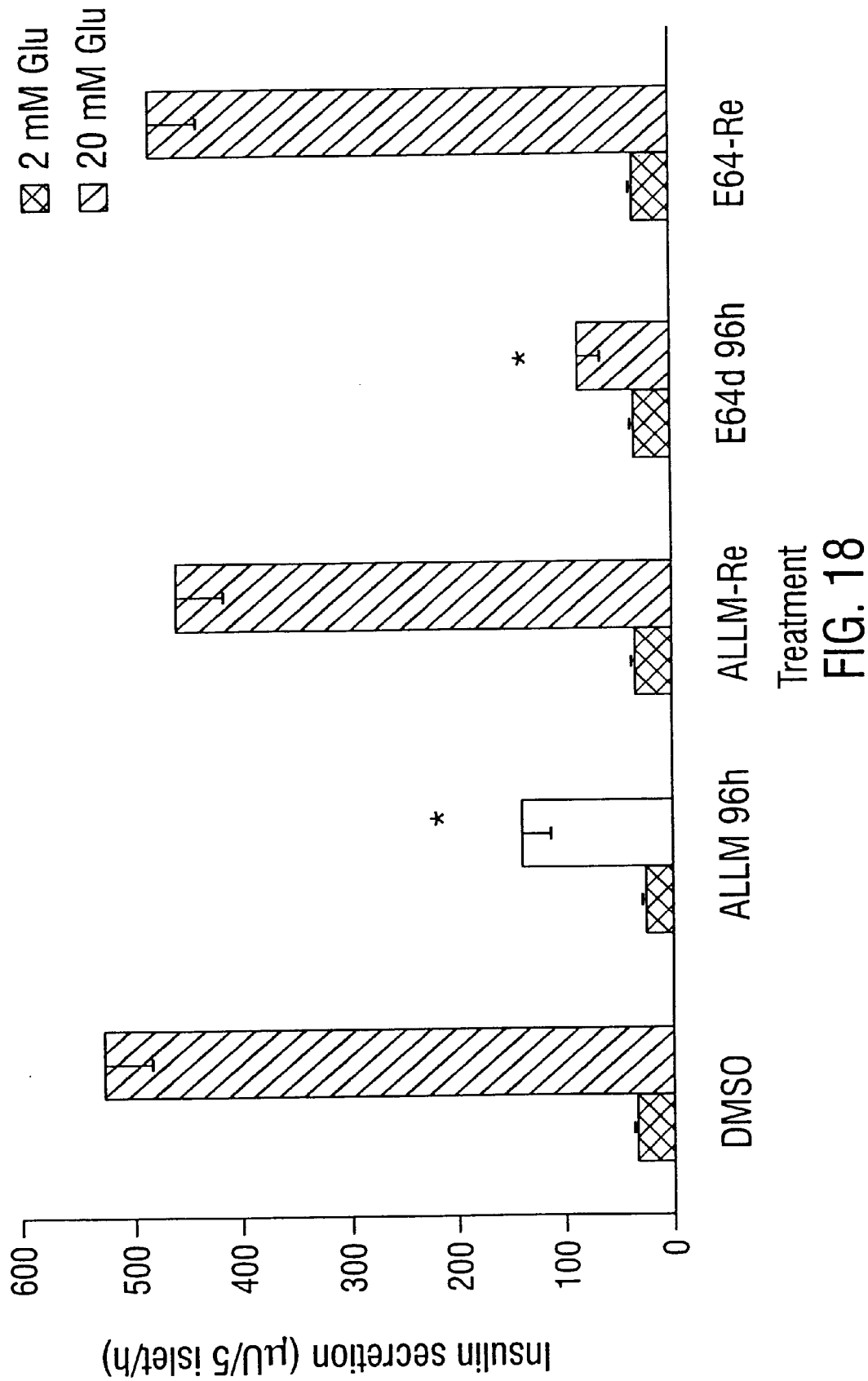
FIG. 18. Recovery of normal glucose stimulated insulin secretion after two days in islets following 48 hour calpain inhibitor treatment.

Insulin secretory responses to glucose in islets that had been treated with calpain inhibitor 2 (ALLM) and E-64-d were measured. As shown in FIG. 14, 48 hours exposure to 100 μM of ALLM or 200 μM of E64-d attenuated the insulin secretory response to 20 mM glucose by approximately 50–60% relative to islets treated with vehicle. There was no significant difference in the basal insulin secretion (at 2 mM glucose) between inhibitor- and control-treated islets. Also, the insulin content in islets treated for 48 hours with the two inhibitors were comparable to that in control islets (FIG. 15). In experiments performed to document the dose response relationship between calpain inhibitor II concentration and inhibition of insulin secretion, inhibition was achieved with 25 μM of ALLM (FIG. 16). The long-term inhibitory effects of calpain inhibitors on glucose-induced insulin secretion were also demonstrated in a dynamic perifusion system (FIG. 17A and FIG. 17B). To confirm the viability of islets treated with the cysteine protease inhibitors, we tested the reversibility of the inhibitory effect of ALLM and E-64-d on insulin secretion. Islets were treated with 100 μM ALLM or 200 μM E-64-d for 48 h, and then cultured for a further 48 h either in the presence or absence of the inhibitors. In this set of experiments, glucose-induced insulin secretion (20 mM) was inhibited by more than 80% in islets treated with ALLM or E-64-d for 96 h. In contrast, those islets that had been allowed to recover for 2 days following 48-h treatment with the inhibitors exhibited an essentially normal insulin secretory response to 20 mM glucose (FIG. 18). In conjunction with the normal insulin contents in 48-hr treated islets, these data exclude the possibility of cell death or non-specific toxic effects resulting from 48 h treatment with the cysteine protease inhibitors.

Figure 19:
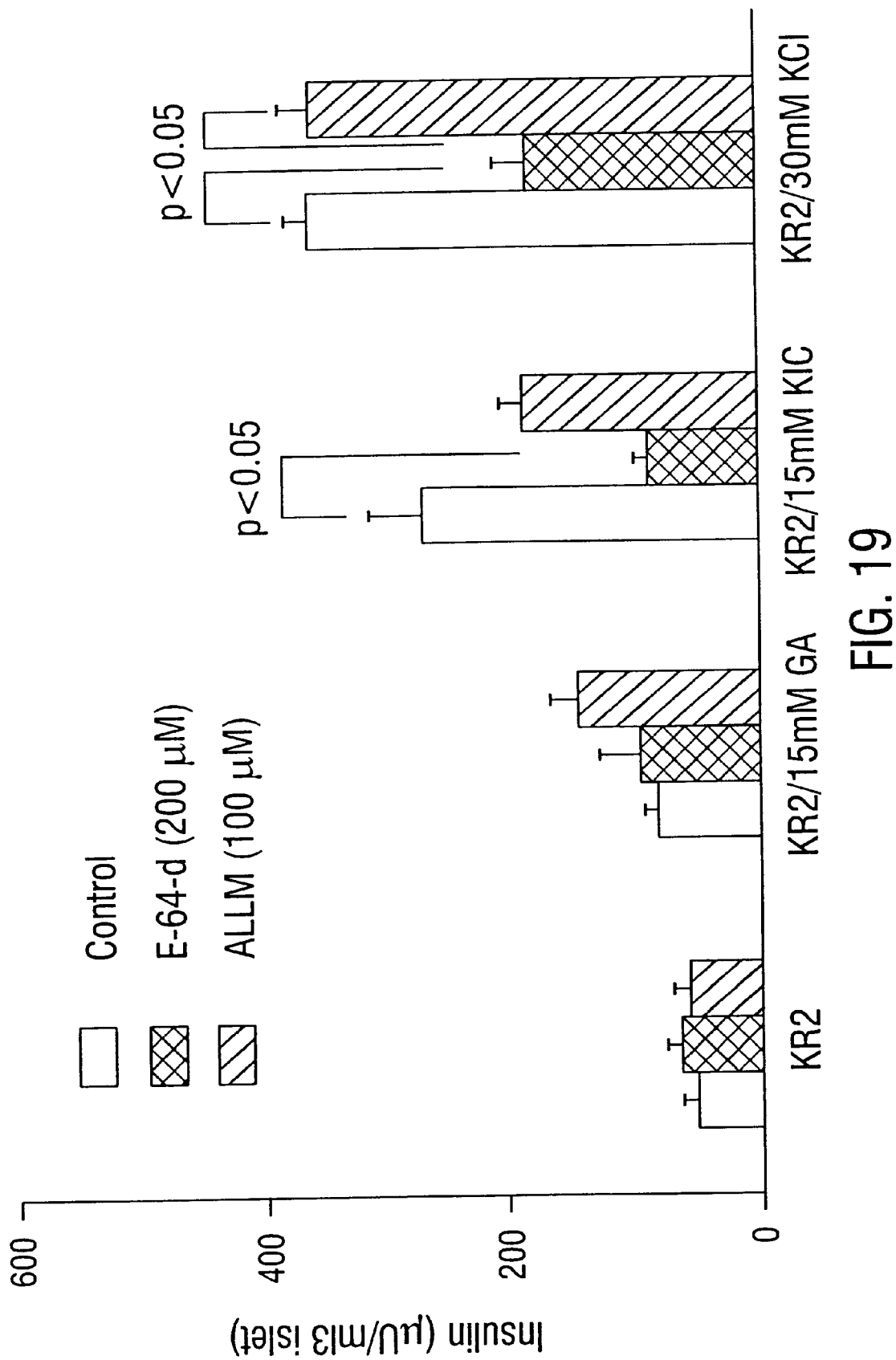
FIG. 19. Stimulated insulin secretory response to glyceraldehyde, keto-isocaproic acid (KIC) and KCl following 48 hour calpain inhibitor treatment.
Figure 20:
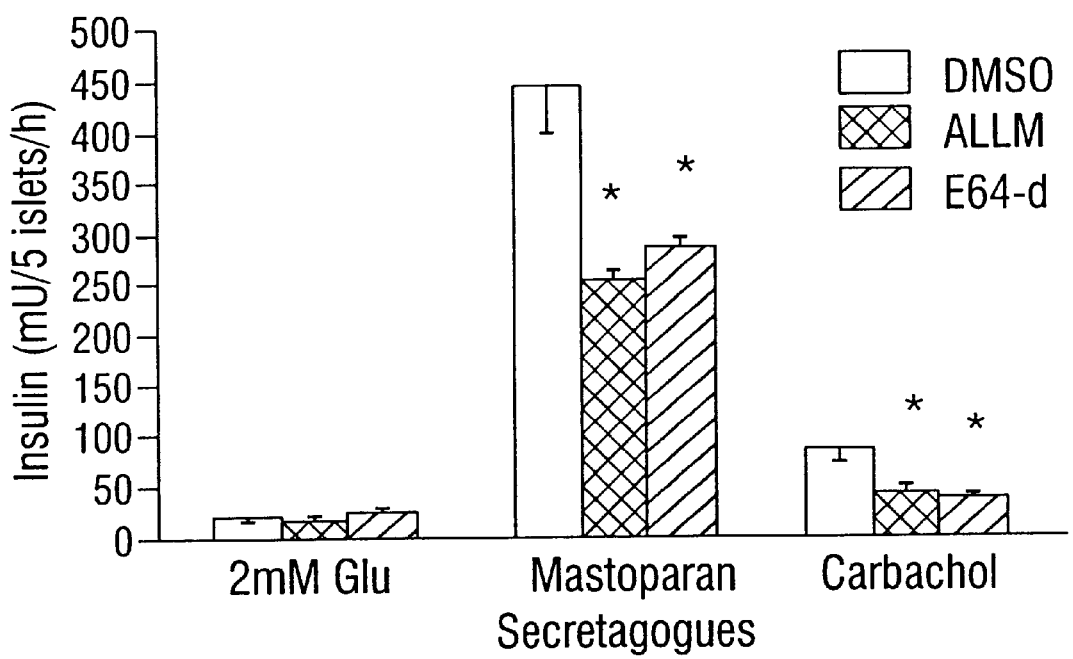
FIG. 20. Stimulated insulin secretory response to mastoparan and carbachol following 48 hour calpain inhibitor treatment.

To further characterize the defect in glucose induced insulin secretion, insulin secretory responses to secretagogues that enter the signal transduction pathway at different levels were studied. As shown in FIG. 19, ALLM or E-64-d treated islets responded normally to glyceraldehyde. However the insulin-secretory responses to keto-isocarproic acid (KIC, a nutrient that stimulates mitochondrial metabolism directly (FIG. 19)) were decreased. The insulin secretory response to 30 mM KCl, which directly depolarizes the β-cell membrane, was significantly reduced in E-64-d treated islets (FIG. 19). Insulin secretory responses to mastoparan, a G-protein activator known to be a potent stimulator of secretion, and carbachol, a muscarinic agonist that stimulates insulin secretion through activation of phospholipase C and release of intracellular $Ca^{2+}$ stores, were attenuated in calpain-inhibitor treated islets were attenuated in islets that had been treated for 48 h with ALLM or E-64-d (FIG. 20).

Due to their lack of the specificity for calpain, (ALLM and E-64-d may also inhibit cathepsins and other proteases, such as those of proteasome), the effects of additional protease inhibitors on insulin secretion were tested. As listed in Table 8, treatment of mouse islets with 100 μM of ALLN (calpain inhibitor I, is a small peptide inhibitor of calpain structurally similar to ALLM) for 48 h inhibited 20 mM glucose-stimulated insulin secretion by 88±9% (P<0.001, N=4). A similar result was obtained with MDL28170 (another cell-permeable peptide calpain inhibitor) —48 hr exposure to 50 μM MDL28170 inhibited insulin secretion by approximately 60% (P<0.05, N=4). Therefore, these two different calpain inhibitors were equally effective in blocking insulin secretion as ALLM and E-64d. In contrast, culturing islets with 100 μM Cathepsin B Inhibitor II (a small peptide, inhibitor of cathepsin B) or 20 μM Lactacystin (a Streptomyces metabolite, which is a specific cell-permeable, irreversible inhibitor of proteasome) for 48 h did not significantly affect either basal or glucose-stimulated insulin secretion, indicating that inhibition of the activities of cathepsin B and proteasome are unlikely to be the cause of defective insulin secretion associated with long term treatment of ALLM or E-64-d.

TABLE 8

Glucose-induced insulin secretion in islets treated with different protease inhibitors for 48 h.

| Inhibitors | (μM) | N | Insulin secretion (% of control treated islets) | |
|---|---|---|---|---|
| | | | 2 mM glucose | 20 mM glucose |
| ALLM | 100 | 5 | 136 ± 25 | 31 ± 4 |
| ALLN | 100 | 3 | 110 ± 8 | 12 ± 2 |
| MDL28170 | 100 | 4 | 111 ± 35 | 41 ± 18 |
| Cath B Inhibitor II | 50 | 3 | 114 ± 19 | 89 ± 25 |
| Lactacystin | 20 | 3 | 88 ± 15 | 95 ± 13 |

Figure 21A:
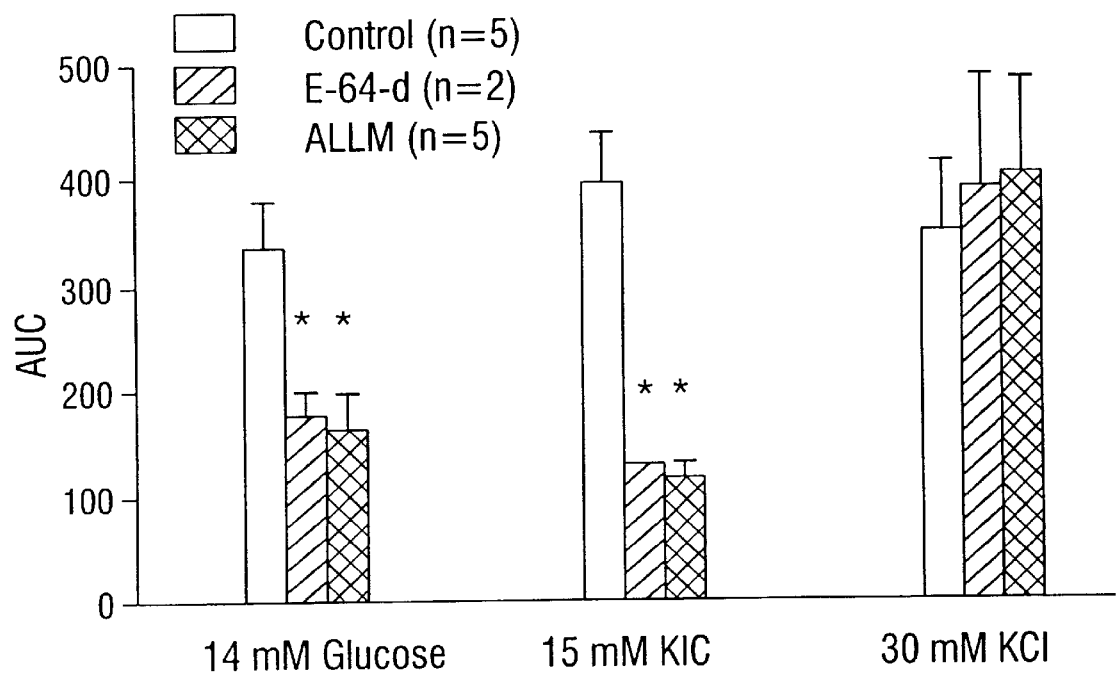
FIG. 21A and FIG. 21B. Intracellular free calcium responses to glucose, KIC and KCl in islets following 48 hour calpain inhibitor treatment.
Figure 21B:
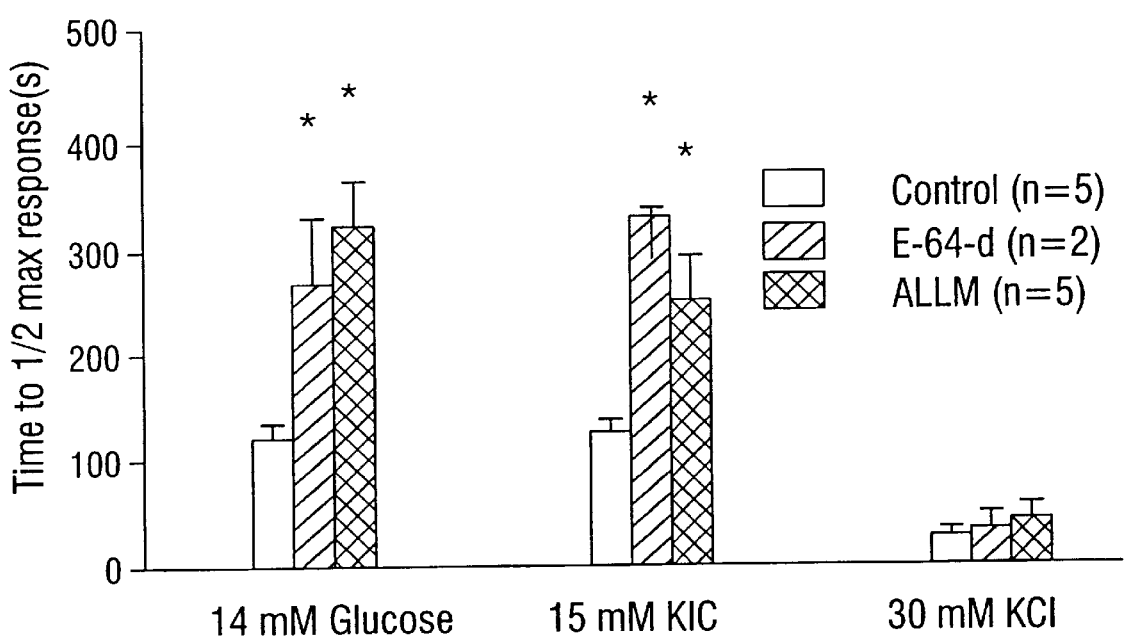

Insulin secretory responses to glucose and most other secretagogues is mediated by a rise in intracellular free calcium ($[Ca^{2+}]_i$). We therefore measured $[Ca^{2+}]_i$ responses to glucose, KIC and KCl using Fura-2 as the $Ca^{2+}$ indicator. In comparison to the responses from the control islets, the most prominent abnormality in $[Ca^{2+}]_i$ responses to glucose and KIC was a delay of the $[Ca^{2+}]_i$ responses (FIG. 21A and FIG. 21B). The mean time interval between administration of 14 mM glucose and the point of half maximal response ($T_{1/2}$) was 120±14 seconds in control islets. The $T_{1/2}$ of $[Ca^{2+}]_i$ responses to glucose in ALLM and E-64-d treated islets were significantly delayed to 319±42 and 265±65 sec. respectively (P<0.001 for both groups, n=5). The $[Ca^{2+}]_i$ responses to KIC in ALLM and E-64-d treated islets were also delayed (251±42 and 330±7 seconds respectively) compared to control islets (125±9, P<0.001 for each group). In addition to the delay in $[Ca^{2+}]_i$ responses to the two nutrients, the integrated $[Ca^{2+}]_i$ responses in the inhibitor-treated islets, calculated as the area under the curves of the $[Ca^{2+}]_i$ responses, were significantly smaller than that of the control islets (FIG. 21A and FIG. 21B). The diminished $[Ca^{2+}]_i$ response to glucose in ALLM and E-64-d treated islets was also documented in ramp experiments in which a gradually increasing level of glucose (from 2 to 26 mM) over 48 mins was applied to islets while changes in $[Ca^{2+}]_i$ were monitored. The $[Ca^{2+}]_i$ responses to 30 mM KCl were not different between control and ALLM or E-64-d treated islets. There was no delay in the appearance of $[Ca\ 2+]_i$ response to KCl, nor was the magnitude of the response reduced.

Figure 22A:
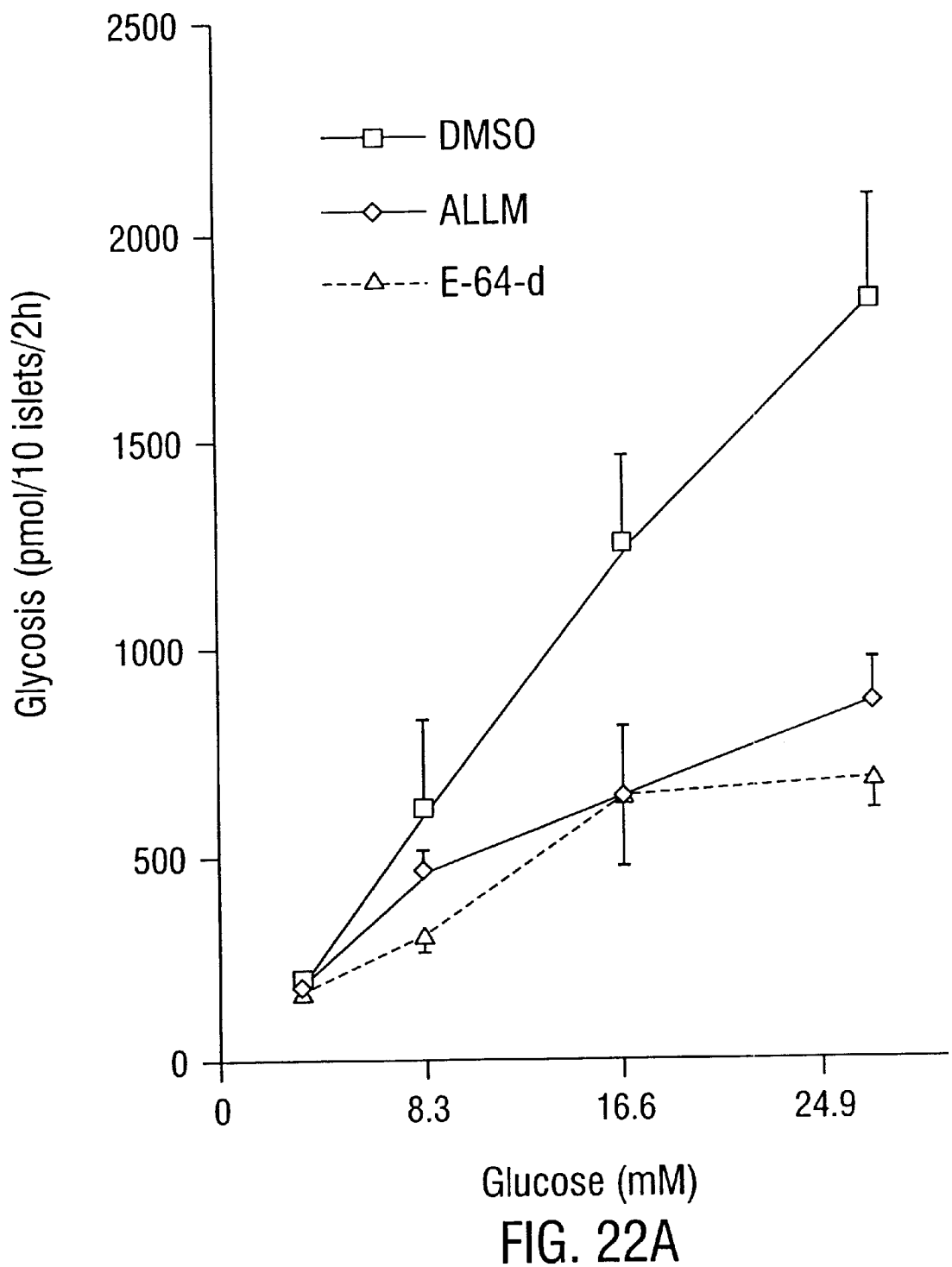
FIG. 22A and FIG. 22B. Glucose metabolism in islets following 48 hour calpain inhibitor treatment.
Figure 22B:
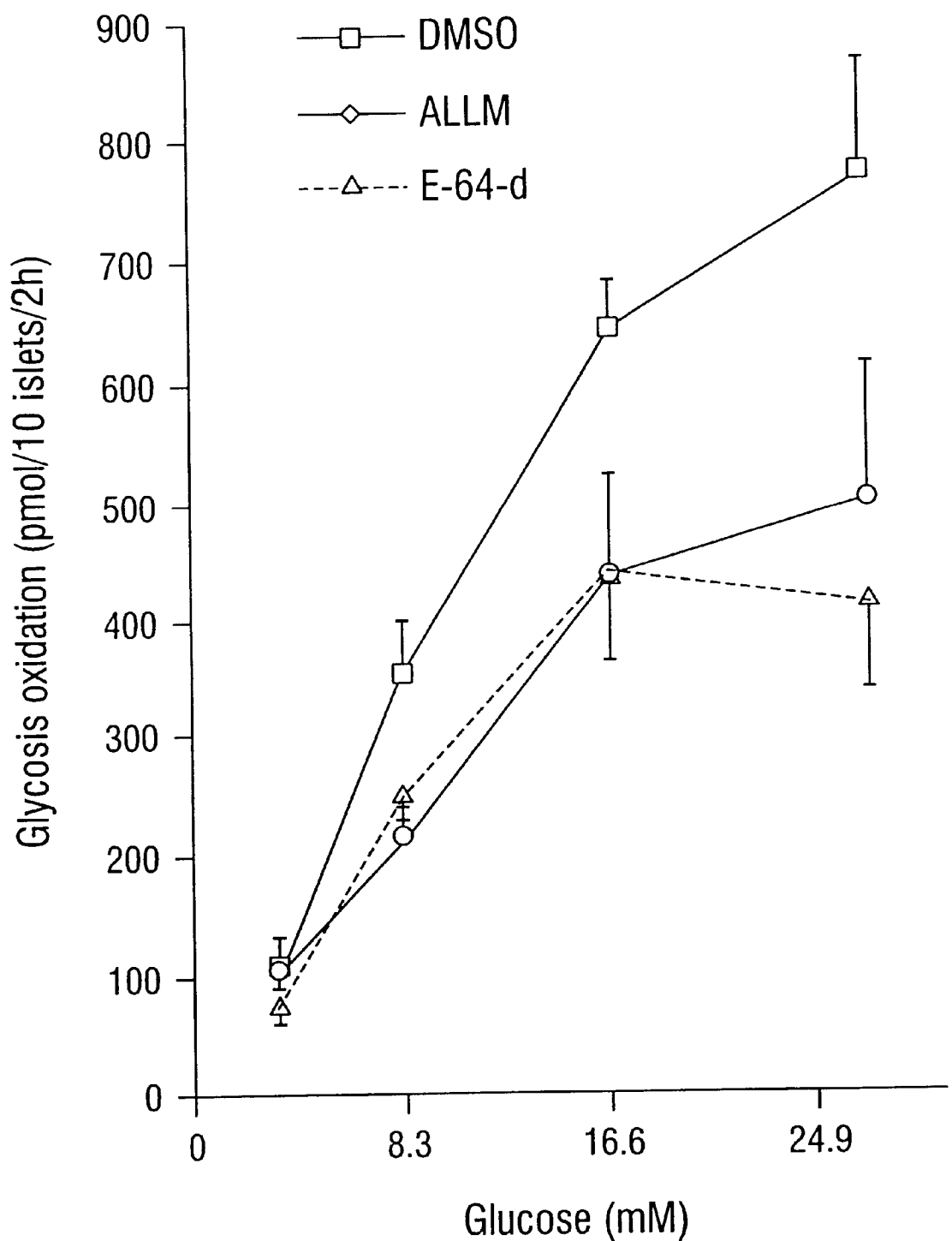

The attenuated insulin secretory and $[Ca^{2+}]_i$ responses to glucose and KIC suggests a possible defect in glucose metabolism, more specifically in mitochondrial metabolism. Therefore glucose metabolism in islets that had been treated with ALLM and E-64-d for 48 h was measured. As depicted in FIG. 22A and FIG. 22B, no significant changes were observed in rate of basal glucose utilization and oxidation at 3.3 mM glucose in islets treated with either inhibitor. However, the rates of glycolysis and glucose oxidation at stimulating concentrations of glucose were significantly reduced in ALLM or E-64-d treated islets compared to the controls. This is again distinct from the acute treatment, where rates of glucose utilization and oxidation were not changed by the 4-h treatment with the inhibitors.

Figure 23:
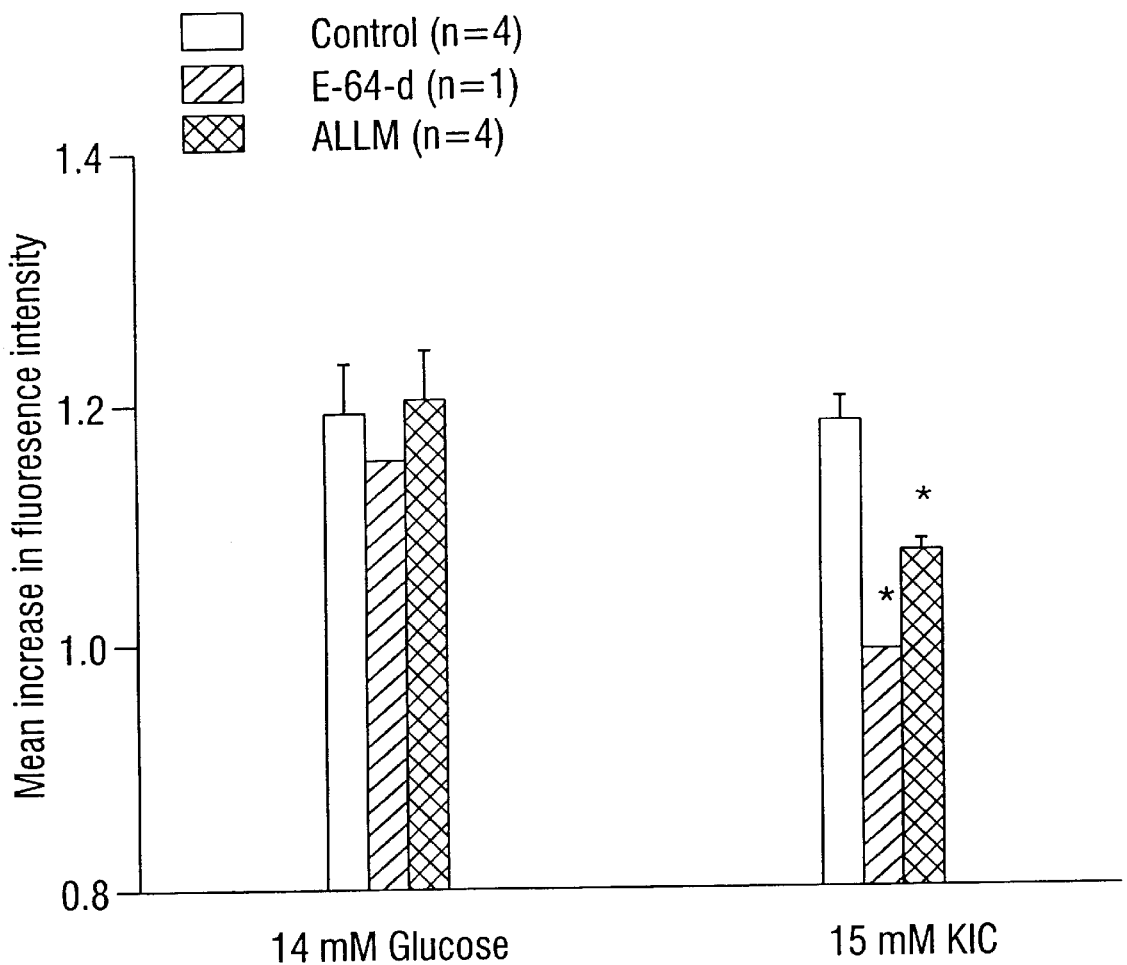
FIG. 23. NAD(P)H autofluorescence changes in response to glucose or KIC in islets following 48 hour calpain inhibitor treatment.

As an additional measurement of glucose metabolism, we monitored NAD(P)H autofluorescence changes in responses to glucose and KIC. NAD(P)H responses to glucose were comparable in control and treated islets, whereas the responses to KIC in ALLM or E-64-d treated islets were significantly reduced in comparison with control islets (FIG. 23). Unlike the $[Ca^{2+}]_I$ responses, there was no significant delay in the onset of NAD(P)H responses to glucose and KIC.

Figure 24A:
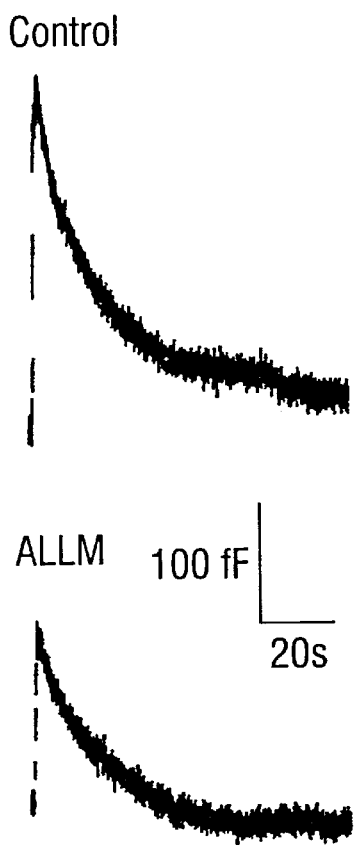
FIG. 24A and FIG. 24B. Lower rates of exocytosis in beta cells following 4 day calpain inhibitor treatment.
Figure 24B:
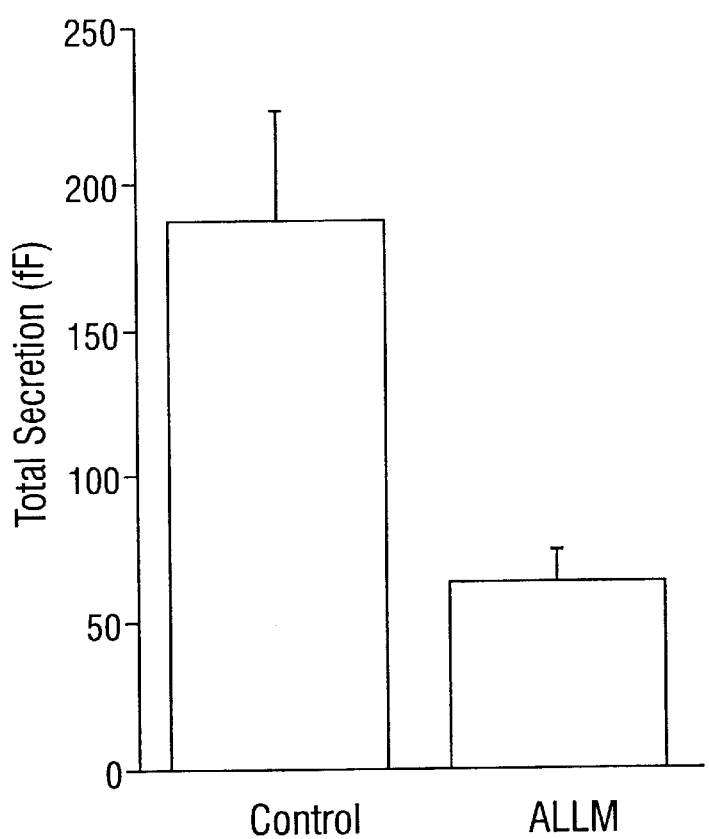

In a previous work, we have demonstrated that in a short-term incubation condition, ALLM and E-64-d enhanced insulin secretion via a direct activation of the exocytosis of insulin. After 4 days culture with the same two calpain inhibitors, significantly lower rates of exocytosis in β-cells were demonstrated (FIG. 24A and FIG. 24B). Moreover, significantly enlarged vesicles were observed in ALLM and E-64-d treated β-cells stained with 1 μM quinacrin (FIG. 25). Quinacrin is a dye specifically partitioned to acidic vesicles. Using confocal microscopy, control treated β-cell were found to contain a large number of vesicles of around 100 micrometer in size (FIG. 25). In ALLM and E-64-d-treated (48 h) cells, the size of those quinacrin-stained vesicles was increased more than 3-fold (FIG. 25). Together with the capacitance measurement and insulin secretion assay, these data indicate that long-term inhibition of cysteine proteases have a direct impact on the exocytotic machinery of the β-cells.

Figure 26:
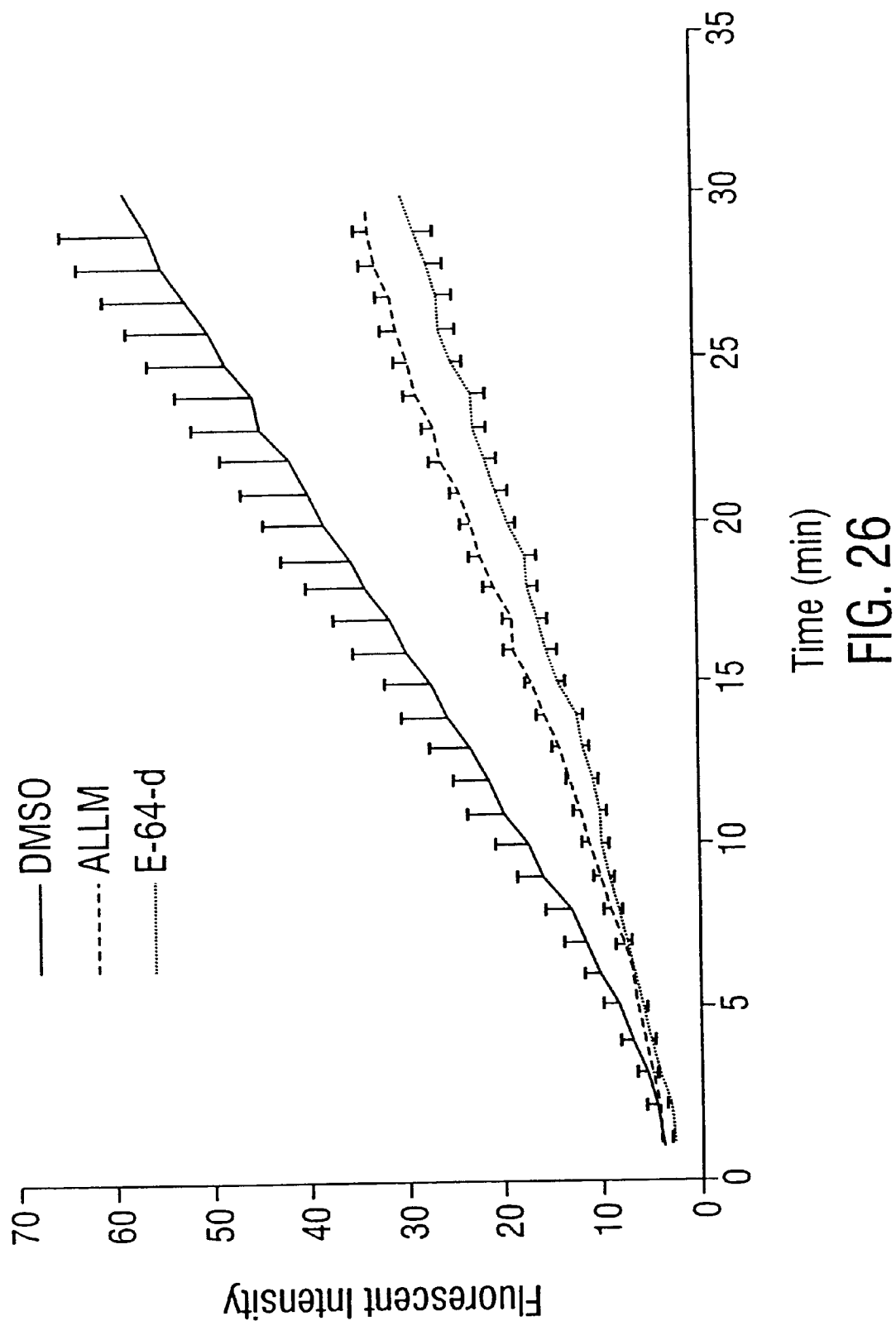
FIG. 26. Residual calpain activity in intact islets following 48 hour calpain inhibitor treatment.

Following 48 h treatment with 100 μM ALLM or 200 μM E-64-d, the residual calpain activity in intact islets, determined by monitoring the cleavage of a specific fluorogenic substrate, was 54±3% and 55±4% of control treated islets (FIG. 26).

Example 10

Use of Animal Models to Deduce the Mechanisms Causing Impairment of Insulin Function in Persons having the GG Phenotype Transgenic models will be created in mice in which calpain proteases and particularly calpain 10 containing the variant GG at UCSNP-43 will be overexpressed in tissues relevant to diabetes (muscle, liver and the pancreatic beta cell). Experiments will be performed to determine if this targeted tissue overexpression of calpains results in dysfunction of the target tissue, e.g., reduced glucose induced insulin secretion, insulin resistance, increased hepatic glucose production. Embryonic stem cell technology will be used to eliminate specific forms of the calpains either in the whole animal or in the specific tissues listed above. Physiological studies in the animals will characterize alterations that occur in each of these target tissues resulting from a lack of calpain expression.

In addition, experiments will be performed to determine if altered calpain expression and/or action is playing a role in the pathophysiology of existing models of type 2 diabetes, i.e., the ob/ob mouse, the db/db mouse and the ZDF rat (Baetens et al., 1978, Coleman, 1979, and Friedman et al., 1991).

Example 11

Use of Calpain Inhibitors in Animals and Humans to Treat Diabetes

The present example describes methods of treating diabetes by modulating the function of one or more calpains in at least one of a β-cell, muscle cell, or fat cell with a modulator of calpain function. A preffered embodiment would be a method of treating diabetes comprising stimulating calpain activity in a fat call or muscle cell with a modulator of calpain function and inhibiting calpain activity in a β-cell with a modulator of calpain function.

Calpain modulators, such as those described in this application, can be administered to animals models of diabetes, including the existing models of type 2 diabetes, i.e., the ob/ob mouse, the db/db mouse and the ZDF rat (Baetens et al., 1978, Coleman, 1979, and Friedman et al., 1991). These modulators can also be administered to transgenic animals, such as those described in Example 9. These modulators can be formulated and administered by any of the means described in this application to better deliniate optimal dosages, routes of delivery, formulations and so on. Physiological studies in the animals will characterize effects of the calpain modulators on varios parameters, including measurements of glucose induced insulin secretion, insulin resistance, and hepatic glucose production. Modulators that have anti-diabetic effects in these animal models are candidates for further animal experimentation and eventual human clinical trials.

As experimental animal models and other systems are developed for testing calpain modulators, novel modulators with improved bioactivity can be developed. Improved bioactivty may be defined as optimizing half-life in vivo, preference for target cells, especially β-cells, muscle or fat, reduced side effects such as toxicity and immunogenicity, or any other measure of improved efficacy. These novel modulators can be developed by any means, including but not limited to, combinatorial libraries, random mutagenesis or modifications, and rational drug designs.

Lead compounds having calpain modulating activity and efficacy in animal diabetic models are candidiate compounds for human clinical trials. Human clinical trials will necesitate further definition of optimal dosage, formulation and administration route. Human trials will further evaluate bioactivity, drug half-life, tissue specificity, toxicity and immunogenicity. Human trials will also define patient indications for treatment with calpain inhibitors as well as define combination therapies of calpain modulators with existing or new drugs aimed at treating diabetes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

"The Expert Committee on the Diagnosis and Classification of Diabetes Mellitus. Report of the expert committee on the diagnosis and classification of diabetes mellitus," *Diabetes Care,* 20:1183–1197, 1997.

Abbondanzo et al., *Breast Cancer Res. Treat.,* 16: 182 (#151), 1990.

Allred et al., *Breast Cancer Res. Treat.,* 16: 182(#149), 1990.

American Diabetes Association, "Economic consequences of diabetes mellitus in the U.S. in 1997," *Diabetes Care,* 21:296–309, 1998.

An et al., *Proc. Amer. Assn. Canc. Res.,* 36: 82, 1995.

Antibodies: A Laboratory Manual., Cold Spring Harbor Laboratory, Cold Spring Harbor Press, Cold Spring Harbor, N.Y., 1988.

Aoki et al., FEBS Letters 205:313–317, 1986.

Baetens et al., *Diabetes,* 27(1):1–7, 1978.

Baichwal and Sugden, In: Kucherlapati R, ed. Gene transfer. New York: Plenum Press, pp. 117–148, 1986.

Barnes and Hodgkin, *EMBO J.,* 15:4477–4484, 1996.

Barrett et al., *Biochem J.,* 201:189–198, 1982.

Bellus, *J. Macromol. Sci. Pure Appl. Chem,* A31(1): 1355–1376, 1994.

Benvenisty and Neshif, *Proc. Nat'l Acad. Sci. USA,* 83:9551–9555, 1986.

Bittner et al., *Methods in Enzymol,* 153:516–544, 1987.

Broman et al., *Am. J. Hum. Genet.,* 63:861–869, 1998.

Brown et al., *Breast Cancer Res. Treat.,* 16: 192(#191), 1990.

Brunning et al., *Cell,* 88:561–572, 1997.

Burant et al., *Am. J. Physiol.,* 247(5 Pt 1):E657–66, 1984.

Capaldi et al., *Biochem. Biophys. Res. Comm.,* 76:425, 1977

Carafoli and Molinari, *Biochem. Biophys. Res. Commun.*, 247:193–203, 1998.
Chen and Okayama, *Mol. Cell Biol.*, 7:2745–2752, 1987.
Chen et al. *Genes & Dev.*, 8:2466–2477 (1994).
Chen et al., *Proc. Am. Urol. Assn.*, 153: 267A, 1995.
Ciccarese et al., *Diabetologia*, 40:1366–1367, 1997.
Colberre-Garapin et al., *J. Mol. Biol.*, 150: 1, 1981.
Coleman, *Science*, 203(4381):663–5, 1979.
Cotton, R. G. H., *Biochem J.*, 263:1–10 (1989).
Cox, et al., *Diabetes*, 41:401–407, 1992.
Davey et al., EPO No. 329 822.
Davies et al., *Nature*, 371:130–136, 1994.
Dear et al., *Genomics*, 45:175–184, 1997.
DeLuca et al., Biochim. Biophys. Acta 1216:81–83, 1993.
Donahue et al., *J. Biol. Chem.*, 269: 8604–8609, 1994.
Dubensky et al., *Proc. Nat'l Acad. Sci. USA*, 81:7529–7533, 1984.
Dukes et al., *J. Biol. Chem.*, 273(38):24457–64, 1998.
Ellis, L. A. et al., *Nucleic Acids Res.*, 22:2710–2711 (1994).
Emori et al., *Proc. Natl. Acad. Sci. USA* 84:3590–3594, 1987.
EPA No. 320 308
Fajans, et al., *Life Sci.*, 55:413–422, 1994.
Fajans, S. S., *Diab./Metab. Rev.* 5, 579–606 (1989).
Fechheimer et al., *Proc. Nat'l Acad. Sci. USA*, 84:8463–8467, 1987.
Ferkol et al., *FASEB J.*, 7:1081–1091, 1993.
Figueiredo-Pereira et al., *J Neurochem*, 62:1989–94, 1994.
Flexner, "HIV-protease inhibitors," *N. Engl. J. Med.*, 338:1281–1292, 1998.
Fraley et al., *Proc. Natl. Acad. Sci. USA*, 76:3348–3352, 1979.
Freifelder, *Physical Biochemistry Applications to Biochemistry and Molecular Biology*, 2nd ed. Wm. Freeman and Co., New York, N.Y., 1982.
Freshner, Second Edition, Oxford/New York, IRL Press, Oxford University Press, 1992.
Friedman et al., *Am. J. Physiol.*, 261(6 Pt 1):E782–8, 1991
Froguel, et al., *N. Engl. J. Med.*, 328:697–702, 1993.
Frohman, M. A., In: *PCR PROTOCOLS: A GUIDE TO METHODS AND APPLICATIONS*, Academic Press, N.Y., 1990
Gefter et al., *Somatic Cell Genet.*, 3: 231–236, 1977.
Ghosh and Bachhawat, In: Wu G. and C. Wu ed. Liver diseases, targeted diagnosis and therapy using specific receptors and ligands. New York: Marcel Dekker, pp. 87–104, 1991.
Ghosh et al., *J. Clin. Invest.*, 102:704–709, 1998.
Gibbs, and Caskey, *Science* 236: 303–305 (1987).
Gingeras et al., PCT Application WO 88/10315.
Goding, 1986, In Monoclonal Antibodies: Principles and Practice, 2d ed., Orlando, Fla., Academic Press, 1986, pp. 60–61, 65–66, and 71–74.
Gopal., *Mol Cell Biol*, 5:1188–1190, 1985.
Graham and van der Eb, *Virology*, 52:456–467, 1973.
Hanada et al. in: Proteinase Inhibitors: Medical and biological aspects, Katunuma et al., editors, Springer Verlaag, Berlin, pp. 25–36, 1983.
Hani et al., *Diabetes*, 46:1225–1226, 1997.
Hanis et al., *Nature Genet.*, 13:161–166, 1996.
Harland and Weintraub, *J. Cell Biol.*, 101:1094–1099, 1985.
Harris et al., *Diabetes Care*, 15(7):815–819, 1992.
Hashida et al., *J. Biochem*, 88:1805–1811, 1980.
Hashimoto et al., *Nature*, 371:161–164, 1994.
Hess et al., *J. Adv. Enzyme Reg.*, 7:149, 1968.
Hitzeman et al., *J. Biol. Chem.*, 255:2073, 1980.
Holland et al., *Biochemistry*, 17:4900, 1978.
Horikawa et al., *Nature Genet.*, 17:384–385, 1997.
Imajoh et al., *FEBS Lett.* 187:47–50, 1984.
Innis et al., *PCR Protocols*, Academic Press, Inc., San Diego Calif., 1990.
Inouye et al., *Nucleic Acids Res.*, 13: 3101–3109, 1985.
Ishiura et al., *Biochem. Biophys. Acta* 701:216–223, 1982.
Iwasaki, et al., *Diabetes*, 46:IN PRESS, 1997.
Jackson et al., *Nature Genet.*, 16:303–306, 1997.
Johnson et al., in *BIOTECHNOLOGY AND PHARMACY*, Pezzuto et al., Eds., Chapman and Hall, New York, 1993
Jones, *Genetics*, 85: 12, 1977.
Kaneda et al., *Science*, 243:375–378, 1989.
Kato et al., *J. Biol. Chem.*, 266:3361–3364, 1991.
King et al., *Diabetes Care*, 21:1414–1431, 1998.
Kingsman et al., *Gene*, 7: 141, 1979.
Klein et al., *Nature*, 327:70–73, 1987.
Kohler and Milstein, *Eur. J. Immunol.*, 6:511–519, 1976.
Kohler and Milstein, *Nature*, 256:495–497, 1975.
Kong and Cox, *Am. J. Hum. Genet.*, 61:1179–1188, 1997.
Kozak, *Mammalian Genome*, 7:563–574, 1996.
Kruglyak et al., *Am. J. Hum. Genet.*, 58:1347–1363, 1996.
Kwoh et al., *Proc. Nat. Acad. Sci. USA*, 86: 1173, 1989.
Kyte and Doolittle, *J. Mol Biol.*, 157(1):105–132, 1982.
Lander and Kruglyak, *Nature Genet.*, 11:241–247, 1995.
Lernmark and Ott, *Nature Genet.*, 19:213–214, 1998.
Liang and Pardee, *Science*, 257: 967–971, 1992.
Lishanski et al., *Proc. Nat'l. Acad. Sci USA.*, 91:2674–2678 (1994).
Lowry et al., *Cell*, 22: 817, 1980.
Maassen and Kadowaki, *Diabetologia*, 39:375–382, 1996.
Mahtani et al., *Nature Genet.*, 14:90–94, 1996.
Mehdi, *Trends Biochem. Sci.*, 16:150–153, 1991.
Melton, et al., *Nucleic Acids Res.*, 12:7035–7056, (1984).
Menzel, et al., *Diabetes*, 44:1408–1413, 1995.
Miller et al., PCT Application WO 89/06700.
Mok et al., *Gynecol. Oncol.*, 52: 247–252, 1994.
Mulligan et al., *Proc. Nat'l Acad. Sci. USA*, 78: 2072, 1981.
Myers and Maniatis in U.S. Pat. No. 4,946,733.
Myers and Maniatis, *Cold Spring Harbor Symposium on Quantitative Biology*, Vo. LI, pp. 18275–18284 (1986)
Myers and Maniatis, *Science*, 230:1242–1246 (1985).
Naggert et al., *Nature Genet.*, 10:135–141, 1995.
Nakamura et al., In: *Handbook of Experimental Immunology* (4th Ed.), Weir, E., Herzenberg, L. A., Blackwell, C., Herzenberg, L. (eds). Vol. 1, Chapter 27, Blackwell Scientific Publ., Oxford, 1987.
Nakamura et al., *J. Biochem.* 96:1399–1407, 1984.
Nakamura et al., *J. Biochem.* 98:757–765, 1985.
Nicolas & Rubenstein, In: *Vectors: A survey of molecular cloning vectors and their uses*, Rodriguez & Denhardt (eds.), Stoneham: Butterworth, pp. 493–513, 1988.
Nicolau and Sene, *Biochem. Biophys. Acta*, 721:185–190, 1982.
Nicolau et al., *Methods Enzymol.*, 149:157–176, 1987.
O'Dowd et al., *Genomics*, 47:310–313, 1998.
O'Hare et al., *Proc. Nat'l Acad. Sci. USA*, 78: 1527, 1981.
Ohara et al., *Proc. Nat'l Acad. Sci. USA*, 86: 5673–5677, 1989.
Otsuka et al., *J. Biol Chem.* 262:5839–5851, 1987.
Ott, *Proc. Natl. Acad. Sci. USA*, 86:4175–4178, 1989.
PCT Application No. PCT/US87/00880.
PCT Application No. PCT/US89/01025.
PCT Application No. WO 88/10315.
Perales et al., *Proc. Natl. Acad. Sci. USA*, 91:4086–4090, 1994.
Pontoglio et at., *J. Clin. Inves.* 101(10):2215–22, 1998.
Posmantur et al., *Neuroscience*, 77:875–88, 1997.

Potter et al., *Proc. Nat'l Acad. Sci. USA,* 81:7161–7165, 1984.
Pratley et al., *J. Clin. Invest.,* 101:1757–1764, 1998.
Remington's Pharmaceutical Sciences 15$^{th}$ Edition, pages 1035–1038 and 1570–1580.
Rich, "Inhibitors of cysteine proteinases," in Protease Inhibitors, A. J. Barrett and G. Salversen, Eds., Elsevier, New York, pp153–178, 1986.
Richard et al., *Cell,* 81:27–40, 1995.
Ridgeway, In: Rodriguez R L, Denhardt D T, ed. Vectors: A survey of molecular cloning vectors and their uses. Stoneham: Butterworth, pp. 467–492, 1988.
Rippe et al., *Mol. Cell Biol.,* 10:689–695, 1990.
Rodbell, *J. Biol. Chem.,* 239:375–380, 1964.
Rosser, Powers, Gores, *J. Biol. Chem.,* 268:23593–23600, 1993.
Rothschild, et al., *Am. J. Hum. Genet.,* 52:110–23, 1993.
Sager et al., *FASEB J.,* 7: 964–970, 1993.
Saido et al., *FASEB J.,* 8:814–822, 1994.
Sambrook et al., *Molecular Cloning: A Laboratory Manual.,* 2d Ed., Cold Spring Harbor Laboratory Press, Cold Spring Harbor, N.Y., 1989.
Scheibel et al., "Protease inhibitors and antimalarial effects," In: Malaria and the Red Cell, Progress in Clinical and Biolgoical Research, Alan R. Liss, Inc., NY, pp. 131–142, 1984.
Sharma et al., *J. Biol Chem.* 267:5731–5734, 1992.
Sherwood et al., *Proc. Natl. Acad. Sci. U.S.A.* 90:3353–3357, 1993.
Smith et al., *Mol. Cell. Endocrinol.,* 122:81–92, 1996.
Spielman and Ewens, *Am. J. Hum. Genet.,* 62:450–458, 1998.
Sreenan et al., *Diabetes,* 47:1881–1888, 1998.
Steiner et al., In: *The Metabolic and Molecular Bases of inherited Disease,* Scriver, Beaudet, Sly, Valle (Eds.), McGraw-Hill, Inc., New York, pp 897–904, 1995.
Stinchcomb et al., *Nature,* 282: 39, 1979.
Stoffers et al., *Nature Genet.,* 17:138–139, 1997.
Suarez et al., In: *Generic Approaches to Mental Disorders,* Gershon and Cloninger (Eds.), American Psychiatric Press, Inc., London England, 1994.
Szybalska et al., *Proc. Nat'l Acad. Sci. USA,* 48: 2026, 1962.
Takahashi-Nakamura et al., *J. Biochem.* 90:1583–1589, 1981.
Takano et al., *J. Biochem.* 235:97–102, 1986.
Takano et al., *J. Biochem.* 235:97–102, 1986.
Taylor, In: *The Metabolic and Molecular Bases of Inherited Disease,* Scriver, Beaudet, Sly, Valle (Eds.), McGraw-Hill, Inc., New York, pp 843–896, 1995.
Temin, In: *Gene Transfer,* Kucherlapati (ed.), New York: Plenum Press, pp. 149–188, 1986.
Terauchi et al., *J. Clin. Invest.,* 99(5):861–866, 1997.
Theophilus, et al., *Nucleic Acids Research,* 17:(19):7707–7722, 1989.
Thomas et al., *Hum. Genet.,* 101:212–213, 1997.
Tschemper et al., *Gene,* 10: 157, 1980.
Tsujinaka et al., "Synthesis of a new cell penetrating calpain inhibitor calpeptin," *Biochem. and Biophys. Res. Comm.,* 153(3): 1201–1208, 1988.
Tur-Kaspa et al., *Mol. Cell Biol.,* 6:716–718, 1986.
Ueda et al., *Int. J. Biochem. Cell Biol.,* 30:679–94, 1998.
U.S. Pat. No. 3,817,837
U.S. Pat. No. 3,850,752
U.S. Pat. No. 3,939,350
U.S. Pat. No. 3,996,345
U.S. Pat. No. 4,215,051
U.S. Pat. No. 4,275,149
U.S. Pat. No. 4,277,437
U.S. Pat. No. 4,366,241
U.S. Pat. No. 4,554,101
U.S. Pat. No. 4,683,195
U.S. Pat. No. 4,683,202
U.S. Pat. No. 4,800,159
U.S. Pat. No. 4,883,750
U.S. Pat. No. 4,946,773
U.S. Pat. No. 4,946,773
U.S. Pat. No. 4,946,773
Umezawa, Methods in Enzymology, 45:678–695, 1976.
Velei et al., *J. Bio. Chem.,* 272(41):25802–08, 1997.
Villa et al., *J. Cell. Sci.,* 111:713–22, 1998.
Vionnet et al., *Nature,* 356:721–722, 1992.
Wagner et al., *Science,* 260:1510–1513, 1993.
Wagner et al., *Science,* 260:1510–1513, 1990.
Walker et al., *Proc. Nat'l Acad. Sci. USA* 89:392–396, 1992.
Wang, Yuen, *Trends Pharmacol. Sci.* 15:412–419, 1994.
Watson et al., *Cancer Res.,* 54: 4598–4602, 1994.
Waxman et al., *J. Biol. Chem.* 253:5888–5891, 1978.
Welsh et al., *Nucleic Acids Res.,* 20: 4965–4970, 1992.
WHO Study Group on Diabetes Mellitus, *Technical Report Series* 727, World Health Organization, Geneva, 1985.
Wigler et al., *Cell,* 11: 223, 1977.
Wigler et al., *Proc. Nat'l Acad. Sci. USA,* 77: 3567, 1980.
Winter and Perucho, *Proc. Nat'l Acad. Sci USA,* 82:7575–7579 (1985).
WO 84/03564
WO 98/11254
Wong et al., *Gene,* 10:87–94, 1980.
Wong et al., *Int. J. Oncol.,* 3: 13–17, 1993.
Wu and Wu, *Adv. Drug Delivery Rev.,* 12:159–167, 1993.
Wu and Wu, *Biochemistry,* 27:887–892, 1988.
Wu and Wu, *J. Biol. Chem.,* 262:4429–4432, 1987.
Wu et al., *Genomics,* 4: 560, 1989.
Yamagata et al., *Nature,* 384:455–458, 1996a.
Yamagata et al., *Nature,* 384:458–460, 1996b.
Yamato et al., *Biochem. Biophys. Res. Comm.* 115:715–721, 1983.
Yang et al., *Proc. Nat'l Acad. Sci. USA,* 87:9568–9572, 1990.
Zelenin et al., *FEBS Lett.,* 280:94–96, 1991.
Zhou, Priestman, Randle, Grill, *Am. J. Physiol.,* 270:E988–E994, 1996.
Zimmerman et al., *Biochem. Biophys. Acta.,* 1078:192–198, 1991.
Zimmerman et al., *Cell. Calcium,* 18:1–8, 1995.

What is claimed is:

1. An isolated and purified polynucleotide comprising a region encoding human calpain 10a, human calpain 10b, human calpain 10c, human calpain 10d, human calpain 10e, human calpain 10f, human calpain 10g, human calpain 10h, or mouse calpain 10.

2. The polynucleotide of claim 1, further defined as comprising a region encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

3. The polynucleotide of claim 2, further defined as comprising a region encoding an amino acid sequence as set forth in SEQ ID NO:2.

4. The polynucleotide of claim 2, further defined as comprising a region encoding an amino acid sequence as set forth in SEQ ID NO:4.

5. The polynucleotide of claim 2, further defined as comprising a region encoding an amino acid sequence as set forth in SEQ ID NO:6.

6. The polynucleotide of claim 2, further defined as comprising a region encoding an amino acid sequence as set forth in SEQ ID NO:8.

7. The polynucleotide of claim 2, further defined as comprising a region encoding an amino acid sequence as set forth in SEQ ID NO:10.

8. The polynucleotide of claim 2, further defined as comprising a region encoding an amino acid sequence as set forth in SEQ ID NO:12.

9. The polynucleotide of claim 2, further defined as comprising a region encoding an amino acid sequence as set forth in SEQ ID NO:14.

10. The polynucleotide of claim 2, further defined as comprising a region encoding an amino acid sequence as set forth in SEQ ID NO:16.

11. The polynucleotide of claim 2, further defined as comprising a region encoding an amino acid sequence as set forth in SEQ ID NO:18.

12. The polynucleotide of claim 2, wherein the region has the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19.

13. The polynucleotide of claim 12, wherein the region has the sequence of SEQ ID NO:1.

14. The polynucleotide of claim 12, wherein the region has the sequence of SEQ ID NO:3.

15. The polynucleotide of claim 12, wherein the region has the sequence of SEQ ID NO:5.

16. The polynucleotide of claim 12, wherein the region has the sequence of SEQ ID NO:7.

17. The polynucleotide of claim 12, wherein the region has the sequence of SEQ ID NO:9.

18. The polynucleotide of claim 12, wherein the region has the sequence of SEQ ID NO:11.

19. The polynucleotide of claim 12, wherein the region has the sequence of SEQ ID NO:13.

20. The polynucleotide of claim 12, wherein the region has the sequence of SEQ ID NO:15.

21. The polynucleotide of claim 12, wherein the region has the sequence of SEQ ID NO:17.

22. The polynucleotide of claim 12, wherein the region has the sequence of SEQ ID NO:19.

23. A vector comprising a polynucleotide that encodes human calpain 10a, human calpain 10b, human calpain 10c, human calpain 10d, human calpain 10e, human calpain 10f, human calpain 10g, human calpain 10h, or mouse calpain 10.

24. The vector of claim 23, further defined as comprising a region encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

25. The vector of claim 24, wherein the region has the sequence of SEQ ED NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19.

26. The vector of claim 25, wherein the region has the sequence of SEQ ID NO:1.

27. The vector of claim 25, wherein the region has the sequence of SEQ ID NO:3.

28. The vector of claim 25, wherein the region has the sequence of SEQ ID NO:5.

29. The vector of claim 25, wherein the region has the sequence of SEQ ID NO:7.

30. The vector of claim 25, wherein the region has the sequence of SEQ ID NO:9.

31. The vector of claim 25, wherein the region has the sequence of SEQ ID NO:11.

32. The vector of claim 25, wherein the region has the sequence of SEQ ID NO:13.

33. The vector of claim 25, wherein the region has the sequence of SEQ ID NO:15.

34. The vector of claim 25, wherein the region has the sequence of SEQ ID NO:17.

35. The vector of claim 25, wherein the region has the sequence of SEQ ID NO:19.

36. The vector of claim 23, further comprising a promoter.

37. The vector of claim 23, wherein the vector is a viral vector.

38. The vector of claim 23, wherein the vector is a retroviral vector.

39. The vector of claim 23, wherein the vector is a plasmid.

40. A recombinant host cell comprising a polynucleotide that encodes human calpain 10a, human calpain 10b, human calpain 10c, human calpain 10d, human calpain 10e, human calpain 10f, human calpain 10g, human calpain 10h, or mouse calpain 10.

41. The recombinant host cell of claim 40, further defined as comprising a region encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

42. The recombinant host cell of claim 41, wherein the region has the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19.

43. The recombinant host cell of claim 42, wherein the region has the sequence of SEQ ID NO:1.

44. The recombinant host cell of claim 42, wherein the region has the sequence of SEQ ID NO:3.

45. The recombinant host cell of claim 42, wherein the region has the sequence of SEQ ID NO:5.

46. The recombinant host cell of claim 42, wherein the region has the sequence of SEQ ID NO:7.

47. The recombinant host cell of claim 42, wherein the region has the sequence of SEQ ID NO:9.

48. The recombinant host cell of claim 42, wherein the region has the sequence of SEQ ID NO:11.

49. The recombinant host cell of claim 42, wherein the region has the sequence of SEQ ID NO:13.

50. The recombinant host cell of claim 42, wherein the region has the sequence of SEQ ID NO:15.

51. The recombinant host cell of claim 42, wherein the region has the sequence of SEQ ID NO:17.

52. The recombinant host cell of claim 42, wherein the region has the sequence of SEQ ID NO:19.

53. The recombinant host cell of claim 40 wherein the host cell is further defined as a prokaryotic cell.

54. The recombinant host cell of claim 40, wherein the host cell is a eukaryotic cell.

55. The recombinant host cell of claim 54, wherein the host cell is a mammalian cell.

56. The recombinant host cell of claim 55, wherein the host cell is a human cell.

57. A method of obtaining a human calpain 10a, human calpain 10b, human calpain 10c, human calpain 10d, human calpain 10e, human calpain 10f, human calpain 10g, human calpain 10h, or mouse calpain 10 polypeptide comprising:
   a) obtaining a polynucleotide comprising a region encoding a human calpain 10a, human calpain 10b, human calpain 10c, human calpain 10d, human calpain 10e, human calpain 10f, human calpain 10g, human calpain 10h, or mouse calpain 10;
   b) inserting the polynucleotide into a host cell; and
   c) culturing the host cell under conditions sufficient to allow production of the human calpain 10a, human calpain 10b, human calpain 10c, human calpain 10d, human calpain 10e, human calpain 10f, human calpain 10g, human calpain 10h, or mouse calpain 10 polypeptide;
wherein a human calpain 10a, human calpain 10b, human calpain 10c, human calpain 10d, human calpain 10e, human calpain 10f, human calpain 10g, human calpain 10h, or mouse calpain 10 polypeptide is thereby obtained.

58. The method of claim 57, further comprising the step of isolating the human calpain 10a, human calpain 10b, human calpain 10c, human calpain 10d, human calpain 10e, human calpain 10f, human calpain 10g, human calpain 10h, or mouse calpain 10 polypeptide from the host cell.

59. The method of claim 57, wherein the polynucleotide is further defined as comprising a region encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

60. The method of claim 57, wherein the polynucleotide is further defined as comprising a region encoding an amino acid sequence as set forth in SEQ ID NO:2.

61. The method of claim 57, wherein the polynucleotide is further defined as comprising a region encoding an amino acid sequence as set forth in SEQ ID NO:4.

62. The method of claim 57, wherein the polynucleotide is further defined as comprising a region encoding an amino acid sequence as set forth in SEQ ID NO:6.

63. The method of claim 57, wherein the polynucleotide is further defined as comprising a region encoding an amino acid sequence as set forth in SEQ ID NO:8.

64. The method of claim 57, wherein the polynucleotide is further defined as comprising a region encoding an amino acid sequence as set forth in SEQ ID NO:10.

65. The method of claim 57, wherein the polynucleotide is further defined as comprising a region encoding an amino acid sequence as set forth in SEQ ID NO:12.

66. The method of claim 57, wherein the polynucleotide is further defined as comprising a region encoding an amino acid sequence as set forth in SEQ ID NO:14.

67. The method of claim 57, wherein the polynucleotide is further defined as comprising a region encoding an amino acid sequence as set forth in SEQ ID NO:16.

68. The method of claim 57, wherein the polynucleotide is further defined as comprising a region encoding an amino acid sequence as set forth in SEQ ID NO:18.

69. The method of claim 57, wherein the region has the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19.

70. The method of claim 69, wherein the region has the sequence of SEQ ID NO:1.

71. The method of claim 69, wherein the region has the sequence of SEQ ID NO:3.

72. The method of claim 69, wherein the region has the sequence of SEQ ID NO:5.

73. The method of claim 69, wherein the region has the sequence of SEQ ID NO:7.

74. The method of claim 69, wherein the region has the sequence of SEQ ID NO:9.

75. The method of claim 69, wherein the region has the sequence of SEQ ID NO:11.

76. The method of claim 69, wherein the region has the sequence of SEQ ID NO:13.

77. The method of claim 69, wherein the region has the sequence of SEQ ID NO:15.

78. The method of claim 69, wherein the region has the sequence of SEQ ID NO:17.

79. The method of claim 69, wherein the region has the sequence of SEQ ID NO:19.

80. The method of claim 57, wherein the polynucleotide is comprised in a vector.

81. The method of claim 80, wherein the vector comprises a promoter.

82. The method of claim 80, wherein the vector is a viral vector.

83. The method of claim 80, wherein the vector is a retroviral vector.

84. The method of claim 80, wherein the vector is a plasmid.

85. The method of claim 57, wherein the host cell is further defined as a prokaryotic cell.

86. The method of claim 57, wherein the host cell is a eukaryotic cell.

87. The method of claim 86, wherein the host cell is a mammalian cell.

88. The method of claim 87, wherein the host cell is a human cell.

* * * * *

UNITED STATES PATENT AND TRADEMARK OFFICE
CERTIFICATE OF CORRECTION

PATENT NO. : 6,235,481 B1  Page 1 of 1
DATED : May 22, 2001
INVENTOR(S) : Horikawa et al.

It is certified that error appears in the above-identified patent and that said Letters Patent is hereby corrected as shown below:

Title page,
Item [73], Assignees, please delete "ARCH Development Corporation & Board of Regents, Chicago, IL (US); The University of Texas System, Austin, TX (US)" and insert -- ARCH Development Corporation, Chicago, IL (US); Board of Regents, The University of Texas System, Austin, TX (US) -- therefor.

Column 209,
Line 17, please delete "SEQ ED NO:1" and insert -- SEQ ID NO:1 -- therefor.

Column 210,
Lines 53, 56, 59, 62 and 65, please delete "claim 57" and insert -- claim 59 -- therefor.

Column 211,
Lines 1, 4, 7, 11 and 13, please delete "claim 57" and insert -- claim 59 -- therefor.

Signed and Sealed this

Twenty-sixth Day of November, 2002

*Attest:*

*Attesting Officer*

JAMES E. ROGAN
*Director of the United States Patent and Trademark Office*

SEQUENCE LISTING

<160> NUMBER OF SEQ ID NOS: 30

<210> SEQ ID NO 1
<211> LENGTH: 49136
<212> TYPE: DNA

<213> ORGANISM: Human

<400> SEQUENCE: 1

| | | | | | |
|---|---|---|---|---|---|
| ctgcagaaaa | acagcttcaa | tgtgaccatc | cttgatagtc | cgaggctgag | taaaatggcc | 60 |
| tgaggaggca | aaatctgaaa | agctctatta | ggtggcaaac | tgctgtcact | agaagagttg | 120 |
| aggccccctt | ctcctcccct | gcctgaccgc | cttcattcct | gggaatggaa | caggttcttg | 180 |
| ggcaagggt | gaatcctcga | gcaggtccca | ggatcactat | cctcacctcc | ccgcggcact | 240 |
| gaatggctat | agctgtaaat | gtgcgtccac | ggggtcactg | tccagccacc | aggaccaggt | 300 |
| gcctggccat | ctggggaatc | ggaaaacgct | cagcgggatg | ctctggccac | ctcccctgcc | 360 |
| ctcagttaag | atgtagagcg | ttcaacctaa | aatgcctaga | aacaaagccc | aggcccggga | 420 |
| aggtcgaacg | agtgcgacgc | cgctccctca | agctcttccc | tcggagccgt | ctcatttccc | 480 |
| aaaactccca | acacatcac | agagagaggt | gttgagccag | gtggtcactc | ccttttccag | 540 |
| aaccacagca | agaagttgag | cctgctgggc | tcctaacgaa | ggccctgggg | cccggtggga | 600 |
| tgaaaagccc | tattaggtag | caaacagctg | tcactagagg | ggttgaggcc | ccttctccc | 660 |
| ctgcctgacg | acgacggcgg | caggaactcg | accggcgccg | gacagctcgc | aacttgcctt | 720 |
| accaagcgta | aatctcggtt | cctcccaact | acccgcggcc | acggcctccg | cagcagagcg | 780 |
| ccggaagcag | agacgcgttt | cgggaggaag | gtgcatgctg | ggagcggcgg | cgcatgctgg | 840 |
| gagctgtagt | ctgcgacgca | actcggccga | ggtggctccc | tggtccctga | agctcccaga | 900 |
| gcccgcgtgt | tcaggcggtc | ccgacacccc | ggcccgagcc | tcaccggctg | gaggactgaa | 960 |
| cgcctgccgg | ccctccgggt | atgagcgag | gccgggatag | ccctgggctc | cgccgccccc | 1020 |
| ggaaggaaaa | aatacagtgc | ggtccgccgc | ccgaccacga | aagagcggag | ctcgggagcc | 1080 |
| ccgcccctg | ggcctccgac | gtccgtggcg | ctttccgtcg | cgcgagtgcg | attgggccgc | 1140 |
| ctgtcacgtg | acccgagacc | ccacgcccgg | ttggctgccg | cctggttacc | aatgggagac | 1200 |
| tagcgggccg | gcgtactggc | ctggtccagc | acctgcgggg | ccctcgggct | tggagggctg | 1260 |
| ggccgggcg | ggaacgggcg | gggcgggccg | gaggcggcgg | cggctgactc | gccttctctc | 1320 |
| cggggctgcg | accccgaggc | aaccggctgc | agatgggagc | ccgcggagcc | gaggatgcgg | 1380 |
| gcgggccggg | gcgcgacgcc | ggcgagggag | ctgttccggg | acgccgcctt | ccccgccgcg | 1440 |
| gactcctcgc | tcttctgcga | cttgtctacg | ccgctggccc | agttccgcga | ggacatcacg | 1500 |
| tggaggcggc | cccaggtggg | gccgtgtggg | gtgcggtggg | cgccgtttct | ggtttctgag | 1560 |
| atctccgctc | ctcgcaggga | gcggggcggg | gtgggcggcc | agggtagctc | cgaacgcagg | 1620 |
| gtccgccgtt | gttctcctca | gaagtgggcg | cccggccccc | tcttttcgta | cctccttcat | 1680 |
| accccgccc | agaacgagca | ggactcggcg | ctaccctaag | gacgctaaac | taggtcgtgg | 1740 |
| cctccgcctg | cgagagctcc | aatccaggag | gctcagagcg | ctgcgagagg | cgttttaaca | 1800 |
| gagccccaaa | acccgcccc | acctgtttgc | tttcgccctg | aagagcgttt | gtgtctgctc | 1860 |
| ctcccgcaga | gagggccgct | cgtgcccctc | tgaagtggct | aggccgagcc | cacaaagcaa | 1920 |
| agcgtgatag | aatttcagtt | ttggattttg | tgcacctgcc | tttccagttg | taacacctag | 1980 |
| aaatggcacc | tccaagggat | gccctggccg | agtgctgtgt | tcatattttt | agaaatggtt | 2040 |
| tatctgctga | ataagactgc | ccaagggagc | aaccttgccc | taagtggatg | cggtcttagc | 2100 |
| ggagacaact | gatggccgcc | agtcttcgaa | cagagctgga | acttctgggc | tctcgtgact | 2160 |
| gagatggctt | tgacaggcca | cctggtttcc | ttggacaaca | ctgaagggcc | tgggaggagg | 2220 |
| caagggtcag | accatgtaga | gccttgtcat | tggaatttgg | gttttatttt | gttaaaagat | 2280 |

```
tgattttagg tgcagctgga ggccactaga gggttttggt agaggagtgg ttctcttgga    2340
tgtgtgtttt tacaagctca ctcttgctgc tgggtgggaa gtgggttgtc ggggcaagaa    2400
tgcaagggtc cattgtagtg gtcctggaga aagatgaagg ggctcagatt agcttgacga    2460
ctgttaggat gtgggtttgg agtagattgg tttgagacgt accttgcagg ggggatcgag    2520
aggccatagt gactgattga aatagagggt gaggatagtg gagggatcaa catgccttct    2580
gggtttctgg cctgaacagg tgggtggatg gtggtcctgg acagagcct gggggtgacc     2640 tagagttggg ctttgctctc acgtcttcag gtggagctgt cctggaggca ggtggatctg    2700
tcctggaggc aggtggatac ggagcaggga taggctagag gcattcttct gggaggcgga    2760
gcatattaga tggtttacag tccacagcct gggagagtgt ctcgggggag tatcagtaaa    2820
gaagaagggg gccttgggc tgagccttga ggaaccctaa catttcttgg ggtcaggcag     2880
gtgccctgac agatagactt gagaagcagc aggcagtgag ggagaggaca cccgggagc    2940 atgcggcctc acagaagctg aagtggggac cacctcaggg gcagcagatg gctgttctgc   3000
tgttgtgaat gctgctgagt agttgggaa gagagttggg accaagagaa gcccagtggg    3060
tttgataaca tagaggtgac agcgacattg atcgaggcag tttaggggcc atgattggct   3120
cagaagctag aggagcctgt gtggagagtg aatgggaagc aggtagtggg catggcagct   3180
ctttcaagag ctgtaatgaa gagaagcctg aaggagacta tggtgctgag agataatgtc   3240
ttaaagaaca tggggtggg attctgcccg gggagctgga agggaaggag ttgtgagagg    3300
agcccaggct ctgagggcag gagagagggt caggtccaga agcaggaggc aaggtcgaag   3360
ctcagagggg tgggcaaggg cagtgtggat gttttgagta gacggggaga aaggggaagg   3420
tatatgatag ttaggggggtg tgggaaatgg agcctgctag agaaacagta agatttccag  3480
caggatggag gacacatttg agatttacca gcatgagtaa aaagtgaaac ttttcgaagc   3540
caacatttag ctgttttgag aaggagcttg ctagagtttg ggattttcc agtaaggaag    3600 gaaggcaccc cagaattaag ctggacagag gcatttgaag ccaggagctg aaggacaccc   3660
gctgcaggaa accaccttcc tgtcccttt tgggtaacac tgatgatcgg aaaagctcca    3720
ccccaactcc tgtcatctag agccttgggt tcttagtttg aagggttcca cagcaggcat   3780
gatctaactc tggacaactt tctgtatctc aggagatttg tgccacaccc cggctgtttc   3840
cagatgaccc acgggaaggg caggtgaagc agggctgct gggggattgc tggttcctgt    3900
gtgcctgcgc cgcgctgcag aagagcaggc acctcctgga ccaggtgcgg ggccccttcc   3960
ctgtgtttgt cctggagccg gtttctttt gcgtttctcc agcctgctga gtaccaggag    4020
gccttgcgaa agcagagctg tgccgcagcc ggatctcctg ctgtgttggg ggaaggcagg   4080
agagttccaa ggcagaggct gaggactgca ctctgtccct ctgctgcagg ggggggtgcc   4140
ttggcctgcc agaaggctcc atcagggagg ttcgccctgc tctgtgctct cctgacccc     4200 ggactccatg gagtcagatc accacgttta gaataaagag acaaatgtgc cagctcacag   4260
gaggacgggg ctgctggca gcctctgcct cagatctctc ctcagctagc tcgctggttt    4320
tcttacaggt tttgaatata agtttgcaaa aagttattaa acctgtttct gtgggtagac   4380
agatactctg ggaggagaag gccttctcag gttttcctta cctgggagtg ttcaccgttt   4440
tatgcttggc ttgttgctaa gtgttgctga ttaatgcagc ggcgtcaaca gtgtgacctc   4500
attcagagtt tcactcatgt cccaggcccc atggtaagcg tgtcacagtc actggctttc   4560
agacacatgg tcttaccagc tttgactttt tttttaaacg agagtgctaa aatcactgcc   4620
```

-continued

```
attgtgtttc tggccgtaaa gtggcagagc caggaccgca ccaggtgccg gtgcccagcc    4680
tgcactcccc cgatgctggg tcagaatgct taccccctgaa ggagccctgc ggtggacgct    4740
gtgggtgcaa gcagctggcc cagagtcggg gcgccaggct cccagcagca ggagggggctg   4800 ctgttcctgt ggtgacgtgt tgcttgcagc cagctcggtc aagaactggg tcactcatgc    4860
ccttgaatgt cacatttgtt ttggcttcag gtcagatgct tttagtgagg gcagcagagt    4920
gtgtcccggg atatgtggct ccctcggtgt ggtcctcaag ttttgcaatg agaggtctgt    4980
taatttcatg tgggtgatgc agccctgtgc aggcgccgac atccaggtgt gccgtagagt    5040
tctctgcgac atccaggtgt gccgtagagt tctctgcgac atccaggtgt gccgtagagt    5100
tctctgcgac atccaggtgt gccgtagagt tctctgcgac atccaggtgt gcgttagagt    5160
tctctgcaga ccgcggtgcc tgtggagcac tcagctgtgg ccacaccgcg gccgggacac    5220
tggagtagcg ccggtggtg cttatatcac gctcgccttt tgcttctccc tgtgcatggc    5280
aggtcattcc tccgggacag ccgagctggg ccgaccagga gtaccggggc tccttcacct    5340
gtcgcatttg gcagtttgga cgctgggtgg aggtgaccac agatgaccgc ctgccgtgcc    5400
ttgcagggag actctgtttc tcccgctgcc agagggagga tgtgttctgg ctccccttac    5460
tggaaaaggt ctacgccaag tgcgtgtgct ggggctgaa gggcctggcc tggggcaagt    5520
gggagctgcc actaccatgg gctgcccag gagggtctct gctcactctg ggctgcagag    5580 ccccccttcag ttctgagggt ctggcagctc attctgtgag tcaggctgac aggccaggtg   5640
cagagattct tcttttgggc ctgtggattg cccactccct gctttccctt cccttgttcc    5700
aaagcccagc gtggagtcgt tctccacaga gaacatgtgt gccgtcctcc ttatttatc    5760 ggcccagca agaaagatgc ttctttatat ttgttgtgga atggttggga caggcagact    5820
cattgtgtag tcgttgggga ggagtgaggc tacccagca taccaacact tgtgtatcac    5880
ggtgcttgct ggctcagggg accaggaccc tcaccatgag tcataattga atagccttcc    5940
ctcttagaat gcatttgtct tcttgccaaa ggcaactgga ctgacaggca ggcagggaag    6000
ctggtgaaca tgggaaggct ggctggtgac atcagtgccc agtgagccct tccatcccaa    6060
gggctgtttt aggaaaagca gggttggagc ttgagagcca agggatgtgg gcatccatag    6120
cttccacgcc tcctgccctg ctcctgtgcc cacaccggat gccagagagt ttctgtgtgt    6180
gggcagagga ctgcagggcg ctcacgcttg ctgcgaagta aggcgtttga aggtgaggct    6240
aagccttgac ttggtgagga tgaggaagaa ggcagagggg agtaaagagg tgggattgag    6300
gcagcggttg gacgatttgg ggtgctacag accatgggaa tcagagaggg ggccatgctc    6360
aatgccagag gctcactccc atggtgattg tgtcccctag ggtccatggg tcctacgagc    6420
acctgtgggc cgggcaggtg gcggatgccc tggtggacct gaccggcggc ctggcagaaa    6480
gatggaacct gaagggcgta gcaggaagcg gaggccagca ggacaggcca ggccgctggg    6540
agcacaggac ttgtcggcag ctgctccacc tgaaggacca gtgtctgatc agctgctgcg    6600
tgctcagccc cagagcaggt gaggcacgtg ccaacatgg gagggctgca gccagcgtgc    6660
cccccactgc caggcctcag gcacactgta gcttttatg tgactggcta cacagccctg    6720
tcaggactaa gtgggaagaa gtaagcttgt tctcaagggt ggtgtcctca gtttgtgacc    6780
ttcccctgct gtcctcttcc agagggacgt ggcccttctc tcccctgacc agtcctttcc    6840
actagtgcga ggcaggaaga ggtggcaccg agtcaaagcc cactgtctgt gccatccctg    6900
gcccagctgg caacctggca aaatcaaaac ctgttttta ttttagtgat agataacatt    6960
cgttaaaaac agtttgtctc caaaaaatga aggggccag gtgtggtggc tcacacctgt    7020
```

```
aatcccagaa ctttgggagg ctgaggtggg agtatcgctg gagcccagga gttcaagaga   7080
cccgcctggg caacatggca agatctcatc tctacaaaaa atgaaggaaa aaaatcactt   7140
agatggaacc acatgtgact tttgagtgcg ctctcagttt tccatgagca cgcacggttt   7200
acgtgttccc ttccgcaccg cttctcacac tgccacacac gcgctgtcaa atgttcgccc   7260
catgagcggg tttgccacag tctcttaatc attccctga  tgttggatat taagatctct   7320
ctggttttat ataattataa gcagtatcaa tgaacatctt tatcattttt ttcatactta   7380
ggattatttt aaaatatggg ttaaagaata tgaatatcac agtaaactga aacaagttgt   7440
cataggcctt ggtctgggtc ccccataagc agaccctgag atgaggttca ggagcacgtt   7500
gagaggttca gagagcctgg agggcgtgta ctccccgcca gccccgctgg ggtgccagga   7560
aggacgctgg cctcagagcc tcccacctgg gagtgagggc gctggtctgg tgggcattag   7620
ctcggggagc tgttggtttt gggtgctcca gggtggggta gcgctaagtc ctagcacttc   7680
aggctttaga ggaagccccc aggcagagag agatggcagc tggcactgac tggaggtgca   7740
ttggagcctg ctgaggtggc aaggggccgc ggcgtgggcg agactgaagt ccttccagga   7800
gaccctcctc tctagaccgt tgccccgcca cagatgtggc cttcctctct gtttggctct   7860
ttcttttcta tgcccatctg tctcaaggtc tctggccagg tggagctgtt gcccccctgg   7920
gcctccatgc ctccagtggg cttctagcca gggcactatc tgaatgtcct acctctagca   7980
ggctttgcca agagaaacac tctctagatt tctggcagtt gcagatgcat ctgtgcagca   8040
tgtttgagaa ctggtgctgt gccaggcatc gtgcacagat gggtacggac gatgactgag   8100
gcctagagaa ggggatgact tacccagcac cagacccgga tggcagccga gtcaggcccc   8160
gtgtgcttgc tcctggagat gctcctgagc tgatgggtca cagctgctaa gaaaggagct   8220
ctcgtggtcc atgggatct   ggggtctccc gtgtagccat agtggggtgg gctggagcat   8280
ctccagagga ggaggcagag gcctgtgtgt ccttgtcagt ttgggactcc atggtgccct   8340
tcctgcctgt gcctgcgcca ttcctcatgc aggtgcccgg gagctggggg agttccatgc   8400
cttcattgtc tcggacctgc gggagctcca gggtcaggcg ggccagtgca tcctgctgct   8460
gcggatccag aacccctggg gccggcggtg ctggcagggg ctctggagag aggggtgagt   8520
gctggggcct ggaccatgct gctgtcggga gggggcccca gtgccagtct ggcctgtgtc   8580
ctggtcacct tcagctgtca ggactgtact tggctgtctc cagcaaggcc cctgagtccc   8640
tgctctcgtg acaccatgct tgtcttggct ccaggcaatc cttgtgaggc ctgggaccaa   8700
ggtggccatt gggcctgggg tttcaatagg gcagacatca tcacgggctc gggcagcagt   8760
cctgggaaga cgcatccaga ggcgtgaagt tcctctggga aaagagggg  ctccagggtg   8820 gccgctgccc agaaggccct gtgctgcaga gctgcttcgg gtgtgggagg gctgcagag   8880 ctggggcacg ggtcgctgg  caggaactca gggctctctg gtcccctcc  aggcttcccc   8940 ccagcctgcc ggcaagttga cactaccagt tctcgggagg ggcttctgct gagatgaggt   9000
ttcttccagg ggtgaagggt ggagccaggt agatgcagcg gtagcatctg agctcctgtc   9060
ccagctccag gaagggagt  tctgggtgga ggaggaggag ttcctcaggg agtttgacga   9120
gctcaccgtt ggctacccgg tcacggaggc cgccacctgc agagcctcta cacaggtagt   9180
gccccgaggg gctgtgctgg gcacgtgctc tgcctgccga agtgaggagg ctgggcacgg   9240
tgcctggggt ttccccctgc ccaggcccagtt tggttctctt cagcgtggag agatgattct   9300
gtcccaggag ccgggaggag ggtgatgatt ctgtcccagg agctggagg  agggtgggct   9360
```

-continued

```
tgtgggaggg gctggctctg tctgtggccg tagctgctgc ttagaccctg ccagggttca  9420
tgaggccacc gtggcgggag gccagcgagg agccgtgtcc cacagctgat gcctggtgtt  9480
ttctcactag agaggctgct ctgccatacg cgggcgctgc ctggggcctg ggtcaagggc  9540
cagtcagcat gaggctgccg gaacaacagc ggctttccca gcaacccaa attctggctg   9600
cgggtctcag aaccgagtga ggtgtacatt gccgtcctgc agagatccag gctgcacgcg  9660
gcggactggg caggccgggc ccgggcactg gtgggtgaca gtcatacttc gtggagccca  9720
gcgagcatcc cgggcaagca ctaccaggct gtgggtctgc acctctggaa ggtaactcag  9780
ccccgtctgg ctcacgctcg gttcagcagg tggtgtggag gcccatggag gtctgggttc  9840
taggactggc tctgccggga cacatgtgac tctgccacgg gccccaccag tctccccct   9900
ccttgggctg ttgcacgggg ttgacgtctg ctggtgctcc cagacccggc tctgacctga  9960
gactgcaggt ctttctgcct tgccgtgtgc ctcattggcc aaaggaaagc aacagagtct 10020
gcagccaggg caggacccgc aggaggggcc tggacccggg gggctcctgg cagcgccgtg 10080
cctttctgag gcaaggaggt agagccagcg gctgaggacc tgtcagggcc agtcccagct 10140
ctgcagcttg ctgtgtgacc tggcacacat cctctccctg cctccctcag tctcttcccc 10200
tgcaagacgg ggtcctgaca cggatctcat gggattgctc tgaggccag gcagtcccag  10260
gctcaaccac tggttcacaa agtgtgttgt ttccaggaag aacagatggg ggcgcctgag 10320
ggcaaagggc ctgagtgtgg tcgaggatat gccggctgct cgctcagggg ctgggttttc 10380
atcttgtgtg tcttgacagg gtgtgacact tggcaccaca ctgttccctg tcccttcatg 10440
gatgtggccc acatgatgtt cctttcctct tgcaaaagaa gttgctggaa ggcccactgt 10500
ccagcagccc ccaggttgcc tgggccacgg tgcctttgtg ggcccagcta caaggaggac 10560
ttgcaggctc gtgtctggga cagatactgg cgccagggcc aagtgaagcc cgggattggt 10620
gggcatctct agctggtccc tgagagaggg tggaggggtgc tgacaggcct ggcgctttc  10680
atctgtcaac tccagaggcc cttgtgcttg cagcagggag gtcaaggcca gggcgtctga 10740
ccccggccgc tcctccacac tgagcctcct gcacgtgctc acaggtagag aagcggcggg 10800
tcaatctgcc tagggtcctg tccatgcccc ccgtggctgg caccgtgtgc catgcatacg 10860
accgggaggt ccacctgcgt tgtgagctct caccgggcta ctacctggct gtccccagca 10920
ccttcctgaa ggacgcgcca ggggagttcc tgctccgagt cttctctacc gggcgagtct 10980
cccttaggtg agaggaaccg cgcagtgctg ctggctctcc gaggccacag gcccttccaa 11040
ggcaggattt gggcactttc cctctgtggt tggcaggtgt ccatgtggga actgaggcca 11100
ctgggaacct gctgccagcg ccctcccatg tttgtcttct tggcagcgcc atcagggcag 11160
tggccaagaa caccaccccc ggggcagccc tgcctgcggg ggagtggggg accgtgcagc 11220
tacggggttc ttgagagtc ggccagacgg cggggggcag caggaacttt gcctcatacc  11280
ccaccaaccc ctgcttcccc ttctcggtcc ccagggccc tggccccgc tgcgtccgca   11340
tcactctgca tcagcactgc cggccccagt acaccgagtt ccaccccatc ggcttccata 11400
tcttccaggc aagctccttg ccccagggag ggaggggag cagaagggc cctcagagaa   11460
tttgcatctt ggcctccatt gtcccaacag agggctctgg gctcagtcac ttgggctccc 11520
cctgcccttc gaggcgctgc ctagaaaccg cacagggccc tctcccatct ccaacctctc 11580
agaggcaagg ccgaagatgg cctctggaag ggcgggggc ctgggaggtg gcagggctg   11640
atccaggcag ggcaggtttc cagaggaggt ggtgagtggg aggaaggga gaagtttgga  11700
gaggacagga ggccgaggtt gagaccagcg ggggtgggtc gagccctggc ttgggaacgc 11760
```

```
aggggggctga tggactcagg agtgagagga ggggaggccc aggctggctg ccacagcag   11820 cccctcgggt gtgaggaagt ccacagtcac tgagctcagc cagcagcccc tgtccactta   11880
ccctgactca gaatgactgt gtcccaaggt tcattctctg cagacatgtg tccctggaa    11940 tgcaggggcc ctgacgagga aggcactgca accctcggtt cacagtgggc tgcctgggga   12000
cccttggacc ctcgctgttt gccctgggcc accggctcag gtcccctaga gctctgagga   12060
aaacacatgc cagggccagt gggagccctt ggggcgggct gggcagtcac aggtgttaaa   12120 gccctgatg atgtgacagg cctccaggcg ggggcccac tgccggcacc ttctggcaag    12180
ggtggccagg ccttggtgag gaggcgagtc cagtgtccag gcctggcagc ccctcctcag   12240 agaagggct gtatgtgact caagagggcc aagggcatcc gagcagatgg ccctgggctg    12300
ggctccctac cccaaggctg ccccctca gtctgagcct gcgctttcct caggtcccag     12360 aggtggaag gagccaggac gcaccccac tgctgctgca ggagccgctg ctgagctgcg    12420
tgccacatcg ctacgcccag gaggtgagcc ggctctgcct cctgctgcg ggcacctaca    12480 aggttgtgcc ctccacctac ctgccggaca cagagggggc cttcacagtg accatcgcaa   12540
ccaggattga caggtggggc tctgggactt gggggcggcc agctggaggc tggggtgctg   12600
gagtcttagt gctcgcctgt ccccccacgt ctcctgcctg ccctcaccc tcaagccccct   12660 atctgtcctg cagaccagg gctgtcctgc ctacctgggg acccttcctt gctggtctga    12720
gcctggaaga agagtctagt gggaggtggg ccaggagcac acagccactt gtgtgacaag   12780
tgcagtctgg gagcgctgat ctggtgtctc tccacaggcc atccattcac agccaggaga   12840
tgctgggcca gttcctccaa gaggtgtgta tgcagcccg ccagcccggc tcacctgcct    12900
ggggctgcct ggtggcctag gtctacctg caacctcagg caggtggttt ctgcctggga    12960
cgtgaggtgc ccttgactct tcctgtgaga gccccgggcg gtgccttgaa gggcaggggg   13020
agctgaggct gcgtcccatt ccctggctgc actcggggtg gggtgtgaga agggcgagt    13080 gccaccgctg cccgggcccc ccatctgtct ttgcaggtct ccgtcatggc agtgatgaaa    13140
acctaacagg gtggccccct gtgccagctc aggtgactgg agcccgaggg cctgacaggt   13200
tcccagcagc tgggccggcc agccttgcac tgtgggggct ggtcctgagt cttggcctgc   13260
ctcccagccc tgccaggggg ctgcggccta ggggtccacg ggaagcctcc gtcaggagag   13320
acgcagccct gggggccagc tggtgctgca aggaagggtg ggaagcttgc tggcttctgt   13380
tgcgccactg agacggcaga gaccccagga tcccagagct tcccaggatc cctcccagat   13440
cctctgctga ctccatatgg aggccccaca cccagagggt agggcagcag atcttctta    13500 taactattta ttgttcgaat cacttttagg atgtaacttt ataaataaac atgagcgctg   13560
atgatttgca gatcagtctt gctccaggta gttccaggct gtgcctgctc ttgccaagca   13620
ggctgtgggg agggctgggt gcctgccgag atggtgagga tgaggatggc ctctggaggg   13680 gctggggggcc tggaggtgg gcagagccaa cccaggcagg gcaggtttca ggggagatg     13740 gtgagtgggg aggagggggag aagtttggag gggcgggccc agggcatgcc ccaggccagg   13800
gggctgaggt tgaggctggc cgggggcaggt caagccctgg tcttggggga cacagactga   13860
tagactgggg agtgagggggt ggggagagcc agcgaaggca ctgccaaggc tgtggcgaag   13920
aaggacatct cggaaacggg tgttagaacc ggagttgcgc agagggagga acccaggttc   13980
acgtggactg ggagccttgg atctggacgg ctcctctgcc tccagccagg gttcacctgc   14040
gcagtgtcct gggattgttt atttccccag gcctctctcc ctcgtccctc acaccaaatg   14100
```

-continued

```
ctgtgatgag agctgtagtg tcactgaacg gtgcagaaga cagttccaga catgggtggg    14160
gagggctgtc actaagccct tttgttttag agacagggtc ttgctctgtt gctcaggctg    14220
gagtgcagtg gcatgatcat agctcactgc agcctcgacc ttctgggctc aggtgatcct    14280
ccctcttcag cctcccaggt gggtaggaaa acaggcgcac actccatgcc tggttagttt    14340
tttcaagttt tgaatgctta gggtcttag tatgtggttg cctaggctgg cctcagtgat     14400
cctcctgcct tggcctccca agcactaag attgcaggca tgaccgccaa ccccagctct     14460
aatccctttt aaattccatt cgcttcctga gtcccttttgt gcctggggag accccgtgta   14520
ttggtccttt ttcacattgc tgtaaacaac tctgagactg gtaatttata agaaaagag    14580 gtttgattgc ctcagttccg aagactgtac aggaagcatg gctggggagg cctcaggaaa    14640
cttagaatca tggcggaggg aaagcaggca gtctgcaggt gtctggagaa ggaggaagag    14700
agcgaagggg aggtgctgtg cacttttaaa tgaccagatc ttaggagaac tcactatcac    14760
caaaacagca agggggatat ccgctcccat gatccaatca tctcccacca ggctcctcca    14820
acactgggga ttataattcg acatgagatt tgggcaggaa cacaaattca aaccatagca    14880
cccagtgagc ctgatttggg ccttgctgcc cgatcacgac catctctgga gtcctggtgt    14940
ctgttcccac tgggacctgt gccgctgtcc ccctctccac gccctggcca cgccaagcca    15000
ccctcctgac tcacccacag gaagctgccc tggccctgga gcctgcccccg tgagcccctc   15060 tgcttgctgg ttcaatggcc ctccagcagc agtggctgtg gcagctgggt tctcggcatc    15120
ttcagacacg gattcttgag cagcaggatg gggctccatc tccctgcgtg cagagcctgc    15180
cacagatctc cctcatccac tggcttctgt gctgacttcg gatgaagcca gtggtgccgc    15240 ctattgggt acagcaactc agggcgaaca gtgaggggcg gctcaccaaa gaaatacccc     15300
gcagggcagt gcccaagcca gaggcttgag ctgggtcgga gctgccctag atccctgggt    15360
ttgtgggcgc acaggtcctg tgcagggcgc ctgatggtgc aggttgaggt gggacagttg    15420
gggtcaaggt atttctcagg cacagtgcct atgaagggaa gacagttgca gggactgtgt    15480
ccatgtcagg atagactggt ggggaccccg tgaagagttc tggagcaaac cctgcctgca    15540
gggccccacc tgggctggcc aggcccttat gttgagcatc ccttcccca ggccctcagg     15600 agccactgtc cccgaggcag gccctgaagg tggcggcaaa accctcctgc tgggcagctc    15660
tgcccaaagg ccacagccag gacctgcttc ccgcgtccag gctactgcct gagaggaggc    15720
ctcgaaagcg cagggttccg tgactttaga ggccatggtt ggcacccatc atcgccccag    15780
tgtagattgg ctccactcga cctggctgct ttggccattt ggtctaccag ctggaaccat    15840
gttcctgggt gtgaaaacg ctccctccga agctgcgga gagccctgag gccttgtgct     15900
tccttctgat gggaggttcc agatgcagtt ggaggggatg tctggcaggg ctctaacccc    15960
cagccaacct aaacatttct ggtgcagaag gccccggcct ggtgttgttt gtccctggct    16020
gcctcctgct ctgacaccat cagcatcctg ttgccaaggt catggatcag tgcggtgctc    16080
ttcagggtgt ccggccagct ggggtctctg tcctgtattc cggcagaggc cccaggagaa    16140
acagcaaatg cctttgtcca ttccatacaa atttcatata aatgtgagca gcttctgatc    16200
ttccgtggcg tattcgtcca gttgatggcc aaccctgggt acctgaccct ccaggacctg    16260
ctgcactggg ctgcccctcg gctgtgtgtg cactcgccac gtggccctcc aggaatccca    16320
tcccacgggg ccacactgaa ccaaatggag agagcagggc caccacccte tctccgcatg    16380 ccacggctgc tctgggaccc gggcaggagg ggacagtctt ggccttccag tgtccctctt    16440
ggccttccca cggccatctc taccccaagg atgcagcaga gatatcggtc gctccccagg    16500
```

```
tgtcaatccc agtcacaggc tcagagaccg ggacatggcc ccgggtgggt ctgtaggccc    16560
tgtgggctca tgtgagctgg tcttgggcag gactccatta ttaactgcct gtgatgtgtc    16620
ccactgtcat ggagccctgg tgactcttgg ggaccagcat cagcttgggg cctgtgtgct    16680
cagtggctcc cagatgcctg gatattctct tcctggtgca catagtcccc ggggaggtcc    16740
ttgtcatgca cacttgctga tgtggggagt gtccttcatc ttgcaggcct ggccacctct    16800
tcagtcagca gatacctggg ctgaaaaccg actcgggcag tgtgggccca actgggctc    16860 tatcggagtg accaccctca gccctcctgg acccctctgc cggctccacc tgagcgctgc    16920
cctcgctggc agccctgcct tgctctgctg ccattccgta agccctgcag gcaggcccct    16980
tggcgccctt cagccgtgtt catgattgtc tcctggcctc tgctgtttag aggtctaatg    17040
ccctccgccc ccggcgagcc aaacccagtg atggtggttc ctgccaccag cttcctgtgg    17100
caccgctgcc actcccgcca ggctcctggg gcaccgccgc cactcccgcc aggctcctgg    17160
ggcaccgccg gccactcccg ccaggctcct ggggcaccgc cgcccactcc ctccaggctc    17220
ctggggcacc gccgccactc ccgccaggct cctggggcac cgccgccact cctgccagcc    17280
tcctgcggca cagctgccac tccctattaa ccagcatggc acaggtgagc ggtgtgacct    17340
tggtcttccc agggaaccag tgcttggcag ctcacaccac acacgcctac gcctaccctc    17400
caccagccac agcagttgtg gcatctctac cctgcccagc aaaagtggaa gtgttgcctg    17460
tgccgctagg aacctccagg tttgctccac ctccaggggc cttgcaggg tgtcaaacct    17520 gtgtctcggg acactgctgt taggtctcca gcttccctat caggcgcctc agcacccagt    17580
cctaccagtg ctcccgcctc ccgtcccag tggctgggc ctgcagcccc ctcctgtgcc    17640
ccgagctggc cgggcccgca gcccactccc tggtcactgg atgttgctga cacttcactc    17700
ggtcagagcc ctagcaccca aggggggcca gggcctgacg ggggtggagc gagggggtgg    17760
gccgcgtctg tgcaggctca agaagcttcc taagaggctg gagagtggaa ccttcaggca    17820
ccacgcactg cctcctccct gcccacggtc ctgggtttct ccagatgggg ccttggcctt    17880
ggctaggtgt tgatcaggag ctgggagtgc tgcgccccgc ccaacttctc caaactccag    17940
ccagggcacc tcagtgaggc ctcagccacc tgcgccttat ttgcttcctc cttggaggcc    18000
ctcgtgtctg ttcattcatc aaacagcagc tggggccccc agcagacccc cttccccaac    18060
tttcccactg gacactggaa ccagtttcac aactggactg gacagggacg accaccttgt    18120
gccaggcgcc agctatctcc cctgaccagt gatgggtcct cattgccgt gggccgtgag    18180 tgacccagtt ccaaatccca aattagtgac tctcttctcc aatgggggtt ggattctcca    18240
gaagcagagg cagacataga atttgggtgc aaggtatttc ggaggggaagg tggaagaggt    18300 ggggttggtg agggagaagc ctggagtgtc ggtggccggg gtgccccac ctggctgaaa    18360 cgcctggtct ttgtgccctg cctggctcag cctcccagg cagactaccc catggcatcc    18420
ctggacaagg ctgcccccaa gaacgctgcc cacagcccag ccatgggcct tcccttgggg    18480
ctaccgcccc ggctcacacc tgctggccag cgtatttact ccttgctggc tgcaccctct    18540
cagcagtggc tgtgtagacc ataaccctgg gaacacctgc ggggagaagc gcccttggcc    18600
tggcggcttg ggggagacac ctgggtgtc aggaggaag gaaggcaagc aggggtgagg    18660
cactgtggga ctttcctgc tttctgggcc agtggccaca ggccacccag tgacatttct    18720
ctctcagcgt ctgctgggt ggactctgca gcggctgcag ccagcctgga tcggctcctc    18780
gcacagctct gcttgagggt gaaggccatc tagaaaccct cagtcccctc tcagcctcag    18840
```

```
agctgatagc gctgcctgac catcagcaag cttgtaatca gcaccacctc cagcatgcct    18900
gctcctggat ctccgtgagg ctcccctgcc tgtgtcaccc aggggcctct agggtgctc     18960 tggagctggg agccactgtc cagcacttcc tgccctctcc ggcctctctt ggctgtctgc    19020
caagcagtca ctcagtctcc tattgaccac tcgttttgcc gcaaggctgc tggtttacgt    19080
gaaaatagag aaagccaaag agtttcctca cccctgtaag atttactggc tcttctggca    19140
ttgcacctgc ctgagttcct tggtggggcc cctctttgag ttcctttggg ctgctgtaac    19200
aaagcaccat agcctgggca gctcgtaaac agtggaaatg cgttgctctt tgttctggag    19260
gctgcaagtc caagattgag gcactggaag acctggtgcc tggtgaggac ctgcttcctg    19320
gtccagagac agcaccttct ctctgtgtcc tgatgtggtg aagggcaaa ggaactccct     19380 ggggcccgtt ttatgtgggc actcatccca ttcgtgacgc ctctgccttc atgacctcat    19440
cacctaccag aggtccccac cttttcattc ctcaccttgg ggatgaggac ttcagtatgt    19500
gaatttcggg gacataaatg tgtcatctat agaagggccc atctcttaca caaatgctgg    19560
gtccccagtg gcctgtgtcc tagcaaatga gagccaccct gaaaaataaa atcctgtctc    19620
cccaacgcca gccctggcaa ggcacccaga actctccgga atgcttgaag gcagggcctg    19680
gcctttccat ggggtccagg gctgtggggt ccctggcggt actgtgggcc tgcagagtgg    19740
ggcatgtggg ctgaagaccg tctcccacc atggtgggaa aggacaaagg gtggccctgg     19800
cagatccgga cgggcaggac tgggtgtgtc ccatgagagc acctccttcc tggccttttcc   19860 tgtggacttt gtcccacacc acctgcctgg gttccttcct ttagtcactt ccagctccag    19920
gcacagcagt tggtgactcc ttggtgggag ccgtgtccca cccggtcctg atactgccgt    19980
cttctctttc acagtcctcc aggcttgggc cagccttggg ggcagcagag cttctggggt    20040
gagtgtcgag atcctgtgtc ctgagagcgg tagtcaggga gagggctggt cggggcaggg    20100
ctgcccgggc aggacacagg atgcggccgg ccaggctggg gccaaggtgt tcagacctgg    20160
actttgggct cgtgctttct tcatggttgc gccttgctcg ctgtcccttg gagtcttcat    20220
ttggttttgc ttttttttgtt tgtttgtttt cacctaattt ttgccagact taagctagtt    20280
ttgctgcctt ttgaaactag tggaagaatc attttattcc tggggataat ttggggcctt    20340
ttgatcccaa cgtgaagccc tgcacatggc tgcttcatca ggggaagggt cttttctgct    20400
ttggaggaaa ggctttggca ggcaggctga cctgggagtc tccggagctc ttggctctct    20460
gtagcatcct ggggagctca gaccatggct gcagggctct ggccatagct tgcaggccat    20520
ctggttagtg ctgccccca aacccggcca ttcctctcta gtccccagca ggtatagcca     20580
gtgtccacat agacagcact gcctcagatc tgggctggga ccacaacact cactcaggga    20640
tcccagggaa catggcacca ggtttagtag gtttagtcgg gcatatgcag tgtcccttac    20700
ccaggtcaag gctcaggctg ggcccatctt agctgcctgg gacacccagt ccttttatga    20760
atctgccagg ggaggagcag ccaggcttgg gctggggcct ggatggacgt gacatcgggc    20820
actgtggcat tgtgtgcctg tctctgtgtt gcaggctgga catgggctca ttgctccttc    20880
tccaagccct ctgaggacat caaaagcgtg gacgcatcac tttccaccat cttgctgccc    20940
actgtccctc catcctgagg cctcctaagc acatgtgtgg ggtggcaggc acactgctga    21000
tagctgtgga tgcggccgtg acatccttca cccctgcccc catggcatgc atgatccatt    21060
agggaggacc gtctgcacaa aggtaatcca ttgactcaga caggggggttc atagaagaac   21120 aggtgagagt ggcaggggg gtattccttg accagctgag ggtcagccaa gggcaggaaa    21180
ggggctgggc accctcaggg aattgaaaga agctctctgt gcctgcagtg cggggagtgg    21240
```

-continued

```
gcttggagaa tatggcaaga gctgaggctg gagatgtaag caggggcctt aagtgttgtt   21300
taaggagcct gagtcttatc tcctgggcaa ttgggagcca ctacatagtt taaagcaggg   21360
cctaacatac atatgtttga aatctttctc tggctgaagt ctcgaggatg aattggaagt   21420
agaggaccaa ctaaaaagtt gttgcacgac attaaggtgg tgtcctgggt taggtgggag   21480
gtgatggaga ggagaatagg ctagtgttga catataccca ggaagcaaaa ccattggggc   21540
atggtgctta atgcttgatt ggattgatca catagatgac tatgaggagg actgacatat   21600
ttcaatctat gaacgtggta tacccatcca tttacttatt tttaatttt taaaaatttt   21660 tttttttttt gagacaggat ctcactctgt tgtccaggc tgaagtccag tggcaggatt   21720
tcagctcact gcagcctcaa cctcctgggc tcaggtgatt ctcccacctt agcctcccga   21780
gtagctggga ctacaagcac agatcaccac acctggctaa ttttttgcat ttttgttttt   21840
tagtagaaac agggtttcgc tatgttgccc aggctagtct caaacgcctg gactccaaca   21900
atccacccac cttggcctcc cggagtgctg gattataggc tggggccact gtgctgaacc   21960
ctgtccattt atttggatct tctttaattt ctcccagcaa tattttgaac ttcaagcata   22020
cgtttcccac ttgtgcctag gtactttgtt ttccaatgct tgtaaatggt attgtatctt   22080
tagttttatt ttccaattgt tttttgctag tatatagaag tgcatttttt ggtatattaa   22140
tcttgtatcc tgtaaccttg ataatgcatt tattagttca tagtgttttt tgcttctttt   22200
gttcttttct ggtaaatgcc ttaggatttt cttttctcc cgactcccg ccttcctcct   22260 cttcttttc ttctgcctta ggattttctt tttcttcttt ctcctccttc tcttcctcct   22320
cctcctcctc ctcttctttc ttctttcttc ttcttcttct cttctttgtt tttaaattga   22380
gacaggggct cactctgttg cccaggctgg agtacagtga tgcaatctta actcactgta   22440
gtctcaaact cctgggctca agtgatcctc ccacctcagc ttcccaagta gccaggacta   22500
caggtgtgca ccatcatgcc tggctaattt ttatatgttt tgtagagatt gggtcttgct   22560
atgttgctcg ggctggtctt gaactcctat cttcaagcga tcttctcact tcagcctccc   22620
cacatgttgg gattacaggc ctgagctact gtgccaagct gaattttcta catgcatgat   22680
tatgtcacat gtgaccatag gtaattttac ttcttccttt tctatctgct ttttcccttt   22740
gccttatttc ctctggctgg gacctccaat accgttttta atagaaatgt gagagccact   22800
tcgtttgttt ctgagtatag tgagaaagtt tggtctttta ccattgccca gcttgaagtt   22860
tcctatagtt tatctatagg tgatctttat cacgttgagg aagttctctt ctctttctag   22920
tttgccgaga gtttctctca ttcatggatg ttgcattttg tcaaatattt ttctgcatcc   22980
attgagataa atatatacat tttaccattt attctattaa ttgatgttct aatgctaaaa   23040
taaacctttt atttcttgca tacttttca tgatgtgtta tttgttttat atattgctgg   23100
atttgatttg ctaatatttt attaaggatt ttatgtctat gtttatgcat gatattggcc   23160
tgtagttttc ttttcttgta atatctttgt ccagttttgg tacagggtaa aacttgactt   23220
agaaaatgag ctggccagtg tttctccttt tttctgatgt ggttaagatt ggtattattt   23280
tattcttaag tgtttgatgg aattcatcag taacaccatc tgggtgaggt attttctttg   23340
tagaaaggct tcaaattatg aattcaacaa ctttaataga tataagcttg ttacatttta   23400 ttttcttgt gtaaattttg gcaagttgtg actttcagta gatgtttttc catttcatca   23460
agatgtcaaa tgtaatttca tgatgttctt actaatattc ttgtattatt cttctgatgt   23520
ctgtagggtc tgaagggatg tctcatcttt tattcctgat attagtaatt tgtggatttt   23580
```

```
ttttctttga tcaatctagc cagagctttc tcaattttttt ttctttttca ataaccaat    23640 ctccatttta ttgattttcg ttttttttctg ctagtacatc aaattttcac tctttcttat    23700
ttcttctgct tacttgggtt tcattttgtt cttggtgttg ttgttttcta gattctcaaa    23760
gtggaatctt aggtaatgat tttagacctt tcttctttcc taacatgaac actgagagct    23820
acagattttc ctctaagcat cacactaacc ttatctcaca aagaccggaa agttgcattt    23880
ttatcatcac ttagttcaaa gtattttctt atgtctcctt gattacttct ttgatccctg    23940
agttatttaa atgtgttgct taattttcaa atatttgggc attctttgtg tgtcttatac    24000
cttgttgcta ttgatttcta attaagctct gttgtagtta gagaacatat tctgtataac    24060
ttaaatcttt ttaattttat ggaggcttaa tttatggcct agcagatgga ctattttgga    24120
aaatgttcaa tgtgcacctg aaaagaatat atattctgct gttgttgggc atagtgttct    24180
ataaacatca gtttggataa gatgattggt gttgctcagg gctatcatat tcttactaat    24240
ttttggttta cttgttctgt gagttactga gatgagggtg tcataataac cgatcacaat    24300
catgaatttg tctgtttatc ctttcagttc tatcagcttc cttcatttt tggattcttt    24360 gtaattaggt acatacacat ttagaattgt tagatattct tgatgaattg acccttttt    24420 catatgaaat atccttttt tttttttgag atggagtctc gctctgtcaa ccaggctaga    24480
gtgcagtggc gcaatctcag ctcactgcaa cctccgcctc ctgggttcaa gtgattctcc    24540
tgcctcagcc tcctgagtag ctgggattac aggtgcccac cactgcgcct ggctaatttt    24600
tgtattttta gtagagacgg ggtttcacca tcttggccag gctggtctca gctcctgac    24660 cttgtggtct gcccacctca gcctcccaaa gtgctgggat tacaggcgtg agccaacacg    24720
ctggtccgtg aaatgtccct ttttttattt tgcaatattc cctatactaa agtctacttt    24780
gatgttaata ttttattcc tgctttctta taattaatgc ttgcatttta taatttttc    24840 cattctttta cattgttttc attctttttac ttttaacttt tgtttatatt taaagtatat    24900
atcatatcag gcagacagca tattgtcatt tcttgctttc ttttcccta agacgaagag    24960 tctcctgtca ctcagcctgg aatacagtgg taccatcagg gctcactgca gcctcaaact    25020
cctagattca agcaatcctc ccatctcagc ctcccaagta gctaggacta caggcatgtg    25080
gcaccacacg tggctaagtt tttaactttt tttttctttt ttttgagaca gtcttggtct    25140
gtcgcccagg ctggagtgca gtggcgtgat ctccactcac ttcaagctcc gcctcccggg    25200
ttcacgccat tctcctgcct cggcctcccg agtagctggg actacaggcg cccgccacca    25260
cacccggcta attttttttt ttagtagaga cggggtttca ctgtgctagc caggacggtc    25320
tcgatctcct cacctcatga tccgcccgcc tcggcctccc agtccctagt ccttttaaa    25380 aaatgtttta ataagatgtt gagtagatct aaatgaacac caatgcaccc accgtgaaag    25440
tgaaggaaca gaacttaaga tgatctttga ggccccttg cactttgccc tgaaacatcc    25500
ttctgccaat gtcccagaag taaccacaaa gccacttcct cgtgtggcct ccatgacaca    25560
cgcctccttg ttttgctcct tcgctggcct ctcctttcat ctctactgtc ctgcatttgg    25620
gtccctaaaa tgttggggct cctcagggtt tggtcctgga ctcttcctgt cccatcgcac    25680
gttctgcatc cacagactac cttgttccca ttcattcaac agtcaccct ctgcccttca    25740 ccctagagc cagctccagc cccggacact gccctgagct ctggacctcg taaagaaatg    25800
tctaccaggt atctcctctt ggatgcctca gaagcacttt aaatgcaact tgtccaaaac    25860
tgaccacatc atccagccct ttcatcactc cccaaactaa tcttccttca aagtctccat    25920
ctcagagagt ggttcctctt gttacccagg ccacatatgt cagtgtcatt ttggaatctt    25980
```

```
tctcccccca ttcctcctac atccaatcaa tcataaataa gttaaatatg catatcataa    26040
accctattgc agctaatgaa atgataaaac aaggaagtat aatagtctag aagagataag    26100
tgaaatacaa aatagtcaac taatccaaaa gaaggcagaa aaagaggagg gaaaatgagt    26160
acaaagaaca gaggagatga ataggaaaca aatagcagat ggtaggttca aacccaacca    26220
tatcaaccat tacattaaat gtgactgagg taaacaatcc agttaaaaga caaagactat    26280
tggccaggca cggtgtctca tgcctgtaac cccagaactt tgtgaggccg aggtgggtgg    26340
atcatttggg gtcaggagtt cgagaccagc ctaaccaaca tagggaaatc cccatctcta    26400
ctaaaactac cgaaaaaaaa caaaaacaaa aacaaacaaa caaaaaaaca cagctgggcg    26460
tagtggcacg cacctgtaat cccagctact caggaggctg aggcatgaga atcacttgaa    26520
cctgggaagt ggaggttgta gtgagcagag ttcatgccac tgcacactag cctgggtgac    26580
acagtgagac ttcatctcaa aaaaacaaaa agacaggccg ggtgcagtgg ctcatgcctg    26640 taacccagc actttgggtg gctgagacag gcagatcacg aggtcaggag atcaagacca    26700
tcctggctaa cacagtgaag ccccatctct actaaaaaaa aaaaaattaa ccgggcgtgg    26760
tggcgggcgc ctgtagtcca gctactcggg aggctgaggc aggagaatca cgtgaaccag    26820
ggaggtggag gttgcagtga gtggagatca ggccactgca ctccaagcct gggcgacaga    26880
ccaagactct gtctcaaaaa aaaaaaaaa aaaaaggact agggacttac tgacttggcc    26940
aaaggctgct ggtgggtgcg tggaggtgct gcctgtcagc tgtgctctgg gctctaggga    27000
catgggagtc caaagggctc tcacctcctc agtgagaggt tctggtgggc tgaccatggt    27060
gggatccaga tttcagcagg tggaccccga gggggtgtga ggaaatggac tctgtgagtg    27120
ggaacttctc tttcagagga atttgcaaga ctggcctgag ccgcacacgg ctcttcagca    27180
gggcttggca gccagcgggg cctcgggagg aggcaaacag ctgatcaaat ccgggcttct    27240
ccagaggaag aaggggaagg gcaggtctgg ggaggtcaga gcgtgggtga gaaccgtggc    27300
catgggtggg atccacatcc cagcctgcag ggcctcctgg tgatggttct ccagaattct    27360
gcgattggag ctgtgctcac agagtcactg tccccgacct cccaggggcg cggacataac    27420
ccagcctcag ctgcagacag cagagactct gcacaactgc agaagctgag caatcagcct    27480
catcagtggc aattcctgga actccaacct caactgtaac atgagctgtg gcagaccttc    27540
agtaacccca gacgaggagt gaggcagagc ctgatagctc agggaccagc tgggatgctc    27600
agtaaacaag agctccagaa gatacgcgga acaggagaag gtgaagtgtg gggacagcag    27660
gcgctgcagg ccacccagaa ggaggaggag aggggacaag aaacactgac caggccttca    27720
agatgaggag tgagcagaga ggacagcaga acatgggaaa acctacctgg cactatgagg    27780
gtggagaggg gagtgttgga gggtgtgcat ttgagtgcaa gtgtgtaaaa gaggccctgg    27840
acaaggagtg aagaatctca tcagatggtt aaagtgaggg agcaccaagt aaaccataat    27900
gaaccataag tcatgtggac cccaacccta atgctaatca taaacctaaa cctcgtgtgg    27960
cctggaaccc taacctgaac ccaaatccta accataaccc taaccataac cataaatcat    28020
gtggactcca accctaatgc taaccataac cctaaaattc aggcagaacc gaacctaact    28080
cgaacccaaa ccctaacgaa aactctaacc ctaaccctaa ctcaattcaa accttaaccc    28140
taaacctaac cataacacta actccaccct attccgaacc ttaaagctaa ttaacaatgc    28200
ctcatatgga cccgaacccct aaccctaacc gaaacctaa ctctaaccct aaccctaact    28260
caacccaaac cttaacccta accataacac taactccaac tacaaccata accctaacca    28320
```

-continued

```
aaactctaac cctaacccta actcaaccca aaccttaccc ctaaccataa cactaactcc    28380
aacaaccata accctaaccg aaactctaac cctaacccta actcaaccca aaccttaccc    28440
ctaaccataa caccaactac aaccctaacc atatcccgag ccctaaacct aattaacaat    28500
gcctcatgtg ggccctaacg ctaaccctaa ccatgcctca tatggacccg aaccctaacc    28560
cctaattcca accctaaccc taagcctaac cctaacacta accctagcca aaaccctagc    28620
actaacccta actccaaccc aaaccctaat cctaagtctc atgttgacca taacctggct    28680
caaaccctaa cctgaaccct aaccctaagc cttgtattga ccacagcctg gctctaaccc    28740
taaccctgac tctagtcctc actgtaattc tacctctagc cttaattcta accctaactc    28800
caatcctaac cctaatccaa atgcaccctc tgatcgcaaa caactcttca gccaatgtca    28860
gacctcacct taaccgtcac cttcacgatc accattccag ttctcccttc agacttccca    28920
gggacttgag ccagcccctg gcccccaggc cttggtttcc ccacctgtgc agcatggatt    28980
tggggctgag ggtacaaaga ctggcaccca cctgagccgt tggaacaggc ctgcccctgg    29040
tcccgaggag gactctgctc tcccggttct ccccttgccc atgtggaagg gggctcatcc    29100
ccccagcatg ggtgcttcct gcctggtgtc catctctgtg tgagttcctt tagggaggga    29160
ccgggtaggc gcagttggca tggcaccgcc atgcccctgg ctcgggctta tgcgggctga    29220
cagtcctgtc cctccaccca gaggcccctc caatgatgta gcttatcaga gtgtgtgtgt    29280
atgtgcacat gtgcatgtgt gtatgttgta tgtgtatata tctatgtatg tatatgtagt    29340
atctatatat atgtgtatgt gtatatatgt atatatgtgt gcatatatat gcatttgtgt    29400
gtgcttgtgt gtatgcatgt ttatgtgtgt atttgtatat gtatctatgt gtgtttatat    29460
gcgagtgtgc atgtgtgtat gcagtgcttg tgtgatgtgt ctgtttttat gtgtgtgcat    29520
gtgtatagta tatgtgcatg tgtgtatgtt tacatgtgtc tgtgtgtgta tgtatatgcc    29580
tgtgcttgtg tgtgtgtgtg tgtacacata cacgtggaca ggcagggag aagctgtatt    29640 gcaccaccac ccaggccctt ggagcccaag tgcagtctcc ccaggctca cgaggcccca    29700 gcacgctgcc ctcctgctca gatggtgccc aaaagcccct tgccgagtcc tctctaagcc    29760
tcatgtagac ccgtgagtcc cttctccgtc tgtttcccct gcctgtgatg cttagggatc    29820
gttcatttca gggccagtga ggaaacccca tcttctcctg cactgccgtg gagttaaagg    29880
agaaggccac aacacactcc cacgttttct acagactagc agtggggtgt ttggccacct    29940
ttggttttga cctttttattt tggaaatgtt cagactgaaa taagcagaag tgtaataacc    30000
ccttgtgccc atcaccccac ctttggcaag agccaaagag tcacaactga ttgtgcttca    30060
ccacactcca tctatgggct caaaatgttt tgagataagt gccagacatc atatccttct    30120
atctacaaaa aatgccacat gaataaaaga taaggacttt taaaaacaca tgaccacagt    30180
aagcattatc acatctagcc aagaaatgaa cctttcctta attgcaacaa acaggagtta    30240 actttttacat tttctctact tctacaattt tttagagaac agtaaggtag actttattca    30300
acggaggcta ccacaatgga gttttgcagc agggaaggga gatgaggctc aattcccacc    30360
ttatacgttt ttaaaaagag cttatttggt tgaattggat ctgaggagtc tggctgcagg    30420
ccaaaatcct ctgtgtgatc attcaggccc aaccgcagtt gttgccagca ggccccacag    30480
gagaagcagc cctcctgccc cagacggcac tttccaccct tagcctcctc cacggttccc    30540
caggccagat ccttttgttt gagccttctg tttcgcctgc ttggtagtga gatcatctcc    30600
ccatctgcct gatgtcatcc aggggcaaa atgggacgt agaggagccg gcaccttttt    30660
ccttctgttt gcctcttgcc tgcactattg cagtcgtgaa tacaggcctg agggtgacct    30720
```

-continued

```
tccattgggc tcgtggtccc aacctcgaca gcagtgactc cacaggatgc atacgaggtc    30780
cccgcggtcc cggccgacat acctgttggg ttcttagttg gcagcttcct cctccgtctc    30840
tctattcccc tcctaggtct cttgcccgt gcagcttcct gcagactgga cttgcaaagt    30900
ccagcctgta tggctggagt tcccatgcct gccaatctcc tgtcgactgc gagtcagctc    30960
cgatacttca ccagattcag gtgagagttt tggttttttg acaagcccac ttcatcagca    31020
gggcatgcat ttctgccagg gggctcatga tatctggtgg tctctttgtg aggccagcag    31080
ccaccaatga tcacgaatgt ggcaggaagc tgccaagaga ccccccagtg ggtgattcct    31140
gcctcctgct gtcatgcaat tccctcctga agggtggctg gacttactca cttataacaa    31200
acaatacagt aaaaaaaaaa aaaaaaaaaa aaagtgatgt gttgtctctt ccgtgattag    31260
gttgaaagag accatggcat ctgtcttgga tgcatactct ctctcgctgg ctctggggta    31320
gccagatgcc atgctgtgtg ctgccctgtg aagaggcatg gccagtaagg aactgagggc    31380
aggaaccagg gaagatttgg ggtcctcagg ccagctgccc attgggaatg aaactctacc    31440
aacagccacc tgggggagct ggaagtgaat ctcatcttag ctgagccttc tgatgagact    31500
gcagccccag ctgacacctg gattgcagac tcatgaaaga cctgaaactc taccaacagc    31560
cacctggggg agctggaagt gaatctcctc gtagctgagc cttctgatga gactgcagcc    31620
ccggctgaca cctggattgc agactcatga agacctgaa actctaccaa cagccacctg    31680
ggggagctgg aagtgaatct cctcgtagct gagccttctg atgagactgc agccccggct    31740
gacacctgga ttgcagactc atgaaagacc ctgagcagag gacccagttt ggcagagccc    31800
gaattcctga cccacaggaa ctgggagata aaactctgtg gttttaatct tctcattttc    31860
gaggtaattt ttttgtgtag caataggtag ctgacaatgc acagctaaaa taatagataa    31920
ttaaccctaa tgctagtttc attcatccat cagggttttgc aaagtagtga tattctactt    31980
ctgtcttcct tcattattta ttagcagaaa tgtatctata aaagaagtg ttccttcatt    32040
aactctttgg tcatgttgag gtacagtttg cataggaaag gcagggcaaa tgcttgattc    32100
tttcccttcc tttcctcatt tataaaataa tgaactgttt tcctggcatc tttcaacaat    32160
gactaatgag tttttaaagt ataattacaa gttcatgagt ttaaacattt tttgatgttc    32220
ccattaacat tattatcctt attgatattc agatcttcct gtctttgtcc agtgccagcc    32280
tatttgattt aactcctgag cccctttggc actgccctaa taatcttga cagctacttt    32340
gttctctggc ataagaagac attccagaat tacattagac atttcctaac ccagattgga    32400
cagcatacac ttctctccaa gagcccctct tcctcttcaa gagaaatggt acttagagac    32460
cacagtctgg gtgttaggtg tgcttgtggt tactggattt gtcgtcattt ttaggccttg    32520
tcagtggaca gaactaaggc ttttttttt gaaagacaca ttatgagtac aaatggatac    32580
tttctattta aattcggatt tacatagttt ttacttaatc ttattgataa tatatctgca    32640
tctcctttct cccacaccaa aaatctcaaa caatacccaa catagttatt catttgtttt    32700
atcctgtaac acacacaata ttttcaaaat gactttacca acactaccat caacagtata    32760
taaccactga aaatagtta aaattatttt tagatacttt taaagtcctt gggttgtgtc    32820
gacgtacaga caaaacagtg ttttaaaatt atttggaaaa tgattactta aaataatgaa    32880
aacttctttt gccattcttt cttgttgtca ggctatatgg atatacatcc aaatgactgg    32940
attttaaaat cacttggaag agtttggtag gttcatattg tcaacccata atgcaagtca    33000
gttagtttca ttttgctttc aattttaaga attccttta caagttaatt taattaaatt    33060
```

-continued

```
aagtaattac acaaacattt gacatgagtc taaatccaaa tctagaaacc aagatatggt    33120
cacagaagtc cgtccctatc cccatcccat ttccacctgt ttcctacagg taacagttta    33180
atttaaagca aattttgtgg cttatctttc catttgtaaa acatacagct gatggctcca    33240
tctaaaaaca catcaattgt ctatatgtac ataaacatgc ttttttttcat ttacaaatac    33300 attctggaga tgaccatatg acagtgtgta gaaatatttc tccctcctct ttgcaagtgc    33360
tcagtgtcct gtggtgtgaa cacgcttcat tcaacctggg cccttgggag agatgctgag    33420
tggttcccgg gctgtcccca ctccacaccg tggcagtgaa gagctgctga agtacatgct    33480
tcatagtcct gcgtctctct gtgagtacat tcctagaagt ggggttattg ggtcaaagag    33540
taaatgcatc tctaatttgg ctaagatatt gccaaatcca cctgcctggg ggtttgtgcc    33600
accttagaga tcagtgatca atgggtgata tccgaggacg tctttctatt gtggtcagac    33660
tcttggattt tgacctgact aatggaggag aaatggtgtt gcagtgaact tttgatttgt    33720
gtttctcttt ttatgatcgt tttgagctta atttgtgttt ctcttttat gatcgttttg    33780 agcatcgttt cgtatcttta aggagcaatt tacatctcct ctgtgagcgt ctactcccat    33840
ctctatcagc aggcgtcttg cctggctccg gaggaagtgt ctctgaaggc tggtggtccc    33900
aggatagggc aaaagaacgg gagtgagaac tctccacaca gtgcttcttc tggggttaag    33960
gaccctctgc ctcagtggct cctgggcgtg attaaacttt gccatttcct gggcccatcc    34020
tagacaggct gctgcaagcc agccaggccg ggatcctgct gccccgggga ggacgtgggg    34080
aaaatccctg ctggagggac tgcccccttcc ttgtccagcc actgggtgtt tatggttcag    34140
tttagggcgg ggatgacagc acacgacaca cactccgctc tcaagagtta ctcctccctc    34200
cccgccagac tcccccaacc ggaggtctcc ccagagtgga ggaccttcca gcggctggca    34260
ggcggcctca ggcaggcagt ggggagcctc tgcaggttcc cgagccagga agtggcactt    34320
aggagtgagg atcttaggag cggggctctt ggacaggagg gcgagtgagt tgggagggcc    34380
tcaagcgggg acccgatggc tctctctgct gagaagggag ggccctaggg atggggacag    34440
agagctggca gttgaaggc caaggagcag gcagcttccc agtcacagag ccttgtgcag    34500
aggaagggga aggagtccga gagggtggcc ctgctgtcca gggccaagaa aagggaaagc    34560
cgctggaaat agcagaaacc tggctggggc agcacccaag gcccacccg aggccaggtg    34620 gggaccccag cggggcatct ggcagcagtg ggtccccagg agcaggcagt gggagccatc    34680
agggtgagtg agctggcggg ggtggcccag gggctggggt cacctgccct cagcccaagg    34740
agcctcttct ggcctttggt ggccagggct gggatctccc tgctggtggc cagatgcctc    34800 gacacccat aggctgggtg aaggtggggc aggagttcca aggcgtggag acggcccctg    34860
agtgcccagg ggcctcctgc tgcaggtggg cagagctgga ggctccactg tgagggtgcc    34920
tggtgaaggg aggcgtgggc acggggagg cagggaaggg ccctgggtgc gacttgcagc    34980
ccctcagacc ctctcaggac ccctcctgcc cccatcgtgg tcctctcagg gccctcagg    35040 atcccttcca gaccctgggg acccgtgtc ccctgctcgt cctgcggtgg tgcccagctc    35100
ctgccaaggg ccctgcactt gggctgtggg gaccccctgt ggggatgggg ccatcacagg    35160
aggctgagca cagggcgggg tcttggctgg aggggaccctt aggccacagg tgctagtctt    35220
ctgcagccac ccccaggac ccctgcccgc tacctcctct gccccacagc tgacaggctt    35280
tgccctcccc tgcccctctg tggccacaca ctcagttctc tatacacttt tattatggaa    35340
aacatcaaat acacacaaaa gcagggcatc taggacagaa ccctgtgtc ctggtcccca    35400 gcccctcaca gtgacaccgc caggctttag gcaagatcag tggggagggg gagtttccca    35460
```

```
gcaggacgtg cacttccaga cctggttctg tgaagagggg aacagaaagt gctgagggtg    35520
acagggaaac ctcgagaaga gggaggtgta ctcacatcct ctctcggggt ccacaactga    35580
gcccccacac agaggacccc actggtctgc ctgagctgct gggtgggcaa gtgaggcact    35640
ggcctcgggg gcacagcgct tgaagggaca ccagaaaaac agtcataaag ataaaccgta    35700
atgtgttgtt ttatttctta tttatttatt tatttatttt tgagatggag tctccctctg    35760
tcgcccaggc tggagtgcag tggcgtgatc tcggctcacc acaacctccg cctcccgggt    35820
tcaagcaatt ctcttgttct cagcttcccg agtagctggg actacaggca cgcgccacca    35880
cgcccagcta ttttttgtat ttttagtaga gatggggttt caccatgtcg gccaggctgg    35940
tcttgaactc ctgacctcgt gatccccctg cctcggcctc tcaaagtgct gggattacag    36000
atgtgagcca ctgcacccag ccaatgtgtt gttttagtaa accaaaacta tgcaaaggac    36060
gcatgaggat ccaagcgact catttaggat ggcagcttca ctgcaaaagg agtctcgatt    36120
cagacctcaa gacatgcttc gtgggtctca ctcaggaagg aagtggaggc aagtcagaat    36180
gtggtgagaa gagagggttt attgaaagtt gctccattac agagcagggt gtcgtcagaa    36240
agcaagaggg ggaacacccc agctttaact ttttctcata caggggtctc gtctgtgtaa    36300
agactaagct aaactgtgcc taacatgtat tattctattg atttaaagaa aactgtctgt    36360
cacggggtct tgctctgttg caaccaggct ggagtgcagt agcacgatct cagctcattg    36420
caatctctgc ctcccaggct caggtgctcc tcccgcctta gcctcctgag taactgggat    36480
tacaggcatg caccccatg cgtggctaat tttttttttt tttactttt gtaaagatgg     36540 ggtcttgcta tgttgcccag gctggtctca aacttctggg ctcaagccaa cctcccacct    36600
tggcctccca aagtgctggg attagaggcc tgagccaccg cgtccggcca agggtagttg    36660
tctgaaaagc atatattgtt ctggatacca gggcacttgg acactttgct gtcatagaag    36720
tgtgtccacg caggcgtcac tggctgctgc tttagctgta aacatcgtat gaccatgggc    36780
tgtggctggc agtatgtgc ctcattggtc tcaaggtgga gctgaacgta aacggctttt    36840
ctctggctct cccaggctcc tgcttccctg acatcccctc acagacttcc cttcaaagca    36900
gggctgtcca atcttttggc ttccccgggc cgcattggaa taagaagaat tgccttgggc    36960
caaacatgaa atacactaac actcacgata gctgatgagc aaaaaaaggt ctctgcgtaa    37020
atctcataat gttttaagaa agtttacaat ttgtgttggg ccacattcaa agcccgcagc    37080
ccgagtgttg gacaagcttg ctgcagaggc tcccctagat agggctgcag gggtggcgtc    37140
cggcagctct agctggagaa gcaggaggaa gggcaggaag gaatcctgtt cggagctctc    37200
gcgtcacaca tacagcccag cggggtgaag tgggaggggc tggcgctgct gcaggggct     37260 aaccttgggg gtgaggggc agcctcggag aggaagctgc ccaggagcag aggctggggg    37320
cggagggccc cggcagtgc ccccgtgccc acagcaggac cctggctgcc agttctccgc     37380
agagggccag gtggtctgaa gctgcccagc agggagagaa caggcctggc ctggactgga    37440
aacctgccat ctggcctctc tgaacctggg gactccgggt gtcctcgaag aagggcctga    37500
gcagcagcag aggaccccag gcgactgcct gagccgggcg ccgacgacga ctgagcacct    37560
gatacgtccc cggcactcgc agcccgcgcg ccggagtcgc tgtgggtgag cggtcgtcga    37620
gcttcacaga ggccgggctc tgtgccaggg ccccgacagg gcaggaagca gatagagtcc    37680
cacaaggcac aagcccagtg cgcagaaagg gttacttaaa aataagttct gtgataaaat    37740
caaacagggt gaagggctgg aacaggtcat gagggtgcaa acaggtcgtg agggcgcaaa    37800
```

-continued

```
caggtcgtga gggcgcaaac aggtcgtgag ggtgcaaaca ggtcgtgagg gtgcaaacag    37860
gtcgtgaggg tgcaaacagg tcatgagggc gcaaacaggt cgtgagggtg caaacaggtc    37920
gtgagggcgc aaacaggtcg tgagggtgca aacaggtcgt gagggtgcaa acaggtcgtg    37980
agggtgcagc tttggggaga gaggggccct ggggtgagc ggggagctag gagagaaaca     38040
gcgctctgga ggggcccggg caaggcctgc ctgagtggga gggggcagag cacgagggcc    38100
caggctccag gctgggtggg actgccctga agtgcctgcg agacagcca aggggcagat     38160 ggagagaggt aggggtggg ctggggacag cgtttcctgt acacaggtgg aacctggcgg     38220 caagggccc ttcccagaga cagtcagagt ctctaaatgt ccagtttctt ccccaagtcc     38280
acacagccca gaagaatccg ctgggaccat gtggccctgc ccagtggggc ttcccttcca    38340
gtgtgtgagg agcacaggtg ccaggccacg tcagggaggc caggcctggt ggggacgggg    38400
tgccccaggc cactgctggg gagagtgat gcccagcaga gggggcacgg tggagttcat     38460
ggctggcctg gtggtgggg gggtggggga gctctgcagg gccctggctc tggtgggctg     38520
ggtaggcctg cttggggcac catctgatct gccagaggtg gaaggagcac tcctgggaga    38580
tgccgtgccc tgcacctcca gtccctgctt gacggcggcc gggcttggac tgatcaggtg    38640
ccgtgccttc tgctgaccc agaggccaga ccctgtggcc agagtgaggg atgggagttg     38700
agatcgggcg gatgaaaacc caaatctgag cctcctgccc gaggatgagg ccctctcca    38760 atgaacatca tggcccatgg agactgggca gggaacccaa gggcgcacac tggggactgg    38820
gcctggaggg acagccgggg aagcaggagg aagggcagga aggacagcag gaggaagcag    38880
gaagaaaggg acaggaacca ggcccgggat gacagcagag aaggaccaat gccagccag     38940 ggcttcctca cgtgcctctg ggtagagagc cctggtctgg ctcaggaggc ccaggcactg    39000
gtctcagacc tgccaccacc tgtgtgacgc tgggccaagc gcttcccttc cctgggcgtc    39060
cgtttccacc gctgtaaagt ggggagggt gaaactgaag ctctccccag cctatcccag     39120
ccgttgagga gggagaggct gtggtcaggg gctgtgggc ccacgttgag gagacgaggc     39180
tcctgccctc aggtgggaca gggcccagga aggggtgct ctgcaccatg ggggcgcagc     39240
ctgggcctac gggctccccc accatgagct cagaaggaag atgtccgctg aggagttggg    39300
ggccagggag aatattctag accagatagg ggtggtctgg gtaggcttct gagggggtgg    39360
gcttggagga ggggccggtg gccaagtcgg ggggaagcag gggaggagcc agcctgcctg    39420
cgtgtgcctc tcacctgtgt gcattggcgt gtgcatgtgt gtgtgcatgt gtgccagcgt    39480
gtgtgtgtgt attggaaggc gcccacggag cgtgtctgca tgaaccagga tgagtgtgcg    39540
tgctgcaccc tgtcttgggg ctgggcatga ggcgctgggg agggcgagct gaccgcagac    39600
cctgggaggg ctgggccctg ggaaggtttc cgagatgaca gggcagaagt gggctgggga    39660
ggaggaaggc tccgtgggcg gggctggagc gtctctggtt ttgctgtctg tctctcacgc    39720
tgtttccaga acaaatgtgt gccctcagca aggatgctgg ctcttcagag gtgtcagcac    39780
aggcagccgg cacccacttt ccctcccaga aatcccccac gccctctagc tggggctggt    39840
gcaggagcag tgggaactc ctgttacccc tgacctgctg ccgtcagtca gccgcccgcc     39900
cccccacctt aaggaggggc agagtcaggg accagccctg aggggtggct cacccccagct   39960 tcacttcccc cagcccttct cagacagcca ctgtgcaggc tttggcagcg gggtcacac     40020 actccacccg ggaggccaaa gctgcatgca ggtcagtgcc gcccactgcc ctaggggcct    40080
cccagcgggg caggggcatg gtgggggtct cagagtgggg cgaggctgtg atgggggtct    40140
cagagcaggg tgaggctgtg ttggggtctc aggtgggctg aggctgttgg ggtctcaggg    40200
```

-continued

```
gtggctgagg ctgatgaaga cttggagcct gtgtctgggt agcagcttgt tggagtgtgg    40260
gatgtgacat ttaaaaacaa gaataaagaa taccccgtgc tgtggcccg aggtgagcag     40320 ctactttggt gaactcgtgt cactcacagc cccatcctgg gtcctgggt gtggtgtgct     40380 gtgtggggcc caggcccagt ggggtcacag gtacggggga ctctggtgcc tgggccacag    40440
ggatctgcac ctcactgcgt gccccacgt cttcagcagt ggttggggcc tgtggtctca     40500
atcccaggcc agccaggcac tctggggtct gggcgggtcc cgggtccaga caggggaag     40560 ggctggggag gggctctggt gtggctggat cgcccgtcta tggccaggtt tctctcctgg    40620
atcactcagt gcagaatcaa agggcacttt tctgcttttg tgtgcagaag ccgagggtga    40680
ccttgtcatc agaaggggaa gtggggcctc agaggcgtgc tgctggctcc aatccccaaa    40740
gcctcctggg caggaagtgg aagggcccca tccccacggt ccctggcagc gggagctccc    40800
tgaggctgat ggtgctggtg tctgtcgagg aagacaggcc tgaggagctg aggcgggagg    40860
ccagctacgg tccacggcct ggacacagat tcctgtgcgg gactggggca gtaggtgggc    40920
atctgtgctg gccatgttag ctcccagggg ccccatgcca tctgggctaa agcctgggcc    40980
ttgatttcct gaacttttct gggaggcact ccacgggcga gacaaggacc catgaacagg    41040
gcacttcttc gaagcctacg tgcacctcga aactcttgca acatttgcat ttttctccct    41100
aatagttcag tgtttgtttt attataaaca ggaaaattta aatattgtag ttagagtttt    41160
tttcttcttc ttagagatgg ggtttcactc tgtctcctaa ggctggagtg cagtggtggg    41220
atcatagctc acttcagcct caacctcctg ggctcaagcc gtcttcctgc ctcagcctcc    41280
cgagtagcac gcatcaccag cccagctaat tttctgtctt tttttttttt tttttttttt    41340 ttttttttgta gagacggggt ctccctgtga tgcccaggtt gttcttaaac ttctggcctc    41400
aagtcatcct cctgtctcag cctcccaaag tgttgggatt acaggcatga gccaccgtgc    41460
ctgcctgcag ttaaacattc ccccacaaaa tactgggcca caccgaggct agtatgaaag    41520
ttgcagccct gggtatgtgt gacctgagag ccccttggca gccatgggga gcgatggggg    41580 aagctgggc aatgggaagg ggtctaggca cacgagccct cgggtcctca cctcccacga    41640
ggcagggtcc caggctgcct ctactcaagg tggggcagca aaagaatcgc cctctagctg    41700
tgcagacccc ctccccctcc aggtctgcac accgcccaag gctggccctg gacttctggt    41760
ggattcaagt actcaggtgg ggagagtagg aggccagtcg cacggagccc tccccaacgc    41820
acagtgcctg cccagctcag gtgcctctga ggtgtagatt ctgagcaggt tctgggatct    41880
cctggccccc agcgggggct gccacaggag tataggccca acaggaaggg aagatcccag    41940
cgattggttc cagtgggttc tggggatgtc ctcggagcct ggcctggctc agggtccctc    42000
caaaagtccc tggaacgagg gtgaagtgtt gctcatgaat cagagagaaa gcaagcagga    42060
ccctcaagaa gggaggagag agaccattgg gcgtgcagca ctttgcactc ggggaaggg    42120 ctcctgaaac ttggaagtca gcaaatatct gctgtacttc accagaggtg ggatctaagg    42180
agacagaatg aagccagggg gcagaatgtt tcgtttctgt ctgaaacctg tgccctgcat    42240
ccctcatgga ctggggacct ggagttcccg ggaccaccg tggggaaatg cgtcccagca    42300
ctaatggtcc ccagcagctg cagtcacggg gtttgggcgc tctcccctcc tgatttgggg    42360 gacctttgt gctcctctgg gcagagggag gaggcagagg gaggaggaag gcccttcgct    42420
gtgggctgag tccttcccac cttccatacc agccagcag gaagccactg caggatgccc    42480
cagaggacag cctgatggtt gggggagagg cttctcccgc cctcacccct ccgggttctt    42540
```

-continued

```
cctggaccca ctgagtaacc caggtggtgg gacgtgtggc tgtgagtcct ggactctggg    42600
cgctcaccag cagctccgtc tcacacctgc ctgcgtgtga caccagcacc ccttatgatg    42660
aggaaacaag tttgcccagc tgcaggggtg gccgagtcag gatgactcta gcccgtgtcc    42720
tggacaccag accctgccca ggtccagccg gggctggtct cagccttcct gggctatgtc    42780
gcggagggtg ttggggacag cgagaggctg gcgtggacag tggaggggtg actttgtggg    42840
tggtcctgat agtgacggag aggaggatac tcagctccac ccctgggcgg ccctgagca    42900 gcacggctgg gcctgaaggg gcagggctgc cgtcacaggc tctggcccct gggagctcaa    42960
ggggtgaatc cctgatccca ggtgtgggac tgggatgggg cctcaggctg atgcaggcag    43020
gacctccaga gctcaggact gggtgggtgg gctcacaggg aggtaggggc aggccagagt    43080
cccagctgtc ctggactctg ctgtggggaa gggctgatgc agtgtggag tcaaatgtgg    43140 gtgcctcctg cagccgggtg ccaggagggg tggaggggcc accctgggct tgtccggga    43200 gcctggtctt cccgtccttg ggctgacagg tgctgctgcc tctgagccct ccctgctaag    43260
agctgtgtgc tgggtaaggc tggtggccct ttgggctccc tgtccaggat ttgtgctctg    43320
gagggtaggg cttgctgggc tggggactgg aggggaacgt ggagctcctt ctgcctcctt    43380
tcctgcccca tgacagcagg cagatcccag gagagaagag ctcaggagat gggaagagga    43440
tctgtccagg ggttagacct caaggtgac ttggagttct ttacggcacc catgctttct    43500
ttgaggagtt ttgtgtttgt gggtgtgggg tcgggctca cctcctccca catccctgcc    43560
cagaggtggg cagagtgggg gcagtgcctt gctcccctg ctcgctctct gctgacctcc    43620
ggctccctgt gctgcccag gaccatgaat ggcacctaca acacctgtgg ctccagcgac    43680
ctcacctggc ccccagcgat caagctgggc ttctacgcct acttgggcgt cctgctggtg    43740
ctaggcctgc tgctcaacag cctggcgctc tgggtgttct gctgccgcat gcagcagtgg    43800
acggagaccc gcatctacat gaccaacctg gcggtggccg acctctgcct gctgtgcacc    43860 ttgccctcg tgctgcactc cctgcgagac acctcagaca cgccgctgtg ccagctctcc    43920
cagggcatct acctgaccaa caggtacatg agcatcagcc tggtcacggc catcgccgtg    43980
gaccgctatg tggccgtgcg gcacccgctg cgtgcccgcg ggctgcggtc cccaggcag    44040 gctgcggccg tgtgcgcggt cctctgggtg ctggtcatcg gctccctggt ggctcgctgg    44100
ctcctgggga ttcaggaggg cggcttctgc ttcaggagca cccggcacaa tttcaactcc    44160
atggcgttcc cgctgctggg attctacctg ccctggccg tggtggtctt ctgctccctg    44220
aaggtggtga ctgccctggc ccagaggcca cccaccgacg tggggcaggc agaggccacc    44280
cgcaaggctg cccgcatggt ctgggccaac ctcctggtgt tcgtggtctg cttcctgccc    44340
ctgcacgtgg ggctgacagt gcgcctcgca gtgggctgga acgcctgtgc cctcctggag    44400
acgatccgtc gcgccctgta cataaccagc aagctctcag atgccaactg ctgcctggac    44460
gccatctgct actactacat ggccaaggag ttccaggagg cgtctgcact ggccgtggct    44520
cccagtgcta aggcccacaa aagccaggac tctctgtgcg tgaccctcgc ctaagaggcg    44580
tgctgtgggc gctgtgggcc aggtctcggg ggctccggga ggtgctgcct gcagggaa    44640 gctggaacca gtagcaagga gcccgggatc agccctgaac tcactgtgta ttctcttgga    44700
gccttgggtg ggcagggacg gcccaggtac ctgctctctt gggaagagag agggacaggg    44760
acaagggcaa gaggactgag gccagagcaa ggccaatgtc agagacccc gggatgggc    44820 ctcacacttg ccaccccag aaccagctca cctggcagga gtgggttcct gctggccagg    44880
gtgcagcctt gatgacacct gccgctgccc ctcggggctg gaataaaact ccccacccag    44940
```

-continued

```
agtcagtcct agtggggccc tctgtgtttc gcactcgtgt ggtgggaggc agggagggag   45000
cgcgtggctc ggagggctgg cggacatctt ccagggaccc ttcggggctc ttcactttga   45060
ggtccccctt ggacccttc accccttccc accccaccc acctggagcg tgagcagggg    45120
ctgttggaag ctcctggcag gaccacagta gaggcccca gcccaggttt ccttgctcaa    45180
gacagggctg ggagcagctg atctccatgt aggggctgca cagcggtgca aggggggtg   45240 accaaggtca agcaggtgag ggtgggttgg ggtgggtggc agtgaaggg gtggccaggg    45300 tctgtcaagg aacccagccc tcttctcctt ccttcaggga aaggctggaa accatgtctg   45360 gcagggcag gggttgggtg cccactcagg taaaggcacg atgtcctgct ggtttctgcc    45420
tctcctgtac tcctgcatgg agggcatctc gaaacccaag ctggaaggac agggcactcc   45480
agagacctcc tgtgagtgtg ggccagcacg gcctgggctc aaaccccatc ctgtcatccc   45540
atattgcatg tccacaggca ccgccccacc ctgttccatg ttccacagga ctggagagag   45600
atggcagtca tgttctggca gggacatggc acaagcatgc ggctgatggc atctcacagg   45660
accccaggct ccggagggcc catgcccagg agagccccat aagggctctg tgcctaaaag   45720
ggtgcatgcc caggtgggcc catgcccagg aaggtccatg tctaggggg ttccgtgccc    45780 aggaaggtcc atgcccagga tggtccatga gcaggaggc ctcattccca ggagggtccc    45840
gtgcccagga gggctctatg cccaaaaggg tcccatgtcc aggagggtcc atacgcaagg   45900
gtgtccatgc ctggttgggg ggggtctat gtccaggagg gtcccatgcc tggaagggtc    45960
catgctcagg agggttcatg cccaggagag tttatgccct ggagggcccc atgcccggga   46020
gagtcacgtg cacagagggc cctgtgctca ggaggataca tgtccaggag tgtccctgtc   46080
caggaggctc catgcccagg aggctccatg tcaagaaaga ttcatgccta ggagggttca   46140
tgcccaggag tgtccctgcc taggaaggtc cattaccaga agggcccatg tcaaggagcg   46200
ttcatgccca ggaaggtcca gcccaggagg gtccatgtca aggaggttcc atgcccagga   46260
gggtccatgc tgaggtgggt ccatgcccag gagggttcat gtccagaaag gtccatgcct   46320
aggagggccc atacacaaca gagccctgtg cccaggaagg accatgtcaa ggagaacccc   46380
atgcccatga gggtccatgc ccagtaaggg ccatgcccat gagatcctca tgcccaggaa   46440
ggcccatgcc caggagggtc caagcccagg ccagttcatg cacaggaggg ccccatgcct   46500
aaaagtgtcc atgcccagga aggtccatgt ccagaagagt ccatacccag gagggctgat   46560
atggttaggc tttgtgtctc cacccaaatc tcatcttgaa ttgtaatccc tataataacc   46620
atagtcccca tgtgtcaagg gagagaccag gtggaggcaa ttggatcatg ggggctgttt   46680
cccacatgct gttctcatga tagtgagtga gttctcatga gatctgatgg tttataagg    46740 ggctcttccc ttcacttctc cttcctactg tcttatgaag aaggttcctt gcttcccctt   46800
caccttctgc catgattgta agtttcctga ggcctcccta gccatgctga agtgtgagtc   46860
aattaaacct ctttccttta aaattaccca gtcttgggca gttctttata acagtatgaa   46920
aacagacgaa tgcagtaaat tggtaccaca gagagtgggg tgctgctgta aagataccca   46980
aaaatgtcga agcaactttg gaactggta atagtcagag gttggaacag tttggagggc    47040
tcagaagaag acagaaagat gtgggaaagt atggaacttc ctagagactt gttgaatggc   47100
tttgatcaaa atgctgatag ggatatggac aatgaattcc aggttgaggt ggtctcagat   47160
ggagatgagg aatttgctgg aaactggaat aaaggtgatt cttgctatgc tttagcaaag   47220
agattggcag catttttgccc ctgccttaga gatctgtgga actttgaatg tgagagagat   47280
```

-continued

```
gatttagggt atctggcaga agaaatttct aagcagcaaa gcattcaaga gtgctcttaa      47340
aagcattcaa ttttatgcat tcacaaagag atgatttgga attggaactc acatttaaaa      47400
gggaagcaga gcataaaagt ttagaaaatt tgcatcctga ctatgggata gaaagaaaa       47460 actcattttc tgaggagaaa ttcaagccag ctgcagaaat ttgcataagt aactaggagc      47520
cacatgttaa tagcatagac aatgagggaa atgtctccag ggcatgtcag aggtcttcac      47580 agcaaccccca cccatcacag gcctggaggc ttaggaggaa aaatggtttt tgtcgttggg     47640
gcccagggcc ttgctggttt gtgcagtctc aggacttggt gccccacatc ccagcagtgg      47700
ctaaaagggg ccaatgtaca gcttagacct ttgcttcaga ggtgcaagcc ccaagccttg      47760
gtggcttaca tgtggtgttg ggcctgcaga tacacagaag tttgctgcac tggtggaacc      47820
ctcatgtaga acctctgcta gggcagtgta gaagtgatat gtggggttgg agccccccca      47880
cacaatcccc actggggcac tgcctactgc tactggaact gtgagaagaa ggccaccatc      47940
ctccagaccc cagaatggta gatccactga tggcttgaac catgcacctg gaaaagccac      48000
agacactcaa caccagcctg tgaaggcagc tggaagggag gctgtacct gcaaaacaac      48060 agaggcagag ctgcccaagg tcatgggagc ccacctcttg catgagcctg acttgaatgt      48120
gagacatgga gtcaaaggag atcatttggg agctttaagt tttgactgcc cacctggatt      48180
tcggacttgc atgggcctg tggccccttc attttggcca atttatccca tttggaatgg      48240
gtatatttac ccaatgcctg tacccccatt ctatctagga tataactaac ttgcttttga     48300
ttttataggt ttgtaggcag aagggactta ccttgtctca gatgacactt tggtcttgga     48360
cttttgggtt aatgctggaa tgaattaaga cttttggggga cttttgggaa ggcatgactg    48420
gttttgaaat gtaaaagaga catgagattc ggaaggggct aggagcagaa tggtataatt     48480
aggctttgtg tccccaccca aatctcatct tgaattgcag tccccacatg tcaagggaga     48540
gaccaggtgc agtaattga atcatggggg cagtctcttc catgctattc tcatgataga     48600
gagtgagttc tcatgaaatc tgacagtttt ataagggct cttcccctt ggcttggcac      48660 ttcttcttgc tgcgttgtga agaaggtgcc ttgcttcccc ttcgccttcc gccatgactg     48720
taagtttcct gagacttccc cagccatgct gaactgtgag tcaattaaac ctctttcctt     48780
tataaattac ccagtctcgg gcagttcctt atagcagtat gaaaacagaa taatataagg     48840
ctgcatgcca ggcagtccca tgcctaggag ggtccatgtc tcgggtccc tcccaggaag      48900 gtccatgtcc aggggtccct gcccaggagg gttcatgcct aggaggaccc atacccagta     48960
gagtcatgtt caggagggtc tattcacagc agagttcatg cccaggaggg tccatgacca     49020
ggaggggtct gtgcccagga aggtccatgc caaccaagga ggatcaatgc ccaggaggac     49080
ccatgtctag gagggtctac gtccaggagg acccattccc aggagggcat acccag         49136
```

<210> SEQ ID NO 2
<211> LENGTH: 672
<212> TYPE: PRT
<213> ORGANISM: Human

<400> SEQUENCE: 2

```
Met Arg Ala Gly Arg Gly Ala Thr Pro Ala Arg Glu Leu Phe Arg Asp
 1               5                   10                  15

Ala Ala Phe Pro Ala Ala Asp Ser Ser Leu Phe Cys Asp Leu Ser Thr
            20                  25                  30

Pro Leu Ala Gln Phe Arg Glu Asp Ile Thr Trp Arg Arg Pro Gln Glu
        35                  40                  45
```

```
Ile Cys Ala Thr Pro Arg Leu Phe Pro Asp Pro Arg Glu Gly Gln
 50                  55                  60

Val Lys Gln Gly Leu Leu Gly Asp Cys Trp Phe Leu Cys Ala Cys
 65                  70                  75                  80

Ala Leu Gln Lys Ser Arg His Leu Leu Asp Gln Val Ile Pro Pro Gly
                 85                  90                  95

Gln Pro Ser Trp Ala Asp Gln Glu Tyr Arg Gly Ser Phe Thr Cys Arg
            100                 105                 110

Ile Trp Gln Phe Gly Arg Trp Val Glu Val Thr Thr Asp Asp Arg Leu
            115                 120                 125

Pro Cys Leu Ala Gly Arg Leu Cys Phe Ser Arg Cys Gln Arg Glu Asp
            130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Gly Leu Ala Glu Arg Trp Asn Leu Lys Gly Val Ala Gly
            180                 185                 190

Ser Gly Gly Gln Gln Asp Arg Pro Gly Arg Trp Glu His Arg Thr Cys
            195                 200                 205

Arg Gln Leu Leu His Leu Lys Asp Gln Cys Leu Ile Ser Cys Cys Val
210                 215                 220

Leu Ser Pro Arg Ala Gly Ala Arg Glu Leu Gly Glu Phe His Ala Phe
225                 230                 235                 240

Ile Val Ser Asp Leu Arg Glu Leu Gln Gly Gln Ala Gly Gln Cys Ile
            245                 250                 255

Leu Leu Leu Arg Ile Gln Asn Pro Trp Gly Arg Arg Cys Trp Gln Gly
            260                 265                 270

Leu Trp Arg Glu Gly Gly Glu Gly Trp Ser Gln Val Asp Ala Ala Val
            275                 280                 285

Ala Ser Glu Leu Leu Ser Gln Leu Gln Glu Gly Glu Phe Trp Val Glu
290                 295                 300

Glu Glu Glu Phe Leu Arg Glu Phe Asp Glu Leu Thr Val Gly Tyr Pro
305                 310                 315                 320

Val Thr Glu Ala Gly His Leu Gln Ser Leu Tyr Thr Glu Arg Leu Leu
            325                 330                 335

Cys His Thr Arg Ala Leu Pro Gly Ala Trp Val Lys Gly Gln Ser Ala
            340                 345                 350

Gly Gly Cys Arg Asn Asn Ser Gly Phe Pro Ser Asn Pro Lys Phe Trp
            355                 360                 365

Leu Arg Val Ser Glu Pro Ser Glu Val Tyr Ile Ala Val Leu Gln Arg
370                 375                 380

Ser Arg Leu His Ala Ala Asp Trp Ala Gly Arg Ala Arg Ala Leu Val
385                 390                 395                 400

Gly Asp Ser His Thr Ser Trp Ser Pro Ala Ser Ile Pro Gly Lys His
            405                 410                 415

Tyr Gln Ala Val Gly Leu His Leu Trp Lys Val Glu Lys Arg Arg Val
            420                 425                 430

Asn Leu Pro Arg Val Leu Ser Met Pro Pro Val Ala Gly Thr Ala Cys
            435                 440                 445

His Ala Tyr Asp Arg Glu Val His Leu Arg Cys Glu Leu Ser Pro Gly
450                 455                 460

Tyr Tyr Leu Ala Val Pro Ser Thr Phe Leu Lys Asp Ala Pro Gly Glu
```

```
                    465                 470                 475                 480
            Phe Leu Leu Arg Val Phe Ser Thr Gly Arg Val Ser Leu Ser Ala Ile
                            485                 490                 495

Arg Ala Val Ala Lys Asn Thr Thr Pro Gly Ala Ala Leu Pro Ala Gly
                        500                 505                 510

Glu Trp Gly Thr Val Gln Leu Arg Gly Ser Trp Arg Val Gly Gln Thr
                    515                 520                 525

Ala Gly Gly Ser Arg Asn Phe Ala Ser Tyr Pro Thr Asn Pro Cys Phe
                530                 535                 540

Pro Phe Ser Val Pro Glu Gly Pro Gly Pro Arg Cys Val Arg Ile Thr
            545                 550                 555                 560

Leu His Gln His Cys Arg Pro Ser Asp Thr Glu Phe His Pro Ile Gly
                            565                 570                 575

Phe His Ile Phe Gln Val Pro Glu Gly Gly Arg Ser Gln Asp Ala Pro
                        580                 585                 590

Pro Leu Leu Leu Gln Glu Pro Leu Leu Ser Cys Val Pro His Arg Tyr
                    595                 600                 605

Ala Gln Glu Val Ser Arg Leu Cys Leu Leu Pro Ala Gly Thr Tyr Lys
                610                 615                 620

Val Val Pro Ser Thr Tyr Leu Pro Asp Thr Glu Gly Ala Phe Thr Val
            625                 630                 635                 640

Thr Ile Ala Thr Arg Ile Asp Arg Pro Ser Ile His Ser Gln Glu Met
                            645                 650                 655

Leu Gly Gln Phe Leu Gln Glu Val Ser Val Met Ala Val Met Lys Thr
                        660                 665                 670

<210> SEQ ID NO 3
<211> LENGTH: 2620
<212> TYPE: DNA
<213> ORGANISM: Human

<400> SEQUENCE: 3
gactagcggg ccggcgtact ggcctggtcc agcacctgcg gggccctcgg gcttggaggg      60
ctgggccggg cggggaacgg gcggggcggg ccggaggcgg cggcggctga ctcgccttct     120
ctccggggct gcgaccccga ggcaaccggc tgcagatggg agcccgcgga gccgaggatg     180
cgggcgggcc ggggcgcgac gccggcgagg gagctgttcc gggacgccgc cttccccgcc     240
gcggactcct cgctcttctg cgacttgtct acgccgctgg cccagttccg cgaggacatc     300
acgtggaggc ggccccagga gatttgtgcc acaccccggc tgtttccaga tgacccacgg     360
gaagggcagg tgaagcaggg gctgctgggg gattgctggt tcctgtgtgc ctgcgccgcg     420
ctgcagaaga gcaggcacct cctggaccag gtcattcctc cgggacagcc gagctgggcc     480
gaccaggagt accggggctc cttcacctgt cgcatttggc agtttggacg ctgggtggag     540
gtgaccacag atgaccgcct gccgtgcctt gcagggagac tctgtttctc ccgctgccag     600
agggaggatg tgttctggct ccccttactg gaaaaggtct acgccaaggt ccatgggtcc     660
tacgagcacc tgtgggccgg gcaggtggcg gatgccctgg tggacctgac cggcggcctg     720
gcagaaagat ggaacctgaa gggcgtagca ggaagcggag ccagcaggga caggccaggc     780
cgctgggagc acaggacttg tcggcagctg ctccacctga aggaccagtg tctgatcagc     840
tgctgcgtgc tcagcccccag agcaggtgcc cgggagctgg gggagttcca tgccttcatt     900
gtctcggacc tgcgggagct ccaggtcag gcggggccagt gcatcctgct gctgcggatc     960
cagaacccct gggggccggcg gtgctggcag gggctctgga gagagggggg tgaagggtgg    1020
```

```
agccaggtag atgcagcggt agcatctgag ctcctgtccc agctccagga agggagttc    1080 tgggtggagg aggaggagtt cctcagggag tttgacgagc tcaccgttgg ctacccggtc   1140
acggaggccg gccacctgca gagcctctac acagagaggc tgctctgcca tacgcgggcg   1200
ctgcctgggg cctgggtcaa gggccagtca gcaggaggct gccggaacaa cagcggcttt   1260
cccagcaacc ccaaattctg gctgcgggtc tcagaaccga gtgaggtgta cattgccgtc   1320
ctgcagagat ccaggctgca cgcggcggac tgggcaggcc gggcccgggc actggtgggt   1380
gacagtcata cttcgtggag cccagcgagc atcccgggca agcactacca ggctgtgggt   1440
ctgcacctct ggaaggtaga gaagcggcgg tcaatctgc ctagggtcct gtccatgccc    1500
cccgtggctg gcaccgcgtg ccatgcatac gaccgggagg tccacctgcg ttgtgagctc   1560
tcaccgggct actacctggc tgtccccagc accttcctga aggacgcgcc aggggagttc   1620
ctgctccgag tcttctctac cggcgagtc tcccttagcg ccatcagggc agtggccaag    1680
aacaccaccc ccggggcagc cctgcctgcg ggggagtggg ggaccgtgca gctacggggt   1740
tcttggagag tcggccagac ggcggggggc agcaggaact ttgcctcata ccccaccaac   1800
ccctgcttcc ccttctcggt ccccgagggc ctggccccc gctgcgtccg catcactctg    1860
catcagcact gccggcccag tgacaccgag ttccacccca tcggcttcca tatcttccag   1920
gtcccagagg gtggaaggag ccaggacgca cccccactgc tgctgcagga ccgctgctg    1980 agctgcgtgc acatcgcta cgcccaggag gtgagccggc tctgcctcct gcctgcaggc    2040
acctacaagg ttgtgccctc cacctacctg ccggacacag agggggcctt cacagtgacc   2100
atcgcaacca ggattgacag gccatccatt cacagccagg agatgctggg ccagttcctc   2160
caagaggtct ccgtcatggc agtgatgaaa acctaacagg gtggccccct gtgccagctc   2220
aggtgactgg agcccgaggg cctgacaggt tccagcagc tgggccggcc agccttgcac    2280
tgtgggggct ggtcctgagt cttggcctgc ctcccagccc tgccagggggg ctgcggccta  2340 ggggtccacg ggaagcctcc gtcaggagag acgcagccct gggggccagc tggtgctgca   2400
aggaagggtg ggaagcttgc tggcttctgt tgcgccactg agacggcaga gaccccagga   2460
tcccagagct tcccaggatc cctcccagat cctctgctga ctccatatgg aggcctcaca   2520
cccagagggt agggcagcag atcttctttta taactattta ttgttcgaat cactttttagg 2580 atgtaacttt ataaataaac atgagcgctg atgatttgca                         2620
```

<210> SEQ ID NO 4
<211> LENGTH: 544
<212> TYPE: PRT
<213> ORGANISM: Human

<400> SEQUENCE: 4

```
Met Arg Ala Gly Arg Gly Ala Thr Pro Ala Arg Glu Leu Phe Arg Asp
  1               5                  10                  15

Ala Ala Phe Pro Ala Ala Asp Ser Ser Leu Phe Cys Asp Leu Ser Thr
                 20                  25                  30

Pro Leu Ala Gln Phe Arg Glu Asp Ile Thr Trp Arg Arg Pro Gln Glu
             35                  40                  45

Ile Cys Ala Thr Pro Arg Leu Phe Pro Asp Pro Arg Glu Gly Gln
         50                  55                  60

Val Lys Gln Gly Leu Leu Gly Asp Cys Trp Phe Leu Cys Ala Cys Ala
 65                  70                  75                  80

Ala Leu Gln Lys Ser Arg His Leu Leu Asp Gln Val Ile Pro Pro Gly
```

-continued

```
                        85                  90                  95
Gln Pro Ser Trp Ala Asp Gln Glu Tyr Arg Gly Ser Phe Thr Cys Arg
                100                 105                 110

Ile Trp Gln Phe Gly Arg Trp Val Glu Val Thr Thr Asp Asp Arg Leu
        115                 120                 125

Pro Cys Leu Ala Gly Arg Leu Cys Phe Ser Arg Cys Gln Arg Glu Asp
        130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Gly Leu Ala Glu Arg Trp Asn Leu Lys Gly Val Ala Gly
                180                 185                 190

Ser Gly Gly Gln Gln Asp Arg Pro Gly Arg Trp Glu His Arg Thr Cys
                195                 200                 205

Arg Gln Leu Leu His Leu Lys Asp Gln Cys Leu Ile Ser Cys Cys Val
        210                 215                 220

Leu Ser Pro Arg Ala Gly Ala Arg Glu Leu Gly Glu Phe His Ala Phe
225                 230                 235                 240

Ile Val Ser Asp Leu Arg Glu Leu Gln Gly Gln Ala Gly Gln Cys Ile
                245                 250                 255

Leu Leu Leu Arg Ile Gln Asn Pro Trp Gly Arg Arg Cys Trp Gln Gly
        260                 265                 270

Leu Trp Arg Glu Gly Gly Glu Gly Trp Ser Gln Val Asp Ala Ala Val
        275                 280                 285

Ala Ser Glu Leu Leu Ser Gln Leu Gln Glu Gly Glu Phe Trp Val Glu
290                 295                 300

Glu Glu Glu Phe Leu Arg Glu Phe Asp Glu Leu Thr Val Gly Tyr Pro
305                 310                 315                 320

Val Thr Glu Ala Gly His Leu Gln Ser Leu Tyr Thr Glu Arg Leu Leu
                325                 330                 335

Cys His Thr Arg Ala Leu Pro Gly Ala Trp Val Lys Gly Gln Ser Ala
                340                 345                 350

Gly Gly Cys Arg Asn Asn Ser Gly Phe Pro Ser Asn Pro Lys Phe Trp
        355                 360                 365

Leu Arg Val Ser Glu Pro Ser Glu Val Tyr Ile Ala Val Leu Gln Arg
        370                 375                 380

Ser Arg Leu His Ala Ala Asp Trp Ala Gly Arg Ala Arg Ala Leu Val
385                 390                 395                 400

Gly Asp Ser His Thr Ser Trp Ser Pro Ala Ser Ile Pro Gly Lys His
                405                 410                 415

Tyr Gln Ala Val Gly Leu His Leu Trp Lys Val Glu Lys Arg Arg Val
                420                 425                 430

Asn Leu Pro Arg Val Leu Ser Met Pro Pro Val Ala Gly Thr Ala Cys
        435                 440                 445

His Ala Tyr Asp Arg Glu Val His Leu Arg Cys Glu Leu Ser Pro Gly
        450                 455                 460

Tyr Tyr Leu Ala Val Pro Ser Thr Phe Leu Lys Asp Ala Pro Gly Glu
465                 470                 475                 480

Phe Leu Leu Arg Val Phe Ser Thr Gly Arg Val Ser Leu Arg Ala Leu
                485                 490                 495

Ala Pro Ala Ala Ser Ala Ser Leu Cys Ile Ser Thr Ala Gly Pro Val
                500                 505                 510
```

```
Thr Pro Ser Ser Thr Pro Ser Ala Ser Ile Ser Ser Arg Ser Gln Arg
        515                 520                 525

Val Glu Gly Ala Arg Thr His Pro His Cys Cys Cys Arg Ser Arg Cys
        530                 535                 540

<210> SEQ ID NO 5
<211> LENGTH: 2297
<212> TYPE: DNA
<213> ORGANISM: Human

<400> SEQUENCE: 5
ccgaggcaac cggctgcaga tgggagcccg cggagccgag gatgcgggcg ggccggggcg      60
cgacgccggc gagggagctg ttccgggacg ccgccttccc cgccgcggac tcctcgctct     120
tctgcgactt gtctacgccg ctggcccagt tccgcgagga catcacgtgg aggcggcccc     180
aggagatttg tgccacaccc cggctgtttc cagatgaccc acgggaaggg caggtgaagc     240
aggggctgct gggggattgc tggttcctgt gtgcctgcgc cgcgctgcag aagagcaggc     300
acctcctgga ccaggtcatt cctccgggac agccgagctg gccgaccag gagtaccggg      360
gctccttcac ctgtcgcatt ggcagtttg gacgctgggt ggaggtgacc acagatgacc      420
gcctgccgtg ccttgcaggg agactctgtt tctcccgctg ccagagggag gatgtgttct     480
ggctccccctt actggaaaag gtctacgcca aggtccatgg gtcctacgag cacctgtggg    540
ccgggcaggt ggcggatgcc ctggtggacc tgaccgcgg cctggcagaa agatggaacc      600
tgaagggcgt agcaggaagc ggaggccagc aggacaggcc aggccgctgg gagcacagga     660
cttgtcggca gctgctccac ctgaaggacc agtgtctgat cagctgctgc gtgctcagcc     720
ccagagcagg tgcccgggag ctgggggagt tccatgcctt cattgtctcg gacctgcggg     780
agctccaggg tcaggcgggc cagtgcatcc tgctgctgcg gatccagaac ccctggggcc     840
ggcggtgctg gcagggctc tggagagagg ggggtgaagg gtggagccag gtagatgcag      900
cggtagcatc tgagctcctg tcccagctcc aggaagggga gttctgggtg gaggaggagg     960
agttcctcag ggagtttgac gagctcaccg ttggctaccc ggtcacggag gccggccacc    1020
tgcagagcct ctacacagag aggctgctct gccatacgcg ggcgctgcct ggggcctggg    1080
tcaagggcca gtcagcagga ggctgccgga caacagcgg ctttcccagc aaccccaaat     1140
tctggctgcg ggtctcagaa ccgagtgagg tgtacattgc cgtcctgcag agatccaggc    1200
tgcacgcggc ggactgggca ggccgggccc gggcactggt gggtgacagt catacttcgt    1260
ggagcccagc gagcatcccg ggcaagcact accaggctgt gggtctgcac ctctggaagg    1320
tagagaagcg gcgggtcaat ctgcctaggg tcctgtccat gccccccgtg gctggcaccg    1380
cgtgccatgc atacgaccgg gaggtccacc tgcgttgtga gctctcaccg ggctactacc    1440
tggctgtccc cagcaccttc ctgaaggacg cgccagggga gttcctgctc cgagtctttct    1500
ctaccgggcg agtctcccctt agggccctgg ccccgctgc gtccgcatca ctctgcatca    1560
gcactgccgg cccagtgaca ccgagttcca ccccatcggc ttccatatct tccaggtccc    1620
agagggtgga aggagccagg acgcacccc actgctgctg caggagccgc tgctgagctg    1680
cgtgccacat cgctacgccc aggaggtgag ccggctctgc ctcctgcctg caggcaccta    1740
caaggttgtg ccctccacct acctgccgga cacagagggg gccttcacag tgaccatcgc    1800
aaccaggatt gacaggccat ccattcacag ccaggagatg ctgggccagt tcctccaaga    1860
ggtctccgtc atggcagtga tgaaaaccta acagggtggc ccctgtgcc agctcaggtg    1920
```

-continued

```
actggagccc gagggcctga caggttccca gcagctgggc cggccagcct tgcactgtgg      1980
gggctggtcc tgagtcttgg cctgcctccc agccctgcca gggggctgcg gcctagggt       2040 ccacgggaag cctccgtcag gagagacgca gccctggggg ccagctggtg ctgcaaggaa      2100
gggtgggaag cttgctggct tctgttgcgc cactgagacg gcagagaccc caggatccca     2160
gagcttccca ggatccctcc cagatcctct gctgactcca tatggaggcc tcacacccag     2220
agggtagggc agcagatctt ctttataact atttattgtt cgaatcactt ttaggatgta     2280
actttataaa taaacct                                                    2297
```

<210> SEQ ID NO 6
<211> LENGTH: 517
<212> TYPE: PRT
<213> ORGANISM: Human

<400> SEQUENCE: 6

```
Met Arg Ala Gly Arg Gly Ala Thr Pro Ala Arg Glu Leu Phe Arg Asp
 1               5                  10                  15

Ala Ala Phe Pro Ala Ala Asp Ser Ser Leu Phe Cys Asp Leu Ser Thr
            20                  25                  30

Pro Leu Ala Gln Phe Arg Glu Asp Ile Thr Trp Arg Arg Pro Gln Glu
        35                  40                  45

Ile Cys Ala Thr Pro Arg Leu Phe Pro Asp Pro Arg Glu Gly Gln
    50                  55                  60

Val Lys Gln Gly Leu Leu Gly Asp Cys Trp Phe Leu Cys Ala Cys Ala
65                  70                  75                  80

Ala Leu Gln Lys Ser Arg His Leu Leu Asp Gln Val Ile Pro Pro Gly
                85                  90                  95

Gln Pro Ser Trp Ala Asp Gln Glu Tyr Arg Gly Ser Phe Thr Cys Arg
            100                 105                 110

Ile Trp Gln Phe Gly Arg Trp Val Glu Val Thr Thr Asp Asp Arg Leu
        115                 120                 125

Pro Cys Leu Ala Gly Arg Leu Cys Phe Ser Arg Cys Gln Arg Glu Asp
    130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Gly Leu Ala Glu Arg Trp Asn Leu Lys Gly Val Ala Gly
            180                 185                 190

Ser Gly Gly Gln Gln Asp Arg Pro Gly Arg Trp Glu His Arg Thr Cys
        195                 200                 205

Arg Gln Leu Leu His Leu Lys Asp Gln Cys Leu Ile Ser Cys Cys Val
    210                 215                 220

Leu Ser Pro Arg Ala Gly Ala Arg Glu Leu Gly Glu Phe His Ala Phe
225                 230                 235                 240

Ile Val Ser Asp Leu Arg Glu Leu Gln Gly Gln Ala Gly Gln Cys Ile
                245                 250                 255

Leu Leu Leu Arg Ile Gln Asn Pro Trp Gly Arg Arg Cys Trp Gln Gly
            260                 265                 270

Leu Trp Arg Glu Gly Gly Glu Gly Trp Ser Gln Val Asp Ala Ala Val
        275                 280                 285

Ala Ser Glu Leu Leu Ser Gln Leu Gln Glu Gly Glu Phe Trp Val Glu
    290                 295                 300
```

Glu Glu Glu Phe Leu Arg Glu Phe Asp Glu Leu Thr Val Gly Tyr Pro
305                 310                 315                 320

Val Thr Glu Ala Gly His Leu Gln Ser Leu Tyr Thr Glu Arg Leu Leu
            325                 330                 335

Cys His Thr Arg Ala Leu Pro Gly Ala Trp Val Lys Gly Gln Ser Ala
            340                 345                 350

Gly Gly Cys Arg Asn Asn Ser Gly Phe Pro Ser Asn Pro Lys Phe Trp
            355                 360                 365

Leu Arg Val Ser Lys Pro Ser Glu Val Tyr Ile Ala Val Leu Gln Arg
        370                 375                 380

Ser Arg Leu His Ala Ala Asp Trp Ala Gly Arg Ala Arg Ala Leu Val
385                 390                 395                 400

Gly Asp Ser His Thr Ser Trp Ser Pro Ala Ser Ile Pro Gly Lys His
                405                 410                 415

Tyr Gln Ala Val Gly Leu His Leu Trp Lys Val Pro Glu Gly Gly Arg
            420                 425                 430

Ser Gln Asp Ala Pro Pro Leu Leu Leu Gln Glu Pro Leu Leu Ser Cys
        435                 440                 445

Val Pro His Arg Tyr Ala Gln Glu Val Ser Arg Leu Cys Leu Leu Pro
    450                 455                 460

Ala Gly Thr Tyr Lys Val Val Pro Ser Thr Tyr Leu Pro Asp Thr Glu
465                 470                 475                 480

Gly Ala Phe Thr Val Thr Ile Ala Thr Arg Ile Asp Arg Pro Ser Ile
                485                 490                 495

His Ser Gln Glu Met Leu Gly Gln Phe Leu Gln Glu Val Ser Val Met
            500                 505                 510

Ala Val Met Lys Thr
            515

<210> SEQ ID NO 7
<211> LENGTH: 2001
<212> TYPE: DNA
<213> ORGANISM: Human

<400> SEQUENCE: 7
ccgaggcaac cggctgcaga tgggagcccg cggagccgag gatgcgggcg ggccggggcg      60
cgacgccggc gagggagctg ttccgggacg ccgccttccc cgccgcggac tcctcgctct     120
tctgcgactt gtctacgccg ctggcccagt tccgcgagga catcacgtgg aggcggcccc     180
aggagatttg tgccacaccc cggctgtttc agatgacccc acgggaaggg caggtgaagc     240 agggggctgct gggggattgc tggttcctgt gtgcctgcgc cgcgctgcag aagagcaggc     300
acctcctgga ccaggtcatt cctccgggac agccgagctg ggccgaccag gagtaccggg     360
gctccttcac ctgtcgcatt tggcagtttg acgctgggt ggaggtgacc acagatgacc      420
gcctgccgtg ccttgcaggg agactctgtt tctcccgctg ccagagggag gatgtgttct     480
ggctcccctt actggaaaag gtctacgcca aggtccatgg gtcctacgag cacctgtggg     540
ccgggcaggt ggcggatgcc ctggtggacc tgaccggcgg cctggcagaa agatggaacc     600
tgaagggcgt agcaggaagc ggaggccagc aggacaggcc aggccgctgg gagcacagga     660
cttgtcggca gctgctccac ctgaaggacc agtgtctgat cagctgctgc gtgctcagcc     720
ccagagcagg tgcccgggag ctgggggagt ccatgccttc cattgtctcg gacctgcggg     780
agctccaggg tcaggcgggc cagtgcatcc tgctgctgcg gatccagaac ccctggggcc     840
ggcggtgctg gcaggggctc tggagagagg ggggtgaagg gtggagccag gtagatgcag     900

```
cggtagcatc tgagctcctg tcccagctcc aggaaggggga gttctgggtg gaggaggagg    960
agttcctcag ggagtttgac gagctcaccg ttggctaccc ggtcacggag gccggccacc   1020
tgcagagcct ctacacagag aggctgctct gccatacgcg ggcgctgcct ggggcctggg   1080
tcaaggcca gtcagcagga ggctgccgga caacagcgg ctttcccagc aaccccaaat    1140
tctggctgcg ggtctcaaaa ccgagtgagg tgtacattgc cgtcctgcag agatccaggc   1200
tgcacgcggc ggactgggca ggccgggccc gggcactggt gggtgacagt catacttcgt   1260
ggagcccagc gagcatcccg ggcaagcact accaggctgt gggtctgcac ctctggaagg   1320
tcccagaggg tggaaggagc caggacgcac ccccactgct gctgcaggag ccgctgctga   1380
gctgcgtgcc acatcgctac gcccaggagg tgagccggct ctgcctcctg cctgcaggca   1440
cctacaaggt tgtgccctcc acctacctgc cggacacaga gggggccttc acagtgacca   1500
tcgcaaccag gattgacagg ccatccattc acagccagga gatgctgggc cagttcctcc   1560
aagaggtctc cgtcatggca gtgatgaaaa cctaacaggg tggcccctg tgccagctca   1620
ggtgactgga gcccgagggc ctgacaggtt cccagcagct gggccggcca gccttgcact   1680
gtggggctg gtcctgagtc ttggcctgcc tcccagccct gccaggggc tgcggcctag   1740
gggtccacgg gaagcctccg tcaggagaga cgcagccctg ggggccagct ggtgctgcaa   1800
ggaagggtgg gaagcttgct ggcttctgtt gcgccactga gacggcagag accccaggat   1860
cccagagctt cccaggatcc ctcccagatc ctctgctgac tccatatgga ggcctcacac   1920
ccagagggta gggcagcaga tcttctttat aactatttat tgttcgaatc acttttagga   1980
tgtaacttta taaataaacc t                                              2001
```

<210> SEQ ID NO 8
<211> LENGTH: 513
<212> TYPE: PRT
<213> ORGANISM: Human

<400> SEQUENCE: 8

```
Met Arg Ala Gly Arg Gly Ala Thr Pro Ala Arg Glu Leu Phe Arg Asp
  1               5                  10                  15

Ala Ala Phe Pro Ala Ala Asp Ser Ser Leu Phe Cys Asp Leu Ser Thr
                 20                  25                  30

Pro Leu Ala Gln Phe Arg Glu Asp Ile Thr Trp Arg Arg Pro Gln Glu
             35                  40                  45

Ile Cys Ala Thr Pro Arg Leu Phe Pro Asp Pro Arg Glu Gly Gln
         50                  55                  60

Val Lys Gln Gly Leu Leu Gly Asp Cys Trp Phe Leu Cys Ala Cys Ala
 65                  70                  75                  80

Ala Leu Gln Lys Ser Arg His Leu Leu Asp Gln Val Ile Pro Pro Gly
                 85                  90                  95

Gln Pro Ser Trp Ala Asp Gln Glu Tyr Arg Gly Ser Phe Thr Cys Arg
            100                 105                 110

Ile Trp Gln Phe Gly Arg Trp Val Glu Val Thr Thr Asp Asp Arg Leu
        115                 120                 125

Pro Cys Leu Ala Gly Arg Leu Cys Phe Ser Arg Cys Gln Arg Glu Asp
    130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175
```

```
Leu Thr Gly Gly Leu Ala Glu Arg Trp Asn Leu Lys Gly Val Ala Gly
            180                 185                 190
Ser Gly Gly Gln Gln Asp Arg Pro Gly Arg Trp Glu His Arg Thr Cys
        195                 200                 205
Arg Gln Leu Leu His Leu Lys Asp Gln Cys Leu Ile Ser Cys Cys Val
    210                 215                 220
Leu Ser Pro Arg Ala Gly Ala Arg Glu Leu Gly Glu Phe His Ala Phe
225                 230                 235                 240
Ile Val Ser Asp Leu Arg Glu Leu Gln Gly Gln Ala Gly Gln Cys Ile
                245                 250                 255
Leu Leu Leu Arg Ile Gln Asn Pro Trp Gly Arg Arg Cys Trp Gln Gly
            260                 265                 270
Leu Trp Arg Glu Gly Gly Glu Gly Trp Ser Gln Val Asp Ala Ala Val
        275                 280                 285
Ala Ser Glu Leu Leu Ser Leu Gln Glu Gly Glu Phe Trp Val Glu
    290                 295                 300
Glu Glu Glu Phe Leu Arg Glu Phe Asp Glu Leu Thr Val Gly Tyr Pro
305                 310                 315                 320
Val Thr Glu Ala Gly His Leu Gln Ser Leu Tyr Thr Glu Arg Leu Leu
                325                 330                 335
Cys His Thr Arg Ala Leu Pro Gly Ala Trp Val Lys Gly Gln Ser Ala
            340                 345                 350
Gly Gly Cys Arg Asn Asn Ser Gly Phe Pro Ser Asn Pro Lys Phe Trp
        355                 360                 365
Leu Arg Val Ser Glu Pro Ser Glu Val Tyr Ile Ala Val Leu Gln Arg
    370                 375                 380
Ser Arg Leu His Ala Ala Asp Trp Ala Gly Arg Ala Arg Ala Leu Val
385                 390                 395                 400
Gly Asp Ser His Thr Ser Trp Ser Pro Ala Ser Ile Pro Gly Lys His
                405                 410                 415
Tyr Gln Ala Val Gly Leu His Leu Trp Lys Val Glu Lys Arg Arg Val
            420                 425                 430
Asn Leu Pro Arg Val Leu Ser Met Pro Pro Val Ala Gly Thr Ala Cys
        435                 440                 445
His Ala Tyr Asp Arg Glu Val His Leu Arg Cys Glu Leu Ser Pro Gly
    450                 455                 460
Tyr Tyr Leu Ala Val Pro Ser Thr Phe Leu Lys Asp Ala Pro Gly Glu
465                 470                 475                 480
Phe Leu Leu Arg Val Phe Ser Thr Gly Arg Val Ser Leu Arg Ser Gln
                485                 490                 495
Arg Val Glu Gly Ala Arg Thr His Pro His Cys Cys Cys Arg Ser Arg
            500                 505                 510
Cys

<210> SEQ ID NO 9
<211> LENGTH: 2204
<212> TYPE: DNA
<213> ORGANISM: Human

<400> SEQUENCE: 9
ccgaggcaac cggctgcaga tgggagcccg cggagccgag gatgcgggcg ggccggggcg      60
cgacgccggc gagggagctg ttccgggacg ccgccttccc cgccgcggac tcctcgctct     120
tctgcgactt gtctacgccg ctggcccagt tccgcgagga catcacgtgg aggcggcccc     180
```

-continued

| | |
|---|---|
| aggagatttg tgccacaccc cggctgtttc cagatgaccc acgggaaggg caggtgaagc | 240 |
| aggggctgct gggggattgc tggttcctgt gtgcctgcgc cgcgctgcag aagagcaggc | 300 |
| acctcctgga ccaggtcatt cctccgggac agccgagctg ggccgaccag gagtaccggg | 360 |
| gctccttcac ctgtcgcatt tggcagtttg acgctgggt ggaggtgacc acagatgacc | 420 |
| gcctgccgtg ccttgcaggg agactctgtt tctcccgctg ccagagggag gatgtgttct | 480 |
| ggctcccctt actggaaaag gtctacgcca aggtccatgg gtcctacgag cacctgtggg | 540 |
| ccgggcaggt ggcggatgcc ctggtggacc tgaccggcgc cctggcagaa agatggaacc | 600 |
| tgaagggcgt agcaggaagc ggaggccagc aggacaggcc aggccgctgg gagcacagga | 660 |
| cttgtcggca gctgctccac ctgaaggacc agtgtctgat cagctgctgc gtgctcagcc | 720 |
| ccagagcagg tgcccgggag ctgggggagt ccatgccttc attgtctcg gacctgcggg | 780 |
| agctccaggt tcaggcgggc cagtgcatcc tgctgctgcg gatccagaac ccctggggcc | 840 |
| ggcggtgctg gcagggctc tggagagagg gggtgaagg gtggagccag gtagatgcag | 900 |
| cggtagcatc tgagctcctg tcccagctcc aggaagggga gttctgggtg gaggaggagg | 960 |
| agttcctcag ggagtttgac gagctcaccg ttggctaccc ggtcacggag gccggccacc | 1020 |
| tgcagagcct ctacacagag aggctgctct gccatacgcg ggcgctgcct ggggcctggg | 1080 |
| tcaagggcca gtcagcagga ggctgccgga caacagcgg ctttcccagc aaccccaaat | 1140 |
| tctggctgcg ggtctcagaa ccgagtgagg tgtacattgc cgtcctgcag agatccaggc | 1200 |
| tgcacgcggc ggactgggca ggccgggccc gggcactggt gggtgacagt catacttcgt | 1260 |
| ggagcccagc gagcatcccg ggcaagcact accaggctgt gggtctgcac ctctggaagg | 1320 |
| tagagaagcg gcgggtcaat ctgcctaggg tcctgtccat gcccccgtg gctggcaccg | 1380 |
| cgtgccatgc atacgaccgg gagtccacc tgcgttgtga gctctcaccg ggctactacc | 1440 |
| tggctgtccc cagcaccttc ctgaaggacg cgccagggga gttcctgctc cgagtcttct | 1500 |
| ctaccgggcg agtctccctt aggtcccaga gggtggaagg agccaggacg cacccccact | 1560 |
| gctgctgcag gagccgctgc tgagctgcgt gccacatcgc tacgcccagg aggtgagccg | 1620 |
| gctctgcctc ctgcctgcag gcacctacaa ggttgtgccc tccacctacc tgccggacac | 1680 |
| agaggggggcc ttcacagtga ccatcgcaac caggattgac aggccatcca ttcacagcca | 1740 |
| ggagatgctg ggccagttcc tccaagaggt ctccgtcatg gcagtgatga aaacctaaca | 1800 |
| gggtggcccc ctgtgccagc tcaggtgact ggagcccgag ggcctgacag gttcccagca | 1860 |
| gctgggccgg ccagccttgc actgtggggg ctggtcctga gtcttggcct gcctcccagc | 1920 |
| cctgccaggg ggctgcggcc tagggtcca cgggaagcct ccgtcaggag agacgcagcc | 1980 |
| ctgggggcca gctggtgctg caaggaaggg tgggaagctt gctggcttct gttgcgccac | 2040 |
| tgagacggca gagaccccag gatcccagag cttcccagga tccctcccag atcctctgct | 2100 |
| gactccatat ggaggcctca cacccagagg gtagggcagc agatcttctt tataactatt | 2160 |
| tattgttcga atcacttta ggatgtaact ttataaataa acct | 2204 |

<210> SEQ ID NO 10
<211> LENGTH: 444
<212> TYPE: PRT
<213> ORGANISM: Human

<400> SEQUENCE: 10

Met Arg Ala Gly Arg Gly Ala Thr Pro Ala Arg Glu Leu Phe Arg Asp
 1               5                  10                  15

-continued

```
Ala Ala Phe Pro Ala Ala Asp Ser Ser Leu Phe Cys Asp Leu Ser Thr
            20                  25                  30
Pro Leu Ala Gln Phe Arg Glu Asp Ile Thr Trp Arg Arg Pro Gln Glu
        35                  40                  45
Ile Cys Ala Thr Pro Arg Leu Phe Pro Asp Asp Pro Arg Glu Gly Gln
    50                  55                  60
Val Lys Gln Gly Leu Leu Gly Asp Cys Trp Phe Leu Cys Ala Cys Ala
65                  70                  75                  80
Ala Leu Gln Lys Ser Arg His Leu Leu Asp Gln Val Ile Pro Pro Gly
                85                  90                  95
Gln Pro Ser Trp Ala Asp Gln Glu Tyr Arg Gly Ser Phe Thr Cys Arg
            100                 105                 110
Ile Trp Gln Phe Gly Arg Trp Val Glu Val Thr Thr Asp Asp Arg Leu
        115                 120                 125
Pro Cys Leu Ala Gly Arg Leu Cys Phe Ser Arg Cys Gln Arg Glu Asp
    130                 135                 140
Val Phe Trp Leu Pro Leu Leu Glu Lys Val Tyr Ala Lys Val His Gly
145                 150                 155                 160
Ser Tyr Glu His Leu Trp Ala Gly Gln Val Ala Asp Ala Leu Val Asp
                165                 170                 175
Leu Thr Gly Gly Leu Ala Glu Arg Trp Asn Leu Lys Gly Val Ala Gly
            180                 185                 190
Ser Gly Gly Gln Gln Asp Arg Pro Gly Arg Trp Glu His Arg Thr Cys
        195                 200                 205
Arg Gln Leu Leu His Leu Lys Asp Gln Cys Leu Ile Ser Cys Cys Val
    210                 215                 220
Leu Ser Pro Arg Ala Gly Ala Arg Glu Leu Gly Glu Phe His Ala Phe
225                 230                 235                 240
Ile Val Ser Asp Leu Arg Glu Leu Gln Gly Gln Ala Gly Gln Cys Ile
                245                 250                 255
Leu Leu Leu Arg Ile Gln Asn Pro Trp Gly Arg Arg Cys Trp Gln Gly
            260                 265                 270
Leu Trp Arg Glu Gly Gly Glu Gly Trp Ser Gln Val Asp Ala Ala Val
        275                 280                 285
Ala Ser Glu Leu Leu Ser Gln Leu Gln Glu Gly Glu Phe Trp Val Glu
290                 295                 300
Glu Glu Glu Phe Leu Arg Glu Phe Asp Glu Leu Thr Val Gly Tyr Pro
305                 310                 315                 320
Val Thr Glu Ala Gly His Leu Gln Ser Leu Tyr Thr Glu Arg Leu Leu
                325                 330                 335
Cys His Thr Arg Ala Leu Pro Gly Ala Trp Val Lys Gly Gln Ser Ala
            340                 345                 350
Gly Gly Cys Arg Asn Asn Ser Gly Phe Pro Ser Asn Pro Lys Phe Trp
        355                 360                 365
Leu Arg Val Ser Lys Pro Ser Glu Val Tyr Ile Ala Val Leu Gln Arg
    370                 375                 380
Ser Arg Leu His Ala Ala Asp Trp Ala Gly Arg Ala Arg Ala Leu Val
385                 390                 395                 400
Gly Asp Ser His Thr Ser Trp Ser Pro Ala Ser Ile Pro Gly Lys His
                405                 410                 415
Tyr Gln Ala Val Gly Leu His Leu Trp Lys Gly Val Thr Leu Gly Thr
            420                 425                 430
```

Thr Leu Phe Pro Val Pro Ser Trp Met Trp Pro Thr
     435                 440

<210> SEQ ID NO 11
<211> LENGTH: 2516
<212> TYPE: DNA
<213> ORGANISM: Human

<400> SEQUENCE: 11

| | | | | | |
|---|---|---|---|---|---|
| ccgaggcaac | cggctgcaga | tgggagcccg | cggagccgag | gatgcgggcg | ggccggggcg | 60 |
| cgacgccggc | gagggagctg | ttccgggacg | ccgccttccc | cgccgcggac | tcctcgctct | 120 |
| tctgcgactt | gtctacgccg | ctggcccagt | tccgcgagga | catcacgtgg | aggcggcccc | 180 |
| aggagatttg | tgccacaccc | cggctgtttc | cagatgaccc | acgggaaggg | caggtgaagc | 240 |
| aggggctgct | gggggattgc | tggttcctgt | gtgcctgcgc | cgcgctgcag | aagagcaggc | 300 |
| acctcctgga | ccaggtcatt | cctccgggac | agccgagctg | gccgaccag | gagtaccggg | 360 |
| gctccttcac | ctgtcgcatt | tggcagtttg | gacgctgggt | ggaggtgacc | acagatgacc | 420 |
| gcctgccgtg | ccttgcaggg | agactctgtt | tctcccgctg | ccagagggag | gatgtgttct | 480 |
| ggctcccctt | actggaaaag | gtctacgcca | aggtccatgg | gtcctacgag | cacctgtggg | 540 |
| ccgggcaggt | ggcggatgcc | ctggtggacc | tgaccgcgg | cctggcagaa | agatggaacc | 600 |
| tgaagggcgt | agcaggaagc | ggaggccagc | aggacaggcc | aggccgctgg | gagcacagga | 660 |
| cttgtcggca | gctgctccac | ctgaaggacc | agtgtctgat | cagctgctgc | gtgctcagcc | 720 |
| ccagagcagg | tgcccgggag | ctgggggagt | tccatgcctt | cattgtctcg | gacctgcggg | 780 |
| agctccaggg | tcaggcgggc | cagtgcatcc | tgctgctgcg | gatccagaac | ccctggggcc | 840 |
| ggcggtgctg | gcagggctc | tggagagagg | ggggtgaagg | gtggagccag | gtagatgcag | 900 |
| cggtagcatc | tgagctcctg | tcccagctcc | aggaagggga | gttctgggtg | gaggaggagg | 960 |
| agttcctcag | ggagtttgac | gagctcaccg | ttggctaccc | ggtcacggag | gccggccacc | 1020 |
| tgcagagcct | ctacacagag | aggctgctct | gccatacgcg | ggcgctgcct | ggggcctggg | 1080 |
| tcaagggcca | gtcagcagga | ggctgccgga | caacagcgg | ctttcccagc | aaccccaaat | 1140 |
| tctggctgcg | ggtctcaaaa | ccgagtgagg | tgtacattgc | cgtcctgcag | agatccaggc | 1200 |
| tgcacgcggc | ggactgggca | ggccgggccc | gggcactggt | gggtgacagt | catacttcgt | 1260 |
| ggagcccagc | gagcatcccg | ggcaagcact | accaggctgt | gggtctgcac | ctctggaagg | 1320 |
| gtgtgacact | tggcaccaca | ctgttccctg | tcccttcatg | gatgtggccc | acatgatgtt | 1380 |
| cctttcctct | tgcaaaagaa | gttgctggaa | ggcccactgt | ccagcagccc | ccaggttgcc | 1440 |
| tgggccacgg | tgcctttgtg | ggcccagcta | caaggaggac | ttgcaggctc | gtgtctggga | 1500 |
| cagatactgg | cgccagggcc | aagtgaagcc | cgggattggt | agagaagcgg | cgggtcaatc | 1560 |
| tgcctagggt | cctgtccatg | cccccgtgg | ctggcaccgc | gtgccatgca | tacgaccggg | 1620 |
| aggtccacct | gcgttgtgag | ctctcaccgg | gctactacct | ggctgtcccc | agcaccttcc | 1680 |
| tgaaggacgc | gccaggggag | ttcctgctcc | gagtcttctc | taccgggcga | gtctccctta | 1740 |
| gggccctggc | ccccgctgcg | tccgcatcac | tctgcatcag | cactgccggc | ccagtgacac | 1800 |
| cgagttccac | cccatcggct | tccatatctt | ccaggtccca | gagggtggaa | ggagccagga | 1860 |
| cgcacccca | ctgctgctgc | aggagccgct | gctgagctgc | gtgccacatc | gctacgccca | 1920 |
| ggaggtgagc | cggctctgcc | tcctgcctgc | aggcacctac | aaggttgtgc | cctccaccta | 1980 |
| cctgccggac | acagaggggg | ccttcacagt | gaccatcgca | accaggattg | acaggccatc | 2040 |

-continued

```
cattcacagc caggagatgc tgggccagtt cctccaagag gtctccgtca tggcagtgat    2100
gaaaacctaa cagggtggcc ccctgtgcca gctcaggtga ctggagcccg agggcctgac    2160
aggttcccag cagctgggcc ggccagcctt gcactgtggg ggctggtcct gagtcttggc    2220
ctgcctccca gccctgccag ggggctgcgg cctagggtc cacgggaagc ctccgtcagg     2280
agagacgcag ccctggggc cagctggtgc tgcaaggaag ggtgggaagc ttgctggctt     2340
ctgttgcgcc actgagacgg cagagacccc aggatcccag agcttccag gatccctccc     2400 agatcctctg ctgactccat atggaggcct acacccaga gggtagggca gcagatcttc     2460
tttataacta tttattgttc gaatcacttt taggatgtaa ctttataaat aaacct        2516
```

<210> SEQ ID NO 12
<211> LENGTH: 274
<212> TYPE: PRT
<213> ORGANISM: Human

<400> SEQUENCE: 12

```
Met Arg Ala Gly Arg Gly Ala Thr Pro Ala Arg Glu Leu Phe Arg Asp
  1               5                  10                  15
Ala Ala Phe Pro Ala Ala Asp Ser Ser Leu Phe Cys Asp Leu Ser Thr
                 20                  25                  30
Pro Leu Ala Gln Phe Arg Glu Asp Ile Thr Trp Arg Arg Pro Gln Glu
             35                  40                  45
Ile Cys Ala Thr Pro Arg Leu Phe Pro Asp Asp Pro Arg Glu Gly Gln
         50                  55                  60
Val Lys Gln Gly Leu Leu Gly Asp Cys Trp Phe Leu Cys Ala Cys Ala
 65                  70                  75                  80
Ala Leu Gln Lys Ser Arg His Leu Leu Asp Gln Val Ile Pro Pro Gly
                 85                  90                  95
Gln Pro Ser Trp Ala Asp Gln Glu Tyr Arg Gly Ser Phe Thr Cys Arg
            100                 105                 110
Ile Trp Gln Phe Gly Arg Trp Val Glu Val Thr Thr Asp Asp Arg Leu
        115                 120                 125
Pro Cys Leu Ala Gly Arg Leu Cys Phe Ser Arg Cys Gln Arg Glu Asp
    130                 135                 140
Val Phe Trp Leu Pro Leu Leu Glu Lys Gly Pro Trp Val Leu Arg Ala
145                 150                 155                 160
Pro Val Gly Arg Ala Gly Gly Gly Cys Pro Gly Gly Pro Asp Arg Arg
                165                 170                 175
Pro Gly Arg Lys Met Glu Pro Glu Gly Arg Ser Arg Lys Arg Arg Pro
            180                 185                 190
Ala Gly Gln Ala Arg Pro Leu Gly Ala Gln Asp Leu Ser Ala Ala Ala
        195                 200                 205
Pro Pro Glu Gly Pro Val Ser Asp Gln Leu Leu Arg Ala Gln Pro Gln
    210                 215                 220
Ser Arg Cys Pro Gly Ala Gly Gly Val Pro Cys Leu His Cys Leu Gly
225                 230                 235                 240
Pro Ala Gly Ala Pro Gly Ser Gly Gly Pro Val His Pro Ala Ala Ala
                245                 250                 255
Asp Pro Glu Pro Leu Gly Pro Ala Val Leu Ala Gly Ala Leu Glu Arg
            260                 265                 270
Gly Gly
```

<210> SEQ ID NO 13

```
<211> LENGTH: 2455
<212> TYPE: DNA
<213> ORGANISM: Human

<400> SEQUENCE: 13
ccgaggcaac cggctgcaga tgggagcccg cggagccgag gatgcgggcg ggccggggcg      60
cgacgccggc gagggagctg ttccgggacg ccgccttccc cgccgcggac tcctcgctct     120
tctgcgactt gtctacgccg ctggcccagt tccgcgagga catcacgtgg aggcggcccc     180
aggagatttg tgccacaccc cggctgtttc cagatgaccc acgggaaggg caggtgaagc     240 agggctgct gggggattgc tggttcctgt gtgcctgcgc cgcgctgcag aagagcaggc     300
acctcctgga ccaggtcatt cctccgggac agccgagctg ggccgaccag gagtaccggg     360
gctccttcac ctgtcgcatt tggcagtttg gacgctgggt ggaggtgacc acagatgacc     420
gcctgccgtg ccttgcaggg agactctgtt tctcccgctg ccagagggag gatgtgttct     480 ggctccccctt actggaaaag ggtccatggg tcctacgagc acctgtgggc cgggcaggtg     540
gcggatgccc tggtggacct gaccggcggc ctggcagaaa gatggaacct gaagggcgta     600
gcaggaagcg gaggccagca ggacaggcca ggccgctggg agcacaggac ttgtcggcag     660
ctgctccacc tgaaggacca gtgtctgatc agctgctgcg tgctcagccc cagagcaggt     720
gcccgggagc tgggggagtt ccatgccttc attgtctcgg acctgcggga gctccagggt     780
caggcgggcc agtgcatcct gctgctgcgg atccagaacc cctggggccg gcggtgctgg     840
caggggctct ggagagaggg gggtgaaggg tggagccagg tagatgcagc ggtagcatct     900
gagctcctgt cccagctcca ggaagggag ttctgggtgg aggaggagga gttcctcagg     960
gagtttgacg agctcaccgt tggctacccg gtcacggagg ccggccacct gcagagcctc    1020
tacacagaga ggctgctctg ccatacgcgg gcgctgcctg gggcctgggt caagggccag    1080
tcagcaggag gctgccggaa caacagcggc tttcccagca accccaaatt ctggctgcgg    1140
gtctcagaac cgagtgaggt gtacattgcc gtcctgcaga gatccaggct gcacgcggcg    1200
gactgggcag gccgggcccg ggcactggtg ggtgacagtc atacttcgtg gagcccagcg    1260
agcatcccgg gcaagcacta ccaggctgtg ggtctgcacc tctggaaggt agagaagcgg    1320
cgggtcaatc tgcctagggt cctgtccatg ccccccgtgg ctggcaccgc gtgccatgca    1380
tacgaccggg aggtccacct gcgttgtgag ctctcaccgg gctactacct ggctgtcccc    1440
agcaccttcc tgaaggacgc gccaggggag ttcctgctcc gagtcttctc taccgggcga    1500
gtctccctta gcgccatcag ggcagtggcc aagaacacca ccccggggc agccctgcct    1560 gcggggagt gggggaccgt gcagctacgg ggttcttgga gagtcggcca gacgcgggg    1620 ggcagcagga actttgcctc ataccccacc aaccctgct tccccttctc ggtccccgag    1680
ggccctggcc ccgctgcgt ccgcatcact ctgcatcagc actgccggcc cagtgacacc    1740
gagttccacc ccatcggctt ccatatcttc caggtcccag agggtggaag gagccaggac    1800
gcacccccac tgctgctgca ggagccgctg ctgagctgcg tgccacatcg ctacgcccag    1860
gaggtgagcc ggctctgcct cctgcctgca ggcacctaca aggttgtgcc ctccacctac    1920
ctgccggaca cagaggggc cttcacagtg accatcgcaa ccaggattga caggccatcc    1980
attcacagcc aggagatgct gggccagttc ctccaagagg tctccgtcat ggcagtgatg    2040
aaaacctaac agggtggccc cctgtgccaa ctcaggtgac tggagcccga gggcctgaca    2100
ggttcccagc agctgggccg gccagccttg cactgtgggg gctggtcctg agtcttggcc    2160
tgcctcccag ccctgccagg gggctgcggc ctaggggtcc acgggaagcc tccgtcagga    2220
```

```
gagacgcagc cctgggggcc agctggtgct gcaaggaagg gtgggaagct tgctggcttc   2280
tgttgcgcca ctgagacggc agagacccca ggatcccaga gcttcccagg atccctccca   2340
gatcctctgc tgactccata tggaggcctc acacccagag ggtagggcag cagatcttct   2400
ttataactat ttattgttcg aatcactttt aggatgtaac tttataaata aacct        2455
```

<210> SEQ ID NO 14
<211> LENGTH: 139
<212> TYPE: PRT
<213> ORGANISM: Human

<400> SEQUENCE: 14

```
Met Arg Ala Gly Arg Gly Ala Thr Pro Ala Arg Glu Leu Phe Arg Asp
 1               5                  10                  15

Ala Ala Phe Pro Ala Ala Asp Ser Ser Leu Phe Cys Asp Leu Ser Thr
                20                  25                  30

Pro Leu Ala Gln Phe Arg Glu Asp Ile Thr Trp Arg Arg Pro Gln Glu
            35                  40                  45

Ile Cys Ala Thr Pro Arg Leu Phe Pro Asp Asp Pro Arg Glu Gly Gln
        50                  55                  60

Val Lys Gln Gly Leu Leu Gly Asp Cys Trp Phe Leu Cys Ala Cys Ala
65                  70                  75                  80

Ala Leu Gln Lys Ser Arg His Leu Leu Asp Gln Val Ser Cys Pro Val
                85                  90                  95

Gln Leu Pro Ala Asp Trp Thr Cys Lys Val Gln Pro Val Trp Leu Glu
           100                 105                 110

Phe Pro Cys Leu Pro Ile Ser Cys Arg Leu Arg Val Ser Ser Asp Thr
           115                 120                 125

Ser Pro Asp Ser Ala Thr Trp Gly Ser Trp Lys
           130                 135
```

<210> SEQ ID NO 15
<211> LENGTH: 1267
<212> TYPE: DNA
<213> ORGANISM: Human

<400> SEQUENCE: 15

```
gcggggccct cgggcttgga gggctgggcc gggcgggaa cgggcggggc gggccggagg    60
cggcggcggc tgactcgcct tctctccggg gctgcgaccc cgaggcaacc ggctgcagat   120
gggagcccgc ggagccgagg atgcgggcgg gccggggcgc gacgccggcg agggagctgt   180
tccgggacgc cgccttcccc gccgcggact cctcgctctt ctgcgacttg tctacgccgc   240
tggcccagtt ccgcgaggac atcacgtgga ggcggcccca ggagatttgt gccacacccc   300
ggctgtttcc agatgaccca cgggaagggc aggtgaagca ggggctgctg ggggattgct   360
ggttcctgtg tgcctgcgcc gcgctgcaga agagcaggca cctcctggac caggtctctt   420
gccctgtgca gcttcctgca gactggactt gcaaagtcca gcctgtatgg ctggagttcc   480
catgcctgcc aatctcctgt cgactgcgag tcagctccga tacttcacca gattcagcca   540
cctgggggag ctggaagtga atctcatctt agctgagcct tctgatgaga ctgcagcccc   600
agctgacacc tggattgcag actcatgaaa gacctgaaac tctaccaaca gccacctggg   660
ggagctggaa gtgaatctcc tcgtagctga gccttctgat gagactgcag ccccggctga   720
cacctggatt gcagactcat gaaagacctg aaactctacc aacagccacc tggggagct   780 ggaagtgaat ctcctcgtag ctgagccttc tgatgagact gcagccccgg ctgacacctg   840
```

| | |
|---|---|
| gattgcagac tcatgaaaga ccctgagcag aggacccagt ttggcagagc ccgaattcct | 900 |
| gacccacagg aactgggaga taaaactctg tggtttaat cttctcattt tagaggtaat | 960 |
| ttttttgtgt agcaataggt agctgacaat gcacagctaa aataatagat aattaaccct | 1020 |
| aatgctagtt tcattcatcc atcagggttt gcaaagtagt gatattctac ttctgtcttc | 1080 |
| cttcattatt tattagcaga aatgtatcta taaaaagaag tgttccttca ttaactcttt | 1140 |
| ggtcatgttg aggtacagtt tgcataggaa aggcagggca aatgcttgat tctttcccctt | 1200 |
| cctttcctca tttataaaat aatgaactgt tttcctggca tctttcaaca atgactaatg | 1260 |
| agttttt | 1267 |

<210> SEQ ID NO 16
<211> LENGTH: 138
<212> TYPE: PRT
<213> ORGANISM: Human

<400> SEQUENCE: 16

```
Met Arg Ala Gly Arg Gly Ala Thr Pro Ala Arg Glu Leu Phe Arg Asp
  1               5                  10                  15

Ala Ala Phe Pro Ala Ala Asp Ser Ser Leu Phe Cys Asp Leu Ser Thr
                 20                  25                  30

Pro Leu Ala Gln Phe Arg Glu Asp Ile Thr Trp Arg Arg Pro Gln Val
             35                  40                  45

Pro Glu Gly Gly Arg Ser Gln Asp Ala Pro Leu Leu Leu Gln Glu
         50                  55                  60

Pro Leu Leu Ser Cys Val Pro His Arg Tyr Ala Gln Glu Val Ser Arg
 65                  70                  75                  80

Leu Cys Leu Leu Pro Ala Gly Thr Tyr Lys Val Val Pro Ser Thr Tyr
                 85                  90                  95

Leu Pro Asp Thr Glu Gly Ala Phe Thr Val Thr Ile Ala Thr Arg Ile
                100                 105                 110

Asp Arg Pro Ser Ile His Ser Gln Glu Met Leu Gly Gln Phe Leu Gln
            115                 120                 125

Glu Val Ser Val Met Ala Val Met Lys Thr
        130                 135
```

<210> SEQ ID NO 17
<211> LENGTH: 864
<212> TYPE: DNA
<213> ORGANISM: Human

<400> SEQUENCE: 17

| | |
|---|---|
| ccgaggcaac cggctgcaga tgggagcccg cggagccgag gatgcgggcg ggccggggcg | 60 |
| cgacgccggc gagggagctg ttccgggacg ccgccttccc cgccgcggac tcctcgctct | 120 |
| tctgcgactt gtctacgccg ctggcccagt tccgcgagga catcacgtgg aggcggcccc | 180 |
| aggtcccaga gggtggaagg agccaggacg caccccact gctgctgcag gagccgctgc | 240 |
| tgagctgcgt gccacatcgc tacgcccagg aggtgagccg gctctgcctc ctgcctgcag | 300 |
| gcacctacaa ggttgtgccc tccacctacc tgccggacac agagggggcc ttcacagtga | 360 |
| ccatcgcaac caggattgac aggccatcca ttcacagcca ggagatgctg gccagttcc | 420 |
| tccaagaggt ctccgtcatg gcagtgatga aaacctaaca gggtggcccc ctgtgccagc | 480 |
| tcaggtgact ggagcccgag ggcctgacag gttcccagca gctgggccgg ccagccttgc | 540 |
| actgtggggg ctggtcctga gtcttggcct gcctcccagc cctgccaggg ggctgcggcc | 600 |

```
tagggggtcca cgggaagcct ccgtcaggag agacgcagcc ctgggggcca gctggtgctg      660
caaggaaggg tgggaagctt gctggcttct gttgcgccac tgagacggca gagaccccag      720
gatcccagag cttcccagga tccctcccag atcctctgct gactccatat ggaggcctca      780
cacccagagg gtagggcagc agatcttctt tataactatt tattgttcga atcacttta       840 ggatgtaact ttataaataa acct                                             864
```

<210> SEQ ID NO 18
<211> LENGTH: 666
<212> TYPE: PRT
<213> ORGANISM: Mus musculus

<400> SEQUENCE: 18

```
Met Arg Ala Val Arg Ala Glu Thr Pro Ala Arg Glu Leu Phe Arg Asp
 1               5                  10                  15

Ala Ala Phe Pro Ala Ser Asp Ser Ser Leu Phe Tyr Asn Leu Ser Thr
            20                  25                  30

Pro Leu Ala Gln Phe Arg Glu Asp Ile Thr Trp Arg Arg Pro Gln Glu
        35                  40                  45

Ile Cys Ala Thr Pro Gln Leu Phe Pro Asp Asn Pro Trp Glu Gly Gln
     50                  55                  60

Val Lys Gln Gly Leu Leu Gly Asp Cys Trp Phe Leu Cys Ala Cys Ala
 65                  70                  75                  80

Ala Leu Gln Lys Ser Gln His Leu Leu Asp Gln Val Phe Pro Pro Gly
                85                  90                  95

Gln Pro Gly Trp Ser Asp Gln Lys Tyr Gln Gly Phe Phe Thr Cys Arg
            100                 105                 110

Ile Trp Gln Phe Gly His Trp Glu Glu Val Thr Ile Asp Asp Arg Leu
        115                 120                 125

Pro Cys Leu Ala Gly Arg Leu Cys Phe Ser Arg Cys Gln Arg Glu Asp
    130                 135                 140

Val Phe Trp Leu Pro Leu Leu Glu Lys Ala Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Ser Leu Ala Glu Arg Trp Ser Leu Lys Asp Val Thr Lys
            180                 185                 190

Ala Ser Gly Gln Gln Asp Arg Pro Ser Gly Glu His Arg Thr Cys
        195                 200                 205

Arg Gln Leu Leu His Leu Lys Asp Arg Cys Leu Ile Ser Cys Ser Val
    210                 215                 220

Leu Ser Pro Arg Ala Gly Ala Arg Glu Leu Gly Glu Phe His Ala Phe
225                 230                 235                 240

Ile Ile Ser Asp Leu Gln Glu Leu Arg Ser Gln Thr Gly Gln Gly Ile
                245                 250                 255

Leu Leu Leu Arg Ile His Asn Pro Trp Gly Arg Arg Cys Trp Gln Gly
            260                 265                 270

Leu Trp Arg Glu Gly Gly Glu Gly Trp Asn Gln Val Glu Pro Ala Lys
        275                 280                 285

Glu Ser Glu Leu Leu Ala Gln Leu Gln Glu Gly Glu Phe Trp Val Glu
    290                 295                 300

Glu Glu Glu Phe Leu Arg Glu Phe Asp Glu Val Thr Ile Gly Tyr Pro
305                 310                 315                 320
```

```
Val Thr Glu Ala Gly His Leu Gln Ser Leu His Thr Glu Arg Val Leu
            325                 330                 335

Cys His Thr Arg Thr Leu Pro Gly Ala Trp Val Thr Gly Gln Ser Ala
            340                 345                 350

Gly Gly Cys Arg Asn Asn Ser Cys Phe Pro Cys Asn Pro Lys Phe Trp
            355                 360                 365

Leu Arg Leu Leu Glu Pro Ser Glu Val Cys Val Ala Val Leu Gln Arg
            370                 375                 380

Pro Arg Arg Leu Val Gly Gln Thr Arg Ala Leu Ala Gly Ala Ser
385                 390                 395                 400

Pro Ala Pro Val Asn Leu Pro Gly Lys Asp Tyr Gln Ala Val Gly Leu
            405                 410                 415

His Ile Trp Lys Val Glu Lys Arg Lys Ile Ser Leu Pro Arg Val Leu
            420                 425                 430

Ser Ala Pro Pro Val Ala Gly Thr Ala Cys His Ala Tyr Asp Arg Glu
            435                 440                 445

Ile His Leu Arg Cys Glu Leu Ser Pro Gly Tyr Tyr Leu Ala Val Pro
            450                 455                 460

Ser Thr Phe Leu Lys Asp Val Pro Gly Gln Phe Leu Leu Arg Val Phe
465                 470                 475                 480

Phe Thr Gly Lys Ile Ser Leu Ser Ala Val Arg Leu Ala Thr Lys Gly
            485                 490                 495

Ala Ser Pro Gly Thr Ala Leu Pro Ala Gly Glu Trp Glu Thr Val Gln
            500                 505                 510

Leu Gln Gly Cys Trp Arg Ala Gly Gln Thr Ala Gly Gly Ser Arg Asn
            515                 520                 525

Phe Ala Ser Tyr Pro Cys Asn Pro Cys Leu Pro Phe Ser Val Pro Glu
            530                 535                 540

Gly Ala Gly Pro Arg Tyr Ile Arg Ile Thr Leu Gln Gln His Cys Arg
545                 550                 555                 560

Leu Ser Asp Ser Gln Leu His Pro Ile Gly Phe His Val Phe Gln Val
            565                 570                 575

Pro Ala Asp Gly Glu Asn Gln Asp Ala Cys Ser Leu Leu Gln Glu
            580                 585                 590

Pro Leu Leu Ser Cys Val Pro His Arg Tyr Ala Gln Glu Val Ser Arg
            595                 600                 605

Leu Cys Leu Leu Ser Val Gly Asn Tyr Arg Ile Val Pro Ser Thr Tyr
            610                 615                 620

Leu Pro Asp Thr Glu Gly Thr Phe Thr Val Thr Ile Ala Thr Arg Ile
625                 630                 635                 640

Asp Arg Gln Ser Ile His Ser Gln Glu Met Leu Gly Gln Leu Leu Gln
            645                 650                 655

Glu Val Ser Phe Met Ala Val Met Lys Ala
            660                 665

<210> SEQ ID NO 19
<211> LENGTH: 2511
<212> TYPE: DNA
<213> ORGANISM: Mus musculus

<400> SEQUENCE: 19
agtaggtctc ccgggctaag caaacacggt ttgcaatgaa ggccgcgcac tcgctcccgg      60
gcggcgaccg agtccacggg ccgcagatgg gagcccaggg cgccgaagat gcggcggtc     120 cgggccgaga cgccggcgcg ggagctcttc cggacgcgg cattccccgc ctcggactcc     180
```

```
tcgctctttt acaacttgtc cacgcctctg gcccagtttc gggaggacat cacttggaga    240 cgacccagg aaatctgtgc cacacctcag ctgtttccag ataacccatg ggagggacag     300
gtgaagcaag ggctgctggg agattgctgg ttcctgtgtg cctgtgccgc ccttcagaag    360
agtcaacacc tcctggacca ggtcttccct ccaggacagc caggctggtc tgaccagaaa    420
taccaaggct tcttcacctg tcggatttgg cagtttggac actgggagga agtgaccata    480
gatgatcgtc tgccttgtct tgccgggaga ctctgctttt cccggtgcca gagagaggat    540
gtgttctggc ttcccttact ggaaaaggcc tatgctaagg tccatggatc gtatgagcac    600
ctgtgggcag ggcaagtggc agatgcctta gtggatctca ctggaagcct ggcagaaagg    660
tggagcttga aggatgtaac gaaagccagc ggccagcagg acagacccag tggtggggag    720
cacagaactt gtcggcagct actccacctg aaggaccggt gtctaatcag ctgctctgtg    780
cttagcccca gagcaggtgc cagggaactc ggagagttcc atgccttcat catctcagat    840
ctgcaggagc tcaggagtca gactggccag ggtatcctcc tgctgcggat tcacaacccc    900
tggggccggg gttgttggca gggcctctgg agagaaggag gtgaagggtg gaaccaggta    960
gagccagcta aggagtctga gctgctggcc caactccagg aaggagagtt ctgggtcgag   1020
gaagaggagt tcctcaggga gtttgatgag gtcaccatcg gctacccagt cacagaggcc   1080
ggccacctac agagtctcca cacagagagg gtgctgtgcc atacgcggac actgcctggt   1140
gcctgggtga caggcagtc agcaggaggc tgccggaaca acagttgctt tccctgcaac   1200
cccaagttct ggttacggct cttggaaccc agcgaggtgt gtgtggctgt tcttcagaga   1260
ccccggaggc gcttagtggg ccagactcgg gcactggcgg gtgccagtcc tgcaccggtg   1320
aacctcccag gcaaagacta ccaggctgtg ggcctgcaca tctggaaggt agagaaacgg   1380
aagatcagcc tgcccagagt cctgtctgca cccctgtgg ctggcactgc atgccatgcg    1440
tatgatcgtg agatccactt gcgttgtgag ctctcaccag gctactacct ggccgtccct   1500
agcacctttt tgaaggatgt gccagggcag ttcctgctca gagtcttctt cactgggaaa   1560
atctccctca gtgccgtcag gctggccacc aagggtgcat cgcctggaac agccctgcct   1620
gcaggcgagt gggagactgt gcagttgcag ggctgctgga gagctggcca gacagctggg   1680
ggcagcagga actttgcctc ttaccctgc aatccctgcc tcccttctc tgttcctgag    1740 ggtgctggcc cccgctacat ccgtatcacc ctacagcaac actgccggct cagtgacagc   1800
cagctgcacc ccattggttt ccatgtcttt caggttccag cagacggtga gaaccaggac   1860
gcgtgttccc tgctgctcca ggagccactg ctaagctgtg taccacatcg ctacgcccag   1920
gaagtgagcc gcctctgcct cctttctgtg gggaactaca ggattgttcc ctccacctac   1980
ctgccagata cagagggtac cttcacggta accatagcaa ccagaatcga taggcagtcc   2040
atccacagcc aggagatgct gggccagctg ctccaggagg tctcctttat ggcagtgatg   2100
aaagcctgac acgagaccct gtgtgccagc catgccaga gcggctgctg cccctgtgcc    2160
cagcatccag gtgcatctcc agccagctac aagccagctt ctcgtcagct ctggaggttg   2220
gctgtggacc ttggggctaa ataggggtgc tttgtcctgg attgaagaca tctcgggtcc   2280
agtgggtgct gcaggcggg gctagaactc ccaagtggta tcttcattcc ttagtgaagg    2340
ccaggagatt cctggggccc gggtttgttg tggaaagctt tgcagaattc acataacctt   2400
ctcgacttcg gaagccttac actaggcagg cggactgtga caaatgctaa aacctatta    2460 ttacttgaaa tattttggga atgtgacttt ataaataaac atgaataatt t            2511
```

<210> SEQ ID NO 20
<211> LENGTH: 309
<212> TYPE: PRT
<213> ORGANISM: Human

<400> SEQUENCE: 20

```
Met Asn Gly Thr Tyr Asn Thr Cys Gly Ser Ser Asp Leu Thr Trp Pro
 1               5                  10                  15

Pro Ala Ile Lys Leu Gly Phe Tyr Ala Tyr Leu Gly Val Leu Leu Val
             20                  25                  30

Leu Gly Leu Leu Leu Asn Ser Leu Ala Leu Trp Val Phe Cys Cys Arg
         35                  40                  45

Met Gln Gln Trp Thr Glu Thr Arg Ile Tyr Met Thr Asn Leu Ala Val
     50                  55                  60

Ala Asp Leu Cys Leu Leu Cys Thr Leu Pro Phe Val Leu His Ser Leu
 65                  70                  75                  80

Arg Asp Thr Ser Asp Thr Pro Leu Cys Gln Leu Ser Gln Gly Ile Tyr
                 85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Arg Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285

Leu Ala Val Ala Pro Arg Ala Lys Ala His Lys Ser Gln Asp Ser Leu
    290                 295                 300

Cys Val Thr Leu Ala
305
```

<210> SEQ ID NO 21
<211> LENGTH: 1875
<212> TYPE: DNA
<213> ORGANISM: Human

<400> SEQUENCE: 21
caggccagag tcccagctgt cctggactct gctgtgggga agggctgatg caggtgtgga     60
gtcaaatgtg ggtgcctcct gcagccgggt gccaggaggg gtggagggc caccctgggc    120

-continued

```
tttgtccggg agcctggtct tcccgtcctt gggctgacag gtgctgctgc ctctgagccc    180
tccctgctaa gagctgtgtg ctgggtaagg ctggtggccc tttgggctcc ctgtccagga    240
tttgtgctct ggagggtagg gcttgctggg ctggggactg aggggaacg tggagctcct     300
tctgcctcct ttcctgcccc atgacagcag gcagatccca ggagagaaga gctcaggaga    360
tgggaagagg atctgtccag gggttagacc tcaagggtga cttggagttc tttacggcac    420
ccatgctttc tttgaggagt tttgtgtttg tgggtgtggg gtcggggctc acctcctccc    480
acatccctgc ccagaggtgg gcagagtggg ggcagtgcct tgctccccct gctcgctctc    540
tgctgacctc cggctccctg tgctgcccca ggaccatgaa tggcacctac aacacctgtg    600
gctccagcga cctcacctgg cccccagcga tcaagctggg cttctacgcc tacttgggcg    660
tcctgctggt gctaggcctg ctgctcaaca gcctggcgct ctgggtgttc tgctgccgca    720
tgcagcagtg gacggagacc cgcatctaca tgaccaacct ggcggtggcc gacctctgcc    780
tgctgtgcac cttgcccttc gtgctgcact ccctgcgaga cacctcagac acgccgctgt    840
gccagctctc ccagggcatc tacctgacca acaggtacat gagcatcagc ctggtcacgg    900
ccatcgccgt ggaccgctat gtggccgtgc ggcacccgct gcgtgcccgc gggctgcggt    960
cccccaggca ggctgcggcc gtgtgcgcgg tcctctgggt gctggtcatc ggctccctgg    1020
tggctcgctg gctcctgggg attcaggagg gcggcttctg cttcaggagc acccggcaca    1080
atttcaactc catggcgttc ccgctgctgg gattctacct gccccctggcc gtggtggtct    1140
tctgctccct gaaggtggtg actgccctgg cccagaggcc acccaccgac gtggggcagg    1200
cagaggccac ccgcaaggct gcccgcatgg tctgggccaa cctcctggtg ttcgtggtct    1260
gcttcctgcc cctgcacgtg gggctgacag tgcgcctcgc agtgggctgg aacgcctgtg    1320
ccctcctgga gacgatccgt cgcgccctgt acataaccag caagctctca gatgccaact    1380
gctgcctgga cgccatctgc tactactaca tggccaagga gttccaggag gcgtctgcac    1440
tggccgtggc tcccagtgct aaggcccaca aaagccagga ctctctgtgc gtgaccctcg    1500
cctaagaggc gtgctgtggg cgctgtgggc caggtctcgg gggctccggg aggtgctgcc    1560
tgccagggga agctggaacc agtagcaagg agcccgggat cagccctgaa ctcactgtgt    1620
attctcttgg agccttgggt gggcagggac ggcccaggta cctgctctct tgggaagaga    1680
gagggacagg gacaagggca agaggactga ggccagagca aggccaatgt cagagacccc    1740
cgggatgggg cctcacactt gccaccccca gaaccagctc acctggccag agtgggttcc    1800
tgctggccag ggtgcagcct tgatgacacc tgccgctgcc cctcgggct ggaataaaac     1860
tccccacccca gagtc                                                    1875
```

<210> SEQ ID NO 22
<211> LENGTH: 714
<212> TYPE: PRT
<213> ORGANISM: Human

<400> SEQUENCE: 22

Met Ser Glu Glu Ile Ile Thr Pro Val Tyr Cys Thr Gly Val Ser Ala
1               5                   10                  15

Gln Val Gln Lys Gln Arg Ala Arg Glu Leu Gly Leu Gly Arg His Glu
            20                  25                  30

Asn Ala Ile Lys Tyr Leu Gly Gln Asp Tyr Glu Gln Leu Arg Val Arg
        35                  40                  45

Cys Leu Gln Ser Gly Thr Leu Phe Arg Asp Glu Ala Phe Pro Pro Val

-continued

```
                 50                     55                     60
Pro Gln Ser Leu Gly Tyr Lys Asp Leu Gly Pro Asn Ser Ser Lys Thr
 65                     70                     75                     80

Tyr Gly Ile Lys Trp Lys Arg Pro Thr Glu Leu Leu Ser Asn Pro Gln
                        85                     90                     95

Phe Ile Val Asp Gly Ala Thr Arg Thr Asp Ile Cys Gln Gly Ala Leu
                       100                    105                    110

Gly Asp Cys Trp Leu Leu Ala Ala Ile Ala Ser Leu Thr Leu Asn Asp
                115                    120                    125

Thr Leu Leu His Arg Val Val Pro His Gly Gln Ser Phe Gln Asn Gly
        130                    135                    140

Tyr Ala Gly Ile Phe His Phe Gln Leu Trp Gln Phe Gly Glu Trp Val
145                    150                    155                    160

Asp Val Val Asp Asp Leu Leu Pro Ile Lys Asp Gly Lys Leu Val
                       165                    170                    175

Phe Val His Ser Ala Glu Gly Asn Glu Phe Trp Ser Ala Leu Leu Glu
                180                    185                    190

Lys Ala Tyr Ala Lys Val Asn Gly Ser Tyr Glu Ala Leu Ser Gly Gly
        195                    200                    205

Ser Thr Ser Glu Gly Phe Glu Asp Phe Thr Gly Val Thr Glu Trp
        210                    215                    220

Tyr Glu Leu Arg Lys Ala Pro Ser Asp Leu Tyr Gln Ile Ile Leu Lys
225                    230                    235                    240

Ala Leu Glu Arg Gly Ser Leu Leu Gly Cys Ser Ile Asp Ile Ser Ser
                245                    250                    255

Val Leu Asp Met Glu Ala Ile Thr Phe Lys Lys Leu Val Lys Gly His
                260                    265                    270

Ala Tyr Ser Val Thr Gly Ala Lys Gln Val Asn Tyr Arg Gly Gln Val
        275                    280                    285

Val Ser Leu Ile Arg Met Arg Asn Pro Trp Gly Glu Val Glu Trp Thr
        290                    295                    300

Gly Ala Trp Ser Asp Ser Ser Glu Trp Asn Asn Val Asp Pro Tyr
305                    310                    315                    320

Glu Arg Asp Gln Leu Arg Val Lys Met Glu Asp Gly Glu Phe Trp Met
                       325                    330                    335

Ser Phe Arg Asp Phe Met Arg Glu Phe Thr Arg Leu Glu Ile Cys Asn
                340                    345                    350

Leu Thr Pro Asp Ala Leu Lys Ser Arg Thr Ile Arg Lys Trp Asn Thr
        355                    360                    365

Thr Leu Tyr Glu Gly Thr Trp Arg Arg Gly Ser Thr Ala Gly Gly Cys
        370                    375                    380

Arg Asn Tyr Pro Ala Thr Phe Trp Val Asn Pro Gln Phe Lys Ile Arg
385                    390                    395                    400

Leu Asp Glu Thr Asp Asp Pro Asp Asp Tyr Gly Asp Arg Glu Ser Gly
                       405                    410                    415

Cys Ser Phe Val Leu Ala Leu Met Gln Lys His Arg Arg Arg Glu Arg
                420                    425                    430

Arg Phe Gly Arg Asp Met Glu Thr Ile Gly Phe Ala Val Tyr Glu Val
                435                    440                    445

Pro Pro Glu Leu Val Gly Gln Pro Ala Val His Leu Lys Arg Asp Phe
        450                    455                    460

Phe Leu Ala Asn Ala Ser Arg Ala Arg Ser Glu Gln Phe Ile Asn Leu
465                    470                    475                    480
```

-continued

```
Arg Glu Val Ser Thr Arg Phe Arg Leu Pro Pro Gly Glu Tyr Val Val
            485                 490                 495

Val Pro Ser Thr Phe Glu Pro Asn Lys Glu Gly Asp Phe Val Leu Arg
            500                 505                 510

Phe Phe Ser Glu Lys Ser Ala Gly Thr Val Glu Leu Asp Asp Gln Ile
            515                 520                 525

Gln Ala Asn Leu Pro Asp Glu Gln Val Leu Ser Glu Glu Ile Asp
    530                 535                 540

Glu Asn Phe Lys Ala Leu Phe Arg Gln Leu Ala Gly Glu Asp Met Glu
545                 550                 555                 560

Ile Ser Val Lys Glu Leu Arg Thr Ile Leu Asn Arg Ile Ile Ser Lys
                565                 570                 575

His Lys Asp Leu Arg Thr Lys Gly Phe Ser Leu Glu Ser Cys Arg Ser
            580                 585                 590

Met Val Asn Leu Met Asp Arg Asp Gly Asn Gly Lys Leu Gly Leu Val
            595                 600                 605

Glu Phe Asn Ile Leu Trp Asn Arg Ile Arg Asn Tyr Leu Ser Ile Phe
    610                 615                 620

Arg Lys Phe Asp Leu Asp Lys Ser Gly Ser Met Ser Ala Tyr Glu Met
625                 630                 635                 640

Arg Met Ala Ile Glu Ser Ala Gly Phe Lys Leu Asn Lys Lys Leu Tyr
                645                 650                 655

Glu Leu Ile Ile Thr Arg Tyr Ser Glu Pro Asp Leu Ala Val Asp Phe
            660                 665                 670

Asp Asn Phe Val Cys Cys Leu Val Arg Leu Glu Thr Met Phe Arg Phe
            675                 680                 685

Phe Lys Thr Leu Asp Thr Asp Leu Asp Gly Val Val Thr Phe Asp Leu
    690                 695                 700

Phe Lys Trp Leu Gln Leu Thr Met Phe Ala
705                 710

<210> SEQ ID NO 23
<211> LENGTH: 700
<212> TYPE: PRT
<213> ORGANISM: Human

<400> SEQUENCE: 23

Met Ala Gly Ile Ala Ala Lys Leu Ala Lys Asp Arg Glu Ala Ala Glu
1               5                   10                  15

Gly Leu Gly Ser His Glu Arg Ala Ile Lys Tyr Leu Asn Gln Asp Tyr
            20                  25                  30

Glu Ala Leu Arg Asn Glu Cys Leu Glu Ala Gly Thr Leu Phe Gln Asp
        35                  40                  45

Pro Ser Phe Pro Ala Ile Pro Ser Ala Leu Gly Phe Lys Glu Leu Gly
    50                  55                  60

Pro Tyr Ser Ser Lys Thr Arg Gly Met Arg Trp Lys Arg Pro Thr Glu
65                  70                  75                  80

Ile Cys Ala Asp Pro Gln Phe Ile Ile Gly Gly Ala Thr Arg Thr Asp
                85                  90                  95

Ile Cys Gln Gly Ala Leu Gly Asp Cys Trp Leu Leu Ala Ala Ile Ala
            100                 105                 110

Ser Leu Thr Leu Asn Glu Glu Ile Leu Ala Arg Val Val Pro Leu Asn
        115                 120                 125

Gln Ser Phe Gln Glu Asn Tyr Ala Gly Ile Phe His Phe Gln Phe Trp
```

```
            130                 135                 140
Gln Tyr Gly Glu Trp Val Glu Val Val Asp Arg Leu Pro Thr
145                 150                 155                 160

Lys Asp Gly Glu Leu Leu Phe Val His Ser Ala Glu Gly Ser Glu Phe
                165                 170                 175

Trp Ser Ala Leu Leu Glu Lys Ala Tyr Ala Lys Ile Asn Gly Cys Tyr
                180                 185                 190

Glu Ala Leu Ser Gly Gly Ala Thr Thr Glu Gly Phe Glu Asp Phe Thr
                195                 200                 205

Gly Gly Ile Ala Glu Trp Tyr Glu Leu Lys Lys Pro Pro Asn Leu
210                 215                 220

Phe Lys Ile Ile Gln Lys Ala Leu Gln Lys Gly Ser Leu Leu Gly Cys
225                 230                 235                 240

Ser Ile Asp Ile Thr Ser Ala Ala Asp Ser Glu Ala Ile Thr Phe Gln
                245                 250                 255

Lys Leu Val Lys Gly His Ala Tyr Ser Val Thr Gly Ala Glu Glu Val
                260                 265                 270

Glu Ser Asn Gly Ser Leu Gln Lys Leu Ile Arg Ile Arg Asn Pro Trp
                275                 280                 285

Gly Glu Val Glu Trp Thr Gly Arg Trp Asn Asp Asn Cys Pro Ser Trp
290                 295                 300

Asn Thr Ile Asp Pro Glu Glu Arg Glu Arg Leu Thr Arg Arg His Glu
305                 310                 315                 320

Asp Gly Glu Phe Trp Met Ser Phe Ser Asp Phe Leu Arg His Tyr Ser
                325                 330                 335

Arg Leu Glu Ile Cys Asn Leu Thr Pro Asp Thr Leu Thr Ser Asp Thr
                340                 345                 350

Tyr Lys Lys Trp Lys Leu Thr Lys Met Asp Gly Asn Trp Arg Arg Gly
                355                 360                 365

Ser Thr Ala Gly Gly Cys Arg Asn Tyr Pro Asn Thr Phe Trp Met Asn
370                 375                 380

Pro Gln Tyr Leu Ile Lys Leu Glu Glu Glu Asp Glu Asp Glu Glu Asp
385                 390                 395                 400

Gly Glu Ser Gly Cys Thr Phe Leu Val Gly Leu Ile Gln Lys His Arg
                405                 410                 415

Arg Arg Gln Arg Lys Met Gly Glu Asp Met His Thr Ile Gly Phe Gly
                420                 425                 430

Ile Tyr Glu Val Pro Glu Glu Leu Ser Gly Gln Thr Asn Ile His Leu
                435                 440                 445

Ser Lys Asn Phe Phe Leu Thr Asn Arg Ala Arg Glu Arg Ser Asp Thr
                450                 455                 460

Phe Ile Asn Leu Arg Glu Val Leu Asn Arg Phe Lys Leu Pro Pro Gly
465                 470                 475                 480

Glu Tyr Ile Leu Val Pro Ser Thr Phe Glu Pro Asn Lys Asp Gly Asp
                485                 490                 495

Phe Cys Ile Arg Val Phe Ser Glu Lys Lys Ala Asp Tyr Gln Ala Val
                500                 505                 510

Asp Asp Glu Ile Glu Ala Asn Leu Glu Glu Phe Asp Ile Ser Glu Asp
                515                 520                 525

Asp Ile Asp Asp Gly Val Arg Arg Leu Phe Ala Gln Leu Ala Gly Glu
                530                 535                 540

Asp Ala Glu Ile Ser Ala Phe Glu Leu Gln Thr Ile Leu Arg Arg Val
545                 550                 555                 560
```

-continued

```
Leu Ala Lys Arg Gln Asp Ile Lys Ser Asp Gly Phe Ser Ile Glu Thr
                565                 570                 575
Cys Lys Ile Met Val Asp Met Leu Asp Ser Asp Gly Ser Gly Lys Leu
            580                 585                 590
Gly Leu Lys Glu Phe Tyr Ile Leu Trp Thr Lys Ile Gln Lys Tyr Gln
        595                 600                 605
Lys Ile Tyr Arg Glu Ile Asp Val Asp Arg Ser Gly Thr Met Asn Ser
    610                 615                 620
Tyr Glu Met Arg Lys Ala Leu Glu Glu Ala Gly Phe Lys Met Pro Cys
625                 630                 635                 640
Gln Leu His Gln Val Ile Val Ala Arg Phe Ala Asp Asp Gln Leu Ile
                645                 650                 655
Ile Asp Phe Asp Asn Phe Val Arg Cys Leu Val Arg Leu Glu Thr Leu
            660                 665                 670
Phe Lys Ile Phe Lys Gln Leu Asp Pro Glu Asn Thr Gly Thr Ile Glu
        675                 680                 685
Leu Asp Leu Ile Ser Trp Leu Cys Phe Ser Val Leu
    690                 695                 700

<210> SEQ ID NO 24
<211> LENGTH: 821
<212> TYPE: PRT
<213> ORGANISM: Human

<400> SEQUENCE: 24

Met Pro Thr Val Ile Ser Ala Ser Val Ala Pro Arg Thr Ala Ala Glu
  1               5                  10                  15
Pro Arg Ser Pro Gly Pro Val Pro His Pro Ala Gln Ser Lys Ala Thr
                 20                  25                  30
Glu Ala Gly Gly Gly Asn Pro Ser Gly Ile Tyr Ser Ala Ile Ile Ser
             35                  40                  45
Arg Asn Phe Pro Ile Ile Gly Val Lys Glu Lys Thr Phe Glu Gln Leu
     50                  55                  60
His Lys Lys Cys Leu Glu Lys Lys Val Leu Tyr Val Asp Pro Glu Phe
 65                  70                  75                  80
Pro Pro Asp Glu Thr Ser Leu Phe Tyr Ser Gln Lys Phe Pro Ile Gln
                 85                  90                  95
Phe Val Trp Lys Arg Pro Pro Glu Ile Cys Glu Asn Pro Arg Phe Ile
                100                 105                 110
Ile Asp Gly Ala Asn Arg Thr Asp Ile Cys Gln Gly Glu Leu Gly Asp
            115                 120                 125
Cys Trp Phe Leu Ala Ala Ile Ala Cys Leu Thr Leu Asn Gln His Leu
130                 135                 140
Leu Phe Arg Val Ile Pro His Asp Gln Ser Phe Ile Glu Asn Tyr Ala
145                 150                 155                 160
Gly Ile Phe His Phe Gln Phe Trp Arg Tyr Gly Glu Trp Val Asp Val
                165                 170                 175
Val Ile Asp Asp Cys Leu Pro Thr Tyr Asn Asn Gln Leu Val Phe Thr
            180                 185                 190
Lys Ser Asn His Arg Asn Glu Phe Trp Ser Ala Leu Leu Glu Lys Ala
        195                 200                 205
Tyr Ala Lys Leu His Gly Ser Tyr Glu Ala Leu Lys Gly Gly Asn Thr
    210                 215                 220
Thr Glu Ala Met Glu Asp Phe Thr Gly Gly Val Ala Glu Phe Phe Glu
```

```
225                 230                 235                 240
Ile Arg Asp Ala Pro Ser Asp Met Tyr Lys Ile Met Lys Ala Ile
                245                 250                 255
Glu Arg Gly Ser Leu Met Gly Cys Ser Ile Asp Asp Gly Thr Asn Met
                260                 265                 270
Thr Tyr Gly Thr Ser Pro Ser Gly Leu Asn Met Gly Glu Leu Ile Ala
            275                 280                 285
Arg Met Val Arg Asn Met Asp Asn Ser Leu Leu Gln Asp Ser Asp Leu
        290                 295                 300
Asp Pro Arg Gly Ser Asp Glu Arg Pro Thr Arg Thr Ile Ile Pro Val
305                 310                 315                 320
Gln Tyr Glu Thr Arg Met Ala Cys Gly Leu Val Arg Gly His Ala Tyr
                325                 330                 335
Ser Val Thr Gly Leu Asp Glu Val Pro Phe Lys Gly Glu Lys Val Lys
                340                 345                 350
Leu Val Arg Leu Arg Asn Pro Trp Gly Gln Val Glu Trp Asn Gly Ser
                355                 360                 365
Trp Ser Asp Arg Trp Lys Asp Trp Ser Phe Val Asp Lys Asp Glu Lys
    370                 375                 380
Ala Arg Leu Gln His Gln Val Thr Glu Asp Gly Glu Phe Trp Met Ser
385                 390                 395                 400
Tyr Glu Asp Phe Ile Tyr His Phe Thr Lys Leu Glu Ile Cys Asn Leu
                405                 410                 415
Thr Ala Asp Ala Leu Gln Ser Asp Lys Leu Gln Thr Trp Thr Val Ser
                420                 425                 430
Val Asn Glu Gly Arg Trp Val Arg Gly Cys Ser Ala Gly Gly Cys Arg
        435                 440                 445
Asn Phe Pro Asp Thr Phe Trp Thr Asn Pro Gln Tyr Arg Leu Lys Leu
    450                 455                 460
Leu Glu Glu Asp Asp Asp Pro Asp Asp Ser Glu Val Ile Cys Ser Phe
465                 470                 475                 480
Leu Val Ala Leu Met Gln Lys Asn Arg Arg Lys Asp Arg Lys Leu Gly
                485                 490                 495
Ala Ser Leu Phe Thr Ile Gly Phe Ala Ile Tyr Glu Val Pro Lys Glu
            500                 505                 510
Met His Gly Asn Lys Gln His Leu Gln Lys Asp Phe Phe Leu Tyr Asn
            515                 520                 525
Ala Ser Lys Ala Arg Ser Lys Thr Tyr Ile Asn Met Arg Glu Val Ser
530                 535                 540
Gln Arg Phe Arg Leu Pro Pro Ser Glu Tyr Val Ile Val Pro Ser Thr
545                 550                 555                 560
Tyr Glu Pro His Gln Glu Gly Glu Phe Ile Leu Arg Val Phe Ser Glu
                565                 570                 575
Lys Arg Asn Leu Ser Glu Glu Val Glu Asn Thr Ile Ser Val Asp Arg
            580                 585                 590
Pro Val Lys Lys Lys Thr Lys Pro Ile Ile Phe Val Ser Asp Arg
        595                 600                 605
Ala Asn Ser Asn Lys Glu Leu Gly Val Asp Gln Glu Ser Glu Glu Gly
        610                 615                 620
Lys Gly Lys Thr Ser Pro Asp Lys Gln Lys Gln Ser Pro Gln Pro Gln
625                 630                 635                 640
Pro Gly Ser Ser Asp Gln Glu Ser Glu Glu Gln Gln Phe Arg Asn
                645                 650                 655
```

-continued

```
Ile Phe Lys Gln Ile Ala Gly Asp Asp Met Glu Ile Cys Ala Asp Glu
            660                 665                 670

Leu Lys Lys Val Leu Asn Thr Val Val Asn Lys His Lys Asp Leu Lys
        675                 680                 685

Thr His Gly Phe Thr Leu Glu Ser Cys Arg Ser Met Ile Ala Leu Met
    690                 695                 700

Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
                725                 730                 735

Asp Gln Ser Gly Thr Ile Asn Ser Tyr Glu Met Arg Asn Ala Val Asn
            740                 745                 750

Asp Ala Gly Phe His Leu Asn Asn Gln Leu Tyr Asp Ile Ile Thr Met
        755                 760                 765

Arg Tyr Ala Asp Lys His Met Asn Ile Asp Phe Asp Ser Phe Ile Cys
    770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
            820

<210> SEQ ID NO 25
<211> LENGTH: 639
<212> TYPE: PRT
<213> ORGANISM: Human

<400> SEQUENCE: 25

Met Phe Ser Cys Val Lys Pro Tyr Glu Asp Gln Asn Tyr Ser Ala Leu
  1               5                  10                  15

Arg Arg Asp Cys Arg Arg Lys Val Leu Phe Glu Asp Pro Leu Phe
                20                  25                  30

Pro Ala Thr Asp Asp Ser Leu Tyr Tyr Lys Gly Thr Pro Gly Pro Ala
            35                  40                  45

Val Arg Arg Lys Arg Pro Lys Gly Ile Cys Glu Asp Pro Arg Leu Phe
        50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Glu
                100                 105                 110

Lys Pro Asn Ala Tyr Ala Gly Ile Phe His Phe His Phe Trp Arg Phe
            115                 120                 125

Gly Trp Val Asp Val Val Ile Asp Asp Arg Leu Pro Thr Val Asn Asn
        130                 135                 140

Gln Leu Ile Tyr Cys His Ser Asn Ser Arg Asn Glu Phe Trp Cys Ala
145                 150                 155                 160

Leu Val Glu Lys Ala Tyr Ala Lys Leu Ala Gly Cys Tyr Gln Ala Leu
                165                 170                 175

Asp Gly Gly Asn Thr Ala Asp Ala Leu Val Asp Phe Thr Gly Gly Val
            180                 185                 190

Ser Glu Pro Ile Asp Leu Thr Glu Gly Asp Phe Ala Asn Asp Glu Thr
```

-continued

```
            195                 200                 205
Lys Arg Asn Gln Leu Phe Glu Arg Met Leu Lys Val His Ser Arg Gly
        210                 215                 220
Gly Leu Ile Ser Ala Ser Ile Lys Ala Val Thr Ala Ala Asp Met Glu
225                 230                 235                 240
Ala Arg Leu Ala Cys Gly Leu Val Lys Gly His Ala Tyr Ala Val Thr
                245                 250                 255
Asp Val Arg Lys Val Arg Leu Gly His Gly Leu Leu Ala Phe Phe Lys
            260                 265                 270
Ser Glu Lys Leu Asp Met Ile Arg Leu Arg Asn Pro Trp Gly Glu Arg
        275                 280                 285
Glu Trp Asn Gly Pro Trp Ser Asp Thr Ser Glu Glu Trp Gln Lys Val
        290                 295                 300
Ser Lys Ser Glu Arg Glu Lys Met Gly Val Thr Val Gln Asp Asp Gly
305                 310                 315                 320
Glu Phe Trp Met Thr Phe Glu Asp Val Cys Arg Tyr Phe Thr Asp Ile
                325                 330                 335
Ile Lys Cys Arg Val Ile Asn Thr Ser His Leu Ser Ile His Lys Thr
            340                 345                 350
Trp Glu Glu Ala Arg Leu His Gly Ala Trp Thr Leu His Glu Asp Pro
        355                 360                 365
Arg Gln Asn Arg Gly Gly Cys Ile Asn His Lys Asp Thr Phe Phe
        370                 375                 380
Gln Asn Pro Gln Tyr Ile Phe Glu Val Lys Lys Pro Glu Asp Glu Val
385                 390                 395                 400
Leu Ile Cys Ile Gln Gln Arg Pro Lys Arg Ser Thr Arg Arg Glu Gly
                405                 410                 415
Lys Gly Glu Asn Leu Ala Ile Gly Phe Asp Ile Tyr Lys Val Glu Glu
            420                 425                 430
Asn Arg Gln Tyr Arg Met His Ser Leu Gln His Lys Ala Ala Ser Ser
        435                 440                 445
Ile Tyr Ile Asn Ser Arg Ser Val Phe Leu Arg Thr Asp Gln Pro Glu
        450                 455                 460
Gly Arg Tyr Val Ile Ile Pro Thr Thr Phe Glu Pro Gly His Thr Gly
465                 470                 475                 480
Glu Phe Leu Leu Arg Val Phe Thr Asp Val Pro Ser Asn Cys Arg Glu
                485                 490                 495
Leu Arg Leu Asp Glu Pro Pro His Thr Cys Trp Ser Ser Leu Cys Gly
            500                 505                 510
Tyr Pro Gln Leu Val Thr Gln Val His Val Leu Gly Ala Ala Gly Leu
        515                 520                 525
Lys Asp Ser Pro Thr Gly Ala Asn Ser Tyr Val Ile Ile Lys Cys Glu
        530                 535                 540
Gly Asp Lys Val Arg Ser Ala Val Gln Lys Gly Thr Ser Thr Pro Glu
545                 550                 555                 560
Tyr Asn Val Lys Gly Ile Phe Tyr Arg Lys Lys Leu Ser Gln Pro Ile
                565                 570                 575
Thr Val Gln Val Trp Asn His Arg Val Leu Lys Asp Glu Phe Leu Gly
            580                 585                 590
Gln Val His Leu Lys Ala Asp Pro Asp Asn Leu Gln Ala Leu His Thr
        595                 600                 605
Leu His Leu Arg Asp Arg Asn Ser Arg Gln Pro Ser Asn Leu Pro Gly
        610                 615                 620
```

-continued

```
Thr Val Ala Val His Ile Leu Ser Ser Thr Ser Leu Met Ala Val
625                 630                 635

<210> SEQ ID NO 26
<211> LENGTH: 641
<212> TYPE: PRT
<213> ORGANISM: Mus musculus

<400> SEQUENCE: 26

Met Gly Pro Pro Leu Lys Leu Phe Lys Asn Gln Lys Tyr Gln Glu Leu
  1               5                  10                  15

Lys Gln Glu Cys Met Lys Asp Gly Arg Leu Phe Cys Asp Pro Thr Phe
             20                  25                  30

Leu Pro Glu Asn Asp Ser Leu Phe Asn Arg Leu Leu Pro Gly Lys
         35                  40                  45

Val Val Trp Lys Arg Pro Gln Asp Ile Ser Asp Pro His Leu Ile
 50                  55                  60

Val Gly Asn Ile Ser Asn His Gln Leu Ile Gln Gly Arg Leu Gly Asn
 65                  70                  75                  80

Lys Ala Met Ile Ser Ala Phe Ser Cys Leu Ala Val Gln Glu Ser His
                 85                  90                  95

Trp Thr Lys Ala Ile Pro Asn His Lys Asp Gln Glu Trp Asp Pro Arg
            100                 105                 110

Lys Pro Glu Lys Tyr Ala Gly Ile Phe His Phe Arg Phe Trp His Phe
        115                 120                 125

Gly Glu Trp Thr Glu Val Val Ile Asp Asp Leu Leu Pro Thr Ile Asn
130                 135                 140

Gly Asp Leu Val Phe Ser Phe Ser Thr Ser Met Asn Glu Phe Trp Asn
145                 150                 155                 160

Ala Leu Leu Glu Lys Ala Tyr Ala Lys Leu Leu Gly Cys Tyr Glu Ala
                165                 170                 175

Leu Asp Gly Leu Thr Ile Thr Asp Ile Ile Met Asp Phe Thr Gly Thr
            180                 185                 190

Leu Ala Glu Ile Ile Asp Met Gln Lys Gly Arg Tyr Thr Asp Leu Val
        195                 200                 205

Glu Glu Lys Tyr Lys Leu Phe Gly Glu Leu Tyr Lys Thr Phe Thr Lys
    210                 215                 220

Gly Gly Leu Ile Cys Cys Ser Ile Glu Ser Pro Ser Gln Glu Glu Gln
225                 230                 235                 240

Glu Val Glu Thr Asp Trp Gly Leu Leu Lys Gly Tyr Thr Tyr Thr Met
                245                 250                 255

Thr Asp Ile Arg Lys Leu Arg Leu Gly Glu Arg Leu Val Glu Val Phe
            260                 265                 270

Ser Thr Glu Lys Leu Tyr Met Val Arg Leu Arg Asn Pro Leu Gly Arg
        275                 280                 285

Gln Glu Trp Ser Gly Pro Trp Ser Glu Ile Ser Glu Glu Trp Gln Gln
    290                 295                 300

Leu Thr Val Thr Asp Arg Lys Asn Leu Gly Leu Val Met Ser Asp Asp
305                 310                 315                 320

Gly Glu Phe Trp Met Ser Leu Glu Asp Phe Cys His Asn Phe His Lys
                325                 330                 335

Leu Asn Val Cys Arg Asn Val Asn Pro Val Phe Gly Arg Lys Glu
            340                 345                 350

Leu Glu Ser Val Val Gly Cys Trp Thr Val Asp Asp Pro Leu Met
```

-continued

```
                355                 360                 365
Asn Arg Ser Gly Gly Cys Tyr Asn Asn Arg Asp Thr Phe Leu Gln Asn
            370                 375                 380
Pro Gln Tyr Ile Phe Thr Val Pro Glu Asp Gly His Lys Val Ile Met
385                 390                 395                 400
Ser Leu Gln Gln Lys Asp Leu Arg Thr Tyr Arg Arg Met Gly Arg Pro
                405                 410                 415
Asp Asn Tyr Ile Ile Gly Phe Glu Leu Phe Lys Val Glu Met Asn Arg
            420                 425                 430
Arg Phe Arg Leu His His Leu Tyr Ile Gln Glu Arg Ala Gly Thr Ser
                435                 440                 445
Thr Tyr Ile Asp Thr Arg Thr Val Phe Leu Ser Lys Tyr Leu Lys Lys
450                 455                 460
Gly Ser Tyr Val Leu Val Pro Thr Met Phe Gln His Gly Arg Thr Ser
465                 470                 475                 480
Glu Phe Leu Leu Arg Ile Phe Ser Glu Val Pro Val Gln Leu Arg Glu
                485                 490                 495
Leu Thr Leu Asp Met Pro Lys Met Ser Cys Trp Asn Leu Ala Arg Gly
                500                 505                 510
Tyr Pro Lys Val Val Thr Gln Ile Thr Val His Ser Ala Glu Gly Leu
            515                 520                 525
Glu Lys Lys Tyr Ala Asn Glu Thr Val Asn Pro Tyr Leu Ile Ile Lys
530                 535                 540
Cys Gly Lys Glu Glu Val Arg Ser Pro Val Gln Lys Asn Thr Val His
545                 550                 555                 560
Ala Ile Phe Asp Thr Gln Ala Val Phe Tyr Arg Arg Thr Thr Asp Ile
                565                 570                 575
Pro Ile Ile Ile Gln Val Trp Asn Ser Arg Lys Phe Cys Asp Gln Phe
            580                 585                 590
Leu Gly Gln Val Thr Leu Asp Ala Asp Pro Ser Asp Cys Arg Asp Leu
                595                 600                 605
Lys Ser Leu Tyr Leu Arg Lys Lys Gly Gly Pro Thr Ala Lys Val Lys
            610                 615                 620
Gln Gly His Ile Ser Phe Lys Val Ile Ser Ser Asp Leu Thr Glu
625                 630                 635                 640
Leu

<210> SEQ ID NO 27
<211> LENGTH: 703
<212> TYPE: PRT
<213> ORGANISM: RAT

<400> SEQUENCE: 27

Met Ala Ala Leu Ala Ala Gly Val Ser Lys Gln Arg Ala Val Ala Glu
  1               5                  10                  15
Gly Leu Gly Ser Asn Gln Asn Ala Val Lys Tyr Leu Gly Gln Asp Phe
                 20                  25                  30
Glu Thr Leu Arg Lys Gln Cys Leu Asn Ser Gly Val Leu Phe Lys Asp
             35                  40                  45
Pro Glu Phe Pro Ala Cys Pro Ser Ala Leu Gly Tyr Lys Asp Leu Gly
         50                  55                  60
Pro Gly Ser Pro Asp Thr Gln Gly Ile Val Trp Lys Arg Pro Thr Glu
 65                  70                  75                  80
Leu Cys Pro Asn Pro Gln Phe Ile Val Gly Gly Ala Thr Arg Thr Asp
```

```
                    85                  90                  95
Ile Arg Gln Gly Gly Leu Gly Asp Cys Trp Leu Leu Ala Ala Ile Ala
                100                 105                 110
Ser Leu Thr Leu Asn Glu Lys Leu Leu Tyr Arg Val Leu Pro Arg Asp
            115                 120                 125
Gln Ser Phe Gln Lys Asp Tyr Ala Gly Ile Phe His Phe Gln Phe Trp
        130                 135                 140
Gln Tyr Gly Glu Trp Val Glu Val Ile Asp Asp Arg Leu Pro Thr
145                 150                 155                 160
Lys Asn Gly Gln Leu Leu Phe Leu His Ser Glu Glu Gly Asn Glu Phe
                165                 170                 175
Trp Ser Ala Leu Leu Glu Lys Ala Tyr Ala Lys Leu Asn Gly Ser Tyr
            180                 185                 190
Glu Ala Leu Val Gly Gly Ser Thr Ile Glu Gly Phe Glu Asp Phe Thr
        195                 200                 205
Gly Gly Ile Ser Glu Phe Tyr Asp Leu Lys Lys Pro Pro Glu Asn Leu
210                 215                 220
Tyr Tyr Ile Ile Gln Lys Ala Leu Arg Lys Gly Ser Leu Leu Gly Cys
225                 230                 235                 240
Ser Ile Asp Val Ser Thr Ala Ala Glu Ala Glu Ala Thr Thr Arg Gln
                245                 250                 255
Lys Leu Val Lys Gly His Ala Tyr Ser Val Thr Gly Val Glu Glu Val
                260                 265                 270
Asn Phe His Gly Arg Pro Glu Lys Leu Ile Arg Leu Arg Asn Pro Trp
            275                 280                 285
Gly Glu Val Glu Trp Ser Gly Ala Trp Ser Asp Asn Ala Pro Glu Trp
        290                 295                 300
Asn Tyr Ile Asp Pro Arg Arg Lys Glu Glu Leu Asp Lys Lys Ala Glu
305                 310                 315                 320
Asp Gly Glu Phe Trp Met Ser Phe Ser Asp Phe Leu Lys Gln Tyr Ser
                325                 330                 335
Arg Leu Glu Ile Cys Asn Leu Ser Pro Asp Ser Leu Ser Ser Glu Glu
            340                 345                 350
Ile His Lys Trp Asn Leu Val Leu Phe Asn Gly Arg Trp Thr Arg Gly
            355                 360                 365
Ser Thr Ala Gly Gly Cys Leu Asn Tyr Pro Gly Thr Tyr Trp Thr Asn
370                 375                 380
Pro Gln Phe Lys Ile His Leu Asp Glu Val Asp Glu Asp Gln Glu Glu
385                 390                 395                 400
Gly Thr Ser Glu Pro Cys Cys Thr Val Leu Leu Gly Leu Met Gln Lys
                405                 410                 415
Asn Arg Arg Gln Lys Arg Ile Gly Gln Gly Met Leu Ser Ile Gly
            420                 425                 430
Tyr Ala Val Tyr Gln Ile Pro Lys Glu Leu Glu Ser His Thr Asp Ala
        435                 440                 445
His Leu Gly Arg Asp Phe Phe Leu Gly Arg Gln Pro Ser Thr Cys Ser
    450                 455                 460
Ser Thr Tyr Met Asn Leu Arg Glu Val Ser Ser Arg Val Arg Leu Pro
465                 470                 475                 480
Pro Gly Gln Tyr Leu Val Val Pro Ser Thr Phe Glu Pro Phe Lys Asp
                485                 490                 495
Gly Asp Phe Cys Leu Arg Val Phe Ser Glu Lys Lys Ala Lys Ala Leu
            500                 505                 510
```

```
Glu Ile Gly Asp Thr Val Ser Gly His Pro His Glu Pro His Pro Arg
            515                 520                 525

Asp Met Asp Glu Glu Asp Glu His Val Arg Ser Leu Phe Glu Phe
530                 535                 540

Val Gly Lys Asp Ser Glu Ile Ser Ala Asn Gln Leu Lys Arg Val Leu
545                 550                 555                 560

Asn Glu Val Leu Ser Lys Arg Thr Asp Met Lys Phe Asp Gly Phe Asn
                565                 570                 575

Ile Asn Thr Cys Arg Glu Met Ile Ser Leu Leu Asp Ser Asp Gly Thr
            580                 585                 590

Gly Ser Leu Gly Pro Met Glu Phe Lys Thr Leu Trp Leu Lys Ile Arg
        595                 600                 605

Thr Tyr Leu Glu Ile Phe Gln Glu Met Asp His Asn His Val Gly Thr
        610                 615                 620

Ile Glu Ala His Glu Met Arg Thr Ala Leu Lys Lys Ala Gly Phe Thr
625                 630                 635                 640

Leu Asn Asn Gln Val Gln Gln Thr Ile Ala Met Arg Tyr Ala Cys Ser
                645                 650                 655

Lys Leu Gly Val Asp Phe Asn Gly Phe Val Ala Cys Met Ile Arg Leu
            660                 665                 670

Glu Thr Leu Phe Lys Leu Phe Arg Leu Leu Asp Lys Asp Gln Asn Gly
        675                 680                 685

Ile Val Gln Leu Ser Leu Ala Glu Trp Leu Cys Cys Val Leu Val
            690                 695                 700

<210> SEQ ID NO 28
<211> LENGTH: 690
<212> TYPE: PRT
<213> ORGANISM: Human

<400> SEQUENCE: 28

Met Pro Tyr Leu Tyr Arg Ala Pro Gly Pro Gln Ala His Pro Val Pro
 1               5                  10                  15

Lys Asp Ala Arg Ile Thr His Ser Ser Gly Gln Ser Phe Glu Gln Met
                20                  25                  30

Arg Gln Glu Cys Leu Gln Arg Gly Thr Leu Phe Glu Asp Ala Asp Phe
            35                  40                  45

Pro Ala Ser Asn Ser Ser Leu Phe Tyr Ser Glu Arg Pro Gln Ile Pro
        50                  55                  60

Phe Val Trp Lys Arg Pro Gly Glu Ile Val Lys Asn Pro Glu Phe Ile
65                  70                  75                  80

Leu Gly Gly Ala Thr Arg Thr Asp Ile Cys Gln Gly Glu Leu Gly Asp
                85                  90                  95

Cys Trp Leu Leu Ala Ala Ile Ala Ser Leu Thr Leu Asn Gln Lys Ala
            100                 105                 110

Leu Ala Arg Val Ile Pro Gln Asp Gln Ser Phe Gly Pro Gly Tyr Ala
        115                 120                 125

Gly Ile Phe His Phe Gln Phe Trp Gln His Ser Glu Trp Leu Asp Val
    130                 135                 140

Val Ile Asp Asp Arg Leu Pro Thr Phe Arg Asp Arg Leu Val Phe Leu
145                 150                 155                 160

His Ser Ala Asp His Asn Glu Phe Trp Ser Ala Leu Leu Glu Lys Ala
                165                 170                 175

Tyr Ala Lys Leu Asn Gly Ser Tyr Glu Ala Leu Lys Gly Gly Ser Ala
```

-continued

```
                180                 185                 190
Ile Glu Ala Met Glu Asp Phe Thr Gly Gly Val Ala Glu Thr Phe Gln
            195                 200                 205

Thr Lys Glu Ala Pro Glu Asn Phe Tyr Glu Ile Leu Glu Lys Ala Leu
    210                 215                 220

Lys Arg Gly Ser Leu Leu Gly Cys Phe Ile Asp Thr Arg Ser Ala Ala
225                 230                 235                 240

Glu Ser Glu Ala Arg Thr Pro Phe Gly Leu Ile Lys Gly His Ala Tyr
                245                 250                 255

Ser Val Thr Gly Ile Asp Gln Val Ser Phe Arg Gly Gln Arg Ile Glu
            260                 265                 270

Leu Ile Arg Ile Arg Asn Pro Trp Gly Gln Val Glu Trp Asn Gly Ser
        275                 280                 285

Trp Ser Asp Ser Ser Pro Glu Trp Arg Ser Val Gly Pro Ala Glu Gln
    290                 295                 300

Lys Arg Leu Cys His Thr Ala Leu Asp Asp Gly Glu Phe Trp Met Ala
305                 310                 315                 320

Phe Lys Asp Phe Lys Ala His Phe Asp Lys Val Glu Ile Cys Asn Leu
                325                 330                 335

Thr Pro Asp Ala Leu Glu Glu Asp Ala Ile His Lys Trp Glu Val Thr
            340                 345                 350

Val His Gln Gly Ser Trp Val Arg Gly Ser Thr Ala Gly Gly Cys Arg
        355                 360                 365

Asn Phe Leu Asp Thr Phe Trp Thr Asn Pro Gln Ile Lys Leu Ser Leu
    370                 375                 380

Thr Glu Lys Asp Glu Gly Gln Glu Glu Cys Ser Phe Leu Val Ala Leu
385                 390                 395                 400

Met Gln Lys Asp Arg Arg Lys Leu Lys Arg Phe Gly Ala Asn Val Leu
                405                 410                 415

Thr Ile Gly Tyr Ala Ile Tyr Glu Cys Pro Asp Lys Asp Glu His Leu
            420                 425                 430

Asn Lys Asp Phe Phe Arg Tyr His Ala Ser Arg Ala Arg Ser Lys Thr
        435                 440                 445

Phe Ile Asn Leu Arg Glu Val Ser Asp Arg Phe Lys Leu Pro Pro Gly
    450                 455                 460

Glu Tyr Ile Leu Ile Pro Ser Thr Phe Glu Pro His Gln Glu Ala Asp
465                 470                 475                 480

Phe Cys Leu Arg Ile Phe Ser Glu Lys Lys Ala Ile Thr Arg Asp Met
                485                 490                 495

Asp Gly Asn Val Asp Ile Asp Leu Pro Glu Pro Lys Pro Thr Pro
            500                 505                 510

Pro Asp Gln Glu Thr Glu Glu Gln Arg Phe Arg Ala Leu Phe Glu
        515                 520                 525

Gln Val Ala Gly Glu Asp Met Glu Val Thr Ala Glu Glu Leu Glu Tyr
    530                 535                 540

Val Leu Asn Ala Val Leu Gln Lys Lys Lys Asp Ile Lys Phe Lys Lys
545                 550                 555                 560

Leu Ser Leu Ile Ser Cys Lys Asn Ile Ile Ser Leu Met Asp Thr Ser
                565                 570                 575

Gly Asn Gly Lys Leu Glu Phe Asp Glu Phe Lys Val Phe Trp Asp Lys
            580                 585                 590

Leu Lys Gln Trp Ile Asn Leu Phe Leu Arg Phe Asp Ala Asp Lys Ser
        595                 600                 605
```

```
Gly Thr Met Ser Thr Tyr Glu Leu Arg Thr Ala Leu Lys Ala Ala Gly
    610                 615                 620

Phe Gln Leu Ser Ser His Leu Leu Gln Leu Ile Val Leu Arg Tyr Ala
625                 630                 635                 640

Asp Glu Glu Leu Gln Leu Asp Phe Asp Asp Phe Leu Asn Cys Leu Val
                645                 650                 655

Arg Leu Glu Asn Ala Ser Arg Val Phe Gln Ala Leu Ser Thr Lys Asn
                660                 665                 670

Lys Glu Phe Ile His Leu Asn Ile Asn Glu Phe Ile His Leu Thr Met
                675                 680                 685

Asn Ile
    690

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 29
tctcagagtg gggtgaggct gtgatgggg                                           29

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 30 aataaa                                                                     6
```